US012746201B2

(12) United States Patent
Patwardhan et al.

(10) Patent No.: US 12,746,201 B2
(45) Date of Patent: Sep. 29, 2026

(54) NANOMATERIALS

(71) Applicant: Guide Therapeutics, LLC, Cambridge, MA (US)

(72) Inventors: Neeraj Narendra Patwardhan, Cambridge, MA (US); Milloni Balwantkumar Chhabra, Cambridge, MA (US); Gregory Lawrence Hamilton, Cambridge, MA (US); Cory Dane Sago, Cambridge, MA (US); Mina Fawzy Gaballa Shehata, Cambridge, MA (US)

(73) Assignee: Guide Therapeutics, LLC, Cambridge, MA (US)

( * ) Notice: Subject to any disclaimer, the term of this patent is extended or adjusted under 35 U.S.C. 154(b) by 291 days.

(21) Appl. No.: 18/673,962

(22) Filed: May 24, 2024

(65) Prior Publication Data

US 2025/0000797 A1 Jan. 2, 2025

Related U.S. Application Data

(63) Continuation of application No. 17/110,070, filed on Dec. 2, 2020, now abandoned.

(60) Provisional application No. 62/944,735, filed on Dec. 6, 2019.

(51) Int. Cl.
*A61K 9/1272* (2025.01)
*A61K 9/1277* (2025.01)
*C12N 15/113* (2010.01)

(52) U.S. Cl.
CPC .......... *A61K 9/1272* (2013.01); *A61K 9/1277* (2013.01); *C12N 15/113* (2013.01)

(58) Field of Classification Search
None
See application file for complete search history.

(56) References Cited

U.S. PATENT DOCUMENTS

| | | | |
|---|---|---|---|
| 3,686,238 | A | 8/1972 | Zaffaroni |
| 8,058,069 | B2 | 11/2011 | Yaworski et al. |
| 9,364,435 | B2 | 6/2016 | Yaworski et al. |
| 9,840,699 | B2 | 12/2017 | Liu et al. |
| 10,113,163 | B2 | 10/2018 | Liu et al. |
| 10,124,065 | B2 | 11/2018 | Baryza et al. |

(Continued)

FOREIGN PATENT DOCUMENTS

| | | | |
|---|---|---|---|
| AU | 2020369940 | A1 | 5/2022 |
| CN | 108368028 | A | 8/2018 |

(Continued)

OTHER PUBLICATIONS

Melissa P. Lokugamage, Cory D. Sago, Zubao Gan, Brandon R. Krupczak, and James E. Dahlman. "Constrained Nanoparticles Deliver siRNA and sgRNA to T Cells In Vivo without Targeting Ligands." Advanced Materials, vol. 31, 2019, 1902251, pp. 1-8 and additional supplementary information. (Year: 2019).*

(Continued)

*Primary Examiner* — Isaac Shomer
(74) *Attorney, Agent, or Firm* — Proskauer Rose LLP

(57) ABSTRACT

Lipid nanoparticle compositions for delivery of nucleic acids are described. The lipid nanoparticle may contain a conformationally constrained ionizable lipid as part of the composition. These compositions may allow for delivery of cargo without the need for a targeting ligand.

20 Claims, 23 Drawing Sheets

(56) References Cited

U.S. PATENT DOCUMENTS

| | | | |
|---|---|---|---|
| 10,167,457 | B2 | 1/2019 | Liu et al. |
| 2003/0083272 | A1 | 5/2003 | Wiederholt et al. |
| 2016/0311759 | A1 | 10/2016 | Brito et al. |
| 2017/0210698 | A1 | 7/2017 | Benenato et al. |
| 2018/0147166 | A1 | 5/2018 | Dong et al. |
| 2018/0290965 | A1 | 10/2018 | Brito et al. |
| 2019/0002393 | A1 | 1/2019 | Beckwith et al. |
| 2019/0076462 | A1 | 3/2019 | Dong et al. |
| 2019/0358170 | A1 | 11/2019 | Brito et al. |
| 2021/0113365 | A1 | 4/2021 | Kim |
| 2021/0130805 | A1 | 5/2021 | Gaudelli et al. |
| 2021/0169804 | A1 | 6/2021 | Patwardhan et al. |
| 2021/0230112 | A1 | 7/2021 | Hamilton et al. |
| 2022/0096381 | A1 | 3/2022 | Endo et al. |
| 2022/0249693 | A1 | 8/2022 | Sago et al. |
| 2022/0249694 | A1 | 8/2022 | Shehata et al. |
| 2022/0273566 | A1 | 9/2022 | Dahlman et al. |
| 2023/0348359 | A1 | 11/2023 | Shehata et al. |

FOREIGN PATENT DOCUMENTS

| | | | | |
|---|---|---|---|---|
| CN | 110520409 | A | 11/2019 | |
| EP | 1164125 | A1 | 12/2001 | |
| EP | 3733211 | A1 | 11/2020 | |
| EP | 3842538 | A1 | 6/2021 | |
| EP | 4069675 | A1 | 10/2022 | |
| GB | 968849 | A | 9/1964 | |
| JP | 2005181734 | A | 7/2005 | |
| WO | 0244321 | A2 | 6/2002 | |
| WO | 03101952 | A2 | 12/2003 | |
| WO | 2008155141 | A2 | 12/2008 | |
| WO | 2011153493 | A2 | 12/2011 | |
| WO | 2013086354 | A1 | 6/2013 | |
| WO | 2014136086 | A1 | 9/2014 | |
| WO | 2015095340 | A1 | 6/2015 | |
| WO | 2015095346 | A1 | 6/2015 | |
| WO | 2016187531 | A1 | 11/2016 | |
| WO | 2017173054 | A1 | 10/2017 | |
| WO | 2018011799 | A1 | 1/2018 | |
| WO | 2018220553 | A1 | 12/2018 | |
| WO | 2019008441 | A1 | 1/2019 | |
| WO | 2019089561 | A1 | 5/2019 | |
| WO | 2019099501 | A1 | 5/2019 | |
| WO | 2019126378 | A1 | 6/2019 | |
| WO | 2020028787 | A1 | 2/2020 | |
| WO | 2020072605 | A1 | 4/2020 | |
| WO | 2020118041 | A1 | 6/2020 | |
| WO | 2020150320 | A1 | 7/2020 | |
| WO | 2020152037 | A1 | 7/2020 | |
| WO | 2020176856 | A1 | 9/2020 | |
| WO | 2020176859 | A1 | 9/2020 | |
| WO | 2020176868 | A1 | 9/2020 | |
| WO | 2020219876 | A1 | 10/2020 | |
| WO | 2020246581 | A1 | 12/2020 | |
| WO | 2020247382 | A1 | 12/2020 | |
| WO | 2021021636 | A1 | 2/2021 | |
| WO | WO-2021021634 | A1 * | 2/2021 | .............. A61P 37/02 |
| WO | 2021080847 | A1 | 4/2021 | |
| WO | 2021113365 | A1 | 6/2021 | |
| WO | 2021141969 | A1 | 7/2021 | |
| WO | 2022060871 | A1 | 3/2022 | |
| WO | 2022140238 | A1 | 6/2022 | |
| WO | 2022140239 | A1 | 6/2022 | |
| WO | 2022140252 | A1 | 6/2022 | |
| WO | 2022159421 | A1 | 7/2022 | |
| WO | 2022159463 | A1 | 7/2022 | |
| WO | 2022159472 | A1 | 7/2022 | |
| WO | 2022159475 | A1 | 7/2022 | |
| WO | 2022251665 | A1 | 12/2022 | |
| WO | 2023056917 | A1 | 4/2023 | |
| WO | 2023121964 | A1 | 6/2023 | |
| WO | 2023121965 | A1 | 6/2023 | |
| WO | 2023121970 | A1 | 6/2023 | |
| WO | 2023121971 | A1 | 6/2023 | |
| WO | 2023121975 | A1 | 6/2023 | |
| WO | 2024019936 | A1 | 1/2024 | |

OTHER PUBLICATIONS

CAS SciFinder Search, Ionizable Lipid, 2025 (21 pages).

Google Search, Is Adamantyl Cycloalkyl, 2025 (4 pages).

Google Search, why is adamantyl group on an ionizable lipid, 2025 (4 pages).

International Search Report for PCT/US2022/012951 dated May 23, 2022 (5 pages).

Partial Search Report for PCT/US2022/012867 dated Mar. 28, 2022 (3 pages).

Partial Search Report for PCT/US2022/012941 dated Mar. 21, 2022 (2 pages).

Partial Search Report for PCT/US2022/012951 dated Mar. 23, 2022 (2 pages).

Partial Search Report for PCT/US2022/012954 dated Mar. 23, 2022 (3 pages).

Kanasty, Rosemary, et al., "Delivery Materials for siRNA Therapeutics", Nature Materials, vol. 12, No. 11, pp. 967-977, Nov. 2013, DOI:10.1038/nmat3765 (11 pages).

Zhang, Xinfu, et al., "Functionalized lipid-like nanoparticles for in vivo mRNA delivery and base editing", Science Advances, vol. 6, No. 34, 2020, eabc2315, DOI: 10.1126/sciadv.abc2315, (9 pages).

CAS Registry No. 751440-44-5; STN Entry Date Sep. 24, 2004; 3-octyl-6-[7-oxo-7-[[2-[(1-oxooctadecyl)oxy]-1-[[(oxooctadecyl)oxy]methyl]ethoxy]heptyl]-4-Cyclohexene-1,2-dicarboxylic acid, (1 page).

International Search Report for PCT/US2020/043512 dated Sep. 23, 2020 (7 pages).

International Search Report for PCT/US2020/062893 dated Jun. 10, 2023 (7 pages).

International Search Report for PCT/US2021/012282 dated Mar. 3, 2021 (5 pages).

International Search Report for PCT/US2022/012867 dated Jun. 8, 2022 (5 pages).

International Search Report for PCT/US2022/053193 dated Jun. 29, 2023 (4 pages).

International Search Report for PCT/US2022/053209 dated Mar. 24, 2023 (5 pages).

International Search Report for PCT/US2023/027741 dated Oct. 13, 2023 (3 pages).

International Search Report for PCT/US22/12951 dated May 23, 2022 (5 pages).

"SID 402741750", PubChem, National Center for Biotechnology Information, SID 402741750, Jan. 23, 2020, retrieved Mar. 21, 2022 from URL: https://pubchem.ncbi.nlm.nih.gov/substance/402741750, (5 pages).

"SID 46481541", PubChem, National Center for Biotechnology Information, SID 46481541, Dec. 12, 2007, retrieved May 10, 2022 from URL: https://pubchem.ncbi.nlm.nih.gov/substance/46481541, (5 pages).

"Tris(deoxycholic acid)1,3,5-benzenetriyltris(methylene) ester", PubChem, National Center for Biotechnology Information, SID 274013917, Dec. 18, 2015, retrieved Mar. 21, 2022 from URL: https://pubchem.ncbi.nlm.nih.gov/substance/274013917, (2 pages).

Adams, David, et al., "Patisiran, an RNAi Therapeutic, for Hereditary Transthyretin Amyloidosis", The New England Journal of Medicine, vol. 379, No. 1, Jul. 5, 2018, pp. 11-21, DOI: 10.1056/NEJMoa1716153 (11 pages).

Augustin, Hellmut G., et al., "Organotypic vasculature: From descriptive heterogeneity to functional pathophysiology", Science, vol. 357, No. 771, Aug. 25, 2017, DOI: 10.1126/science.aal2379 (13 pages).

Belliveau, Nathan M., et al., "Microfluidic Synthesis of Highly Potent Limit-size Lipid Nanoparticles for In Vitro Delivery of siRNA", Molecular Therapy—Nucleic Acids, vol. 1, No. e37, 2012, DOI: 10.1038/mtna.2012.28 (9 pages).

Brown, William H., et al., "Organic Chemistry", Second Edition, Saunders College Publishing, 1995, pp. 169 (3 pages).

(56) References Cited

OTHER PUBLICATIONS

Chen, Delai, et al., "Rapid Discovery of Potent siRNA-Containing Lipid Nanoparticles Enabled by Controlled Microfluidic Formulation", Journal of the American Chemical Society, vol. 134, No. 16, Apr. 25, 2012, pp. 6948-6951, DOI: 10.1025/ja301621z (4 pages).
Cheng, Zhiliang, et al., "Multifunctional Nanoparticles: Cost versus benefit of adding targeting and imaging capabilities", Science, vol. 338, No. 6109, Nov. 16, 2012, pp. 903-910, DOI: 10.1126/science.1226338 (18 pages).
Chenthamara, et al., "Therapeutic efficacy of nanoparticles and routes of administration", Biomaterials Research, vol. 23, No. 20, Nov. 21, 2019, DOI:10.1186/s40824-019-0166-x (29 pages).
Cullis, Pieter R., et al., "Lipid Nanoparticle Systems for Enabling Gene Therapies", Molecular Therapy, vol. 25, No. 7, Jul. 5, 2017, pp. 1467-1475, DOI: 10.1016/j.ymthe.2017.03.013 (9 pages).
Dahlman, James E., et al., "In vivo endothelial siRNA delivery using polymeric nanoparticles with low molecular weight", Nature Nanotechnology, vol. 9, No. 8, Aug. 2014, pp. 648-655, DOI: 10.1038/nnano.2014.84 (17 pages).
Dang, Chi V., et al., "Drugging the 'undruggable' cancer targets", Nature Reviews Cancer, vol. 17, No. 8, Aug. 2017, pp. 502-508, DOI: 10.1038/nrc.2017.36, Author Manuscript (16 pages).
Diab, Hadeer M., et al., "ZnO-Nanoparticles-Catalyzed Synthesis of Poly(tetrahydrobenzimidazo[2,1-b]quinazolin-1(2H)-ones) as Novel Multi-armed Molecules", Synlett, vol. 29, No. 12, 2018, pp. 1627-1633, DOI: 10.1055/s-0037-1609967, (7 pages).
Dixon, Scott J., et al., "Identifying Druggable Disease-Modifying Gene Products", Current Opinion in Chemical Biology, vol. 13, No. 5-6, Dec. 2009, pp. 549-555, DOI: 10.1016/j.cbpa.2009.08.003, Author Manuscript (12 pages).
Elbashir, Sayda M., et al., "Duplexes of 21-nucleotide RNAs mediate RNA interference in cultured mammalian cells", Nature, vol. 411, May 24, 2001, pp. 494-498 (5 pages).
Epand, et al., "Role of the position of unsaturation on the phase behavior and intrinsic curvature of phosphatidylethanolamines", Biophysical Journal, vol. 71, No. 4, pp. 1806-1810, Oct. 1996, DOI:10.1016/S0006-3495(96)79381-5 (5 pages).
Fenton, et al., "Synthesis and Biological Evaluation of Ionizable Lipid Materials for the In Vivo Delivery of Messenger RNA to B Lymphocytes", Advanced materials (Deerfield Beach, Fla.), vol. 29, No. 33, Sep. 2017, DOI:10.1002/adma.201606944 (7 pages).
Funakoshi, Yuka, et al., "Effect of Alkyl Chain Length and Unsaturation of the Phospholipid on the Physicochemical Properties of Lipid Nanoparticles", Chem. Pharm. Bull., vol. 63, No. 9, 2015, pp. 731-736 (6 pages).
Gelsema, W. J., et al., "Benzoolysis of diacylglycerophosphocholines: dephosphorylation and sequential formation of isomeric reaction products", Journal of Lipid Research, vol. 37, 1996, pp. 1224-1233 (10 pages).
Heidenreich, Olaf, et al., "High Activity and Stability of Hammerhead Ribozymes Containing 2'-Modified Pyrimidine Nucleosides and Phosphorothioates", The Journal of Biological Chemistry, vol. 269, Jan. 21, 1994, pp. 2131-2138 (8 pages).
Jenkins, Russell W., et al., "Mechanisms of resistance to immune checkpoint inhibitors", British Journal of Cancer, vol. 118, No. 1, Jan. 2018, pp. 9-16, DOI: 10.1038/bjc.2017.434 (8 pages).
Junquera, Elena, et al., "Recent progress in gene therapy to deliver nucleic acids with multivalent cationic vectors", Advances in Colloid and Interface Science, vol. 233, 2016, pp. 161-175, (15 pages).
Karikó, Katalin, et al., "Incorporation of Pseudouridine Into mRNA Yields Superior Nonimmunogenic Vector With Increased Translational Capacity and Biological Stability", Molecular Therapy, vol. 16, No. 11, Nov. 2008, pp. 1833-1840, DOI:10.1038/mt.2008.200 (8 pages).
Kedmi, Ranit, et al., "A modular platform for targeted RNAi therapeutics", Nature Nanotechnology, vol. 13, Jan. 29, 2018, pp. 214-219, DOI: 10.1038/s41565-017-0043-5 (6 pages).
Khalil, Danny N., et al., "The future of cancer treatment: immunomodulation, CARs and combination immunotherapy", Nature Reviews: Clinical Oncology, vol. 13, No. 5, May 2016, pp. 273-290, DOI: 10.1038/nrclinonc.2016.25, Author Manuscript (40 pages).
Kozak, Marilyn, "An analysis of 5'-noncoding sequences from 699 vertebrate messenger RNAs", Nucleic Acids Research, vol. 15, No. 20, 1987, pp. 8125-8148 (24 pages).
Kumar, Priti, et al., "T Cell-Specific siRNA Delivery Suppresses HIV-1 Infection in Humanized Mice", Cell, vol. 134, Aug. 22, 2008, pp. 577-586, DOI: 10.1016/j.cell.2008.06.034 (10 pages).
Leung, Alex K., et al., "Lipid Nanoparticles Containing siRNA Synthesized by Microfluidic Mixing Exhibit an Electron-Dense Nanostructured Core", The Journal of Physical Chemistry, vol. 116, No. 34, Jul. 18, 2012, pp. 18440-18450, DOI: 10.1021/jp303267y (11 pages).
Lokugamage, Melissa P., et al., "Constrained Nanoparticles Deliver siRNA and sgRNA to T Cells In Vivo without Targeting Ligands", Advanced Materials, vol. 31, Issue 41, No. 1902251, Aug. 29, 2019, DOI: 10.1002/adma.201902251 (8 pages).
Lokugamage, Melissa P., et al., "Constrained Nanoparticles Deliver siRNA and sgRNA to T Cells In Vivo without Targeting Ligands", Advanced Materials, vol. 31, Issue 41, No. 1902251, Aug. 29, 2019, DOI: 10.1002/adma.201902251, Supporting Information (32 pages).
Lokugamage, Melissa P., et al., "Testing thousands of nanoparticles in vivo using DNA barcodes", Current Opinion: Biomedical Engineering, vol. 7, Sep. 2018, p. 1-8, DOI: 10.1016/j.cobme.2018.08.001, Author Manuscript (16 pages).
Lorenzer, Cornelia, et al., "Going beyond the liver: Progress and challenges of targeted delivery of siRNA therapeutics", Journal of Controlled Release, vol. 203, Apr. 10, 2015, pp. 1-15, DOI: 10.1016/j.jconrel.2015.02.003 (15 pages).
Macparland, Sonya A., et al., "Phenotype Determines Nanoparticle Uptake by Human Macrophages from Liver and Blood", ACS Nano, vol. 11, 2017, pp. 2428-2443, DOI: 10.1021/acsnano.6b06245 (16 pages).
Makarova, Kira M., et al., "An updated evolutionary classification of CRISPR-Cas systems", Nature Reviews Microbiology, vol. 13, 2015, pp. 722-736, DOI: 10.1038/nrmicro3569, (15 pages).
Mathiowitz, E., et al., "Novel Microcapsules for Delivery Systems", Reactive Polymers, vol. 6, 1987, pp. 275-283 (9 pages).
Mathiowitz, E., et al., "Polyanhydride Microspheres as Drug Carriers I. Hot-Melt Microencapsulation", Journal of Controlled Release, vol. 5, 1987, pp. 13-22 (10 pages).
Mathiowitz, E., et al., "Polyanhydride Microspheres as Drug Carriers. II. Microencapsulation by Solvent Removal", Journal of Applied Polymer Science, vol. 35, 1988, pp. 755-775 (20 pages).
Paunovska, Kalina, et al., "A direct comparison of in vitro and in vivo nucleic acid delivery mediated by hundreds of nanoparticles reveals a weak correlation", Nano Lett., vol. 18, No. 3, Mar. 14, 2018, pp. 2148-2157, DOI: 10.1021/acs.nanolett.8b00432, Author Manuscript (20 pages).
Paunovska, Kalina, et al., "Analyzing 2,000 in vivo Drug Delivery Data Points Reveals Cholesterol Structure Impacts Nanoparticle Delivery", ACS Nano, vol. 12, No. 8, Aug. 28, 2018, pp. 8341-8349, DOI: 10.1021/acsnano.8b03640, Author Manuscript (17 pages).
Platt, Randall J., et al., "CRISPR-Cas9 Knockin Mice for Genome Editing and Cancer Modeling", Cell, vol. 159, Oct. 9, 2014, pp. 440-455, DOI: 10.1016/j.cell.2014.09.014 (16 pages).
Pollastri, M. P., et al., "Synthesis, structure, and thermal properties of 1,2-dipalmitoylgalloylglycerol (DPGG), a novel self-adhering lipid", Chemistry and Physics of Lipids, vol. 104, 2000, pp. 67-74 (8 pages).
Ramishetti, Srinivas, et al., "Systemic Gene Silencing in Primary T Lymphocytes Using Targeted Lipid Nanoparticles", ACS Nano, vol. 9, No. 7, Jun. 4, 2015, pp. 6706-6716, DOI: 10.1021/acsnano.5b02796 (11 pages).
Reichmuth, et al., "mRNA vaccine delivery using lipid nanoparticles", Therapeutic Delivery, vol. 7, No. 5, pp. 319-334, 2016, DOI:10.4155/tde-2016-0006 (16 pages).
Sago, Cory D., et al., "High-throughput in vivo screen of functional mRNA delivery identifies nanoparticles for endothelial cell gene editing", PNAS, vol. 115, No. 43, 2018, pp. E9944-E9952, DOI: 10.1073/pnas.1811276115, (9 pages).
Sago, Cory D., et al., "Modifying a commonly expressed endocytic receptor retargets nanoparticles in vivo", Nano Lett., vol. 18, No.

(56) References Cited

OTHER PUBLICATIONS

12, Dec. 12, 2018, pp. 7590-7600, DOI: 10.1021/acs.nanolett.8b03149, Author Manuscript (21 pages).
Sago, Cory D., et al., "Nanoparticles That Deliver RNA to Bone Marrow Identified by in Vivo Directed Evolution", Journal of the American Chemical Society, vol. 140, No. 49, 2018, pp. 17095-17105, DOI: 10.1021/jacs.8b08976, Author Manuscript (23 pages).
Scheidt, et al., "The interaction of small molecules with phospholipid membranes studied by 1H NOESY NMR under magic-angle spinning", Acta Pharmacologica Sinica, vol. 29, No. 1, 2008, pp. 35-49, DOI:10.1111/j.1745-7254.2008.00726.x (15 pages).
Sharma, Padmanee , et al., "The future of immune checkpoint therapy", Science, vol. 348, No. 6230, Apr. 3, 2015, pp. 56-61, DOI: 10.1126/science.aaa8172 (6 pages).
Shmakov, Sergey, et al., "Discovery and Functional Characterization of Diverse Class 2 CRISPR-Cas Systems", Molecular Cell, vol. 60, No. 3, 2015, pp. 385-397, DOI: 10.1016/j.molcel.2015.10.008, (14 pages).
Tavares, Anthony J., et al., "Effect and removing Kupffer cells on nanoparticle tumor delivery", Proceedings of the National Academy of Sciences, vol. 114, No. 51, Dec. 5, 2017, pp. E10871-E10880, DOI: 10.1073/pnas.1713390114 (10 pages).
Tsoi, Kim M., et al., "Mechanism of hard nanomaterial clearance by the liver", Nature Materials, vol. 15, No. 11, Nov. 2016, pp. 1212-1221, DOI: 10.1038/nmat4718, Author Manuscript (21 pages).
Ui-Tei, Kumiko, et al., "Sensitive assay of RNA interference in *Drosophila* and Chinese hamster cultured cells using firefly luciferase gene as target", FEBS Letters, vol. 479, 2000, pp. 79-82 (4 pages).
Wang, et al., "Effects of various numbers and positions of cis double bonds in the sn-2 acyl chain of phosphatidylethanolamine on the chain-melting temperature", The Journal of Biological Chemistry, vol. 274, No. 18, pp. 12289-12299. Apr. 30, 1999, DOI:10.1074/jbc.274.18.12289 (11 pages).
Yokoe, Hiroko, et al., "Spatial dynamics of GFP-tagged proteins investigated by local fluorescence enhancement", Nature Biotechnology, vol. 14, Oct. 1996, pp. 1252-1256 (5 pages).
Zetsche, Bernd, et al., "Cpf1 Is a Single RNA-Guided Endonuclease of a Class 2 CRISPR-Cas System", Cell, vol. 163, No. 3, 2015, pp. 759-771, DOI: 10.1016/j.cell.2015.09.038, (15 pages).

* cited by examiner

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 1 | 19 | Cholesterol | DMG-PEG2000 | DMPC | 50 | 38.5 | 1.5 | 10 | 103.31 | 13.05 | |
| 1 | 19 | Cholesterol | DMG-PEG2000 | DMPC | 55 | 33 | 3 | 9 | 85.93 | 9.56 | |
| 1 | 19 | Cholesterol | DMG-PEG2000 | DMPC | 45 | 44 | 2 | 9 | 108.5 | 10.21 | |
| 1 | 19 | Cholesterol | DMG-PEG2000 | DMPC | 35 | 46.5 | 2.5 | 16 | 122.51 | 11.43 | 6.998488 |
| 1 | 19 | Cholesterol | DMG-PEG2000 | DSPC | 50 | 38.5 | 1.5 | 10 | 111.82 | 16.5 | |
| 1 | 19 | Cholesterol | DMG-PEG2000 | DSPC | 55 | 33 | 3 | 9 | 69.88 | 7.42 | |
| 1 | 19 | Cholesterol | DMG-PEG2000 | DSPC | 45 | 44 | 2 | 9 | 102.21 | 17.75 | |
| 1 | 19 | Cholesterol | DMG-PEG2000 | DSPC | 35 | 46.5 | 2.5 | 16 | 96.16 | 7.54 | 7.500638 |
| 1 | 1 | Cholesterol | DMG-PEG2000 | DMPC | 50 | 38.5 | 1.5 | 10 | 161.42 | 21.54 | |
| 1 | 1 | Cholesterol | DMG-PEG2000 | DMPC | 55 | 33 | 3 | 9 | 80.97 | 17.27 | |
| 1 | 1 | Cholesterol | DMG-PEG2000 | DMPC | 45 | 44 | 2 | 9 | 142.28 | 13.93 | |
| 1 | 1 | Cholesterol | DMG-PEG2000 | DMPC | 35 | 46.5 | 2.5 | 16 | 151.17 | 10.87 | |
| 1 | 1 | Cholesterol | DMG-PEG2000 | DSPC | 50 | 38.5 | 1.5 | 10 | 121.4 | 18.69 | |
| 1 | 1 | Cholesterol | DMG-PEG2000 | DSPC | 55 | 33 | 3 | 9 | 91.66 | 12.89 | |
| 1 | 1 | Cholesterol | DMG-PEG2000 | DSPC | 45 | 44 | 2 | 9 | 113.14 | 14.42 | |
| 1 | 1 | Cholesterol | DMG-PEG2000 | DSPC | 35 | 46.5 | 2.5 | 16 | 158.28 | 12.84 | 8.532899 |
| 1 | 18 | Cholesterol | DMG-PEG2000 | DMPC | 50 | 38.5 | 1.5 | 10 | 79.24 | 11.33 | |
| 1 | 18 | Cholesterol | DMG-PEG2000 | DMPC | 55 | 33 | 3 | 9 | 72.78 | 8.13 | |
| 1 | 18 | Cholesterol | DMG-PEG2000 | DMPC | 45 | 44 | 2 | 9 | 72.87 | 11.71 | |
| 1 | 18 | Cholesterol | DMG-PEG2000 | DMPC | 35 | 46.5 | 2.5 | 16 | 118.56 | 8.02 | 7.518114 |
| 1 | 18 | Cholesterol | DMG-PEG2000 | DSPC | 50 | 38.5 | 1.5 | 10 | 97.64 | 28.4 | |
| 1 | 18 | Cholesterol | DMG-PEG2000 | DSPC | 55 | 33 | 3 | 9 | 69.38 | 20.78 | |
| 1 | 18 | Cholesterol | DMG-PEG2000 | DSPC | 45 | 44 | 2 | 9 | 96.81 | 10.76 | |
| 1 | 18 | Cholesterol | DMG-PEG2000 | DSPC | 35 | 46.5 | 2.5 | 16 | 110.28 | 14.97 | 7.59667 |
| 1 | 19 | Cholesterol | DMG-PEG2000 | DMPC | 50 | 38.5 | 1.5 | 10 | 96.78 | 12.29 | |

FIG. 1A

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 1 | 19 | Cholesterol | DMG-PEG2000 | DMPC | 55 | 33 | 3 | 9 | 84.66 | 17.23 | |
| 1 | 19 | Cholesterol | DMG-PEG2000 | DMPC | 45 | 44 | 2 | 9 | 84 | 6.45 | |
| 1 | 19 | Cholesterol | DMG-PEG2000 | DMPC | 35 | 46.5 | 2.5 | 16 | 108.15 | 11.15 | 5.896317 |
| 1 | 19 | Cholesterol | DMG-PEG2000 | DSPC | 50 | 38.5 | 1.5 | 10 | 92.51 | 10.18 | |
| 1 | 19 | Cholesterol | DMG-PEG2000 | DSPC | 55 | 33 | 3 | 9 | 83.16 | 14.8 | |
| 1 | 19 | Cholesterol | DMG-PEG2000 | DSPC | 45 | 44 | 2 | 9 | 87.06 | 9.59 | |
| 1 | 19 | Cholesterol | DMG-PEG2000 | DSPC | 35 | 46.5 | 2.5 | 16 | 96.66 | 12.65 | 5.910653 |
| 1 | 20 | Cholesterol | DMG-PEG2000 | DMPC | 50 | 38.5 | 1.5 | 10 | 95.9 | 10.66 | |
| 1 | 20 | Cholesterol | DMG-PEG2000 | DMPC | 55 | 33 | 3 | 9 | 87.91 | 13.97 | |
| 1 | 20 | Cholesterol | DMG-PEG2000 | DMPC | 45 | 44 | 2 | 9 | 86.71 | 11.97 | |
| 1 | 20 | Cholesterol | DMG-PEG2000 | DMPC | 35 | 46.5 | 2.5 | 16 | 86.45 | 12.07 | 15.48035 |
| 1 | 20 | Cholesterol | DMG-PEG2000 | DSPC | 50 | 38.5 | 1.5 | 10 | 88.65 | 12.02 | |
| 1 | 20 | Cholesterol | DMG-PEG2000 | DSPC | 55 | 33 | 3 | 9 | 96.29 | 14.76 | |
| 1 | 20 | Cholesterol | DMG-PEG2000 | DSPC | 45 | 44 | 2 | 9 | 86.88 | 7.05 | |
| 1 | 20 | Cholesterol | DMG-PEG2000 | DSPC | 35 | 46.5 | 2.5 | 16 | 73.08 | 8.62 | 57.63798 |
| 1 | 2 | Cholesterol | DMG-PEG2000 | DMPC | 50 | 38.5 | 1.5 | 10 | 68.99 | 8.34 | |
| 1 | 2 | Cholesterol | DMG-PEG2000 | DMPC | 55 | 33 | 3 | 9 | 89.31 | 15.53 | |
| 1 | 2 | Cholesterol | DMG-PEG2000 | DMPC | 45 | 44 | 2 | 9 | 94.15 | 14.28 | |
| 1 | 2 | Cholesterol | DMG-PEG2000 | DMPC | 35 | 46.5 | 2.5 | 16 | 90.65 | 7.89 | 7.287803 |
| 1 | 2 | Cholesterol | DMG-PEG2000 | DSPC | 50 | 38.5 | 1.5 | 10 | 93.17 | 21.91 | |
| 1 | 2 | Cholesterol | DMG-PEG2000 | DSPC | 45 | 44 | 2 | 9 | 96.46 | 15.29 | |
| 1 | 2 | Cholesterol | DMG-PEG2000 | DSPC | 35 | 46.5 | 2.5 | 16 | 90.64 | 24.53 | 7.444263 |
| 1 | 3 | Cholesterol | DMG-PEG2000 | DMPC | 50 | 38.5 | 1.5 | 10 | 116.91 | 14.27 | |
| 1 | 3 | Cholesterol | DMG-PEG2000 | DMPC | 55 | 33 | 3 | 9 | 111.6 | 6.22 | |
| 1 | 3 | Cholesterol | DMG-PEG2000 | DMPC | 45 | 44 | 2 | 9 | 119.78 | 10.78 | |
| 1 | 3 | Cholesterol | DMG-PEG2000 | DMPC | 35 | 46.5 | 2.5 | 16 | 156.52 | 9.66 | 7.359571 |
| 1 | 3 | Cholesterol | DMG-PEG2000 | DSPC | 50 | 38.5 | 1.5 | 10 | 102.08 | 14.04 | |

FIG. 1B

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 1 | 3 | Cholesterol | DMG-PEG2000 | DSPC | 55 | 33 | 3 | 9 | 83.09 | 10.11 | |
| 1 | 3 | Cholesterol | DMG-PEG2000 | DSPC | 45 | 44 | 2 | 9 | 110.02 | 10.76 | |
| 1 | 3 | Cholesterol | DMG-PEG2000 | DSPC | 35 | 46.5 | 2.5 | 16 | 131.74 | 6.88 | 7.45842 |
| 1 | 4 | Cholesterol | DMG-PEG2000 | DMPC | 50 | 38.5 | 1.5 | 10 | 85.72 | 22.17 | |
| 1 | 4 | Cholesterol | DMG-PEG2000 | DMPC | 55 | 33 | 3 | 9 | 78.75 | 22.55 | |
| 1 | 4 | Cholesterol | DMG-PEG2000 | DMPC | 45 | 44 | 2 | 9 | 65.8 | 12.17 | |
| 1 | 4 | Cholesterol | DMG-PEG2000 | DMPC | 35 | 46.5 | 2.5 | 16 | 109.28 | 7 | 7.444397 |
| 1 | 4 | Cholesterol | DMG-PEG2000 | DSPC | 50 | 38.5 | 1.5 | 10 | 71.3 | 12.67 | |
| 1 | 4 | Cholesterol | DMG-PEG2000 | DSPC | 55 | 33 | 3 | 9 | 78.26 | 11.46 | |
| 1 | 4 | Cholesterol | DMG-PEG2000 | DSPC | 45 | 44 | 2 | 9 | 105.23 | 21.58 | |
| 1 | 5 | Cholesterol | DMG-PEG2000 | DSPC | 35 | 46.5 | 2.5 | 16 | 114.72 | 12.47 | 7.526844 |
| 2 | 5 | Cholesterol | DMG-PEG2000 | DMPC | 45 | 44 | 2 | 9 | 86.02 | 15.44 | |
| 2 | 5 | Cholesterol | DMG-PEG2000 | DMPC | 50 | 38.5 | 1.5 | 10 | 74.1 | 14.97 | |
| 2 | 5 | Cholesterol | DMG-PEG2000 | DSPC | 35 | 46.5 | 2.5 | 16 | 84.97 | 16.36 | |
| 2 | 5 | Cholesterol | DMG-PEG2000 | DSPC | 45 | 44 | 2 | 9 | 87.64 | 12.33 | |
| 2 | 5 | Cholesterol | DMG-PEG2000 | DSPC | 50 | 38.5 | 1.5 | 10 | 81.46 | 16.02 | |
| 2 | 5 | Cholesterol | DMG-PEG2000 | DMPC | 35 | 46.5 | 2.5 | 16 | 83.71 | 13.48 | 5.488632 |
| 2 | 6 | Cholesterol | DMG-PEG2000 | DMPC | 45 | 44 | 2 | 9 | 94.39 | 15.68 | |
| 2 | 6 | Cholesterol | DMG-PEG2000 | DMPC | 50 | 38.5 | 1.5 | 10 | 97.03 | 12.4 | |
| 2 | 6 | Cholesterol | DMG-PEG2000 | DSPC | 35 | 46.5 | 2.5 | 16 | 101.41 | 7.48 | |
| 2 | 7 | Cholesterol | DMG-PEG2000 | DMPC | 45 | 44 | 2 | 9 | 100.32 | 10.06 | |
| 2 | 7 | Cholesterol | DMG-PEG2000 | DMPC | 50 | 38.5 | 1.5 | 10 | 119.74 | 13.8 | |
| 2 | 7 | Cholesterol | DMG-PEG2000 | DSPC | 45 | 44 | 2 | 9 | 228.75 | 57.08 | |
| 2 | 7 | Cholesterol | DMG-PEG2000 | DSPC | 50 | 38.5 | 1.5 | 10 | 117.89 | 7.79 | |
| 2 | 8 | Cholesterol | DMG-PEG2000 | DMPC | 35 | 46.5 | 2.5 | 16 | 222.26 | 57.08 | 7.16192 |
| 2 | 8 | Cholesterol | DMG-PEG2000 | DMPC | 45 | 44 | 2 | 9 | 38.08 | 57.08 | |
| 2 | 8 | Cholesterol | DMG-PEG2000 | DMPC | 50 | 38.5 | 1.5 | 10 | 10.87 | 57.08 | |

FIG. 1C

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 2 | 8 | Cholesterol | DMG-PEG2000 | DSPC | 35 | 46.5 | 2.5 | 16 | 18.81 | 57.08 | |
| 2 | 8 | Cholesterol | DMG-PEG2000 | DSPC | 50 | 38.5 | 1.5 | 10 | 66.35 | 57.08 | |
| 2 | 9 | Cholesterol | DMG-PEG2000 | DMPC | 45 | 44 | 2 | 9 | 145.3 | 57.08 | |
| 2 | 9 | Cholesterol | DMG-PEG2000 | DMPC | 50 | 38.5 | 1.5 | 10 | 84.13 | 14.26 | |
| 2 | 9 | Cholesterol | DMG-PEG2000 | DSPC | 35 | 46.5 | 2.5 | 16 | 87 | 7.41 | |
| 2 | 9 | Cholesterol | DMG-PEG2000 | DSPC | 45 | 44 | 2 | 9 | 85.99 | 14.03 | |
| 2 | 9 | Cholesterol | DMG-PEG2000 | DSPC | 50 | 38.5 | 1.5 | 10 | 100.4 | 14.29 | |
| 2 | 10 | Cholesterol | DMG-PEG2000 | DMPC | 35 | 46.5 | 2.5 | 16 | 120.01 | 7.86 | 7.05768 |
| 2 | 10 | Cholesterol | DMG-PEG2000 | DMPC | 45 | 44 | 2 | 9 | 122.59 | 14.99 | |
| 2 | 10 | Cholesterol | DMG-PEG2000 | DMPC | 50 | 38.5 | 1.5 | 10 | 130.25 | 8.74 | |
| 2 | 10 | Cholesterol | DMG-PEG2000 | DSPC | 35 | 46.5 | 2.5 | 16 | 126.49 | 13.17 | |
| 2 | 10 | Cholesterol | DMG-PEG2000 | DSPC | 45 | 44 | 2 | 9 | 119.78 | 26.75 | |
| 2 | 10 | Cholesterol | DMG-PEG2000 | DSPC | 50 | 38.5 | 1.5 | 10 | 135.41 | 20.85 | |
| 2 | 11 | Cholesterol | DMG-PEG2000 | DMPC | 35 | 46.5 | 2.5 | 16 | 120.57 | 6.61 | 6.457129 |
| 2 | 11 | Cholesterol | DMG-PEG2000 | DMPC | 45 | 44 | 2 | 9 | 117.55 | 18.52 | |
| 2 | 11 | Cholesterol | DMG-PEG2000 | DMPC | 50 | 38.5 | 1.5 | 10 | 116.12 | 19.08 | |
| 2 | 11 | Cholesterol | DMG-PEG2000 | DSPC | 35 | 46.5 | 2.5 | 16 | 120.36 | 16.36 | |
| 2 | 11 | Cholesterol | DMG-PEG2000 | DSPC | 45 | 44 | 2 | 9 | 173.02 | 57.08 | |
| 2 | 11 | Cholesterol | DMG-PEG2000 | DSPC | 50 | 38.5 | 1.5 | 10 | 127.98 | 9.54 | |
| 2 | 12 | Cholesterol | DMG-PEG2000 | DMPC | 35 | 46.5 | 2.5 | 16 | 105.58 | 16.94 | 6.456879 |
| 2 | 12 | Cholesterol | DMG-PEG2000 | DMPC | 45 | 44 | 2 | 9 | 97.29 | 17.72 | |
| 2 | 12 | Cholesterol | DMG-PEG2000 | DSPC | 50 | 38.5 | 1.5 | 10 | 60.45 | 57.08 | |
| 2 | 12 | Cholesterol | DMG-PEG2000 | DSPC | 35 | 46.5 | 2.5 | 16 | 93.52 | 4.9 | |
| 2 | 12 | Cholesterol | DMG-PEG2000 | DSPC | 45 | 44 | 2 | 9 | 101.48 | 10.6 | |
| 2 | 12 | Cholesterol | DMG-PEG2000 | DSPC | 50 | 38.5 | 1.5 | 10 | 99.01 | 17.91 | |
| 2 | 15 | Cholesterol | DMG-PEG2000 | DMPC | 35 | 46.5 | 2.5 | 16 | 128.7 | 15.44 | 6.396035 |
| 2 | 15 | Cholesterol | DMG-PEG2000 | DMPC | 45 | 44 | 2 | 9 | 100.38 | 3.33 | |

FIG. 1D

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 2 | 15 | Cholesterol | DMG-PEG2000 | DMPC | 50 | 38.5 | 1.5 | 10 | 81.35 | 10.64 | |
| 2 | 15 | Cholesterol | DMG-PEG2000 | DSPC | 35 | 46.5 | 2.5 | 16 | 99.05 | 10.15 | |
| 2 | 15 | Cholesterol | DMG-PEG2000 | DSPC | 45 | 44 | 2 | 9 | 93.16 | 14.71 | |
| 2 | 15 | Cholesterol | DMG-PEG2000 | DSPC | 50 | 38.5 | 1.5 | 10 | 97.08 | 7.61 | |
| 2 | 16 | Cholesterol | DMG-PEG2000 | DMPC | 35 | 46.5 | 2.5 | 16 | 108.37 | 18.64 | 6.275359 |
| 2 | 16 | Cholesterol | DMG-PEG2000 | DMPC | 45 | 44 | 2 | 9 | 92.62 | 7.69 | |
| 2 | 16 | Cholesterol | DMG-PEG2000 | DMPC | 50 | 38.5 | 1.5 | 10 | 205.01 | 36.27 | |
| 2 | 16 | Cholesterol | DMG-PEG2000 | DSPC | 35 | 46.5 | 2.5 | 16 | 99.97 | 3.68 | |
| 2 | 16 | Cholesterol | DMG-PEG2000 | DSPC | 45 | 44 | 2 | 9 | 81.27 | 17.49 | |
| 2 | 16 | Cholesterol | DMG-PEG2000 | DSPC | 50 | 38.5 | 1.5 | 10 | 81.05 | 11.56 | |
| 2 | 21 | Cholesterol | DMG-PEG2000 | DMPC | 35 | 46.5 | 2.5 | 16 | 196.45 | 57.08 | 6.141069 |
| 2 | 21 | Cholesterol | DMG-PEG2000 | DMPC | 45 | 44 | 2 | 9 | 92.17 | 6.75 | |
| 2 | 21 | Cholesterol | DMG-PEG2000 | DMPC | 50 | 38.5 | 1.5 | 10 | 96.22 | 14.53 | |
| 2 | 21 | Cholesterol | DMG-PEG2000 | DSPC | 35 | 46.5 | 2.5 | 16 | 171.44 | 40.53 | |
| 2 | 21 | Cholesterol | DMG-PEG2000 | DSPC | 45 | 44 | 2 | 9 | 126.94 | 30.24 | |
| 2 | 21 | Cholesterol | DMG-PEG2000 | DSPC | 50 | 38.5 | 1.5 | 10 | 70.05 | 48.61 | |
| 2 | 22 | Cholesterol | DMG-PEG2000 | DMPC | 35 | 46.5 | 2.5 | 16 | 121.11 | 9.19 | 5.531161 |
| 2 | 22 | Cholesterol | DMG-PEG2000 | DMPC | 45 | 44 | 2 | 9 | 116.82 | 12.36 | |
| 2 | 22 | Cholesterol | DMG-PEG2000 | DMPC | 50 | 38.5 | 1.5 | 10 | 21.85 | 57.08 | |
| 2 | 22 | Cholesterol | DMG-PEG2000 | DSPC | 35 | 46.5 | 2.5 | 16 | 162.06 | 57.08 | |
| 2 | 22 | Cholesterol | DMG-PEG2000 | DSPC | 45 | 44 | 2 | 9 | 102.77 | 15.2 | |
| 2 | 22 | Cholesterol | DMG-PEG2000 | DSPC | 50 | 38.5 | 1.5 | 10 | 125.84 | 14.35 | |
| 2 | 23 | Cholesterol | DMG-PEG2000 | DMPC | 35 | 46.5 | 2.5 | 16 | 241.16 | 57.08 | 8.429284 |
| 2 | 23 | Cholesterol | DMG-PEG2000 | DMPC | 45 | 44 | 2 | 9 | 144.33 | 10.98 | |
| 2 | 23 | Cholesterol | DMG-PEG2000 | DMPC | 50 | 38.5 | 1.5 | 10 | 104.24 | 11.9 | |
| 2 | 23 | Cholesterol | DMG-PEG2000 | DSPC | 35 | 46.5 | 2.5 | 16 | 113.33 | 10.96 | |
| 2 | 23 | Cholesterol | DMG-PEG2000 | DSPC | 45 | 44 | 2 | 9 | 98.71 | 18.2 | |

FIG. 1E

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 2 | 23 | Cholesterol | DMG-PEG2000 | DSPC | 50 | 38.5 | 1.5 | 10 | 91.31 | 15.93 | |
| 2 | 24 | Cholesterol | DMG-PEG2000 | DMPC | 35 | 46.5 | 2.5 | 16 | 117.3 | 14.76 | 5.564599 |
| 2 | 24 | Cholesterol | DMG-PEG2000 | DMPC | 45 | 44 | 2 | 9 | 137.96 | 6.38 | |
| 2 | 24 | Cholesterol | DMG-PEG2000 | DMPC | 50 | 38.5 | 1.5 | 10 | 117.54 | 11.29 | |
| 2 | 24 | Cholesterol | DMG-PEG2000 | DSPC | 35 | 46.5 | 2.5 | 16 | 96.2 | 9.36 | |
| 2 | 24 | Cholesterol | DMG-PEG2000 | DSPC | 45 | 44 | 2 | 9 | 81.13 | 10.69 | |
| 2 | 24 | Cholesterol | DMG-PEG2000 | DSPC | 50 | 38.5 | 1.5 | 10 | 119.87 | 6.5 | |
| 2 | 25 | Cholesterol | DMG-PEG2000 | DMPC | 35 | 46.5 | 2.5 | 16 | 169.61 | 11.73 | 3.945084 |
| 2 | 25 | Cholesterol | DMG-PEG2000 | DMPC | 45 | 44 | 2 | 9 | 71.54 | 57.08 | |
| 2 | 25 | Cholesterol | DMG-PEG2000 | DMPC | 50 | 38.5 | 1.5 | 10 | 198.26 | 9.22 | |
| 2 | 25 | Cholesterol | DMG-PEG2000 | DSPC | 35 | 46.5 | 2.5 | 16 | 131.68 | 13.01 | |
| 2 | 25 | Cholesterol | DMG-PEG2000 | DSPC | 45 | 44 | 2 | 9 | 172.94 | 11.41 | |
| 2 | 25 | Cholesterol | DMG-PEG2000 | DSPC | 50 | 38.5 | 1.5 | 10 | 162.98 | 7.89 | |
| 2 | 26 | Cholesterol | DMG-PEG2000 | DMPC | 35 | 46.5 | 2.5 | 16 | 271.69 | 57.08 | 5.947456 |
| 2 | 26 | Cholesterol | DMG-PEG2000 | DMPC | 45 | 44 | 2 | 9 | 142.48 | 1.91 | |
| 2 | 26 | Cholesterol | DMG-PEG2000 | DMPC | 50 | 38.5 | 1.5 | 10 | 244.6 | 16.23 | |
| 2 | 26 | Cholesterol | DMG-PEG2000 | DSPC | 50 | 38.5 | 1.5 | 10 | 166.61 | 12.34 | |
| 2 | 27 | Cholesterol | DMG-PEG2000 | DMPC | 35 | 46.5 | 2.5 | 16 | 289.72 | 28.11 | 7.662701 |
| 2 | 27 | Cholesterol | DMG-PEG2000 | DMPC | 50 | 38.5 | 1.5 | 10 | 214.84 | 5.62 | |
| 2 | 27 | Cholesterol | DMG-PEG2000 | DSPC | 35 | 46.5 | 2.5 | 16 | 266.44 | 5.31 | |
| 2 | 27 | Cholesterol | DMG-PEG2000 | DSPC | 45 | 44 | 2 | 9 | 222.13 | 7.46 | |
| 2 | 27 | Cholesterol | DMG-PEG2000 | DSPC | 50 | 38.5 | 1.5 | 10 | 224.46 | 12.01 | |
| 2 | 28 | Cholesterol | DMG-PEG2000 | DMPC | 45 | 44 | 2 | 9 | 134.42 | 12.39 | |
| 2 | 28 | Cholesterol | DMG-PEG2000 | DMPC | 50 | 38.5 | 1.5 | 10 | 136.81 | 10.5 | |
| 2 | 28 | Cholesterol | DMG-PEG2000 | DSPC | 35 | 46.5 | 2.5 | 16 | 141.71 | 10.86 | |
| 2 | 28 | Cholesterol | DMG-PEG2000 | DSPC | 45 | 44 | 2 | 9 | 143.66 | 12.79 | |
| 2 | 28 | Cholesterol | DMG-PEG2000 | DSPC | 50 | 38.5 | 1.5 | 10 | 157.21 | 7.79 | |

FIG. 1F

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 2 | 59 | Cholesterol | DMG-PEG2000 | DMPC | 35 | 46.5 | 2.5 | 16 | 252.24 | 11.31 | 7.446693 |
| 2 | 59 | Cholesterol | DMG-PEG2000 | DMPC | 45 | 44 | 2 | 9 | 263.47 | 8.87 | |
| 2 | 59 | Cholesterol | DMG-PEG2000 | DSPC | 35 | 46.5 | 2.5 | 16 | 202.92 | 2.58 | |
| 2 | 59 | Cholesterol | DMG-PEG2000 | DSPC | 45 | 44 | 2 | 9 | 183.26 | 12.15 | |
| 2 | 59 | Cholesterol | DMG-PEG2000 | DSPC | 50 | 38.5 | 1.5 | 10 | 194.6 | 9.99 | |
| 2 | 60 | Cholesterol | DMG-PEG2000 | DMPC | 35 | 46.5 | 2.5 | 16 | 193.34 | 12.71 | 7.440976 |
| 2 | 60 | Cholesterol | DMG-PEG2000 | DMPC | 45 | 44 | 2 | 9 | 176.66 | 9.05 | |
| 2 | 60 | Cholesterol | DMG-PEG2000 | DMPC | 50 | 38.5 | 1.5 | 10 | 173.15 | 15.27 | |
| 2 | 60 | Cholesterol | DMG-PEG2000 | DSPC | 35 | 46.5 | 2.5 | 16 | 197.45 | 15.86 | |
| 2 | 60 | Cholesterol | DMG-PEG2000 | DSPC | 45 | 44 | 2 | 9 | 149.98 | 10.69 | |
| 2 | 60 | Cholesterol | DMG-PEG2000 | DSPC | 50 | 38.5 | 1.5 | 10 | 176.49 | 9.21 | |
| 2 | 61 | Cholesterol | DMG-PEG2000 | DMPC | 35 | 46.5 | 2.5 | 16 | 219.71 | 0 | 6.525854 |
| 2 | 61 | Cholesterol | DMG-PEG2000 | DMPC | 45 | 44 | 2 | 9 | 179.79 | 11.28 | |
| 2 | 61 | Cholesterol | DMG-PEG2000 | DSPC | 35 | 46.5 | 2.5 | 16 | 163.66 | 10.12 | |
| 2 | 61 | Cholesterol | DMG-PEG2000 | DSPC | 45 | 44 | 2 | 9 | 134.86 | 12.88 | |
| 2 | 61 | Cholesterol | DMG-PEG2000 | DSPC | 50 | 38.5 | 1.5 | 10 | 178.95 | 4.02 | |
| 2 | 62 | Cholesterol | DMG-PEG2000 | DMPC | 35 | 46.5 | 2.5 | 16 | 319.99 | 35.44 | 7.485979 |
| 2 | 62 | Cholesterol | DMG-PEG2000 | DMPC | 50 | 38.5 | 1.5 | 10 | 256.71 | 0 | |
| 2 | 62 | Cholesterol | DMG-PEG2000 | DSPC | 45 | 44 | 2 | 9 | 213.64 | 10.55 | |
| 2 | 62 | Cholesterol | DMG-PEG2000 | DSPC | 50 | 38.5 | 1.5 | 10 | 204.04 | 3.17 | |
| 2 | 63 | Cholesterol | DMG-PEG2000 | DMPC | 35 | 46.5 | 2.5 | 16 | 232.74 | 16.6 | 5.551521 |
| 2 | 63 | Cholesterol | DMG-PEG2000 | DMPC | 45 | 44 | 2 | 9 | 145.8 | 7.66 | |
| 2 | 63 | Cholesterol | DMG-PEG2000 | DMPC | 50 | 38.5 | 1.5 | 10 | 178.3 | 10.2 | |
| 2 | 63 | Cholesterol | DMG-PEG2000 | DSPC | 35 | 46.5 | 2.5 | 16 | 155.23 | 6.59 | |
| 2 | 63 | Cholesterol | DMG-PEG2000 | DSPC | 45 | 44 | 2 | 9 | 160.03 | 18.11 | |
| 2 | 63 | Cholesterol | DMG-PEG2000 | DSPC | 50 | 38.5 | 1.5 | 10 | 141.75 | 10.88 | |
| 2 | 64 | Cholesterol | DMG-PEG2000 | DMPC | 35 | 46.5 | 2.5 | 16 | 205.42 | 13.1 | 6.89979 |

FIG. 1G

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 2 | 64 | Cholesterol | DMG-PEG2000 | DMPC | 45 | 44 | 2 | 9 | 207.68 | 6.45 | |
| 2 | 64 | Cholesterol | DMG-PEG2000 | DSPC | 50 | 38.5 | 1.5 | 10 | 194.52 | 8.36 | |
| 2 | 64 | Cholesterol | DMG-PEG2000 | DSPC | 35 | 46.5 | 2.5 | 16 | 218.14 | 3.76 | |
| 2 | 64 | Cholesterol | DMG-PEG2000 | DSPC | 45 | 44 | 2 | 9 | 259.83 | 8.49 | |
| 2 | 64 | Cholesterol | DMG-PEG2000 | DSPC | 50 | 38.5 | 1.5 | 10 | 228.22 | 6.03 | |
| 2 | 65 | Cholesterol | DMG-PEG2000 | DMPC | 45 | 44 | 2 | 9 | 197.18 | 10.94 | |
| 2 | 65 | Cholesterol | DMG-PEG2000 | DSPC | 35 | 46.5 | 2.5 | 16 | 196.02 | 8.43 | |
| 2 | 65 | Cholesterol | DMG-PEG2000 | DSPC | 45 | 44 | 2 | 9 | 239.71 | 7.11 | |
| 2 | 65 | Cholesterol | DMG-PEG2000 | DSPC | 50 | 38.5 | 1.5 | 10 | 240.6 | 5.73 | |
| 2 | 66 | Cholesterol | DMG-PEG2000 | DMPC | 45 | 44 | 2 | 9 | 289.14 | 20.72 | |
| 2 | 66 | Cholesterol | DMG-PEG2000 | DSPC | 35 | 46.5 | 2.5 | 16 | 247.24 | 4.31 | |
| 2 | 66 | Cholesterol | DMG-PEG2000 | DSPC | 45 | 44 | 2 | 9 | 221.69 | 10.73 | |
| 2 | 66 | Cholesterol | DMG-PEG2000 | DSPC | 50 | 38.5 | 1.5 | 10 | 300.24 | 2.77 | |
| 3 | 4 | Cholesterol | DMG-PEG2000 | DSPC | 50 | 38.5 | 1.5 | 10 | 120.3 | 13.76 | 8.635252 |
| 3 | 4 | Cholesterol | DMG-PEG2000 | DSPC | 45 | 44 | 2 | 9 | 125.4 | 14.49 | |
| 3 | 4 | Cholesterol | DMG-PEG2000 | DSPC | 40 | 42 | 3 | 15 | 96.54 | 16.05 | |
| 3 | 4 | Cholesterol | DMG-PEG2000 | DSPC | 35 | 46.5 | 2.5 | 16 | 120.72 | 16.15 | 8.264557 |
| 3 | 4 | Cholesterol | DSG-PEG2000 | DSPC | 40 | 42 | 3 | 15 | 96.02 | 21.65 | |
| 3 | 4 | Cholesterol | DSG-PEG2000 | DSPC | 35 | 46.5 | 2.5 | 16 | 109.38 | 10.35 | 7.415907 |
| 3 | 1 | Cholesterol | DMG-PEG2000 | DSPC | 50 | 38.5 | 1.5 | 10 | 164.69 | 13.81 | 9.265217 |
| 3 | 1 | Cholesterol | DMG-PEG2000 | DSPC | 40 | 42 | 3 | 15 | 167.25 | 13.53 | |
| 3 | 1 | Cholesterol | DMG-PEG2000 | DSPC | 35 | 46.5 | 2.5 | 16 | 203.57 | 11.52 | 10.35556 |
| 3 | 1 | Cholesterol | DSG-PEG2000 | DSPC | 50 | 38.5 | 1.5 | 10 | 146.35 | 8.58 | 9.513375 |
| 3 | 1 | Cholesterol | DSG-PEG2000 | DSPC | 45 | 44 | 2 | 9 | 105.92 | 17.41 | |
| 3 | 1 | Cholesterol | DSG-PEG2000 | DSPC | 40 | 42 | 3 | 15 | 118.89 | 13.05 | |
| 3 | 1 | Cholesterol | DSG-PEG2000 | DSPC | 35 | 46.5 | 2.5 | 16 | 139.84 | 13.72 | 9.739387 |
| 3 | 39 | Cholesterol | DMG-PEG2000 | DSPC | 50 | 38.5 | 1.5 | 10 | 106.43 | 18.46 | 10.20955 |

FIG. 1H

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 3 | 39 | Cholesterol | DMG-PEG2000 | DSPC | 45 | 44 | 2 | 9 | 115.84 | 16.44 | |
| 3 | 39 | Cholesterol | DMG-PEG2000 | DSPC | 35 | 46.5 | 2.5 | 16 | 110.07 | 23.76 | 3.422403 |
| 3 | 39 | Cholesterol | DSG-PEG2000 | DSPC | 50 | 38.5 | 1.5 | 10 | 102.91 | 24.47 | |
| 3 | 39 | Cholesterol | DSG-PEG2000 | DSPC | 45 | 44 | 2 | 9 | 69.3 | 15.23 | |
| 3 | 39 | Cholesterol | DSG-PEG2000 | DSPC | 40 | 42 | 3 | 15 | 69.9 | 16.02 | |
| 3 | 39 | Cholesterol | DSG-PEG2000 | DSPC | 35 | 46.5 | 2.5 | 16 | 71.84 | 8.91 | 6.193562 |
| 3 | 40 | Cholesterol | DMG-PEG2000 | DSPC | 50 | 38.5 | 1.5 | 10 | 80.35 | 16.33 | |
| 3 | 40 | Cholesterol | DMG-PEG2000 | DSPC | 45 | 44 | 2 | 9 | 83.81 | 13.65 | |
| 3 | 40 | Cholesterol | DMG-PEG2000 | DSPC | 40 | 42 | 3 | 15 | 87.91 | 14.9 | |
| 3 | 40 | Cholesterol | DSG-PEG2000 | DSPC | 50 | 38.5 | 1.5 | 10 | 69.38 | 17.1 | 7.678424 |
| 3 | 40 | Cholesterol | DSG-PEG2000 | DSPC | 45 | 44 | 2 | 9 | 65.92 | 7.65 | |
| 3 | 40 | Cholesterol | DSG-PEG2000 | DSPC | 40 | 42 | 3 | 15 | 64.49 | 9.86 | |
| 3 | 40 | Cholesterol | DSG-PEG2000 | DSPC | 35 | 46.5 | 2.5 | 16 | 92.05 | 24.45 | 12.32939 |
| 3 | 38 | Cholesterol | DMG-PEG2000 | DSPC | 50 | 38.5 | 1.5 | 10 | 100.31 | 30.39 | 2.40102 |
| 3 | 38 | Cholesterol | DMG-PEG2000 | DSPC | 45 | 44 | 2 | 9 | 75.13 | 13.84 | |
| 3 | 38 | Cholesterol | DMG-PEG2000 | DSPC | 40 | 42 | 3 | 15 | 87.03 | 14.64 | |
| 3 | 38 | Cholesterol | DMG-PEG2000 | DSPC | 35 | 46.5 | 2.5 | 16 | 96.72 | 24.5 | |
| 3 | 38 | Cholesterol | DSG-PEG2000 | DSPC | 50 | 38.5 | 1.5 | 10 | 68.69 | 9.71 | |
| 3 | 38 | Cholesterol | DSG-PEG2000 | DSPC | 45 | 44 | 2 | 9 | 93.38 | 36.6 | |
| 3 | 38 | Cholesterol | DSG-PEG2000 | DSPC | 35 | 46.5 | 2.5 | 16 | 61.28 | 9.68 | 4.515903 |
| 3 | 41 | Cholesterol | DMG-PEG2000 | DSPC | 50 | 38.5 | 1.5 | 10 | 79.36 | 15.54 | |
| 3 | 41 | Cholesterol | DMG-PEG2000 | DSPC | 35 | 46.5 | 2.5 | 16 | 83.52 | 14.26 | 11.54628 |
| 3 | 41 | Cholesterol | DSG-PEG2000 | DSPC | 50 | 38.5 | 1.5 | 10 | 85.99 | 13.09 | 7.47881 |
| 3 | 41 | Cholesterol | DSG-PEG2000 | DSPC | 45 | 44 | 2 | 9 | 81.04 | 38.91 | |
| 3 | 41 | Cholesterol | DSG-PEG2000 | DSPC | 40 | 42 | 3 | 15 | 86.61 | 26.9 | |
| 3 | 41 | Cholesterol | DSG-PEG2000 | DSPC | 35 | 46.5 | 2.5 | 16 | 62.75 | 13.6 | 13.52483 |
| 3 | 42 | Cholesterol | DMG-PEG2000 | DSPC | 50 | 38.5 | 1.5 | 10 | 84.77 | 21.5 | 11.97034 |

FIG. 11

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 3 | 42 | Cholesterol | DMG-PEG2000 | DSPC | 45 | 44 | 2 | 9 | 92.02 | 17.05 | |
| 3 | 42 | Cholesterol | DMG-PEG2000 | DSPC | 35 | 46.5 | 2.5 | 16 | 115.73 | 14.3 | 0 |
| 3 | 42 | Cholesterol | DSG-PEG2000 | DSPC | 50 | 38.5 | 1.5 | 10 | 69.9 | 8.1 | 4.490936 |
| 3 | 42 | Cholesterol | DSG-PEG2000 | DSPC | 45 | 44 | 2 | 9 | 66.5 | 7.91 | |
| 3 | 42 | Cholesterol | DSG-PEG2000 | DSPC | 40 | 42 | 3 | 15 | 61.86 | 13.68 | |
| 3 | 42 | Cholesterol | DSG-PEG2000 | DSPC | 35 | 46.5 | 2.5 | 16 | 58.87 | 14.41 | 0 |
| 3 | 43 | Cholesterol | DMG-PEG2000 | DSPC | 50 | 38.5 | 1.5 | 10 | 111.26 | 15.16 | 11.19423 |
| 3 | 43 | Cholesterol | DMG-PEG2000 | DSPC | 45 | 44 | 2 | 9 | 116.16 | 19.43 | |
| 3 | 43 | Cholesterol | DMG-PEG2000 | DSPC | 40 | 42 | 3 | 15 | 100.47 | 19.98 | |
| 3 | 43 | Cholesterol | DMG-PEG2000 | DSPC | 35 | 46.5 | 2.5 | 16 | 121.82 | 19.37 | 10.63488 |
| 3 | 43 | Cholesterol | DSG-PEG2000 | DSPC | 50 | 38.5 | 1.5 | 10 | 90.43 | 13.02 | |
| 3 | 43 | Cholesterol | DSG-PEG2000 | DSPC | 45 | 44 | 2 | 9 | 75.27 | 19.13 | |
| 3 | 43 | Cholesterol | DSG-PEG2000 | DSPC | 40 | 42 | 3 | 15 | 85.91 | 16.4 | |
| 3 | 43 | Cholesterol | DSG-PEG2000 | DSPC | 35 | 46.5 | 2.5 | 16 | 83.8 | 20.07 | 5.742372 |
| 3 | 44 | Cholesterol | DMG-PEG2000 | DSPC | 40 | 42 | 3 | 15 | 94.96 | 18.4 | |
| 3 | 44 | Cholesterol | DMG-PEG2000 | DSPC | 35 | 46.5 | 2.5 | 16 | 96.41 | 14.89 | 12.30343 |
| 3 | 44 | Cholesterol | DSG-PEG2000 | DSPC | 50 | 38.5 | 1.5 | 10 | 104.44 | 27.36 | |
| 3 | 44 | Cholesterol | DSG-PEG2000 | DSPC | 45 | 44 | 2 | 9 | 82.34 | 9.8 | |
| 3 | 44 | Cholesterol | DSG-PEG2000 | DSPC | 35 | 46.5 | 2.5 | 16 | 65.9 | 13.41 | 13.57316 |
| 3 | 45 | Cholesterol | DMG-PEG2000 | DSPC | 50 | 38.5 | 1.5 | 10 | 123.76 | 18.17 | |
| 3 | 45 | Cholesterol | DMG-PEG2000 | DSPC | 45 | 44 | 2 | 9 | 105.04 | 17.02 | |
| 3 | 45 | Cholesterol | DMG-PEG2000 | DSPC | 40 | 42 | 3 | 15 | 121.74 | 18.32 | |
| 3 | 45 | Cholesterol | DMG-PEG2000 | DSPC | 35 | 46.5 | 2.5 | 16 | 94.57 | 10.99 | |
| 3 | 45 | Cholesterol | DSG-PEG2000 | DSPC | 45 | 44 | 2 | 9 | 97.73 | 17.82 | |
| 3 | 45 | Cholesterol | DSG-PEG2000 | DSPC | 40 | 42 | 3 | 15 | 72.51 | 18.8 | |
| 3 | 45 | Cholesterol | DSG-PEG2000 | DSPC | 35 | 46.5 | 2.5 | 16 | 79.57 | 15.19 | |
| 3 | 30 | Cholesterol | DMG-PEG2000 | DSPC | 45 | 44 | 2 | 9 | 199.76 | 28.17 | |

FIG. 1J

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 3 | 30 | Cholesterol | DMG-PEG2000 | DSPC | 40 | 42 | 3 | 15 | 180.02 | 12.19 | |
| 3 | 30 | Cholesterol | DSG-PEG2000 | DSPC | 50 | 38.5 | 1.5 | 10 | 167.22 | 28 | 9.988395 |
| 3 | 30 | Cholesterol | DSG-PEG2000 | DSPC | 45 | 44 | 2 | 9 | 130.81 | 11.65 | |
| 3 | 30 | Cholesterol | DSG-PEG2000 | DSPC | 40 | 42 | 3 | 15 | 136.54 | 11.01 | |
| 3 | 30 | Cholesterol | DSG-PEG2000 | DSPC | 35 | 46.5 | 2.5 | 16 | 182.39 | 10.94 | 10.17186 |
| 3 | 31 | Cholesterol | DMG-PEG2000 | DSPC | 50 | 38.5 | 1.5 | 10 | 165.76 | 12.66 | 7.765531 |
| 3 | 31 | Cholesterol | DMG-PEG2000 | DSPC | 45 | 44 | 2 | 9 | 211.25 | 14.32 | |
| 3 | 31 | Cholesterol | DMG-PEG2000 | DSPC | 40 | 42 | 3 | 15 | 202.8 | 9.54 | |
| 3 | 31 | Cholesterol | DSG-PEG2000 | DSPC | 50 | 38.5 | 1.5 | 10 | 188.27 | 5.99 | 8.905104 |
| 3 | 31 | Cholesterol | DSG-PEG2000 | DSPC | 45 | 44 | 2 | 9 | 137.57 | 10.6 | |
| 3 | 31 | Cholesterol | DSG-PEG2000 | DSPC | 40 | 42 | 3 | 15 | 154.79 | 7.06 | |
| 3 | 32 | Cholesterol | DMG-PEG2000 | DSPC | 50 | 38.5 | 1.5 | 10 | 281.97 | 6.34 | 7.54584 |
| 3 | 32 | Cholesterol | DMG-PEG2000 | DSPC | 45 | 44 | 2 | 9 | 189.91 | 8.8 | |
| 3 | 32 | Cholesterol | DMG-PEG2000 | DSPC | 40 | 42 | 3 | 15 | 219.43 | 14.18 | |
| 3 | 32 | Cholesterol | DSG-PEG2000 | DSPC | 50 | 38.5 | 1.5 | 10 | 148.03 | 6.58 | 8.975779 |
| 3 | 32 | Cholesterol | DSG-PEG2000 | DSPC | 45 | 44 | 2 | 9 | 181.64 | 7.11 | |
| 3 | 32 | Cholesterol | DSG-PEG2000 | DSPC | 40 | 42 | 3 | 15 | 133.77 | 10.05 | |
| 3 | 32 | Cholesterol | DSG-PEG2000 | DSPC | 35 | 46.5 | 2.5 | 16 | 221.38 | 5.77 | 9.027957 |
| 3 | 29 | Cholesterol | DMG-PEG2000 | DSPC | 50 | 38.5 | 1.5 | 10 | 192.54 | 7.44 | 8.555339 |
| 3 | 29 | Cholesterol | DMG-PEG2000 | DSPC | 45 | 44 | 2 | 9 | 145.43 | 14.1 | |
| 3 | 29 | Cholesterol | DMG-PEG2000 | DSPC | 40 | 42 | 3 | 15 | 129.61 | 7.72 | |
| 3 | 29 | Cholesterol | DMG-PEG2000 | DSPC | 35 | 46.5 | 2.5 | 16 | 185.03 | 10.47 | 8.680198 |
| 3 | 29 | Cholesterol | DSG-PEG2000 | DSPC | 50 | 38.5 | 1.5 | 10 | 220.38 | 13.95 | 9.056886 |
| 3 | 29 | Cholesterol | DSG-PEG2000 | DSPC | 45 | 44 | 2 | 9 | 175.34 | 12.35 | |
| 3 | 29 | Cholesterol | DSG-PEG2000 | DSPC | 40 | 42 | 3 | 15 | 152.54 | 13 | |
| 3 | 29 | Cholesterol | DSG-PEG2000 | DSPC | 35 | 46.5 | 2.5 | 16 | 175.9 | 12.33 | 8.603137 |
| 3 | 33 | Cholesterol | DSG-PEG2000 | DSPC | 50 | 38.5 | 1.5 | 10 | 214.61 | 5.53 | 8.805956 |

FIG. 1K

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 3 | 33 | Cholesterol | DSG-PEG2000 | DSPC | 45 | 44 | 2 | 9 | 151.03 | 6.63 | |
| 3 | 33 | Cholesterol | DSG-PEG2000 | DSPC | 40 | 42 | 3 | 15 | 231.04 | 8.91 | |
| 3 | 33 | Cholesterol | DSG-PEG2000 | DSPC | 35 | 46.5 | 2.5 | 16 | 244.11 | 15.01 | 9.798536 |
| 3 | 34 | Cholesterol | DMG-PEG2000 | DSPC | 45 | 44 | 2 | 9 | 286.88 | 17.52 | |
| 3 | 34 | Cholesterol | DMG-PEG2000 | DSPC | 40 | 42 | 3 | 15 | 280.92 | 10.12 | |
| 3 | 34 | Cholesterol | DSG-PEG2000 | DSPC | 45 | 44 | 2 | 9 | 236.92 | 9.57 | |
| 3 | 34 | Cholesterol | DSG-PEG2000 | DSPC | 40 | 42 | 3 | 15 | 255.56 | 8.31 | |
| 3 | 35 | Cholesterol | DMG-PEG2000 | DSPC | 50 | 38.5 | 1.5 | 10 | 206.2 | 6.78 | 8.253902 |
| 3 | 35 | Cholesterol | DMG-PEG2000 | DSPC | 45 | 44 | 2 | 9 | 183.55 | 14.76 | |
| 3 | 35 | Cholesterol | DMG-PEG2000 | DSPC | 40 | 42 | 3 | 15 | 224.14 | 8.04 | |
| 3 | 35 | Cholesterol | DSG-PEG2000 | DSPC | 50 | 38.5 | 1.5 | 10 | 181.02 | 11.84 | 9.095158 |
| 3 | 35 | Cholesterol | DSG-PEG2000 | DSPC | 45 | 44 | 2 | 9 | 130.63 | 9.41 | |
| 3 | 35 | Cholesterol | DSG-PEG2000 | DSPC | 40 | 42 | 3 | 15 | 145.74 | 10.06 | |
| 3 | 35 | Cholesterol | DSG-PEG2000 | DSPC | 35 | 46.5 | 2.5 | 16 | 197.85 | 4.87 | 9.156927 |
| 3 | 36 | Cholesterol | DMG-PEG2000 | DSPC | 45 | 44 | 2 | 9 | 239.83 | 7.21 | |
| 3 | 36 | Cholesterol | DMG-PEG2000 | DSPC | 35 | 46.5 | 2.5 | 16 | 285.61 | 10.16 | 8.995415 |
| 3 | 36 | Cholesterol | DSG-PEG2000 | DSPC | 50 | 38.5 | 1.5 | 10 | 214.94 | 8.97 | 9.251538 |
| 3 | 36 | Cholesterol | DSG-PEG2000 | DSPC | 45 | 44 | 2 | 9 | 179.69 | 10.64 | |
| 3 | 36 | Cholesterol | DSG-PEG2000 | DSPC | 35 | 46.5 | 2.5 | 16 | 280.71 | 11.75 | 9.766873 |
| 3 | 37 | Cholesterol | DMG-PEG2000 | DSPC | 50 | 38.5 | 1.5 | 10 | 250.05 | 12.06 | 7.833347 |
| 3 | 37 | Cholesterol | DMG-PEG2000 | DSPC | 45 | 44 | 2 | 9 | 233.03 | 14.99 | |
| 3 | 37 | Cholesterol | DMG-PEG2000 | DSPC | 40 | 42 | 3 | 15 | 262.7 | 6.74 | |
| 3 | 37 | Cholesterol | DSG-PEG2000 | DSPC | 50 | 38.5 | 1.5 | 10 | 216.35 | 7.05 | 9.230769 |
| 3 | 37 | Cholesterol | DSG-PEG2000 | DSPC | 45 | 44 | 2 | 9 | 162.87 | 14.11 | |
| 3 | 37 | Cholesterol | DSG-PEG2000 | DSPC | 35 | 46.5 | 2.5 | 16 | 256.18 | 8.96 | 9.620949 |
| 3 | 1 | Cholesterol | DMG-PEG2000 | DSPC | 50 | 38.5 | 1.5 | 10 | 229.24 | 7.17 | 8.912077 |
| 3 | 1 | Cholesterol | DMG-PEG2000 | DSPC | 45 | 44 | 2 | 9 | 195.35 | 10.93 | |

FIG. 1L

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 3 | 1 | Cholesterol | DSG-PEG2000 | DSPC | 50 | 38.5 | 1.5 | 10 | 217.98 | 8.17 | 7.621076 |
| 3 | 1 | Cholesterol | DSG-PEG2000 | DSPC | 45 | 44 | 2 | 9 | 143.86 | 7.97 | |
| 3 | 1 | Cholesterol | DSG-PEG2000 | DSPC | 40 | 42 | 3 | 15 | 192.79 | 6.39 | |
| 3 | 1 | Cholesterol | DSG-PEG2000 | DSPC | 35 | 46.5 | 2.5 | 16 | 231.51 | 7.77 | 9.03213 |
| 3 | 25 | Cholesterol | DMG-PEG2000 | DSPC | 50 | 38.5 | 1.5 | 10 | 231.57 | 11.8 | 7.129017 |
| 3 | 25 | Cholesterol | DMG-PEG2000 | DSPC | 45 | 44 | 2 | 9 | 247.65 | 13.66 | |
| 3 | 25 | Cholesterol | DMG-PEG2000 | DSPC | 40 | 42 | 3 | 15 | 237.38 | 8.65 | |
| 3 | 25 | Cholesterol | DMG-PEG2000 | DSPC | 35 | 46.5 | 2.5 | 16 | 282.01 | 22.5 | 7.492182 |
| 3 | 25 | Cholesterol | DSG-PEG2000 | DSPC | 45 | 44 | 2 | 9 | 180.68 | 14.55 | |
| 3 | 25 | Cholesterol | DSG-PEG2000 | DSPC | 40 | 42 | 3 | 15 | 190.52 | 6.33 | |
| 3 | 4 | Cholesterol | DMG-PEG2000 | DSPC | 50 | 38.5 | 1.5 | 10 | 191.01 | 7.09 | 7.490212 |
| 3 | 4 | Cholesterol | DMG-PEG2000 | DSPC | 45 | 44 | 2 | 9 | 136.08 | 12.69 | |
| 3 | 4 | Cholesterol | DMG-PEG2000 | DSPC | 40 | 42 | 3 | 15 | 124.28 | 8.56 | |
| 3 | 4 | Cholesterol | DMG-PEG2000 | DSPC | 35 | 46.5 | 2.5 | 16 | 157.96 | 12.75 | 8.697706 |
| 3 | 4 | Cholesterol | DSG-PEG2000 | DSPC | 50 | 38.5 | 1.5 | 10 | 155.35 | 9.24 | 8.675952 |
| 3 | 4 | Cholesterol | DSG-PEG2000 | DSPC | 45 | 44 | 2 | 9 | 127.03 | 8.11 | |
| 3 | 4 | Cholesterol | DSG-PEG2000 | DSPC | 40 | 42 | 3 | 15 | 129.72 | 20.59 | |
| 3 | 4 | Cholesterol | DSG-PEG2000 | DSPC | 35 | 46.5 | 2.5 | 16 | 122.48 | 10.14 | 8.749084 |
| 4 | 1 | Cholesterol | DMG-PEG2000 | DSPC | 45 | 44 | 2 | 9 | 122.2 | 34.26 | |
| 4 | 1 | Cholesterol | DMG-PEG2000 | DSPC | 35 | 46.5 | 2.5 | 16 | 137.66 | 9.52 | |
| 4 | 1 | Cholesterol | DSG-PEG2000 | DSPC | 50 | 38.5 | 1.5 | 10 | 135.89 | 13.11 | 8.823537 |
| 4 | 1 | Cholesterol | DSG-PEG2000 | DSPC | 45 | 44 | 2 | 9 | 91.82 | 9.34 | |
| 4 | 1 | Cholesterol | DSG-PEG2000 | DSPC | 35 | 46.5 | 2.5 | 16 | 128.8 | 11.2 | |
| 4 | 47 | Cholesterol | DMG-PEG2000 | DSPC | 50 | 38.5 | 1.5 | 10 | 94.57 | 12.03 | 7.829479 |
| 4 | 47 | Cholesterol | DMG-PEG2000 | DSPC | 45 | 44 | 2 | 9 | 101.47 | 17.13 | |
| 4 | 47 | Cholesterol | DMG-PEG2000 | DSPC | 35 | 46.5 | 2.5 | 16 | 92.51 | 19.88 | |
| 4 | 47 | Cholesterol | DSG-PEG2000 | DSPC | 50 | 38.5 | 1.5 | 10 | 117.78 | 8.86 | 7.221584 |

FIG. 1M

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 4 | 47 | Cholesterol | DSG-PEG2000 | DSPC | 45 | 44 | 2 | 9 | 94.85 | 15.21 | |
| 4 | 47 | Cholesterol | DSG-PEG2000 | DSPC | 35 | 46.5 | 2.5 | 16 | 94.72 | 15.92 | |
| 4 | 48 | Cholesterol | DMG-PEG2000 | DSPC | 50 | 38.5 | 1.5 | 10 | 94.25 | 13.94 | 9.919999 |
| 4 | 48 | Cholesterol | DMG-PEG2000 | DSPC | 45 | 44 | 2 | 9 | 104.6 | 16.01 | |
| 4 | 48 | Cholesterol | DMG-PEG2000 | DSPC | 35 | 46.5 | 2.5 | 16 | 91.17 | 20 | |
| 4 | 48 | Cholesterol | DSG-PEG2000 | DSPC | 50 | 38.5 | 1.5 | 10 | 108.6 | 10.49 | 9.874231 |
| 4 | 48 | Cholesterol | DSG-PEG2000 | DSPC | 45 | 44 | 2 | 9 | 110.77 | 8 | |
| 4 | 48 | Cholesterol | DSG-PEG2000 | DSPC | 35 | 46.5 | 2.5 | 16 | 81.52 | 12.01 | |
| 4 | 50 | Cholesterol | DMG-PEG2000 | DSPC | 50 | 38.5 | 1.5 | 10 | 112.26 | 15.68 | 7.665949 |
| 4 | 50 | Cholesterol | DMG-PEG2000 | DSPC | 45 | 44 | 2 | 9 | 98.33 | 12.73 | |
| 4 | 50 | Cholesterol | DMG-PEG2000 | DSPC | 35 | 46.5 | 2.5 | 16 | 82.83 | 23.58 | |
| 4 | 50 | Cholesterol | DSG-PEG2000 | DSPC | 50 | 38.5 | 1.5 | 10 | 127.27 | 9.78 | 7.420054 |
| 4 | 50 | Cholesterol | DSG-PEG2000 | DSPC | 45 | 44 | 2 | 9 | 94.28 | 7.97 | |
| 4 | 50 | Cholesterol | DSG-PEG2000 | DSPC | 35 | 46.5 | 2.5 | 16 | 90.36 | 20.52 | |
| 4 | 53 | Cholesterol | DMG-PEG2000 | DSPC | 50 | 38.5 | 1.5 | 10 | 109.22 | 20.21 | 9.996225 |
| 4 | 53 | Cholesterol | DMG-PEG2000 | DSPC | 45 | 44 | 2 | 9 | 97.88 | 10.33 | |
| 4 | 53 | Cholesterol | DMG-PEG2000 | DSPC | 35 | 46.5 | 2.5 | 16 | 95.93 | 21.85 | |
| 4 | 53 | Cholesterol | DSG-PEG2000 | DSPC | 50 | 38.5 | 1.5 | 10 | 98.86 | 16.18 | 9.932697 |
| 4 | 53 | Cholesterol | DSG-PEG2000 | DSPC | 45 | 44 | 2 | 9 | 75.84 | 26.42 | |
| 4 | 53 | Cholesterol | DSG-PEG2000 | DSPC | 35 | 46.5 | 2.5 | 16 | 84.41 | 16.62 | |
| 4 | 67 | Cholesterol | DMG-PEG2000 | DSPC | 50 | 38.5 | 1.5 | 10 | 154.94 | 7.66 | 6.890504 |
| 4 | 67 | Cholesterol | DMG-PEG2000 | DSPC | 45 | 44 | 2 | 9 | 137.92 | 8.7 | |
| 4 | 67 | Cholesterol | DMG-PEG2000 | DSPC | 35 | 46.5 | 2.5 | 16 | 119.6 | 11.95 | |
| 4 | 67 | Cholesterol | DSG-PEG2000 | DSPC | 50 | 38.5 | 1.5 | 10 | 120 | 9.89 | 7.241026 |
| 4 | 67 | Cholesterol | DSG-PEG2000 | DSPC | 45 | 44 | 2 | 9 | 92.6 | 6.62 | |
| 4 | 67 | Cholesterol | DSG-PEG2000 | DSPC | 35 | 46.5 | 2.5 | 16 | 92.04 | 0.83 | |
| 4 | 68 | Cholesterol | DMG-PEG2000 | DSPC | 50 | 38.5 | 1.5 | 10 | 126.67 | 21.3 | 7.257977 |

FIG. 1N

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 4 | 68 | Cholesterol | DMG-PEG2000 | DSPC | 45 | 44 | 2 | 9 | 106.28 | 14.58 | |
| 4 | 68 | Cholesterol | DSG-PEG2000 | DSPC | 35 | 46.5 | 2.5 | 16 | 132.38 | 6.3 | 7.450841 |
| 4 | 68 | Cholesterol | DSG-PEG2000 | DSPC | 50 | 38.5 | 1.5 | 10 | 195.95 | 57.08 | |
| 4 | 68 | Cholesterol | DSG-PEG2000 | DSPC | 45 | 44 | 2 | 9 | 134.27 | 10.65 | |
| 4 | 68 | Cholesterol | DSG-PEG2000 | DSPC | 35 | 46.5 | 2.5 | 16 | 96.36 | 10.21 | |
| 4 | 49 | Cholesterol | DMG-PEG2000 | DSPC | 50 | 38.5 | 1.5 | 10 | 139.26 | 12.95 | 5.804976 |
| 4 | 49 | Cholesterol | DMG-PEG2000 | DSPC | 45 | 44 | 2 | 9 | 119.94 | 9.88 | |
| 4 | 49 | Cholesterol | DMG-PEG2000 | DSPC | 35 | 46.5 | 2.5 | 16 | 98.43 | 15.45 | |
| 4 | 49 | Cholesterol | DSG-PEG2000 | DSPC | 50 | 38.5 | 1.5 | 10 | 104.23 | 9.17 | 6.270189 |
| 4 | 49 | Cholesterol | DSG-PEG2000 | DSPC | 45 | 44 | 2 | 9 | 111.29 | 7.82 | |
| 4 | 49 | Cholesterol | DSG-PEG2000 | DSPC | 35 | 46.5 | 2.5 | 16 | 120.1 | 8.65 | |
| 4 | 52 | Cholesterol | DMG-PEG2000 | DSPC | 50 | 38.5 | 1.5 | 10 | 104.76 | 7.78 | 2.82E-07 |
| 4 | 52 | Cholesterol | DMG-PEG2000 | DSPC | 45 | 44 | 2 | 9 | 110.78 | 18.77 | |
| 4 | 52 | Cholesterol | DMG-PEG2000 | DSPC | 35 | 46.5 | 2.5 | 16 | 105.37 | 14.1 | |
| 4 | 52 | Cholesterol | DSG-PEG2000 | DSPC | 50 | 38.5 | 1.5 | 10 | 112.08 | 7.16 | 4.474854 |
| 4 | 52 | Cholesterol | DSG-PEG2000 | DSPC | 45 | 44 | 2 | 9 | 92.39 | 21.31 | |
| 4 | 52 | Cholesterol | DSG-PEG2000 | DSPC | 35 | 46.5 | 2.5 | 16 | 95.13 | 10.7 | |
| 4 | 69 | Cholesterol | DMG-PEG2000 | DSPC | 50 | 38.5 | 1.5 | 10 | 134.17 | 4.98 | 7.06667 |
| 4 | 69 | Cholesterol | DMG-PEG2000 | DSPC | 45 | 44 | 2 | 9 | 131.19 | 6.92 | |
| 4 | 69 | Cholesterol | DMG-PEG2000 | DSPC | 35 | 46.5 | 2.5 | 16 | 160.1 | 7.56 | |
| 4 | 69 | Cholesterol | DSG-PEG2000 | DSPC | 50 | 38.5 | 1.5 | 10 | 143.3 | 16.92 | 7.157256 |
| 4 | 69 | Cholesterol | DSG-PEG2000 | DSPC | 45 | 44 | 2 | 9 | 125.03 | 6.53 | |
| 4 | 69 | Cholesterol | DSG-PEG2000 | DSPC | 35 | 46.5 | 2.5 | 16 | 101.48 | 2.85 | |
| 4 | 70 | Cholesterol | DMG-PEG2000 | DSPC | 50 | 38.5 | 1.5 | 10 | 112.76 | 10.55 | 7.275622 |
| 4 | 70 | Cholesterol | DMG-PEG2000 | DSPC | 45 | 44 | 2 | 9 | 117.38 | 18.02 | |
| 4 | 70 | Cholesterol | DMG-PEG2000 | DSPC | 35 | 46.5 | 2.5 | 16 | 104.04 | 23.57 | |
| 4 | 70 | Cholesterol | DSG-PEG2000 | DSPC | 50 | 38.5 | 1.5 | 10 | 120.21 | 19.22 | 6.846701 |

FIG. 1O

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 4 | 70 | Cholesterol | DSG-PEG2000 | DSPC | 45 | 44 | 2 | 9 | 131.32 | 43.73 | |
| 4 | 70 | Cholesterol | DSG-PEG2000 | DSPC | 35 | 46.5 | 2.5 | 16 | 118.67 | 13.47 | |
| 4 | 24 | Cholesterol | DMG-PEG2000 | DSPC | 50 | 38.5 | 1.5 | 10 | 124.97 | 10.66 | 5.548813 |
| 4 | 24 | Cholesterol | DMG-PEG2000 | DSPC | 45 | 44 | 2 | 9 | 116.58 | 15.95 | |
| 4 | 24 | Cholesterol | DMG-PEG2000 | DSPC | 35 | 46.5 | 2.5 | 16 | 103.53 | 14.02 | |
| 4 | 24 | Cholesterol | DSG-PEG2000 | DSPC | 50 | 38.5 | 1.5 | 10 | 123.87 | 11.2 | 5.793184 |
| 4 | 24 | Cholesterol | DSG-PEG2000 | DSPC | 45 | 44 | 2 | 9 | 104.46 | 17.01 | |
| 4 | 24 | Cholesterol | DSG-PEG2000 | DSPC | 35 | 46.5 | 2.5 | 16 | 100 | 16.84 | |
| 4 | 46 | Cholesterol | DMG-PEG2000 | DSPC | 45 | 44 | 2 | 9 | 122.42 | 24.62 | |
| 4 | 46 | Cholesterol | DMG-PEG2000 | DSPC | 35 | 46.5 | 2.5 | 16 | 163.13 | 17 | |
| 4 | 46 | Cholesterol | DSG-PEG2000 | DSPC | 50 | 38.5 | 1.5 | 10 | 104.14 | 32.57 | 9.987067 |
| 4 | 46 | Cholesterol | DSG-PEG2000 | DSPC | 45 | 44 | 2 | 9 | 89.48 | 39.57 | |
| 4 | 46 | Cholesterol | DSG-PEG2000 | DSPC | 35 | 46.5 | 2.5 | 16 | 83.34 | 29.23 | |
| 4 | 53 | Cholesterol | DMG-PEG2000 | DSPC | 50 | 38.5 | 1.5 | 10 | 138.85 | 11.14 | 7.260187 |
| 4 | 53 | Cholesterol | DMG-PEG2000 | DSPC | 35 | 46.5 | 2.5 | 16 | 125.64 | 9.22 | |
| 4 | 53 | Cholesterol | DSG-PEG2000 | DSPC | 50 | 38.5 | 1.5 | 10 | 149.38 | 4.66 | 7.361538 |
| 4 | 53 | Cholesterol | DSG-PEG2000 | DSPC | 45 | 44 | 2 | 9 | 107.14 | 10.55 | |
| 4 | 53 | Cholesterol | DSG-PEG2000 | DSPC | 35 | 46.5 | 2.5 | 16 | 117.69 | 15.61 | |
| 4 | 29 | Cholesterol | DSG-PEG2000 | DSPC | 50 | 38.5 | 1.5 | 10 | 349.97 | 0 | 9.394296 |
| 4 | 29 | Cholesterol | DSG-PEG2000 | DSPC | 45 | 44 | 2 | 9 | 157.55 | 7.43 | |
| 4 | 29 | Cholesterol | DSG-PEG2000 | DSPC | 35 | 46.5 | 2.5 | 16 | 192.78 | 57.08 | |
| 4 | 54 | Cholesterol | DMG-PEG2000 | DSPC | 50 | 38.5 | 1.5 | 10 | 130.09 | 9.68 | 11.13306 |
| 4 | 54 | Cholesterol | DMG-PEG2000 | DSPC | 45 | 44 | 2 | 9 | 254.32 | 45.8 | |
| 4 | 54 | Cholesterol | DMG-PEG2000 | DSPC | 35 | 46.5 | 2.5 | 16 | 118.5 | 8.4 | |
| 4 | 54 | Cholesterol | DSG-PEG2000 | DSPC | 50 | 38.5 | 1.5 | 10 | 172.57 | 57.08 | 10.05967 |
| 4 | 55 | Cholesterol | DMG-PEG2000 | DSPC | 45 | 44 | 2 | 9 | 55.4 | 0 | |
| 4 | 56 | Cholesterol | DMG-PEG2000 | DSPC | 35 | 46.5 | 2.5 | 16 | 130.69 | 10.99 | |

FIG. 1P

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 4 | 56 | Cholesterol | DSG-PEG2000 | DSPC | 50 | 38.5 | 1.5 | 10 | 171.42 | 0 | 7.520197 |
| 4 | 56 | Cholesterol | DSG-PEG2000 | DSPC | 45 | 44 | 2 | 9 | 230.61 | 14.04 | |
| 4 | 57 | Cholesterol | DMG-PEG2000 | DSPC | 50 | 38.5 | 1.5 | 10 | 138.11 | 5.9 | 9.818822 |
| 4 | 57 | Cholesterol | DMG-PEG2000 | DSPC | 45 | 44 | 2 | 9 | 227.28 | 57.08 | |
| 4 | 57 | Cholesterol | DMG-PEG2000 | DSPC | 35 | 46.5 | 2.5 | 16 | 157.51 | 8.37 | |
| 4 | 57 | Cholesterol | DSG-PEG2000 | DSPC | 50 | 38.5 | 1.5 | 10 | 218.16 | 57.08 | 9.948145 |
| 4 | 57 | Cholesterol | DSG-PEG2000 | DSPC | 35 | 46.5 | 2.5 | 16 | 325.46 | 0 | |
| 4 | 58 | Cholesterol | DMG-PEG2000 | DSPC | 45 | 44 | 2 | 9 | 302.21 | 0 | |
| 4 | 19 | Cholesterol | DMG-PEG2000 | DSPC | 50 | 38.5 | 1.5 | 10 | 115.35 | 7.6 | |
| 4 | 19 | Cholesterol | DMG-PEG2000 | DSPC | 45 | 44 | 2 | 9 | 47.58 | 57.08 | |
| 4 | 19 | Cholesterol | DSG-PEG2000 | DSPC | 35 | 46.5 | 2.5 | 16 | 128.65 | 8.09 | |
| 4 | 20 | Cholesterol | DMG-PEG2000 | DSPC | 50 | 38.5 | 1.5 | 10 | 167.42 | 13.7 | |
| 4 | 21 | Cholesterol | DSG-PEG2000 | DSPC | 50 | 38.5 | 1.5 | 10 | 96.21 | 57.08 | 6.076081 |
| 4 | 21 | Cholesterol | DSG-PEG2000 | DSPC | 45 | 44 | 2 | 9 | 112.57 | 7.89 | |
| 4 | 30 | Cholesterol | DMG-PEG2000 | DSPC | 50 | 38.5 | 1.5 | 10 | 105.04 | 4.79 | 9.70389 |
| 4 | 30 | Cholesterol | DMG-PEG2000 | DSPC | 35 | 46.5 | 2.5 | 16 | 111.7 | 8.42 | |
| 4 | 30 | Cholesterol | DSG-PEG2000 | DSPC | 45 | 44 | 2 | 9 | 105 | 18.9 | |
| 4 | 31 | Cholesterol | DSG-PEG2000 | DSPC | 45 | 44 | 2 | 9 | 221.89 | 0 | |
| 4 | 32 | Cholesterol | DMG-PEG2000 | DSPC | 45 | 44 | 2 | 9 | 51.51 | 57.08 | |
| 4 | 32 | Cholesterol | DMG-PEG2000 | DSPC | 35 | 46.5 | 2.5 | 16 | 121.72 | 12.47 | |
| 4 | 32 | Cholesterol | DSG-PEG2000 | DSPC | 50 | 38.5 | 1.5 | 10 | 74.21 | 57.08 | 8.547087 |
| 4 | 32 | Cholesterol | DSG-PEG2000 | DSPC | 45 | 44 | 2 | 9 | 171.23 | 10.55 | |
| 4 | 4 | Cholesterol | DMG-PEG2000 | DSPC | 50 | 38.5 | 1.5 | 10 | 143.69 | 12.62 | 7.532265 |
| 4 | 4 | Cholesterol | DMG-PEG2000 | DSPC | 35 | 46.5 | 2.5 | 16 | 129.97 | 12.47 | |
| 4 | 4 | Cholesterol | DSG-PEG2000 | DSPC | 50 | 38.5 | 1.5 | 10 | 488.1 | 57.08 | 7.410863 |
| 4 | 4 | Cholesterol | DSG-PEG2000 | DSPC | 45 | 44 | 2 | 9 | 210.39 | 4.39 | |
| 4 | 25 | Cholesterol | DMG-PEG2000 | DSPC | 50 | 38.5 | 1.5 | 10 | 226.38 | 0 | 7.41512 |

FIG. 1Q

| Screen Number | Lipid | Cholesterol | PEG | Phospholipid | Lipid Ratio | Cholesterol Ratio | PEG Ratio | Phospholipid Ratio | Diameter | PDI | pKa |
|---|---|---|---|---|---|---|---|---|---|---|---|
| 4 | 25 | Cholesterol | DMG-PEG2000 | DSPC | 35 | 46.5 | 2.5 | 16 | 208.45 | 14.99 | |

FIG. 1R

NANOMATERIALS

RELATED APPLICATION INFORMATION

This application is a continuation of U.S. Patent Application Ser. No. 17/110,070, filed Dec. 2, 2020, which claims priority to U.S. Provisional Application Ser. No. 62/944,735, filed Dec. 6, 2019, the entireties of which are hereby incorporated herein by reference.

BACKGROUND

Field

The present application relates to the fields of chemistry, biology, and medicine. Disclosed herein are drug delivery systems and methods of their use. More particularly, disclosed herein are nanoparticle compositions for delivery of nucleic acids to cells.

Description

T cells, B cells, macrophages, and other immune cells help regulate homeostasis and immunity, which makes them an important target for RNA therapies. While nanoparticles carrying RNA have been directed to immune cells in vivo using protein- and aptamer-based targeting ligands, systemic delivery to immune cells without targeting ligands remains challenging.

SUMMARY

Some embodiments described herein relate to a compound of Formula (I):

(I)

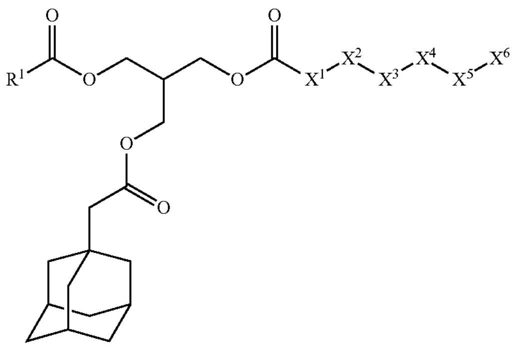

wherein:

$R^1$ is $C_9$-$C_{20}$ alkyl or $C_9$-$C_{20}$ alkenyl with 1-3 units of unsaturation, $X^1$ and $X^2$ are each independently absent or selected from —O—, $NR^2$, and

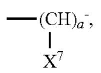

wherein $R^2$ is $C_1$-$C_6$ alkyl, and wherein $X^1$ and $X^2$ are not both —O— or $NR^2$;

a is an integer between 1 and 6;

$X^3$ and $X^4$ are each independently absent or selected from the group consisting of: 4- to 7-membered heterocyclyl optionally substituted with 1 or 2 $C_1$-$C_6$ alkyl groups, 5- to 6-membered heteroaryl optionally substituted with 1 or 2 $C_1$-$C_6$ alkyl groups, and —$NR^3$—, wherein each $R^3$ is a hydrogen atom or $C_1$-$C_6$ alkyl;

$X^5$ is —$(CH_2)_b$—, wherein b is an integer between 0 and 6;

$X^6$ is hydrogen, $C_1$-$C_6$ alkyl, 5- to 6-membered heteroaryl optionally substituted with 1 or 2 $C_1$-$C_6$ alkyl groups, or —$NR^4R^5$, wherein $R^4$ and $R^5$ are each independently hydrogen or $C_1$-$C_6$ alkyl; or alternatively $R^4$ and $R^5$ join together with the nitrogen to which they are bound to form a 4- to 7-membered heterocyclyl optionally substituted with 1 or 2 $C_1$-$C_6$ alkyl groups, wherein the heterocyclyl optionally includes an additional heteroatom selected from oxygen, sulfur, and nitrogen;

$X^7$ is hydrogen or —$NR^6R^7$, wherein $R^6$ and $R^7$ are each independently hydrogen or $C_1$-$C_6$ alkyl; or alternatively $R^6$ and $R^7$ join together with the nitrogen to which they are bound to form a 4- to 7-membered heterocyclyl optionally substituted with 1 or 2 $C_1$-$C_6$ alkyl groups, wherein the heterocyclyl optionally includes an additional heteroatom selected from oxygen, sulfur, and nitrogen;

at least one of $X^1$, $X^2$, $X^3$, $X^4$, and $X^5$ is present; and provided that when either $X^1$ or $X^2$ is —O—, neither $X^3$ nor $X^4$ is

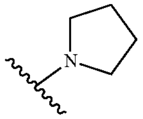, and when either $X^1$ or $X^2$ is —O—, $R^4$ and $R^5$ are not both ethyl.

Additional embodiments feature a compound of Formula (II):

(II)

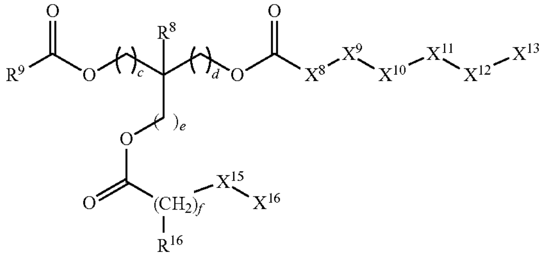

wherein:

$R^8$ is hydrogen or $C_1$-$C_6$ alkyl;

$R^9$ is $C_9$-$C_{20}$ alkyl optionally fused with 1-4 $C_3$-$C_6$ cycloalkyl groups, $C_9$-$C_{20}$ alkenyl with 1-3 units of unsaturation, or —$(CH_2)_g$—$X^{17}$, wherein $X^{17}$ is optionally substituted $C_4$-$C_{12}$ cycloalkyl;

$X^8$ and $X^9$ are each independently absent or selected from —O—, $NR^{10}$, and

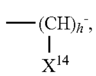

wherein $R^{10}$ is $C_1$-$C_6$ alkyl, and wherein $X^8$ and $X^9$ are not both —O— or $NR^{10}$;

$X^{10}$ and $X^{11}$ are each independently absent or selected from the group consisting of: 4- to 7-membered heterocyclyl optionally substituted with 1 or 2 $C_1$-$C_6$ alkyl groups, 5- to 6-membered heteroaryl optionally substituted with 1 or 2 $C_1$-$C_6$ alkyl groups, and $—NR^{11}—$, wherein $R^{11}$ is a hydrogen atom or $C_1$-$C_6$ alkyl;

$X^{12}$ is $—(CH_2)_i—$;

$X^{13}$ is hydrogen, $C_1$-$C_6$ alkyl, 5- to 6-membered heteroaryl optionally substituted with 1 or 2 $C_1$-$C_6$ alkyl groups, or $—NR^{12}R^{13}$, wherein $R^{12}$ and $R^{13}$ are each independently hydrogen or $C_1$-$C_6$ alkyl; or alternatively $R^{12}$ and $R^{13}$ join together with the nitrogen to which they are bound to form a 4- to 7-membered heterocyclyl optionally substituted with 1 or 2 $C_1$-$C_6$ alkyl groups, wherein the heterocyclyl optionally includes an additional heteroatom selected from oxygen, sulfur, and nitrogen;

$X^{14}$ is hydrogen or $—NR^{14}R^{15}$, wherein $R^{14}$ and $R^{15}$ are each independently hydrogen or $C_1$-$C_6$ alkyl; or alternatively $R^{14}$ and $R^{15}$ join together with the nitrogen to which they are bound to form a 4- to 7-membered heterocyclyl optionally substituted with 1 or 2 $C_1$-$C_6$ alkyl groups, wherein the heterocyclyl optionally includes an additional heteroatom selected from oxygen, sulfur, and nitrogen;

each of c, d, e, f, g, h, and i is independently an integer from 0-6;

at least one of $X^8$, $X^9$, $X^{10}$, $X^{11}$, and $X^{12}$ is present;

$R^{16}$ is hydrogen or optionally substituted $C_5$-$C_6$ aryl;

$X^{15}$ is optionally substituted $C_4$-$C_{12}$ cycloalkyl or optionally substituted $C_5$-$C_{10}$ aryl; and $X^{16}$ is hydrogen or optionally substituted $C_4$-$C_{12}$ cycloalkyl;

provided that when f is 1 and $R^9$ is

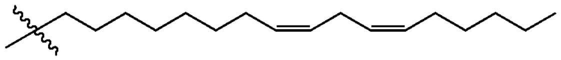, $X^{15}$ is not

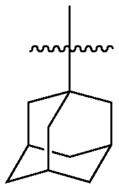.

Some embodiments feature a lipid nanoparticle composition comprising: a conformationally constrained ionizable lipid; a phospholipid; a polyethylene glycol-lipid; a cholesterol; and optionally a nucleic acid. Further embodiments are directed toward a method of delivering a nucleic acid to a subject in need thereof, comprising administering to the subject in need the lipid nanoparticle composition.

These and other embodiments are described in greater detail below.

BRIEF DESCRIPTION OF THE DRAWINGS

FIGS. 1A-1R is a table showing information related to LNP formulation and characterization.

DETAILED DESCRIPTION

Definitions

Figure 2:
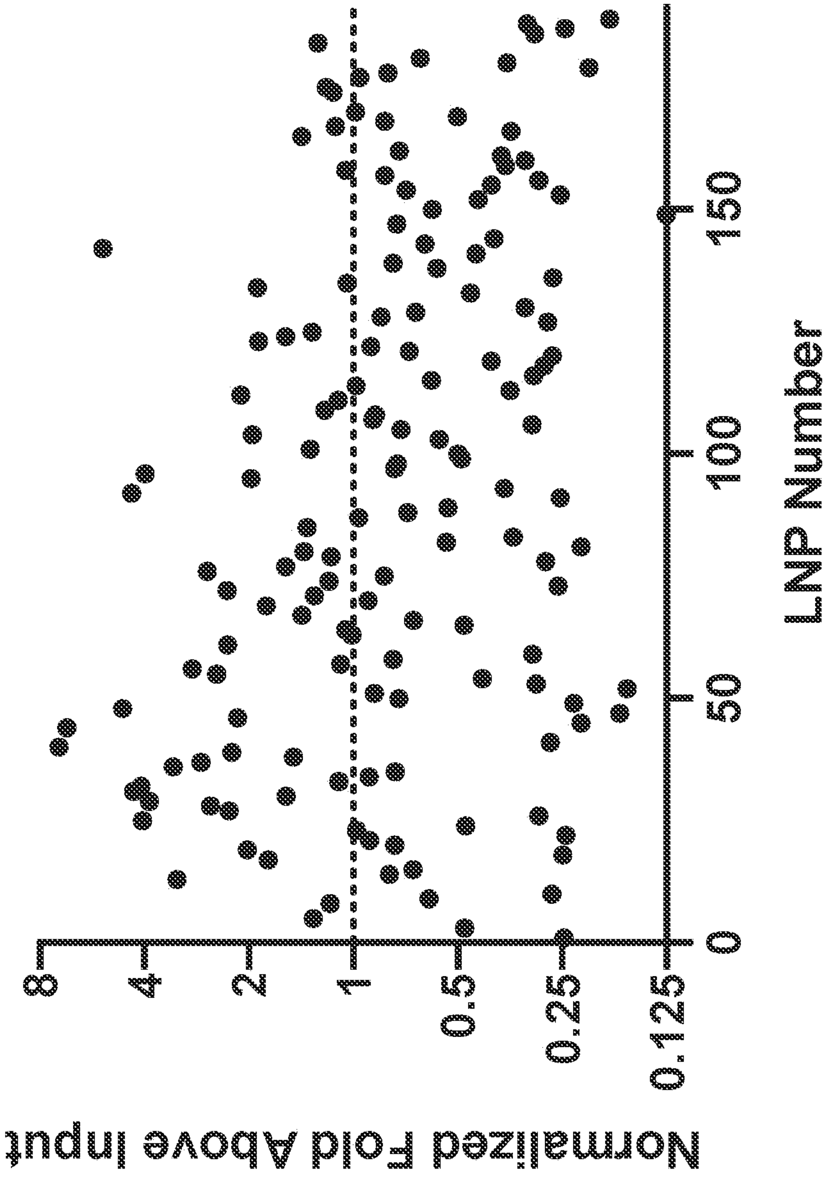
FIG. 2 is a graph showing the normalized frequency DNA barcode counts in FACS isolated samples as compared to the frequency in injected input for selected LNPs as tested in spleen CD3 cells.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" or "X" group(s) such as, without limitation, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$ and $X^{17}$ represent substituents that can be attached to the indicated atom. Such R and X groups may be referred to herein in a general way as "R" groups. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

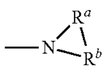

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, acylalkyl, hydroxy, alkoxy, alkoxyalkyl, aminoalkyl, amino acid, aryl, heteroaryl, heterocyclyl, aryl (alkyl), heteroaryl(alkyl), heterocyclyl(alkyl), hydroxyalkyl, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, azido, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heteroalicyclyl group. That is, the alkyl, alkenyl, alkynyl, ring(s) of the cycloalkyl, ring(s) of the cycloalkenyl, ring(s) of the aryl, ring(s) of the heteroaryl or ring(s) of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl, cycloalkenyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Typical mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, bicyclo[2.1.1]heptane, adamantanyl, and norbornanyl; and examples of spiro cycloalkyl groups include spiro[3.3]heptane and spiro[4.5]decane.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s) or 3 to 8 atoms in the ring(s). When composed of two or more rings, the rings may be connected together in a fused fashion. A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one, two, three or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, those described herein and the following: furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused or spiro fashion, as described herein with respect to "cycloalkyl." Additionally, any nitrogens in a heterocyclyl may be quaternized. Heterocyclyl or heteroalicyclic groups may be unsubstituted or substituted. Examples of such "heterocyclyl" or "heteroalicyclyl" groups include, but are not limited to, those described herein and the following: 1,3-dioxin, 1,3-dioxane, 1,4-dioxane, 1,2-dioxolane, 1,3-dioxolane, 1,4-dioxolane, 1,3-oxathiane, 1,4-oxathiin, 1,3,4-oxadiazol-2(3H)-one, 1,2,3-oxadiazol-5(2H)-one, 1,3-oxathiolane, 1,3-dithiole, 1,3-dithiolane, 1,4-oxathiane, tetrahydro-1,4-thiazine, 1,3-thiazinane, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, and 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, imidazolylalkyl and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a heteroalicyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl), and 1,3-thiazinan-4-yl(methyl).

"Lower alkylene groups" are straight-chained $—CH_2—$ tethering groups, forming bonds to connect molecular fragments via their terminal carbon atoms. Examples include but are not limited to methylene ($—CH_2—$), ethylene ($—CH_2CH_2—$), propylene ($—CH_2CH_2CH_2—$), and butylene ($—CH_2CH_2CH_2CH_2—$). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) as defined herein. A non-limiting list of alkoxys are methoxy, ethoxy, n-propoxy, 1-methylethoxy (isopropoxy), cyclopropoxy, n-butoxy, iso-butoxy, sec-butoxy, tert-butoxy, cyclobutoxy, phenoxy and benzoxy. An alkoxy may be substituted or unsubstituted.

As used herein, "acyl" refers to a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl) connected, as substituents, via a carbonyl group. Examples include formyl, acetyl, propanoyl, benzoyl and acryl. An acyl may be substituted or unsubstituted.

As used herein, "acylalkyl" refers to an acyl connected, as a substituent, via a lower alkylene group. Examples include aryl-$C(=O)—(CH_2)_n—$ and heteroaryl-$C(=O)—(CH_2)_n—$, where n is an integer in the range of 1 to 6.

As used herein, "alkoxyalkyl" refers to an alkoxy group connected, as a substituent, via a lower alkylene group. Examples include $C_{1-4}$ alkyl-$O—(CH_2)_n—$, wherein n is an integer in the range of 1 to 6.

As used herein, "aminoalkyl" refers to an optionally substituted amino group connected, as a substituent, via a lower alkylene group. Examples include $H_2N(CH_2)_n—$, wherein n is an integer in the range of 1 to 6.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, chloro-fluoroalkyl, chloro-difluoroalkyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, chloro-fluoroalkyl, chloro-difluoroalkoxy and 2-fluoroisobutoxy. A haloalkoxy may be substituted or unsubstituted.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "$X_3CS(O)_2N(R_A)$—" group wherein each X is a halogen, and $R_A$ hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl).

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "carbonyl" group refers to a C═O group.

An "S-sulfonamido" group refers to a "—$SO_2N(R_AR_B)$" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "$RSO_2N(R_A)$—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carbamyl" group refers to a "—OC(═O)N($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(═O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(═S)—N($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(═S)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(═O)N($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(═O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

A "urea" group refers to "N(R)—C(═O)—$NR_AR_B$ group in which R can be hydrogen or an alkyl, and $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A urea may be substituted or unsubstituted.

An "oxime" group refers to "—C(═N—OH)$R_A$" in which $R_A$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An oxime may be substituted or unsubstituted.

An "acyl hydrozone" refers to "—C(═N—NH-acyl)-$R_A$." in which the acyl portion has the structure as provided herein for "acyl", and $R_A$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An acyl hydrozone may be substituted or unsubstituted.

A "hydrazine" refers to "—$NHNR_AR_B$" in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A hydrazine may be substituted or unsubstituted.

The term "halogen atom" or "halogen" as used herein, means any one of the radio-stable atoms of column 7 of the Periodic Table of the Elements, such as, fluorine, chlorine, bromine and iodine.

As used herein, ═ (dashed) indicates a single or double bond, unless stated otherwise.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The terms "protecting group" and "protecting groups" (and the abbreviation "PG") as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein);

acyclic acetal; cyclic acetal (e.g., those described herein); acyclic hemiacetal; cyclic hemiacetal, cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

The term "leaving group" (and the abbreviation "LG") as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates, mesylates, trifluoroacetates and halogens (e.g., I, Br, and Cl). Non-limiting characteristics and examples of leaving groups can be found, for example in *Organic Chemist,* 2d ed., Francis Carey (1992), pages 328-331*; Introduction to Organic Chemistry,* 2d ed., Andrew Streitwieser and Clayton Heathcock (1981), pages 169-171; and *Organic Chemistry,* $5^{th}$ ed., John McMurry (2000), pages 398 and 408; all of which are incorporated herein by reference for the limited purpose of disclosing characteristics and examples of leaving groups.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless the context indicates otherwise. Similarly, a group of items linked with the conjunction 'or' should not be read as requiring mutual exclusivity among that group, but rather should be read as 'and/or' unless the context indicates otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z, or a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

As used herein, an "RNA" refers to a ribonucleic acid that may be naturally or non-naturally occurring. For example, an RNA may include modified and/or non-naturally occurring components such as one or more nucleobases, nucleosides, nucleotides, or linkers. An RNA may include a cap structure, a chain terminating nucleoside, a stem loop, a polyA sequence, and/or a polyadenylation signal. An RNA may have a nucleotide sequence encoding a polypeptide of interest. For example, an RNA may be a messenger RNA (mRNA). Translation of an mRNA encoding a particular polypeptide, for example, in vivo translation of an mRNA inside a mammalian cell, may produce the encoded polypeptide. RNAs may be selected from the nonlimiting group consisting of small interfering RNA (siRNA), microRNA (miRNA), Dicer-substrate RNA (dsRNA), small hairpin RNA (shRNA), mRNA, single-guide RNA (sgRNA), cas9 mRNA, and mixtures thereof.

The terms "polypeptide", "peptide", and "protein", may be used interchangeably to refer a string of at least three amino acids linked together by peptide bonds. Peptide may refer to an individual peptide or a collection of peptides. Peptides can contain natural amino acids, non-natural amino acids (i.e., compounds that do not occur in nature but that can be incorporated into a polypeptide chain), and/or amino acid analogs. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. Modifications may include cyclization of the peptide, the incorporation of D-amino acids, etc.

As used herein, the terms "treat," "treating," "treatment" and "therapeutic use" refer to the elimination, reduction or amelioration of one or more symptoms of a disease or disorder. As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

The compositions described herein are preferably provided in unit dosage form. As used herein, a "unit dosage form" is a composition containing an amount of a compound or composition that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation. As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman el al., Pharmaceutical Dosage Forms: Tablets (1989); and Ansel, Introduction to Pharmaceutical Dosage Forms 8th Edition (2004).

As used herein, the terms "individual," "host," "subject," and "patient" are used interchangeably herein, and refer to a mammal, including, but not limited to, humans, rodents, such as mice and rats, and other laboratory animals.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the term "conformationally constrained lipid" refers to a lipid whose molecular structure is predominantly in one architecture, such as an adamantane, whose shape resembles an 'armchair'.

The term "PEG-lipid" refers to a lipid modified with polyethylene glycol. Exemplary PEG-lipids, include but are not limited to $C_{14}PEG_{350}$, $C_{14}PEG_{1000}$, $C_{14}PEG_{2000}$, $C_{14}PEG_{3000}$, and $C_{18}PEG_{2000}$.

The term "oligonucleotide" refers to short DNA, RNA, or DNA/RNA molecules or oligomers containing a relatively small number of nucleotides.

A. Lipid Nanoparticles

Effective, targeted delivery of biologically active substances such as small molecule drugs, proteins, and nucleic acids is a continuing challenge in the field of medicine. The delivery of nucleic acids specifically is made difficult by the relative instability and low cell permeability of nucleic acids. It has been discovered that lipid nanoparticles having constrained lipids can more effectively deliver nucleic acids to specific tissues in the body. In one embodiment, lipid nanoparticles can be formulated by mixing nucleic acids with conformationally constrained ionizable lipids, PEG-lipids, phospholipids, cholesterol, and optionally a nucleic acid. In some embodiments, the lipid nanoparticles do not contain a targeting ligand. In some embodiments, the disclosed lipid nanoparticles preferentially target T cells over hepatocytes in the absence of a targeting ligand.

Lipid nanoparticle sizes vary. In one embodiment, the lipid nanoparticles can have an average hydrodynamic diameter from between about 30 to about 170 nm. The lipid nanoparticles can have an average hydrodynamic diameter that is about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, or any range having endpoints defined by any two of the aforementioned values. For example, in an embodiment the nanoparticles have an average hydrodynamic diameter from between 50 nm to 100 nm.

1. Compounds

Some embodiments relate to a compound of Formula (I):

(I)

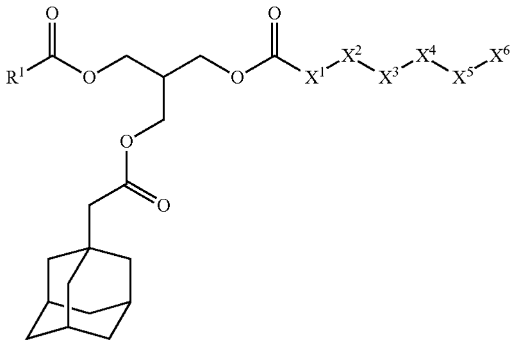

wherein:

$R^1$ is $C_9$-$C_{20}$ alkyl or $C_9$-$C_{20}$ alkenyl with 1-3 units of unsaturation;

$X^1$ and $X^2$ are each independently absent or selected from —O—, $NR^2$, and

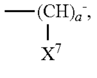

$R^2$ is $C_1$-$C_6$ alkyl, and wherein $X^1$ and $X^2$ are not both —O— or $NR^2$;

a is an integer between 1 and 6;

$X^3$ and $X^4$ are each independently absent or selected from the group consisting of: 4- to 7-membered heterocyclyl optionally substituted with 1 or 2 $C_1$-$C_6$ alkyl groups, 5- to 6-membered heteroaryl optionally substituted with 1 or 2 $C_1$-$C_6$ alkyl groups, and —$NR^3$—, wherein each $R^3$ is a hydrogen atom or $C_1$-$C_6$ alkyl;

$X^5$ is —$(CH_2)_b$—, wherein b is an integer between 0 and 6;

$X^6$ is hydrogen, $C_1$-$C_6$ alkyl, 5- to 6-membered heteroaryl optionally substituted with 1 or 2 $C_1$-$C_6$ alkyl groups, or —$NR^4R^5$, wherein $R^4$ and $R^5$ are each independently hydrogen or $C_1$-$C_6$ alkyl; or alternatively $R^4$ and $R^5$ join together with the nitrogen to which they are bound to form a 4- to 7-membered heterocyclyl optionally substituted with 1 or 2 $C_1$-$C_6$ alkyl groups, wherein the heterocyclyl optionally includes an additional heteroatom selected from oxygen, sulfur, and nitrogen;

$X^7$ is hydrogen or —$NR^6R^7$, wherein $R^6$ and $R^7$ are each independently hydrogen or $C_1$-$C_6$ alkyl; or alternatively $R^6$ and $R^7$ join together with the nitrogen to which they are bound to form a 4- to 7-membered heterocyclyl optionally substituted with 1 or 2 $C_1$-$C_6$ alkyl groups, wherein the heterocyclyl optionally includes an additional heteroatom selected from oxygen, sulfur, and nitrogen;

at least one of $X^1$, $X^2$, $X^3$, $X^4$, and $X^5$ is present; and provided that when either $X^1$ or $X^2$ is —O—, neither $X^3$ nor $X^4$ is

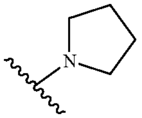, and when either $X^1$ or $X^2$ is —O—, $R^4$ and $R^5$ are not both ethyl.

In other embodiments,

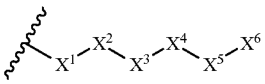

is not selected from the group consisting of:

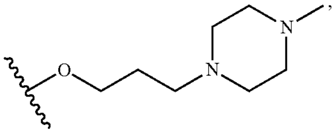,

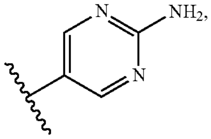 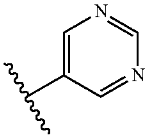, and

-continued
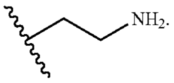
In some embodiments, $R^1$ is
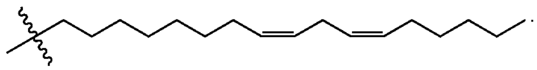 [SMILES: *CCCCCCC/C=C\C/C=C\CCCCC]
Additional embodiments relate to a compound of Formula (Ia):
(Ia)
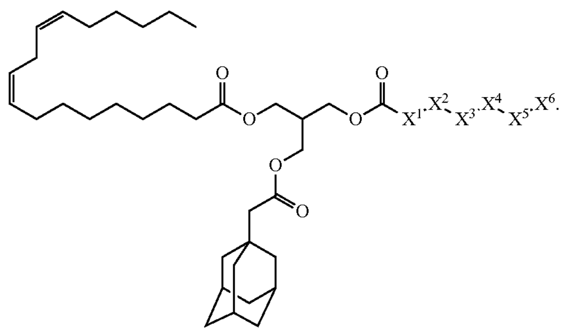
In some embodiments, the compound of Formula (I) is selected from the group consisting of:
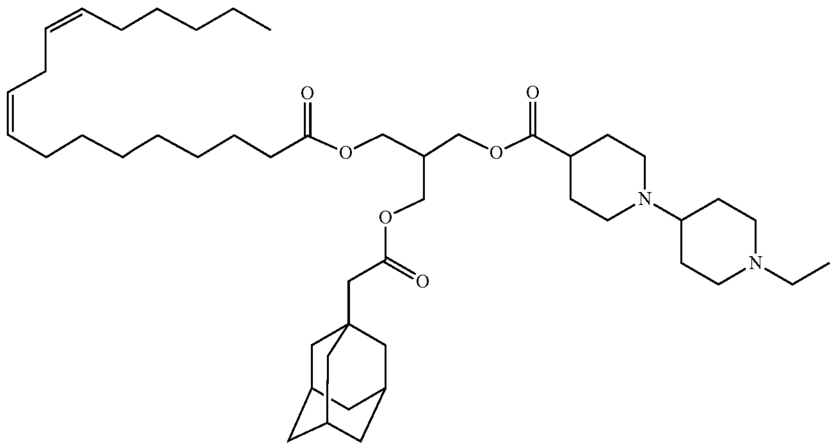
,
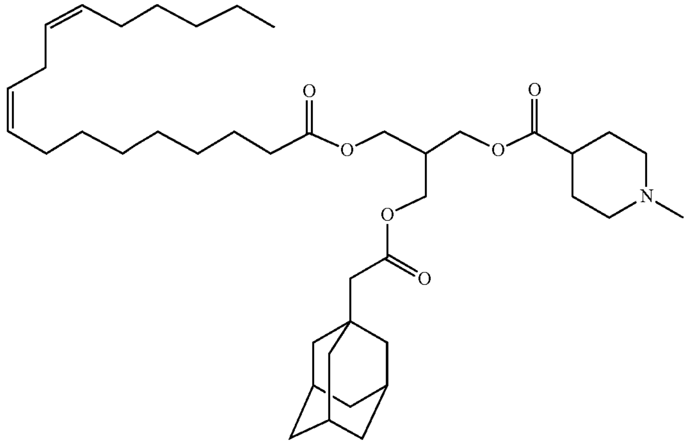
, -continued
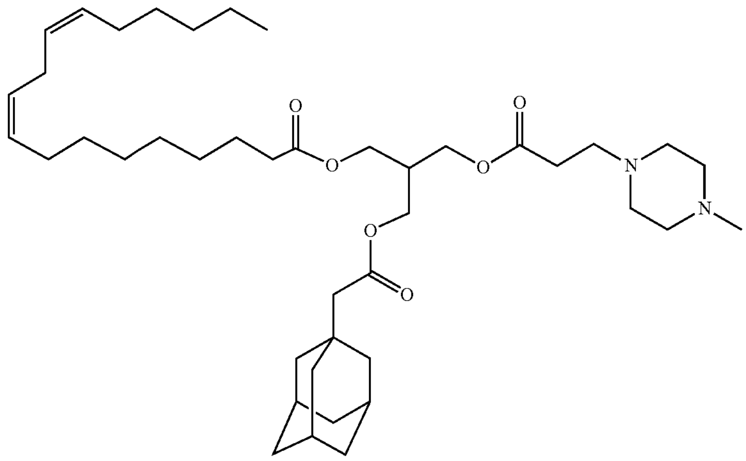
,
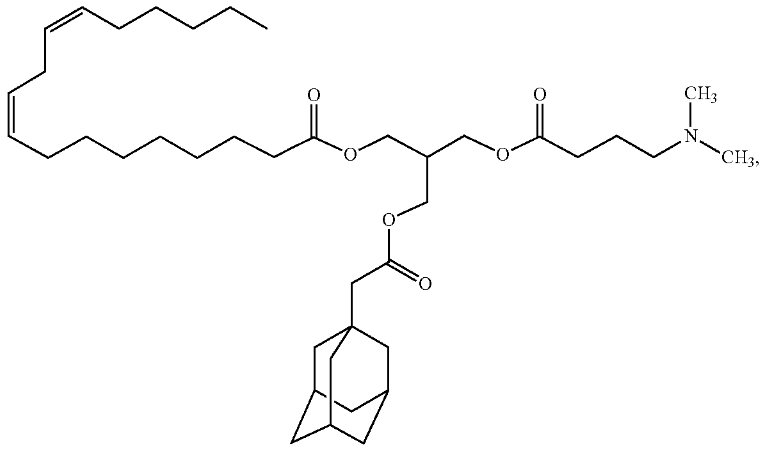
,
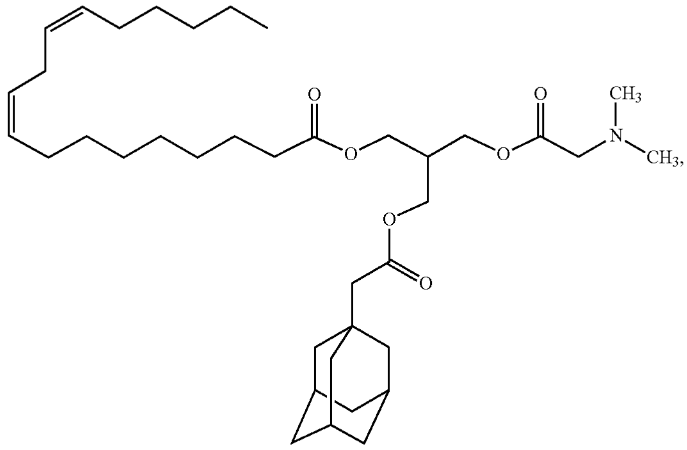
, -continued
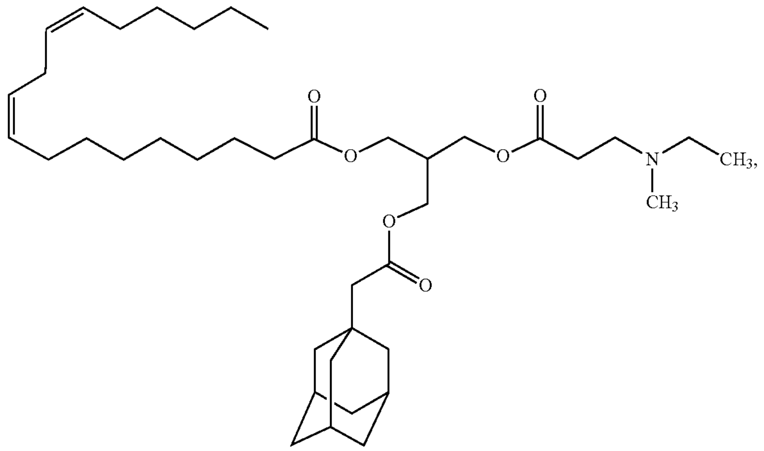
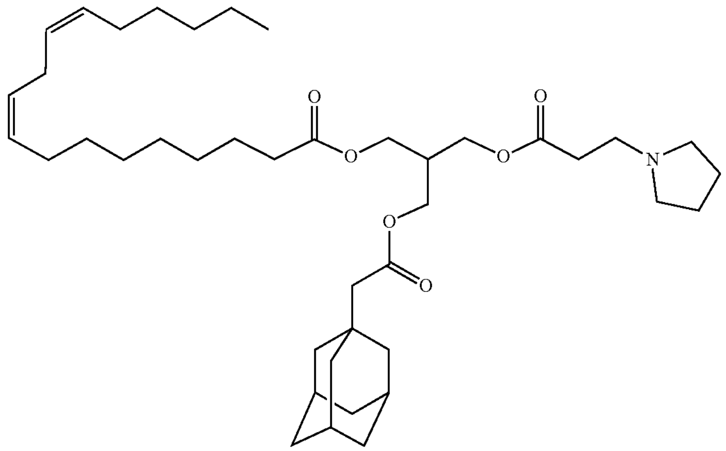
,
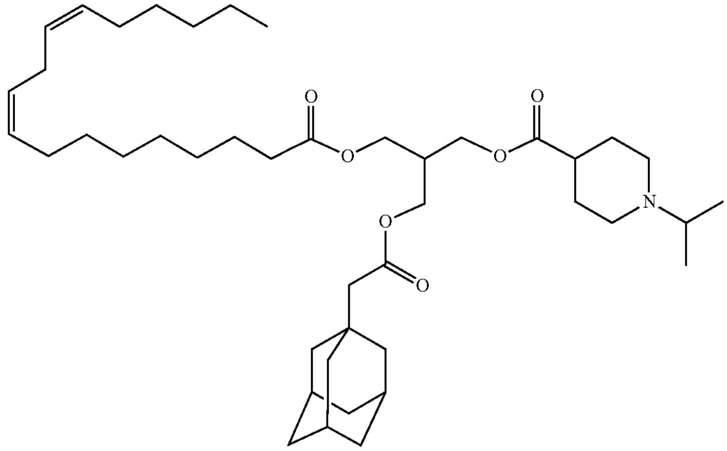
, -continued
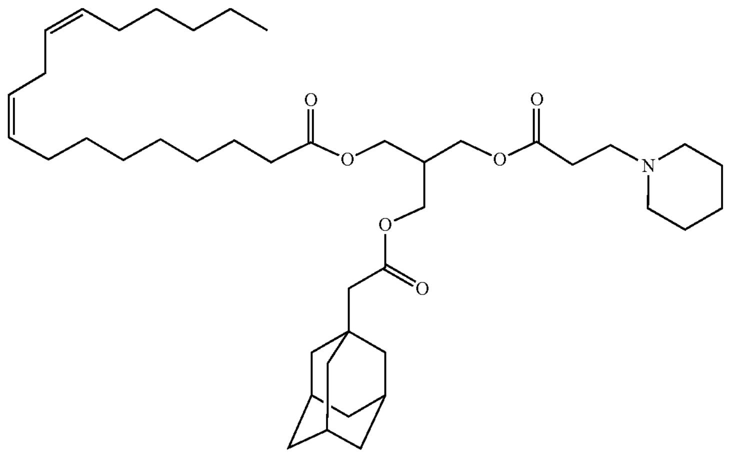
,
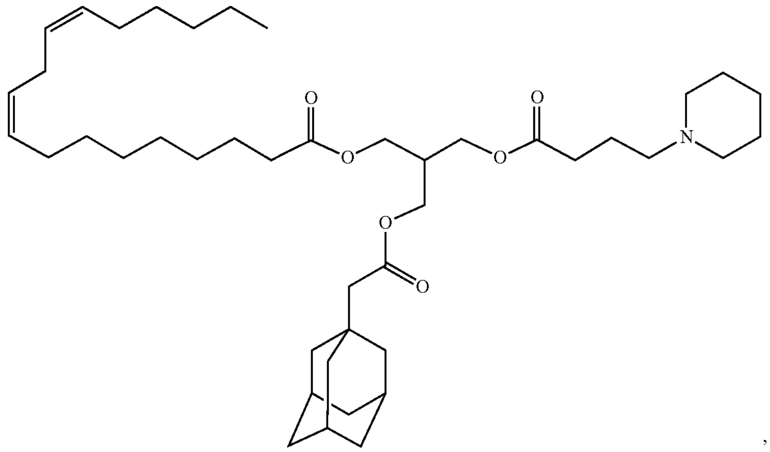
,
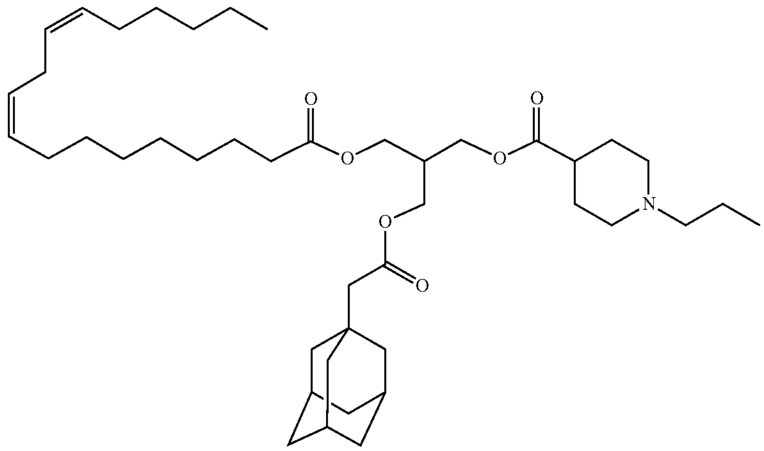
, -continued
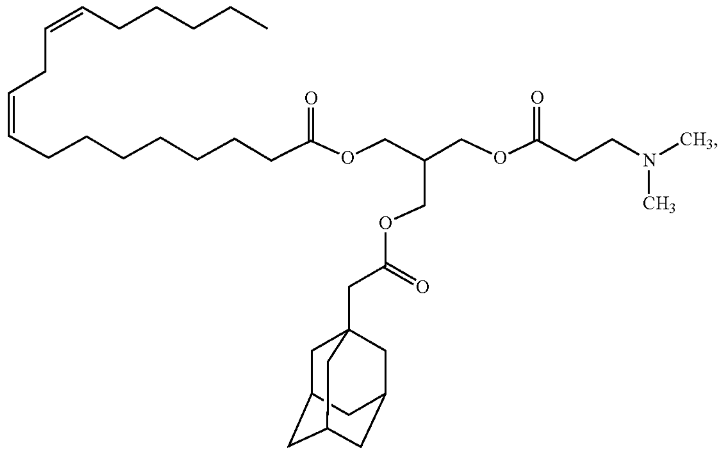
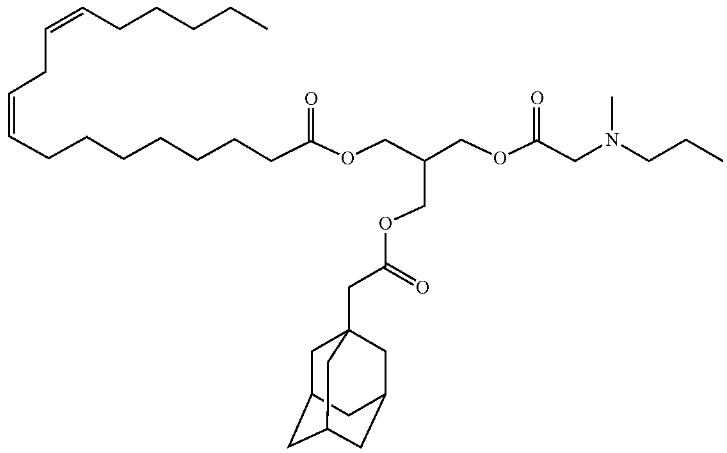
,
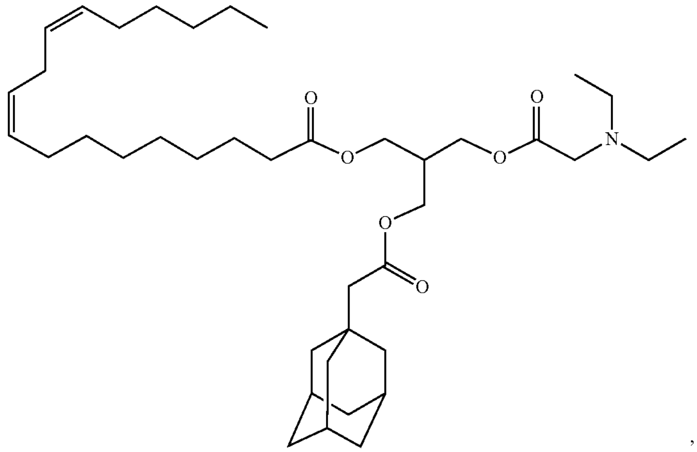
, -continued
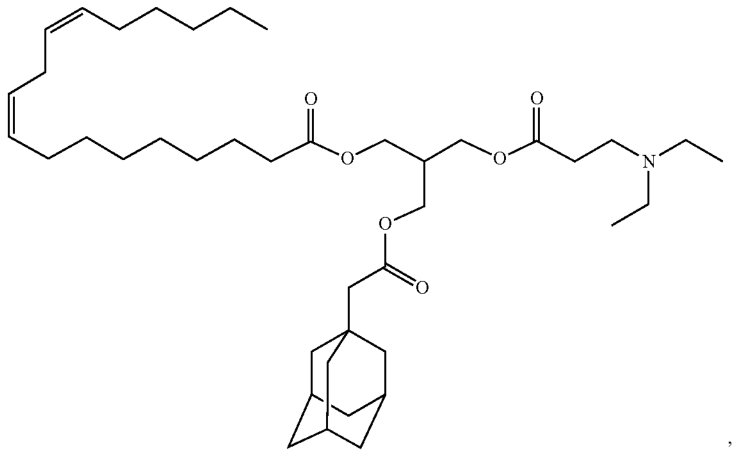
,
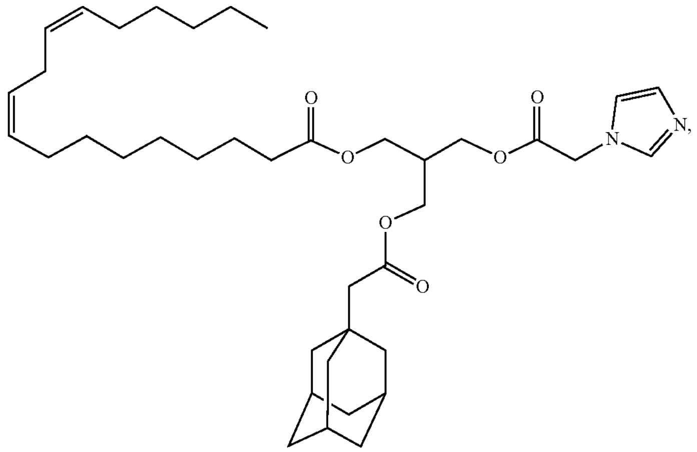
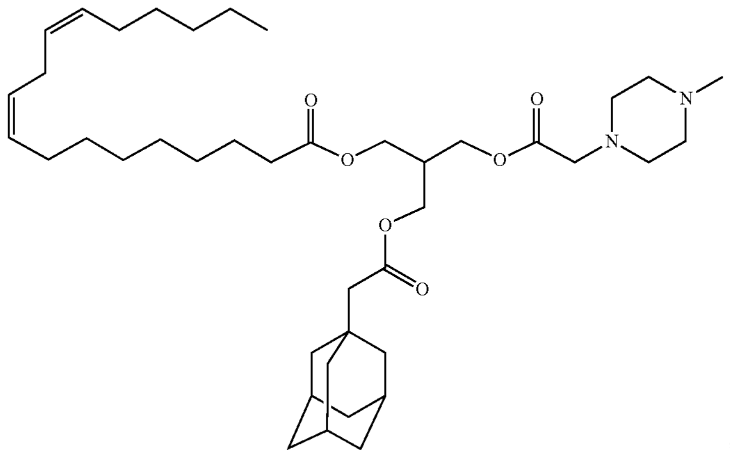
, -continued
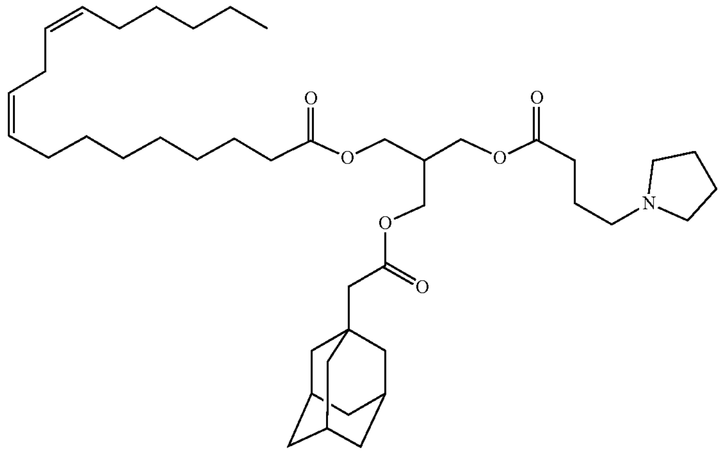
,
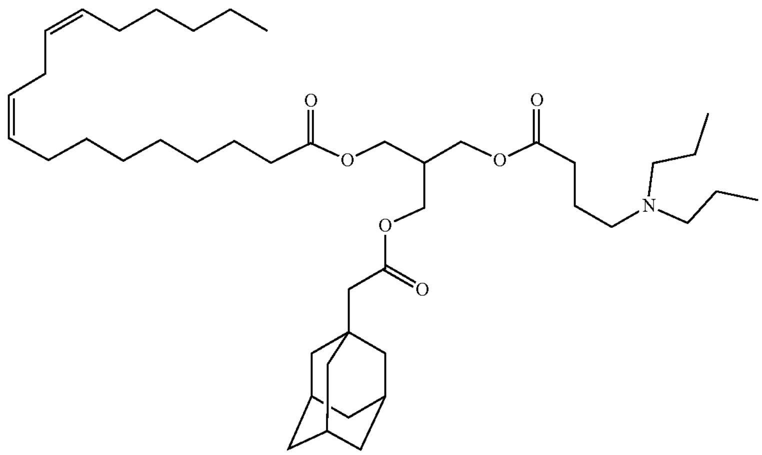
,
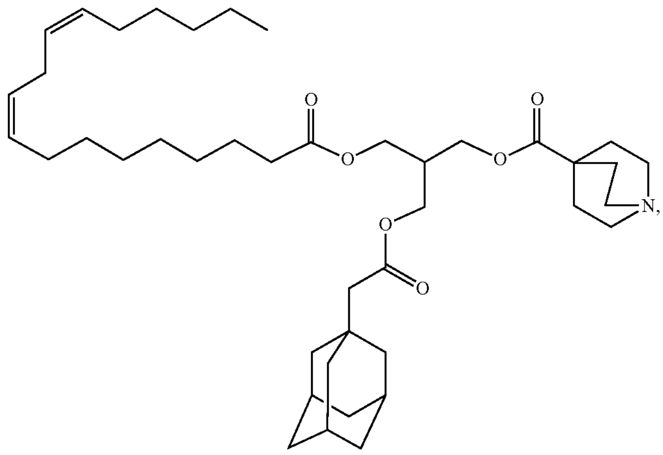
, -continued
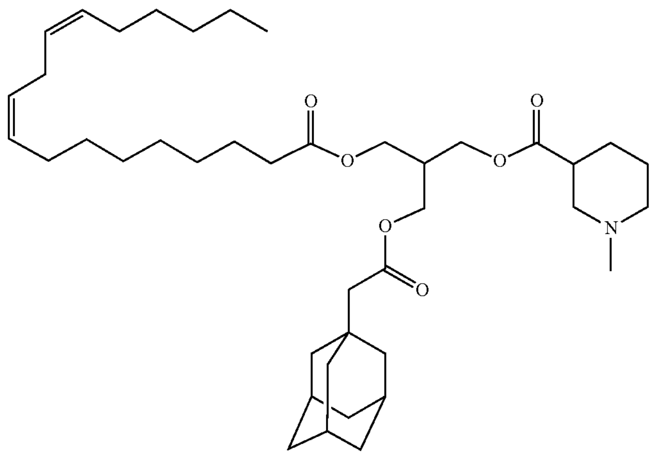
,
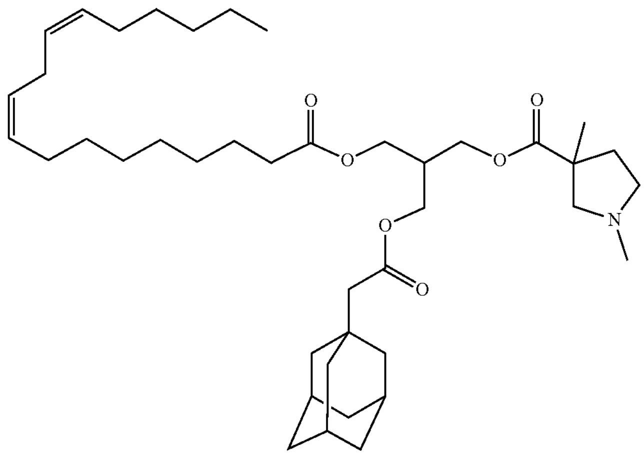
,
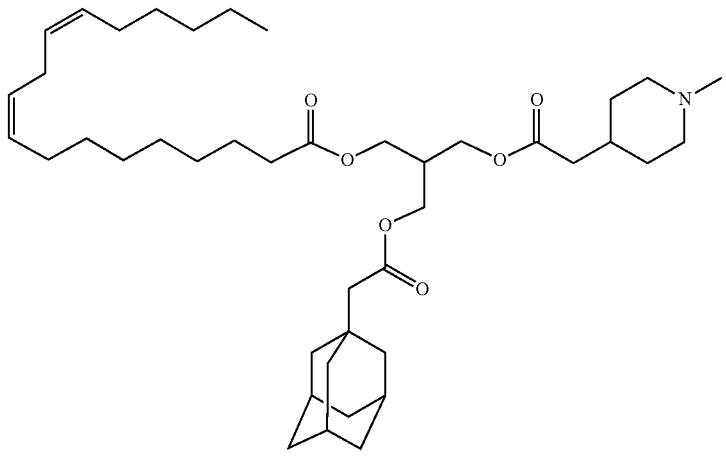
, -continued
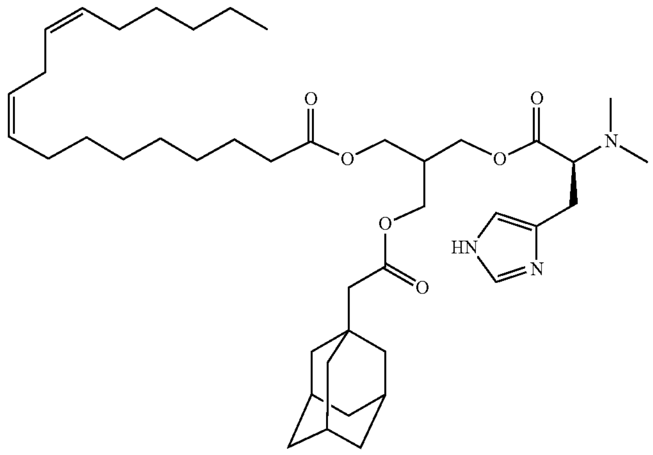
,
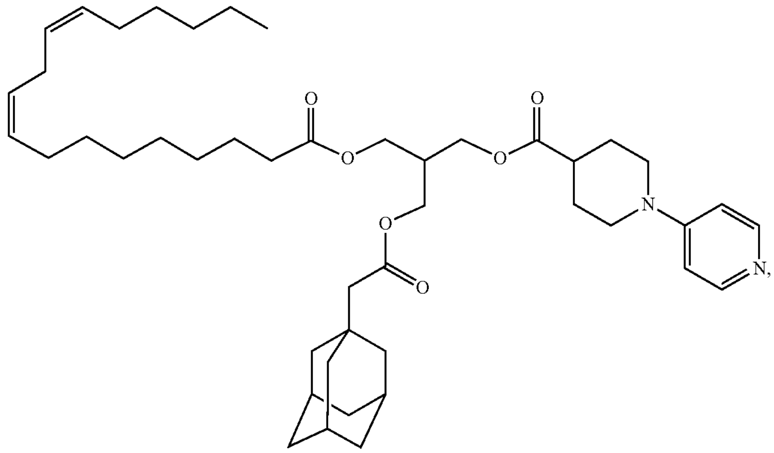
,
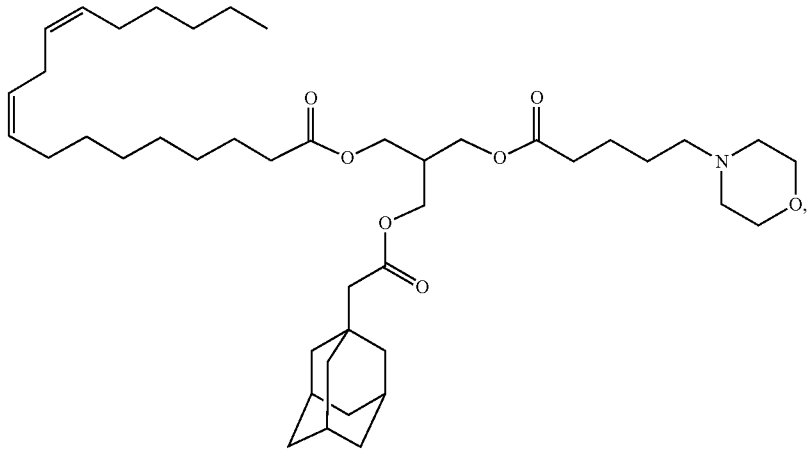
, -continued
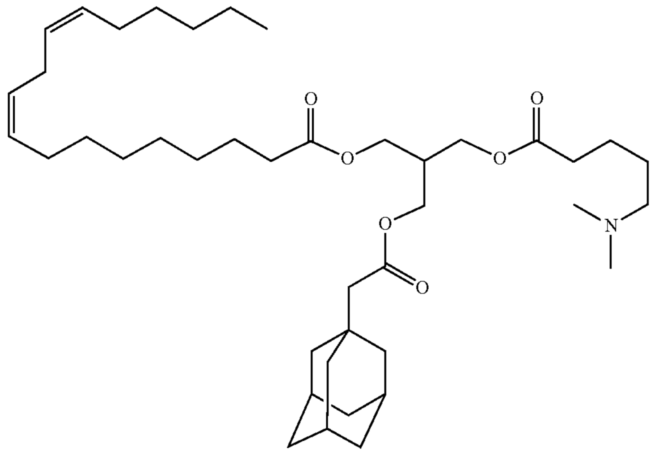
,
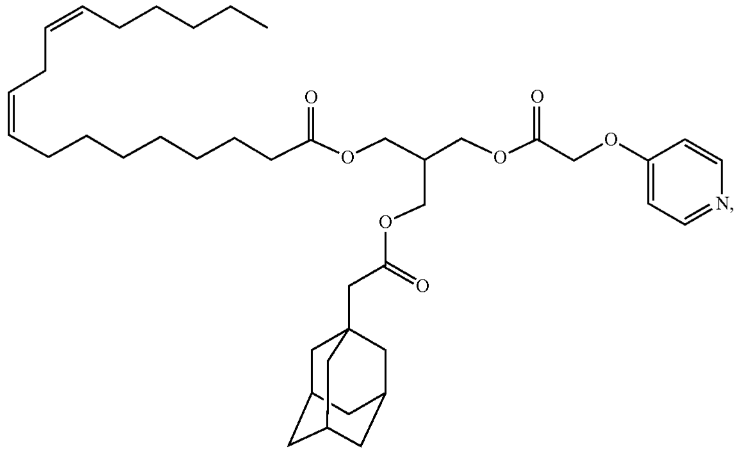
,
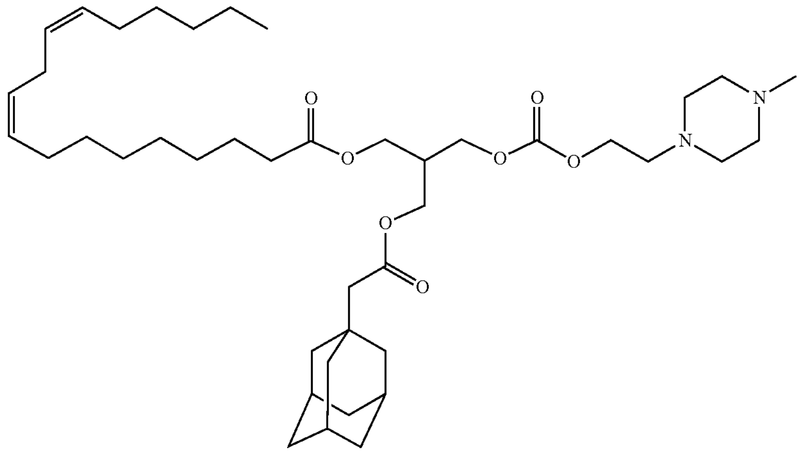
, -continued
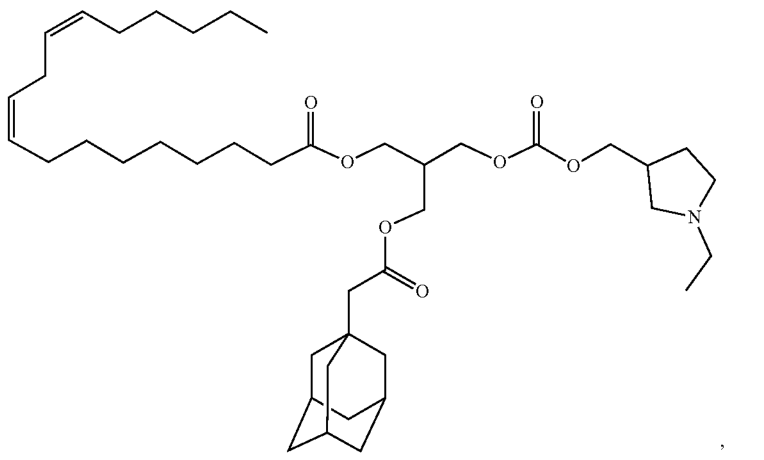
,
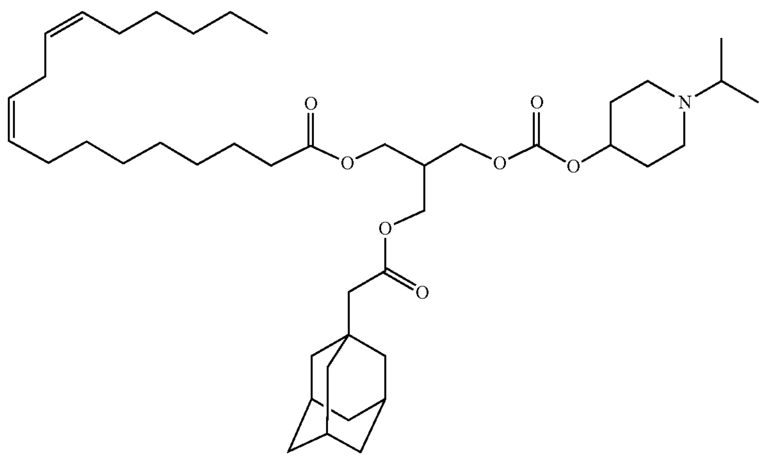
,
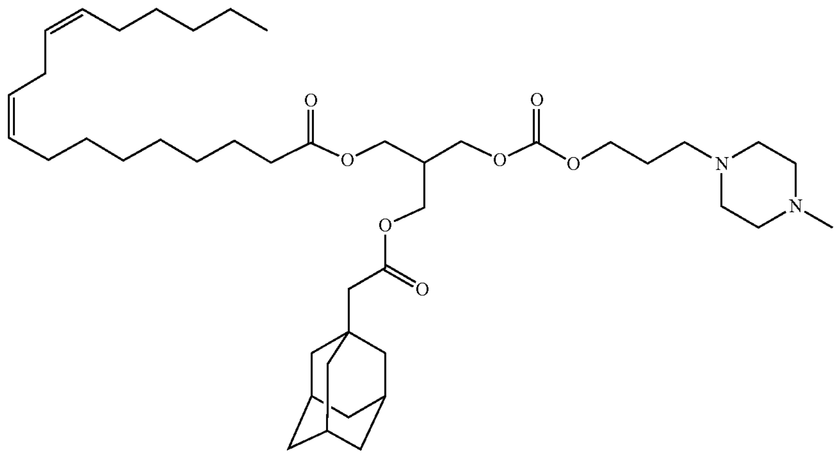
, -continued
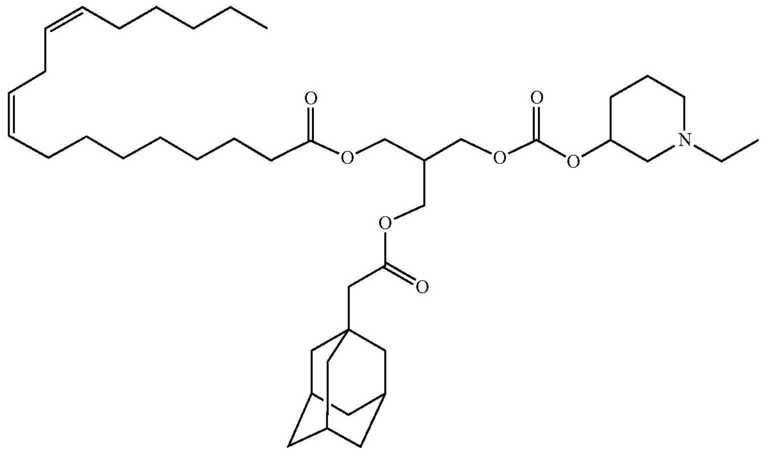
,
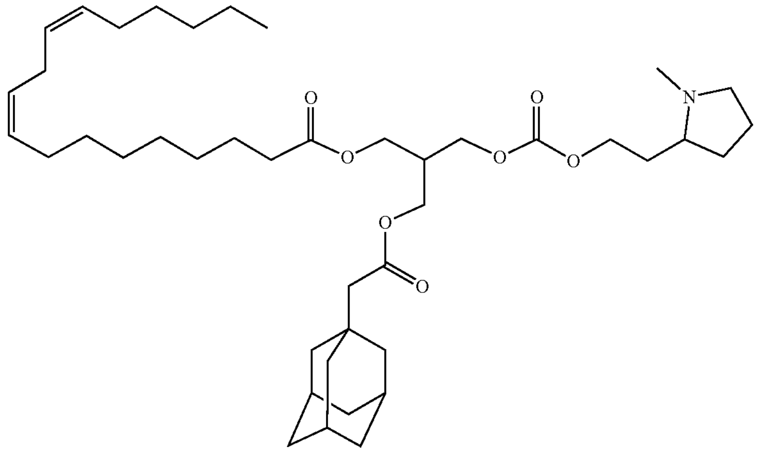
,
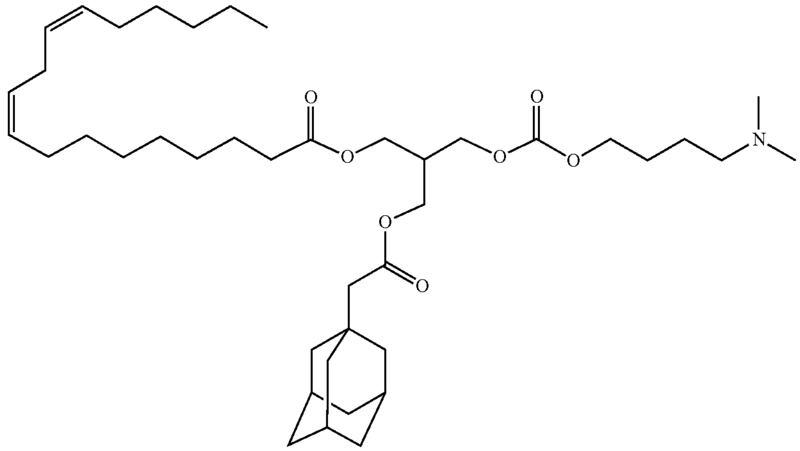
and -continued

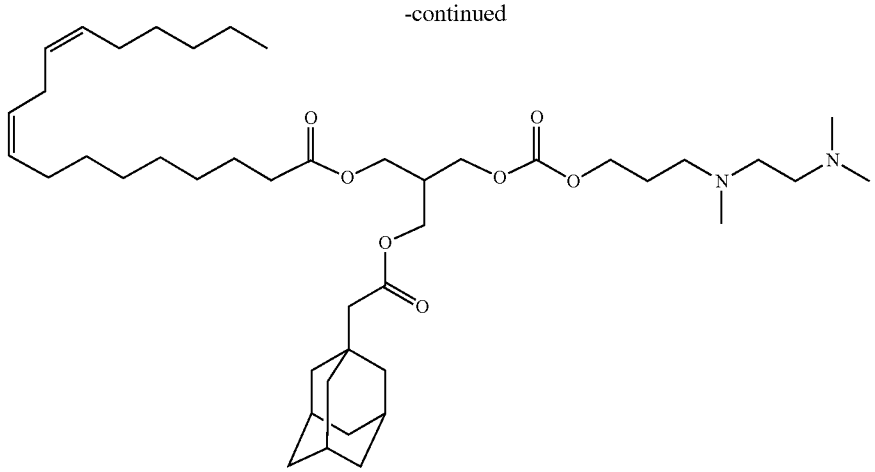

Additional embodiments relate to a compound of Formula (II):

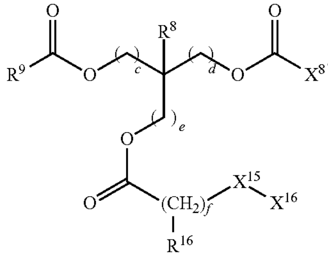

(II)

wherein:

$R^8$ is hydrogen or $C_1$-$C_6$ alkyl;

$R^9$ is $C_9$-$C_{20}$ alkyl optionally fused with 1-4 $C_3$-$C_6$ cycloalkyl groups, $C_9$-$C_{20}$ alkenyl with 1-3 units of unsaturation, or $(CH_2)_g$—$X^7$, wherein $X^{17}$ is optionally substituted $C_4$-$C_{12}$ cycloalkyl;

$X^8$ and $X^9$ are each independently absent or selected from —O—, $NR^{10}$, and

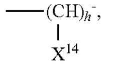

wherein $R^{10}$ is $C_1$-$C_6$ alkyl, and wherein $X^8$ and $X^9$ are not both —O— or $NR^{10}$;

$X^{10}$ and $X^{11}$ are each independently absent or selected from the group consisting of: 4- to 7-membered heterocyclyl optionally substituted with 1 or 2 $C_1$-$C_6$ alkyl groups, 5- to 6-membered heteroaryl optionally substituted with 1 or 2 $C_1$-$C_6$ alkyl groups, and —$NR^{11}$—, wherein $R^{11}$ is a hydrogen atom or $C_1$-$C_6$ alkyl;

$X^{12}$ is —$(CH_2)_i$—;

$X^{13}$ is hydrogen, $C_1$-$C_6$ alkyl, 5- to 6-membered heteroaryl optionally substituted with 1 or 2 $C_1$-$C_6$ alkyl groups, or —$NR^{12}R^{13}$, wherein $R^{12}$ and $R^{13}$ are each independently hydrogen or $C_1$-$C_6$ alkyl; or alternatively $R^{12}$ and $R^{13}$ join together with the nitrogen to which they are bound to form a 4- to 7-membered heterocyclyl optionally substituted with 1 or 2 $C_1$-$C_6$ alkyl groups, wherein the heterocyclyl optionally includes an additional heteroatom selected from oxygen, sulfur, and nitrogen;

$X^{14}$ is hydrogen or —$NR^{14}R^{15}$, wherein $R^{14}$ and $R^{15}$ are each independently hydrogen or $C_1$-$C_6$ alkyl; or alternatively $R^{14}$ and $R^{15}$ join together with the nitrogen to which they are bound to form a 4- to 7-membered heterocyclyl optionally substituted with 1 or 2 $C_1$-$C_6$ alkyl groups, wherein the heterocyclyl optionally includes an additional heteroatom selected from oxygen, sulfur, and nitrogen;

each of c, d, e, f, g, h, and i is independently an integer from 0-6;

at least one of $X^8$, $X^9$, $X^{10}$, $X^{11}$, and $X^{12}$ is present;

$R^{16}$ is hydrogen or optionally substituted $C_5$-$C_6$ aryl;

$X^{15}$ is optionally substituted $C_4$-$C_{12}$ cycloalkyl or optionally substituted $C_5$-$C_{10}$ aryl; and $X^{16}$ is hydrogen or optionally substituted $C_4$-$C_{12}$ cycloalkyl;

provided that when f is 1 and $R^9$ is

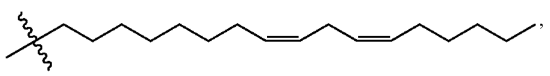 [SMILES: *CCCCCCC/C=C\C/C=C\CCCCC]

$X^{15}$ is not

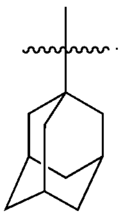 [SMILES: *C12CC3CC(CC(C3)C1)C2]

In some embodiments, $R^9$ is

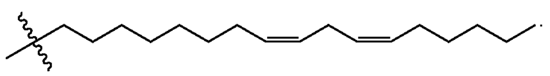 [SMILES: *CCCCCCC/C=C\C/C=C\CCCCC]

In some embodiments, $R^9$ is

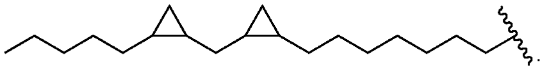 [SMILES: *CCCCCCCC1CC1CC1CC1CCCCC]

In some embodiments, i is 3, $X^8$, $X^9$, $X^{10}$, and $X^{11}$, are absent, $X^{13}$ is —$NR^{12}R^{13}$, and $R^{12}$ and $R^{13}$ are each methyl. In some embodiments, $X^8$, $X^9$, and $X^{11}$ are absent, i is 0, $X^{10}$ is

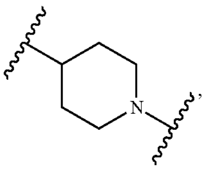 [SMILES: *C1CCN(*)CC1]

and $X^{13}$ is

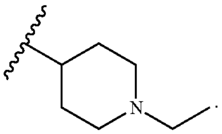 [SMILES: *C1CCN(CC)CC1]

In some embodiments, c, d, and e are each 1. In some embodiments, $R^9$ is

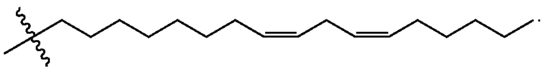 [SMILES: *CCCCCCC/C=C\C/C=C\CCCCC]

In some embodiments, $R^8$ is hydrogen. In some embodiments, $R^9$ and

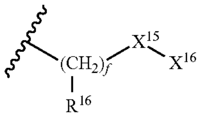

are each

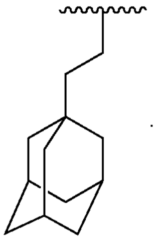 [SMILES: *CCC12CC3CC(CC(C3)C1)C2]

Further embodiments relate to a compound of Formula (IIa), (IIb), or (IIc):

(IIa)

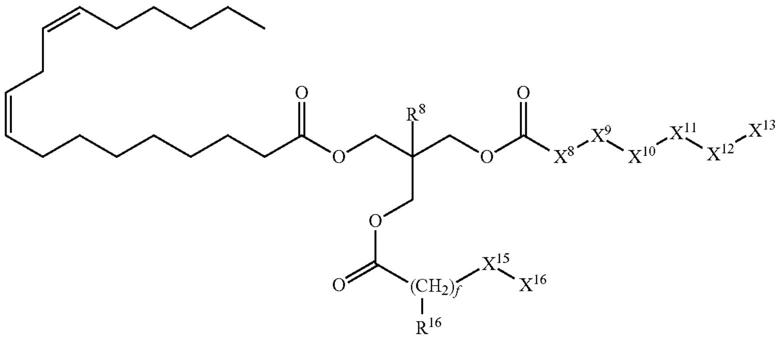

(IIb)

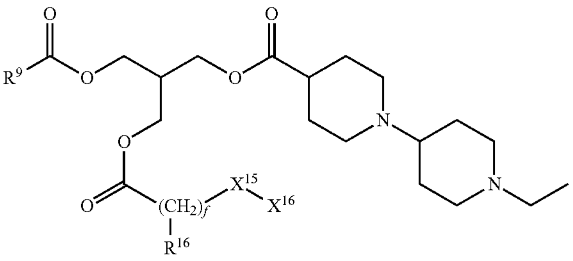

-continued
(IIc)
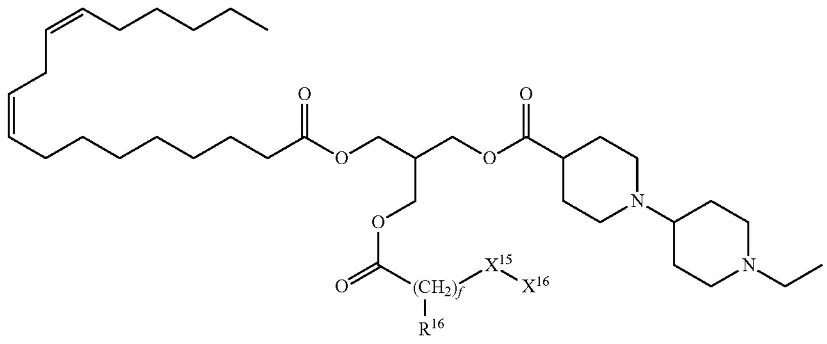
.
In some embodiments, the compound of Formula (II) is selected from the group consisting of:
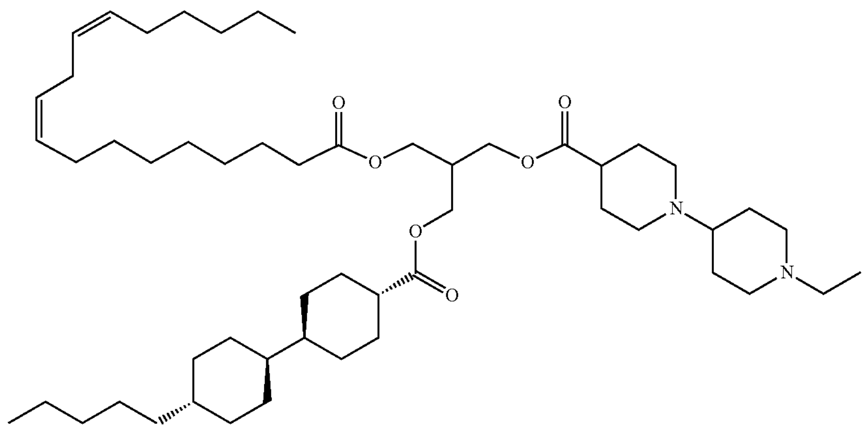
,
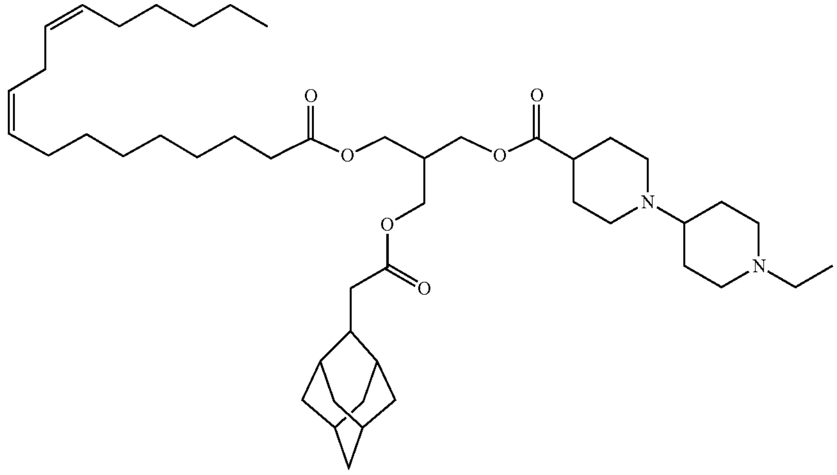
, -continued
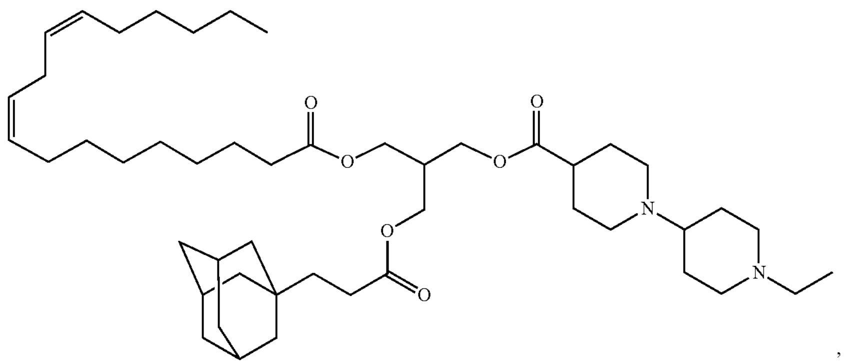
,
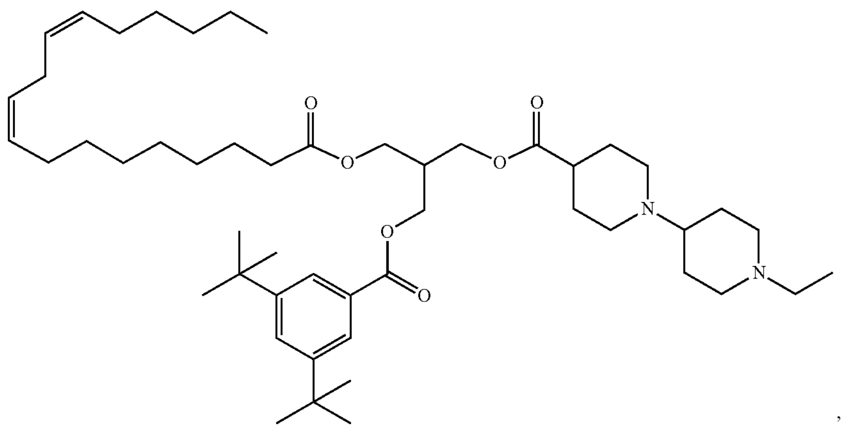
,
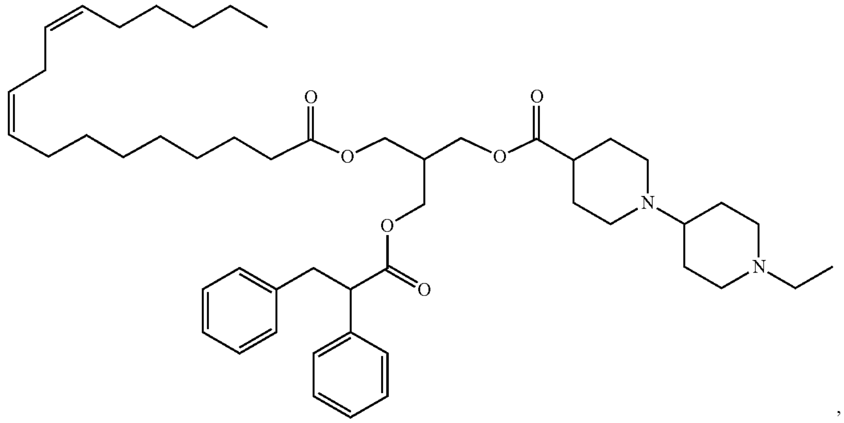
,
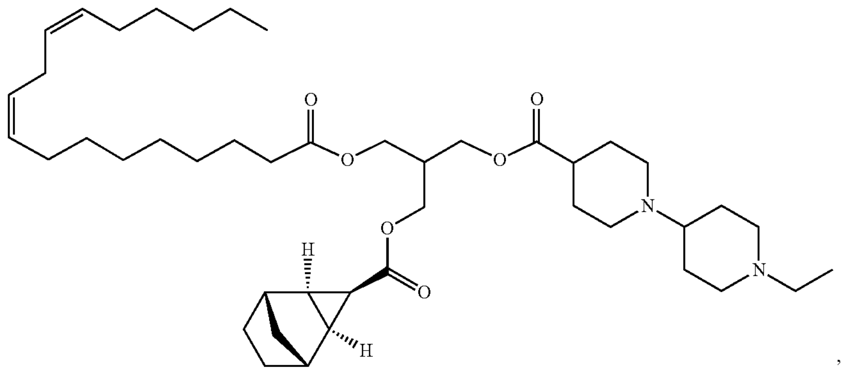
, -continued
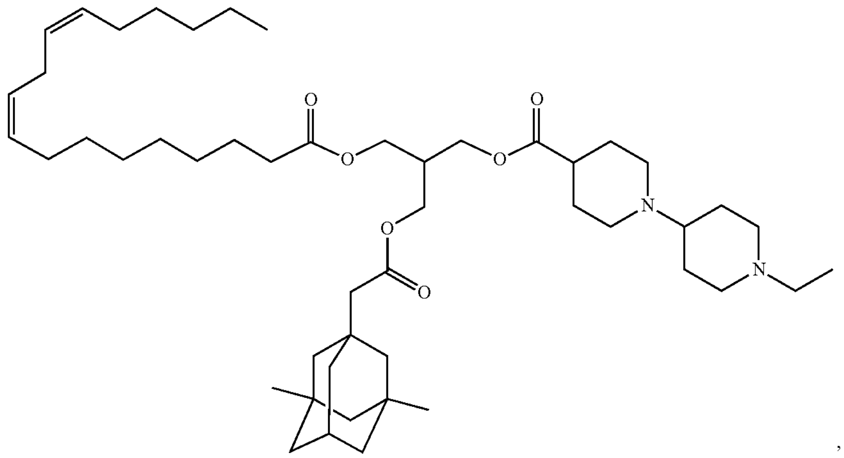
,
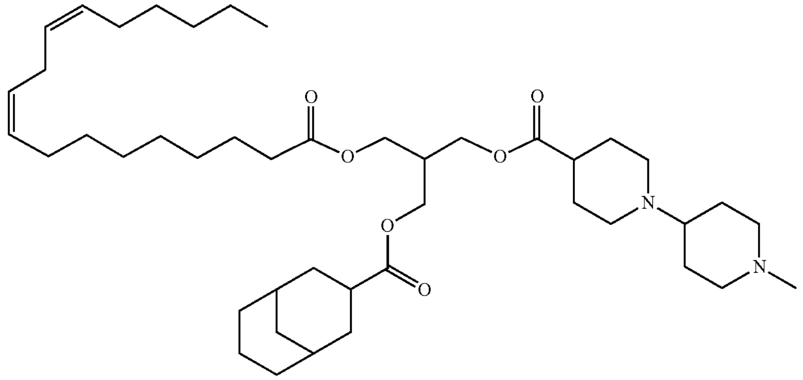
,
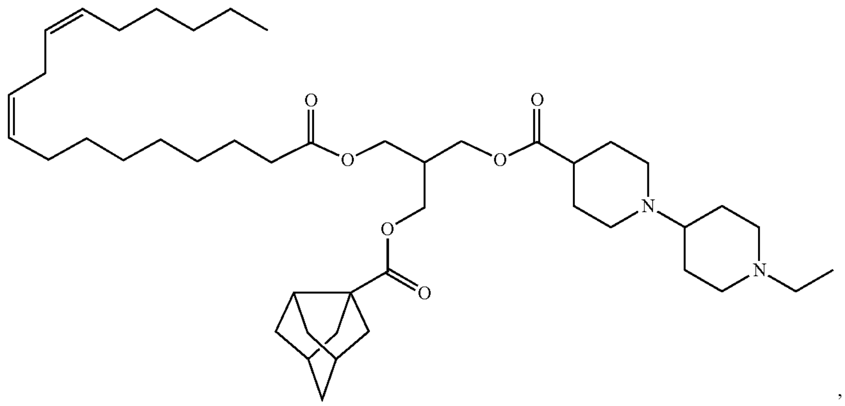
,
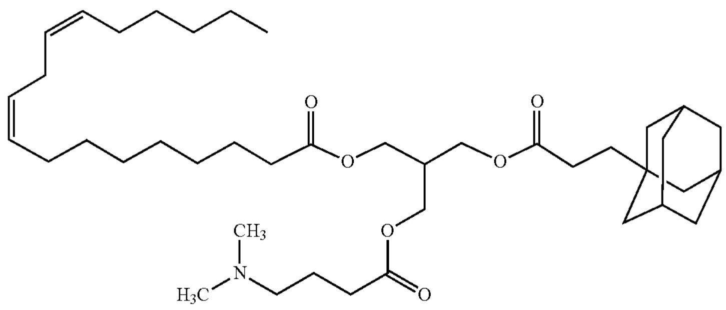
, -continued
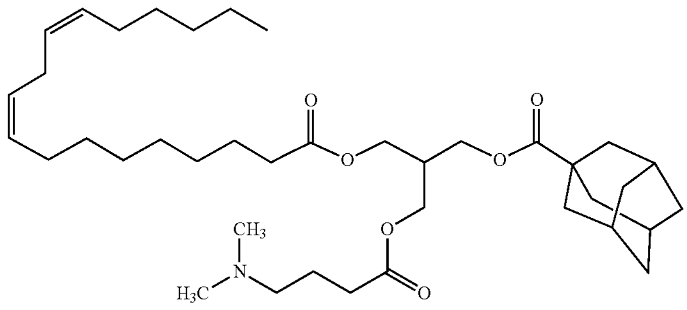
,
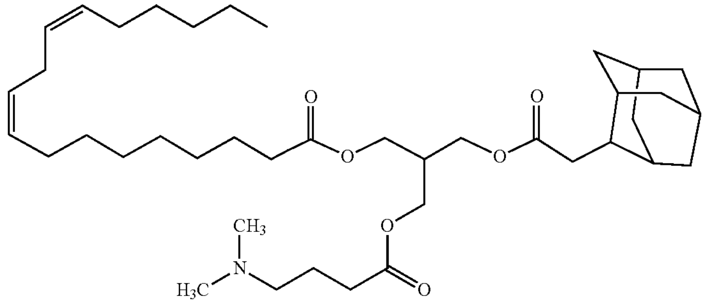
,
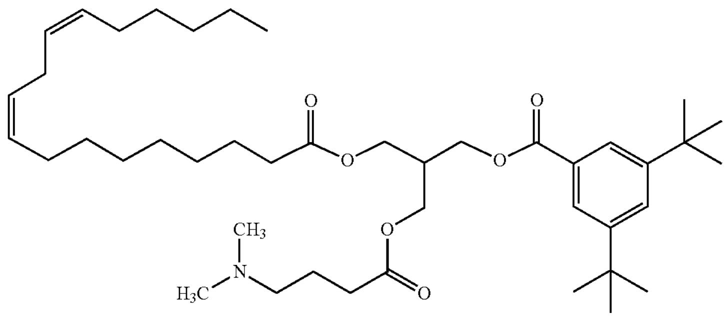
,
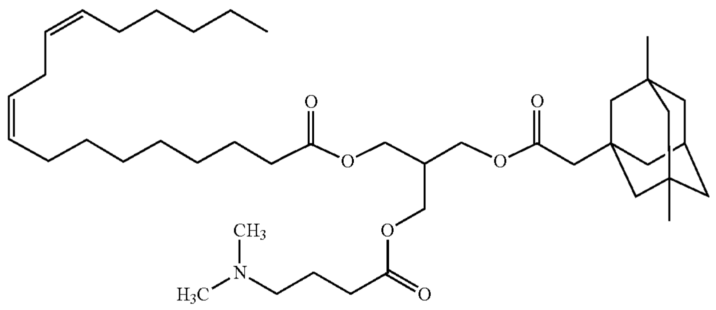
,
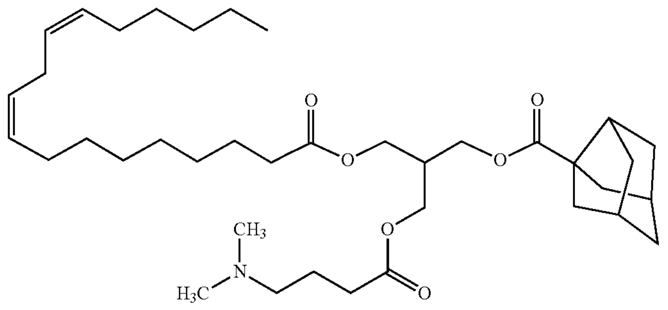
, -continued
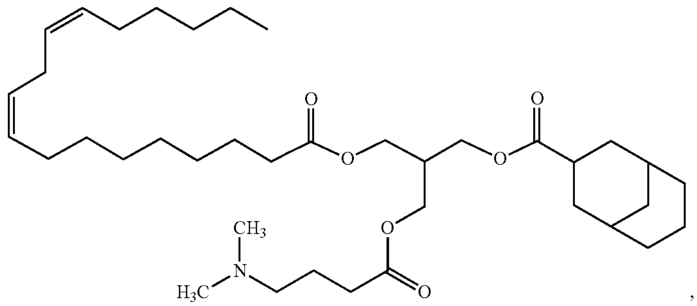
,
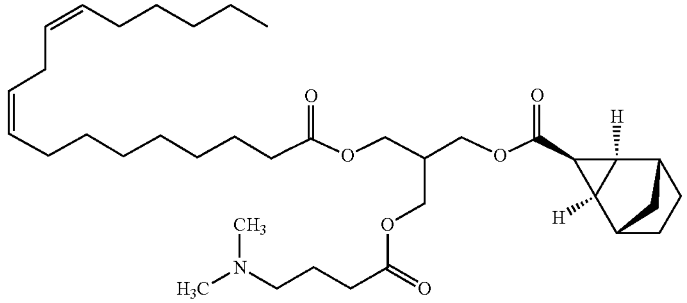
,
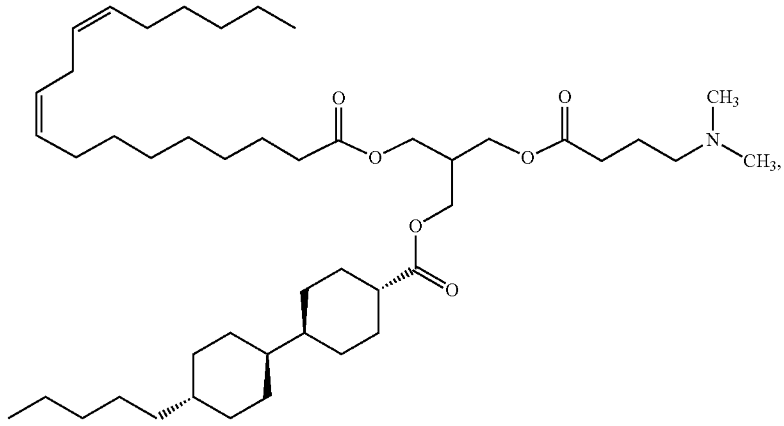
,
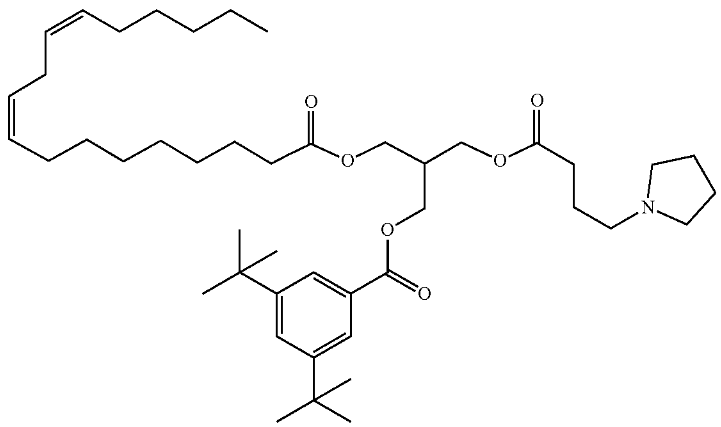
, -continued
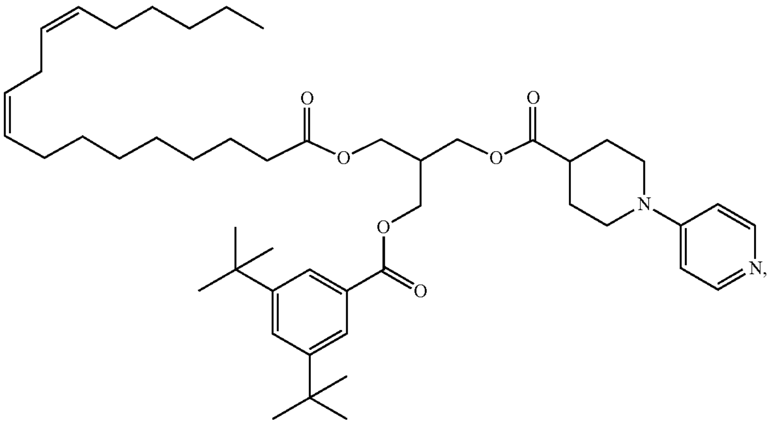
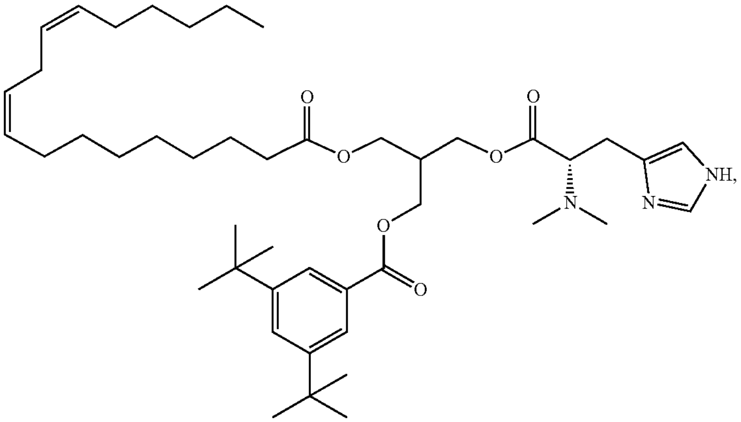
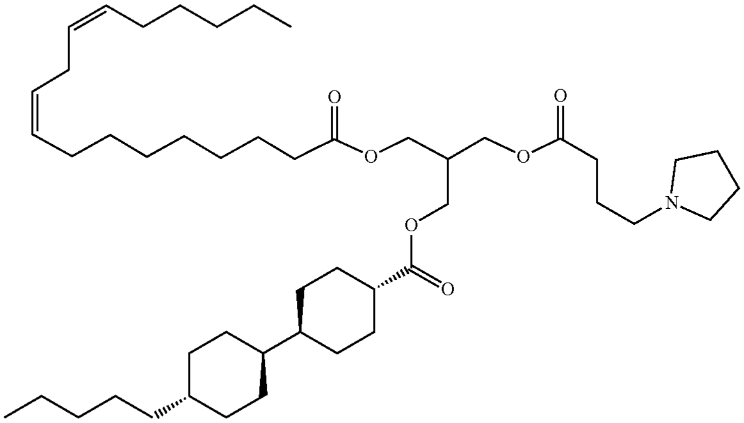
,
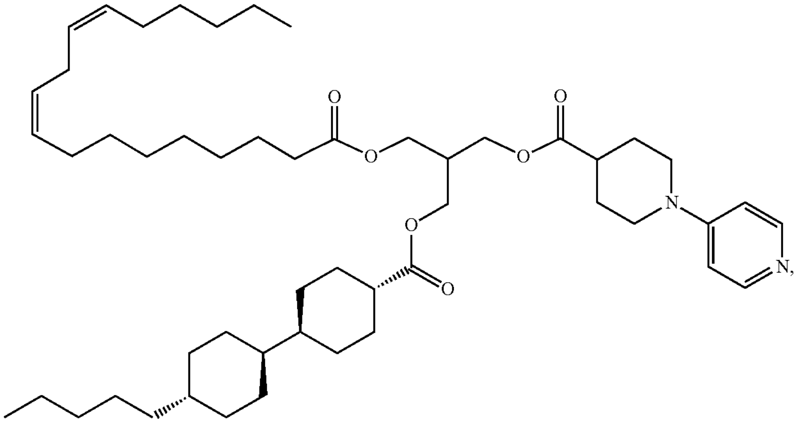

-continued
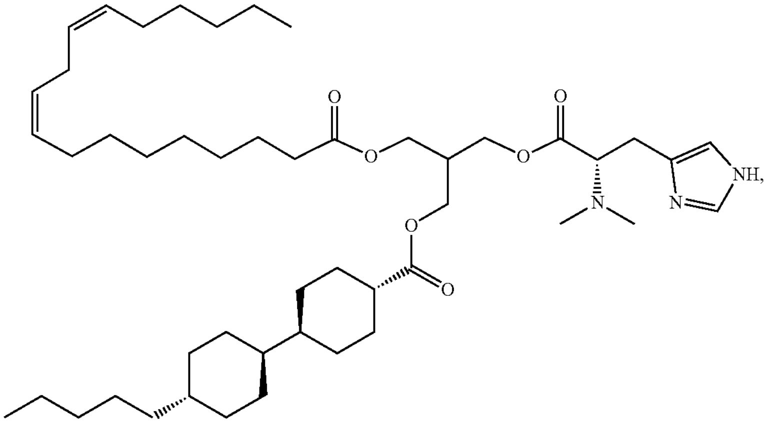
,
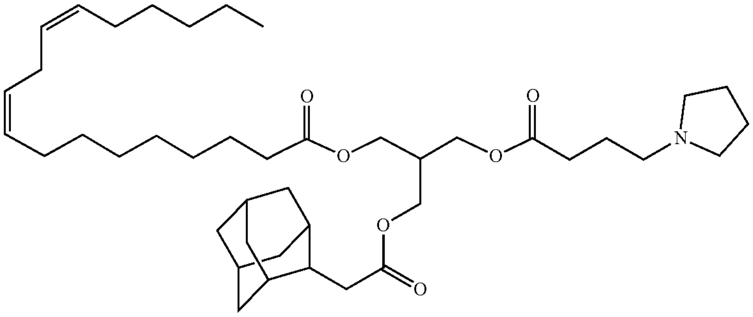
,
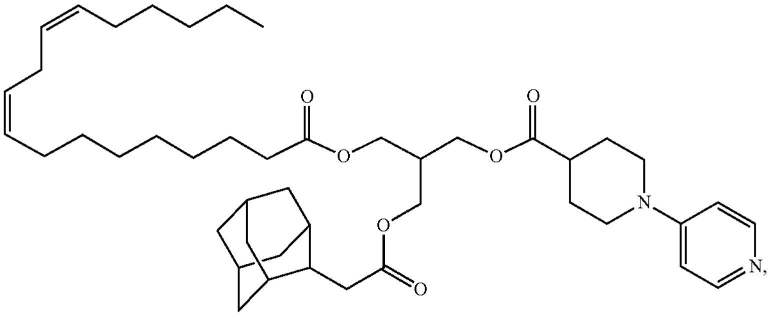
,
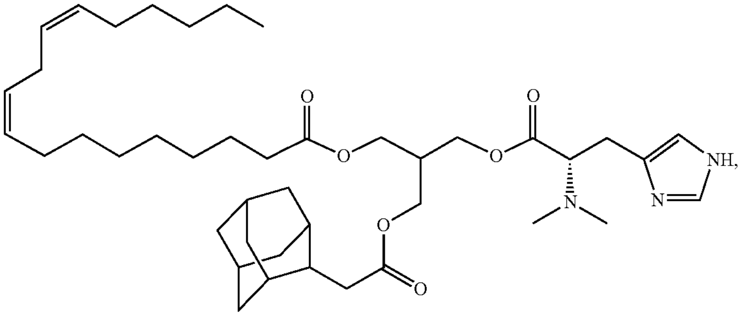
,
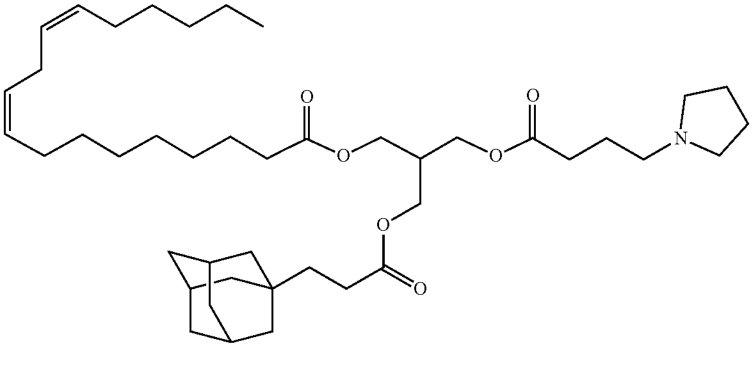
,

-continued
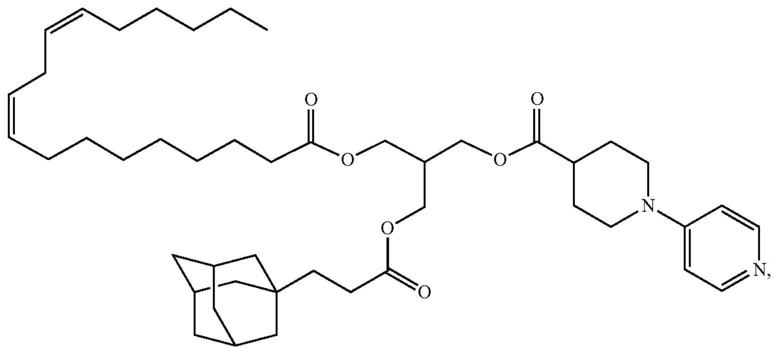
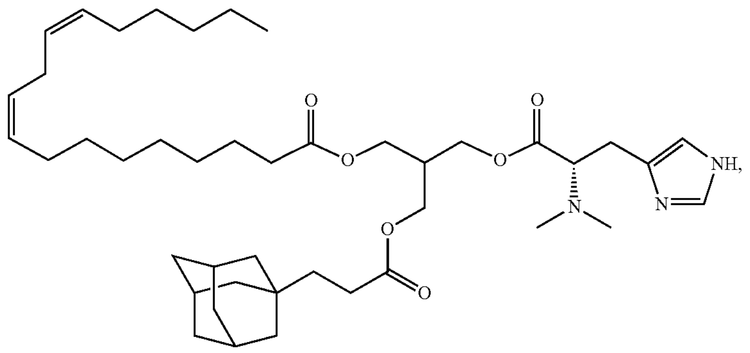
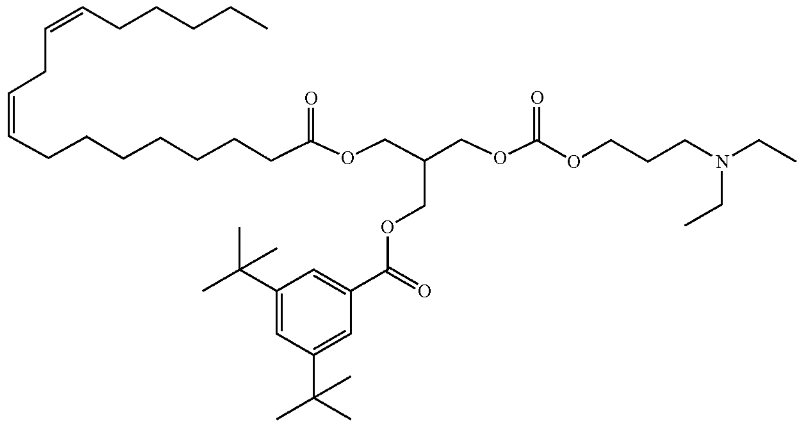
,
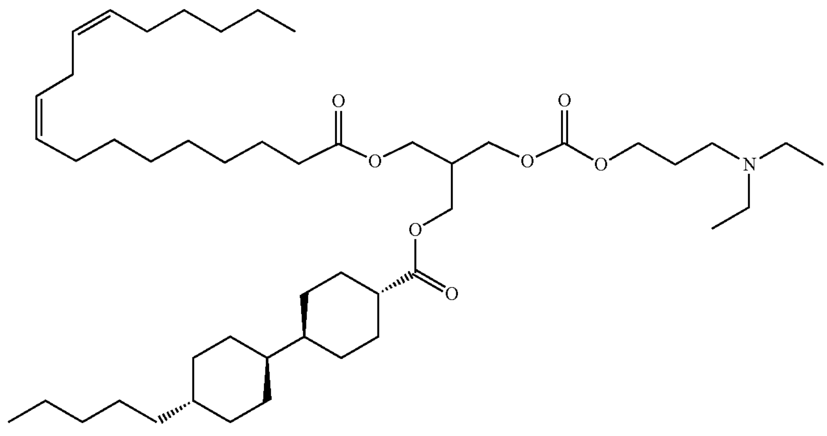
,

-continued

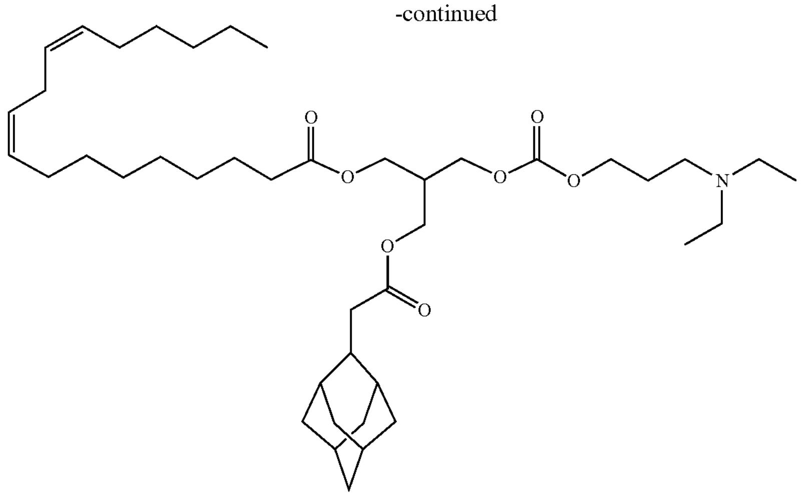

, and

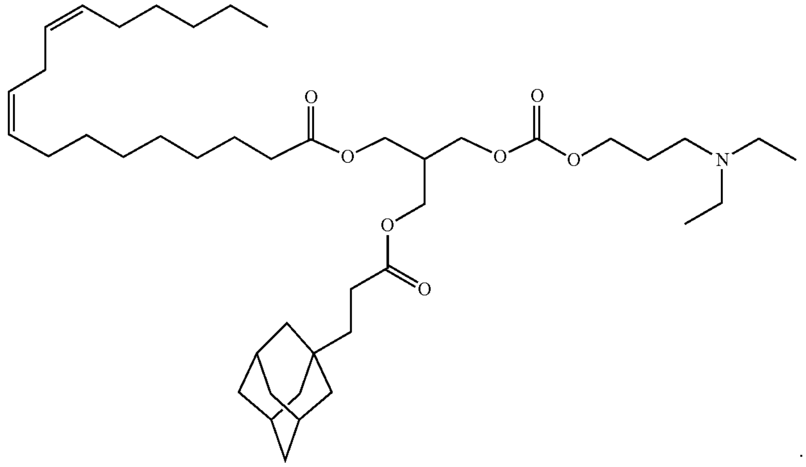

.

2. Ionizable Lipids

In one embodiment, the disclosed lipid nanoparticles include an ionizable lipid. The ionizable lipid typically includes an amine-containing group on the head group. In one embodiment, the ionizable lipid is a conformationally constrained ionizable lipid as described elsewhere herein. In some embodiments, the conformationally constrained lipid is present in the lipid nanoparticle at 35, 45, 50, or 65 mole percent, based on total moles of components of the lipid nanoparticle. In another embodiment, the conformationally constrained lipid is present at about 33 mol % to about 36 mol %, based on total moles of components of the lipid nanoparticle. In yet another embodiment, the conformationally constrained lipid is present at about 35 mol %, based on total moles of components of the lipid nanoparticle.

Additional embodiments relate to a lipid nanoparticle composition comprising: a conformationally constrained ionizable lipid; a phospholipid; a polyethylene glycol-lipid; a cholesterol; and optionally a nucleic acid. In some embodiments, the conformationally constrained ionizable lipid comprises a structure according to any one of Formulas (I), (Ia), (II), (IIa), (IIb), and (IIc). In some embodiments, the amount of conformationally constrained ionizable lipid is present in the range of about 35 to 65 mole percent, based on total moles of components of the lipid nanoparticle.

3. Sterols

In some embodiments, the disclosed lipid nanoparticles include one or more sterols. In one embodiment, the sterol is cholesterol, or a variant or derivative thereof. In some embodiments, the cholesterol is modified, for example oxidized. Unmodified cholesterol can be acted upon by enzymes to form variants that are side-chain or ring oxidized. The cholesterol can be oxidized on the beta-ring structure or on the hydrocarbon tail structure. Exemplary cholesterols that are considered for use in the disclosed lipid nanoparticles include but are not limited to 25-hydroxycholesterol (25-OH), 20α-hydroxycholesterol (20α-OH), 27-hydroxycholesterol, 6-keto-5α-hydroxycholesterol, 7-ketocholesterol, 7β-hydroxycholesterol, 7α-hydroxycholesterol, 7β-25-dihydroxycholesterol, beta-sitosterol, stigmasterol, brassicasterol, campesterol, or combinations thereof. In one embodiment, side-chain oxidized cholesterol can enhance cargo delivery relative to other cholesterol variants. In one embodiment, the cholesterol is an unmodified cholesterol.

4. PEG-Lipids

In some embodiments, the disclosed nanoparticle compositions also include one or more PEG or PEG-modified lipids. Such lipids may be alternately referred to as PEGylated lipids or PEG-lipids. Inclusion of a PEGylating lipid can be used to enhance lipid nanoparticle colloidal stability in vitro and circulation time in vivo. In some embodiments, the PEGylation is reversible in that the PEG moiety is gradually released in blood circulation. Exemplary PEG-lipids include but are not limited to PEG conjugated to saturated or unsaturated alkyl chains having a length of $C_6$-$C_{20}$. PEG-modified phosphatidylethanolamines, PEG-modified phosphatidic acids, PEG-modified ceramides (PEG-CER), PEG-modified dialkylamines, PEG-modified diacylglycerols (PEG-DAG), PEG-modified dialkylglycerols, and mixtures thereof. For example, a PEG lipid may be PEG-c-DOMG, PEG-DMG, PEG-DLPE, PEG-DMPE, PEG-DPPE, PEG-DSG or a PEG-DSPE lipid.

5. Phospholipids

The phospholipid component of the nanoparticle may include one or more phospholipids, such as one or more (poly)unsaturated lipids. The phospholipids may assemble into one or more lipid bilayers. In some embodiments, the phospholipids may include a phospholipid moiety and one or more fatty acid moieties.

In some embodiments, the phospholipid moiety includes but is not limited to phosphatidyl choline, phosphatidyl ethanolamine, phosphatidyl glycerol, phosphatidyl serine, phosphatidic acid, 2-lysophosphatidyl choline, and sphingomyelin. In some embodiments, the fatty acid moiety includes but is not limited to lauric acid, myristic acid, myristoleic acid, palmitic acid, palmitoleic acid, stearic acid, oleic acid, linoleic acid, alpha-linolenic acid, erucic acid, phytanic acid, arachidic acid, arachidonic acid, eicosapentaenoic acid, behenic acid, docosapentaenoic acid, and docosahexaenoic acid. Non-natural species including natural species with modifications and substitutions including branching, oxidation, cyclization, and alkynes are also contemplated. For example, a phospholipid may be functionalized with or cross-linked to one or more alkynes (e.g., an alkenyl group in which one or more double bonds is replaced with a triple bond). Under appropriate reaction conditions, an alkyne group may undergo a copper-catalyzed cycloaddition upon exposure to an azide. Such reactions may be useful in functionalizing a lipid bilayer of a nanoparticle composition to facilitate membrane permeation or cellular recognition or in conjugating a nanoparticle composition to a useful component such as a targeting or imaging moiety (e.g., a dye).

Exemplary phospholipids include but are not limited to 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-0-octadecenyl-sn-glycero-3-phosphocholine (18:0 Diether PC), 1-oleoyl-2-cholesterylhemisuccinoy 1-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoylphosphatidylglycerol (DPPG), palmitoyloleoylphosphatidylethanolamine (POPE), distearoyl-phosphatidyl-ethanolamine (DSPE), dipalmitoyl phosphatidyl ethanolamine (DPPE), dimyristoylphosphoethanolamine (DMPE), 1-stearoyl-2-oleoyl-phosphatidy ethanolamine (SOPE), 1-stearoyl-2-oleoyl-phosphatidyicholine (SOPC), sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine (LPE). In a preferred embodiment, the phospholipid is DSPC. In another embodiment, the phospholipid is DMPC.

E. Cargo

In one embodiment, the disclosed lipid nanoparticle compositions include a therapeutic or prophylactic agent to a subject. In some embodiments, the therapeutic or prophylactic agent is encapsulated by the lipid nanoparticle. In one embodiment, the lipid nanoparticles are loaded with one or more nucleic acids.

Representative nucleic acids include but are not limited to deoxyribonucleic acid (DNA), ribonucleic acid (RNA) RNA, DNA, single-stranded RNA, single-stranded DNA, double-stranded RNA, double stranded DNA, triple-stranded DNA, siRNA, shRNA, sgRNA, mRNA, miRNA, and antisense DNA.

CRISPR (Clustered Regularly Interspaced Short Palindromic Repeats) based gene editing requires two components: a guide-RNA and a CRISPR-associated endonuclease protein (Cas). The guide RNA directs the Cas nuclease to the specific target DNA sequence. Cas then creates a double-strand break in the DNA at that site. In one embodiment, the disclosed lipid nanoparticles can be used to carry the components required for CRISPR-based gene editing. In one lipid nanoparticle, the nucleic acid cargo is a guide-RNA. In such an embodiment, a second lipid nanoparticle can contain nucleic acid cargo that encodes an RNA-guided endonuclease. The two lipid nanoparticles can be administered together. Exemplary RNA-guided endonucleases include but are not limited to Cas9, CasX, CasY, Cas13, or Cpf1.

In one embodiment, the cargo is siRNA. Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, et al. (2001) Nature, 411:494 498) (Ui-Tei, et al. (2000) FEBS Lett 479:79-82.

In one embodiment, the lipid nanoparticle contains less than 1.0 mg/kg inhibitory nucleic acid. The nanoparticle can contain 1.0, 0.9, 0.8, 0.7, 0.6, or 0.5 mg/kg inhibitory nucleic acid. In another embodiment, the lipid nanoparticle contains 0.5 mg/kg inhibitory nucleic acid. This is an advantage over current technology in which nanoparticles require high doses of nucleic acid (>1 mg/kg) to achieve gene silencing, doses of which are not approve for human delivery. The disclosed technology can achieve gene silencing using 0.5 mg/kg inhibitory nucleic acid in a lipid nanoparticle that does not include targeting ligands.

In some embodiments, the nucleic acids, including but not limited to oligonucleotides, are modified or include one more modified nucleotides to increase stability, half-life, and nuclease sensitivity. To limit nuclease sensitivity, the native phosphodiester oligodeoxyribonucleotide, native phosphodiester oligoribonucleotide, ribonucleotide polymers, and deoxyribonucleotide polymers can include one more different modifications. Exemplary modifications, include but are not limited to phosphorothioate (PS) bonds, 2"-O Methyl (2'OMe), 2' Fluoro bases, inverted dT and ddT, phosphorylation of the 3'end of oligonucleotides, locked nucleic acids, and including a phosphoramidite C3 Spacer.

The phosphorothioate bond substitutes a sulfur atom for a non-bridging oxygen in the phosphate backbone of an oligonucleotide. Approximately 50% of the time (due to the 2 resulting stereoisomers that can form), PS modification renders the internucleotide linkage more resistant to nuclease degradation. In some embodiments, the nucleic acids include one or more PS bonds, for example at least 3 PS bonds at the 5' and 3' oligonucleotide ends to inhibit exonuclease degradation. Some nucleic acid include PS bonds throughout the entire oligonucleotide to help reduce attack by endonucleases as well.

A naturally occurring post-transcriptional modification of RNA, 2'OMe is found in tRNA and other small RNAs. In some embodiments, the nucleic acids or oligonucleotides are directly synthesized to contain 2'OMe. This modification increases the Tm of RNA:RNA duplexes, but results in only small changes in RNA:DNA stability. It prevents attack by single-stranded endonucleases, but not exonuclease digestion. In some embodiment, these nucleic acids or oligonucleotides are also end blocked. DNA oligonucleotides that include this modification are typically 5- to 10-fold less susceptible to DNases than unmodified DNA. The 2'OMe modification is commonly used in antisense oligonucleotides as a means to increase stability and binding affinity to target transcripts.

2'-Fluoro bases have a fluorine-modified ribose which increases binding affinity (Tm) and also confers some relative nuclease resistance compared to native RNA. In some embodiments, the nucleic acids or oligonucleotides include 2' fluoro bases in conjunction with PS-modified bonds.

Inverted dT can be incorporated at the 3' end of an oligonucleotide, leading to a 3'-3' linkage that will inhibit degradation by 3' exonucleases and extension by DNA polymerases. In addition, placing an inverted, 2',3' dideoxy-dT base (5' Inverted ddT) at the 5' end of an oligonucleotide prevents spurious ligations and may protect against some forms of enzymatic degradation.

Some embodiments provide nucleic acids or oligonucleotides that include a phosphoramidite C3 Spacer. The phosphoramidite C3 Spacer can be incorporated internally, or at either end of an oligo to introduce a long hydrophilic spacer arm for the attachment of fluorophores or other pendent groups. The C3 spacer also can be used to inhibit degradation by 3' exonucleases.

In some embodiments, the nucleic acids or oligonucleotides include locked nucleic acids. Locked nucleic acids include modified RNA nucleotides in which the 2'-O and 4'-C atoms of the ribose are joined through a methylene bridge. This additional bridge limits the flexibility normally associated with the ring, essentially locking the structure into a rigid conformation. LNAs can be inserted into both RNA and DNA oligonucleotides.

Other types of cargo that can be delivered via the disclosed nanoparticles include but are not limited to chemotherapeutic agents, cytotoxic agents, radioactive ions, small molecules, proteins, polynucleotides, and nucleic acids.

Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

Some embodiments relate to a method of delivering a nucleic acid to a subject in need thereof, comprising administering to the subject a lipid nanoparticle composition as described herein. In some embodiments, the nucleic acid is siRNA, miRNA, anti-sense oligonucleotide, or immunostimulatory oligonucleotide.

B. Exemplary Lipid Nanoparticle Formulations

In one embodiment, the lipid nanoparticle formulation includes about 30 mol % to about 70 mol % conformationally constrained ionizable lipid, about 5 mol % to about 25 mol % phospholipid, about 25 mol % to about 45 mol % cholesterol, and about 0 mol % to about 5 mol % PEG-lipid. In another embodiment, the lipid nanoparticle formulation include about 35 mol % conformationally constrained ionizable lipid, about 16 mol % phospholipid, about 46.5 mol % cholesterol, and about 2.5 mol % PEG-lipid. In another embodiment, the lipid nanoparticle formulation include about 50 mol % conformationally constrained ionizable lipid, about 10 mol % phospholipid, about 38.5 mol % cholesterol, and about 1.5 mol % PEG-lipid.

One embodiment provides a lipid nanoparticle formulation including about 33 mol % to about 36 mol % conformationally constrained ionizable lipid with an adamantane tail, about 15 mol % to about 17 mol % 1-2-distearoyl-sn-glycero-3-phosphocholine, about 2 mol % to about 3 mol % $C_{14}PEG_{2000}$, and about 45 mol % to about 47 mol % cholesterol, based on the total moles of these four ingredients.

Another embodiment provides a lipid nanoparticle formulation including 35 mol % conformationally constrained ionizable lipid with an adamantane tail, 16 mol % 1-2-distearoyl-sn-glycero-3-phosphocholine, and 2.5 mol % $C_{14}PEG_{2000}$, 46 mol % cholesterol, based on the total moles of these four ingredients.

Another embodiment provides a lipid nanoparticle formulation in which the mass ratio of (ionizable lipid, cholesterol, lipid-PEG, and phospholipid):siRNA is between about 2:1 and 50:1.

In yet another embodiment the lipid nanoparticle formulation includes 3-[(1-Adamantanyl)acetoxy]-2-{[3-(diethylamino)propoxycarbonyloxy]methyl}propyl (9Z,12Z)-9,12-octadecadienoate, DSPC, a polyethylene glycol-lipid, cholesterol, and an inhibitory nucleic acid.

One embodiment provides a lipid nanoparticles composition containing 3-[(1-Adamantanyl)acetoxy]-2-{[3-(diethylamino)propoxycarbonyloxy]methyl}propyl (9Z,12Z)-9,12-octadecadienoate, DSPC, a polyethylene glycol-lipid, cholesterol, and sgRNA specific for a gene. Another embodiment provides a lipid nanoparticle including 3-[(1-Adamantanyl)acetoxy]-2-{[3-(diethylamino)propoxycarbonyloxy]methyl}propyl (9Z,12Z)-9,12-octadecadienoate, DSPC, a polyethylene glycol-lipid, cholesterol, and mRNA encoding an RNA guided DNA endonuclease.

C. Pharmaceutical Compositions

Pharmaceutical compositions including the disclosed lipid nanoparticles are provided. The lipid nanoparticle compositions can be formulated in whole or in part as pharmaceutical compositions. Pharmaceutical compositions may include one or more nanoparticle compositions. For example, a pharmaceutical composition may include one or more nanoparticle compositions including one or more different therapeutic and/or prophylactics including but not limited to one or more nucleic acids of different types or encode different agents. In some embodiments the pharmaceutical compositions include one or more pharmaceutically acceptable excipients or accessory ingredients including but not limited to a pharmaceutically acceptable carrier.

Pharmaceutical compositions containing the nanoparticles can be formulated for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the nanoparticle compositions disclosed herein are administered to a subject in a therapeutically effective amount. As used herein the term “effective amount” or “therapeutically effective amount” means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed nanoparticles, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed nanoparticles, generally dosage levels of 0.001 mg to 5 mg of nucleic acid per kg of body weight daily are administered to mammals. More specifically, a preferential dose for the disclosed nanoparticles is 0.01 mg/kg to 0.25 mg/kg. For the disclosed nanoparticles, generally dosage levels of 0.2 mg to 100 mg of the four components (ionizable lipid, cholesterol, PEG-lipid, and phospholipid)/kg of body weight are administered to mammals. More specifically, a preferential dose of the disclosed nanoparticles is 0.05 mg/kg to 0.5 mg/kg of the four components/kg of body weight.

In certain embodiments, the lipid nanoparticle composition is administered locally, for example by injection directly into a site to be treated. Typically, the injection causes an increased localized concentration of the lipid nanoparticle composition which is greater than that which can be achieved by systemic administration. The lipid nanoparticle compositions can be combined with a matrix as described above to assist in creating an increased localized concentration of the polypeptide compositions by reducing the passive diffusion of the polypeptides out of the site to be treated.

1. Formulations for Parenteral Administration

In some embodiments, the nanoparticle compositions disclosed herein, including those containing lipid nanoparticles, are administered in an aqueous solution, by parenteral injection. The formulation may also be in the form of a suspension or emulsion. In general, pharmaceutical compositions are provided including effective amounts of a lipid nanoparticle, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Controlled Delivery Polymeric Matrices

The lipid nanoparticles disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of lipid nanoparticles, although in some embodiments biodegradable matrices are preferred. These may be natural or synthetic polymers, although synthetic polymers are preferred in some embodiments due to the better characterization of degradation and release profiles. The polymer is selected based on the period over which release is desired. In some cases, linear release may be most useful, although in others a pulse release or “bulk release” may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release, 5:13-22 (1987); Mathiowitz, et al., Reactive Polymers, 6:275-283 (1987); and Mathiowitz, et al., J. Appl. Polymer Sci., 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

D. Methods of Manufacturing Lipid Nanoparticles

Methods of manufacturing lipid nanoparticles are known in the art. In one embodiment, the disclosed lipid nanoparticles are manufactured using microfluidics. For exemplary methods of using microfluidics to form lipid nanoparticles, see Leung, A. K. K, et al., *J. Phys Chem,* 116:18440-18450 (2012), Chen, D., et al., *J Am Chem Soc,* 134:6947-6951 (2012), and Belliveau, N. M., et al., *Molecular Therapy—Nucleic Acids,* 1: e37 (2012). Briefly, the cargo, such as an oligonucleotide or siRNA, is prepared in one buffer. The other lipid nanoparticle components (ionizable lipid, PEG-lipid, cholesterol, and DSPC) are prepared in another buffer. A syringe pump introduces the two solutions into a microfluidic device. The two solutions come into contact within the microfluidic device to form lipid nanoparticles encapsulating the cargo.

Methods of screening the disclosed lipid nanoparticles are discussed in International Patent Application No. PCT/US/2018/058171, which is incorporated by reference in its entirety. The screening methods characterizes vehicle delivery formulations to identify formulations with a desired tropism and that deliver functional cargo to the cytoplasm of specific cells. The screening method uses a reporter that has a functionality that can be detected when delivered to the cell. Detecting the function of the reporter in the cell indicates that the formulation of the delivery vehicle will deliver functional cargo to the cell. A chemical composition identifier is included in each different delivery vehicle formulation to keep track of the chemical composition specific for each different delivery vehicle formulation. In one embodiment, the chemical composition identifier is a nucleic acid barcode. The sequence of the nucleic acid bar code is paired to the chemical components used to formulate the delivery vehicle in which it is loaded so that when the nucleic acid bar code is sequenced, the chemical composition of the delivery vehicle that delivered the barcode is identified. Representative reporters include, but are not limited to siRNA, mRNA, nuclease protein, nuclease mRNA, small molecules, epigenetic modifiers, and phenotypic modifiers.

E. Methods of Use

Methods of using the disclosed lipid nanoparticles to deliver cargo, for example nucleic acids, to specific cells or organs are disclosed herein. In some embodiments, the nanoparticles deliver therapeutic or prophylactic agents to specific cells or organs in a subject in need thereof in the absence of a targeting ligand. In another embodiment, the disclosed lipid nanoparticles are useful to treat or prevent diseases in a subject in need thereof.

In some embodiments, the disclosed nanoparticles are delivered directly to the subject. In other embodiments, the lipid nanoparticles are contacted with cells ex vivo, and the treated cells are administered to the subject. The cells can be autologous cells, for example immune cells including but not limited to T cells or cells that differentiate into T cells. In some embodiments, the disclosed lipid nanoparticles may be used as vehicles for adoptive cell transfer.

1. Methods of Delivering Cargo to Cells

Methods of delivering a therapeutic and/or prophylactic nucleic acids to a subject in need thereof are provided herein.

In some embodiments, the disclosed lipid nanoparticle composition targets a particular type or class of cells (e.g., cells of a particular organ or system thereof). For example, a nanoparticle composition including a therapeutic and/or prophylactic of interest may be specifically delivered to immune cells in the subject. Exemplary immune cells include but are not limited to CD8+, CD4+, or CD8+CD4+ cells. In other embodiments, the lipid nanoparticles can be formulated to be delivered in the absence of a targeting ligand to a mammalian liver immune cells, spleen T cells, or lung endothelial cells. Specific delivery to a particular class or type of cells indicates that a higher proportion of lipid nanoparticles are delivered to target type or class of cells. In some embodiments, specific delivery may result in a greater than 2 fold, 5 fold, 10 fold, 15 fold, or 20 fold increase in the amount of therapeutic and/or prophylactic per 1 g of tissue of the targeted destination.

2. Methods of Gene Regulation

Methods of using the disclosed lipid nanoparticles for gene regulation are provided herein. In one embodiment, the lipid nanoparticles can be used for reducing gene expression in a target cell in a subject in need thereof. The lipid nanoparticle can deliver the inhibitory nucleic acid to the target cell in the subject without a targeting ligand. The inhibitory nucleic acid can be siRNA.

Another embodiment provides methods of using the disclosed lipid nanoparticles for editing a gene in a cell in a subject in need thereof.

In one embodiment, the cell that is targeted for gene regulation is an immune cell. The immune cell can be a T cell, such as CD8+ T cell, CD4+ T cell, or T regulatory cell. Other exemplary immune cells for gene editing include but are not limited to macrophages, dendritic cells, B cells or natural killer cells.

Exemplary genes that can be targeted include but are not limited to T cell receptors, B cell receptors, CTLA4, PD1, FOXO1, FOXO3, AKTs, CCR5, CXCR4, LAG3, TIM3, Killer immunoglobulin-like receptors, GITR, BTLA, LFA-4, T4, LFA-1, Bp35, CD27L receptor, TNFRSF8, TNFRSF5, CD47, CD52, ICAM-1, LFA-3, L-selectin, Ki-24, MB1, B7, B70, M-CSFR, TNFR-II, IL-7R, OX-40, CD137, CD137L, CD30L, CD40L, FasL, TRAIL, CD257, LIGHT, TRAIL-R1, TRAILR2, TRAIL-R4, TWEAK-R, TNFR, BCMA, B7DC, BTLA, B7-H1, B7-H2, B7-H3, ICOS, VEGFR2, NKG2D, JAG1, GITR, CD4, CCR2, GATA-3, MTORC1, MTORC2, RAPTOR, GATOR, FOXP3, NFAT, IL2R, and IL7

Exemplary tumor-associated antigens that can be recognized by T cells and are contemplated for targeting, include but are not limited to MAGE1, MAGE3, MAGE6, BAGE, GAGE, NYESO-1, MART1/Melan A, MC1R, GP100, tyrosinase, TRP-1, TRP-2, PSA, CEA, Cyp-B, Her2/Neu, hTERT, MUC1, PRAME, WT1, RAS, CDK-4, MUM-1, KRAS, MSLN and β-catenin.

3. Subjects to be Treated

In some embodiments, the subjects treated are mammals experiencing cancer, autoimmune disease, infections disease, organ transplant, organ failure, or a combination thereof. In some embodiments, the methods described herein may cause T cells to present specific antigens for the treatment of cancer or autoimmune disease. In some embodiments, the methods described herein may be used for T cell priming. In some embodiments, the methods described herein may be used to deliver DNA or mRNA that cause T cells to present MHC-peptide complexes. In some embodiments, the methods described herein may be used to deliver one or more of DNA, siRNA, or mRNA to a T cell to avoid anergy.

EXAMPLES

General notes: All reactions were run using anhydrous grade solvents under an atmosphere of nitrogen in flasks or vials with magnetic stirring, unless otherwise noted. Anhydrous solvents were purchased from Sigma-Aldrich and used as received. Flash column chromatography was performed using a Biotage Selekt or Teledyne-Isco Combiflash Nextgen300+ with prepacked Biotage Sfar silica gel cartridges. Thin layer chromatography was performed using Merck silica gel 60 plates, and compounds were visualized using iodine. Nuclear magnetic resonance (NMR) spectroscopy was performed using a Varian INOVA 500 MHz spectrometer; chemical shifts are reported in δ parts per million (ppm) upfield of tetramethylsilane, referenced to residual solvent peak of $CHCl_3$ at δ=7.26 ppm. Liquid chromatography-mass spectrometry (LCMS) was performed using a Waters Acquity UPLC H-class Plus with QDa detector (ESI) equipped with a Waters Acquity UPLC BEH C18 column (130 Å, 1.7 μM, 2.1 mm×50 mm). Compounds were analyzed using the following general LCMS method unless otherwise noted: solvent A=water+0.1% formic acid, solvent B=acetonitrile; gradient from 90%/A, 10% B to 5% A, 95% B over 3 minutes, then hold at 95% B for 2 minutes, then ramp back to 10% B over 1 minute; flow rate=0.5 mL/min.

List of Abbreviations

AOP: (7-Azabenzotriazol-1-yloxy)tris(dimethylamino) phosphonium hexafluorophosphate
DCM: dichloromethane
DIPEA: N,N-diisopropylethylamine
DMAP: 4-(dimethylamino)pyridine
DMPC: 1,2-Dimyristoyl-sn-glycero-3-phosphocholine
DSPC: 1,2-Distearoyl-sn-glycero-3-phosphocholine
EDC: N-(3-Dimethylaminopropyl)-N'-ethylcarbodiimide hydrochloride
Eq: equivalents
ESI: electrospray ionization
LCMS: liquid chromatography-mass spectrometry
LNP: lipid nanoparticle
NMR: Nuclear magnetic resonance
RT: retention time Example 1: 3-(2-((3r,5r,7r)-adamantan-1-yl)acetoxy)-2-((((9Z,12Z)-octadeca-9,12-dienoyl)oxy)methyl)propyl 1'-ethyl-[1,4'-bipiperidine]-4-carboxylate (1)

(1)

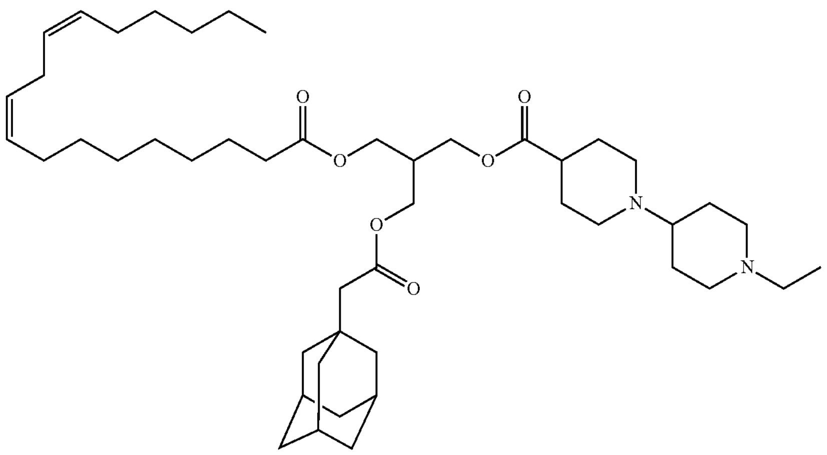

Step 1: 3-hydroxy-2-(hydroxymethyl)propyl (9Z,12Z)-octadeca-9,12-dienoate

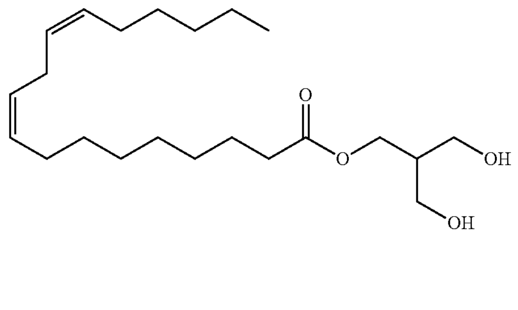 [SMILES: CCCCC/C=C\C/C=C\CCCCCCCC(=O)OCC(CO)CO]

To a mixture of trimethylolmethane (3.0 g, 1 Eq, 28 mmol) in dichloromethane (100 mL) was added linoleic acid (7.9 g, 1 Eq, 28 mmol), DIPEA (5.5 g, 7.4 mL, 1.5 Eq, 42 mmol), and DMAP (0.69 g, 0.2 Eq, 5.7 mmol). Added EDC (8.1 g, 1.5 Eq, 42 mmol) last, and stirred at 23° C. for 18 h. After this time, the reaction mixture was concentrated and purified by flash column chromatography (200 g silica, 0 to 90% ethyl acetate in hexanes over 20 minutes). Obtained 3-hydroxy-2-(hydroxymethyl)propyl (9Z,12Z)-octadeca-9,12-dienoate (2.6 g, 25%) as a colorless oil. $^{1}$H NMR (500 MHz, Chloroform-d) δ 5.43-5.27 (m, 5H), 4.24 (d, J=6.3 Hz, 2H), 3.76 (ddt, J=21.1, 11.1, 5.3 Hz, 4H), 2.77 (d, J=6.8 Hz, 2H), 2.61-2.55 (m, 2H), 2.36-2.29 (m, 2H), 2.10-1.98 (m, 6H), 1.66-1.58 (m, 2H), 1.41-1.21 (m, 12H), 0.92-0.85 (m, 3H).

Step 2: 3-(2-((3r,5r,7r)-adamantan-1-yl)acetoxy)-2-(hydroxymethyl)propyl (9Z,12Z)-octadeca-9,12-dienoate

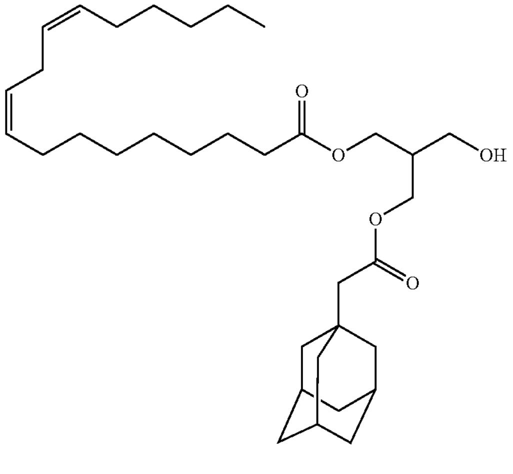 [SMILES: CCCCC/C=C\C/C=C\CCCCCCCC(=O)OCC(CO)COC(=O)CC12CC3CC(CC(C3)C1)C2]

To a solution of 3-hydroxy-2-(hydroxymethyl)propyl (9Z,12Z)-octadeca-9,12-dienoate (2.6 g, 1 Eq, 7.1 mmol) in dichloromethane (30 mL) was added 2-(adamantan-1-yl) acetic acid (1.4 g, 1 Eq, 7.1 mmol), DIPEA (1.8 g, 2 Eq, 14 mmol), and DMAP (0.17 g, 0.2 Eq, 1.4 mmol). Added EDC (2.0 g, 1.5 Eq, 11 mmol) last, and stirred at 23° C. for 18 h. After this time, the reaction mixture was concentrated and purified by flash column chromatography (100 g silica, 0 to 40% ethyl acetate in hexanes over 20 minutes). Obtained 3-(2-((3r,5r,7r)-adamantan-1-yl)acetoxy)-2-(hydroxymethyl)propyl (9Z,12Z)-octadeca-9,12-dienoate (1.86 g, 48%) as a colorless oil. $^{1}$H NMR (500 MHz, Chloroform-d) δ 5.41-5.28 (m, 4H), 4.23-4.10 (m, 5H), 3.62 (t, J=6.0 Hz, 2H), 2.76 (tt, J=6.6, 0.9 Hz, 2H), 2.35-2.27 (m, 3H), 2.19 (hept, J=5.9 Hz, 1H), 2.10-1.99 (m, 6H), 1.97 (p, J=2.9 Hz, 3H), 1.74-1.57 (m, 17H), 1.39-1.23 (m, 10H), 0.92-0.85 (m, 3H).

Step 3: 3-(2-((3r,5r,7r)-adamantan-1-yl)acetoxy)-2-((((9Z,12Z)-octadeca-9,12-dienoyl)oxy)methyl)propyl 1'-ethyl-[1,4'-bipiperidine]-4-carboxylate (1)

(1)

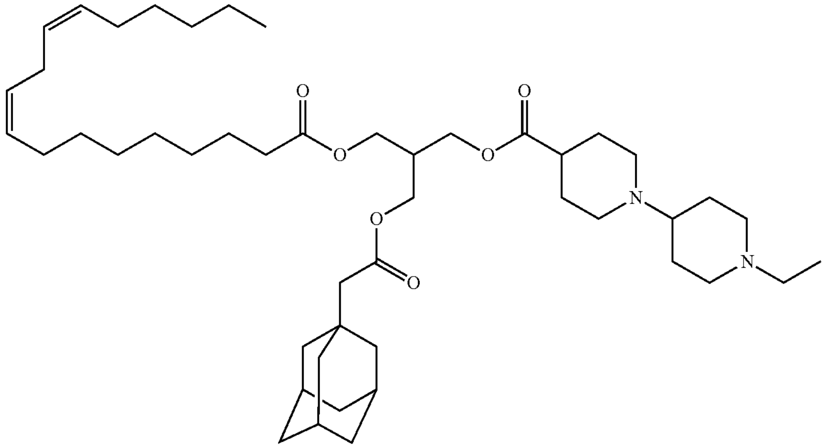

To a solution of 3-(2-((3r,5r,7r)-adamantan-1-yl)acetoxy)-2-(hydroxymethyl)propyl (9Z,12Z)-octadeca-9,12-dienoate (50 mg, 1 Eq, 92 μmol) in dichloromethane (1 mL) was added 1'-ethyl-[1,4'-bipiperidine]-4-carboxylic acid dihydrochloride (29 mg, 1 Eq, 92 μmol), DIPEA (53 mg, 72 μL, 4.5 Eq, 0.41 mmol), and DMAP (2.2 mg, 0.2 Eq, 18 μmol). Added EDC (35 mg, 2 Eq, 0.18 mmol) last, and stirred at 23° C. for 18 h. After this time, the reaction mixture was purified directly by flash column chromatography (10 g silica, 0 to 25% methanol in dichloromethane over 12 minutes). Obtained 3-(2-((3r,5r,7r)-adamantan-1-yl)acetoxy)-2-((((9Z,12Z)-octadeca-9,12-dienoyl)oxy)methyl)propyl 1'-ethyl-[1,4'-bipiperidine]-4-carboxylate (61 mg, 87%) as a colorless oil. $^1$H NMR (500 MHz, Chloroform-d) δ 5.41-5.28 (m, 4H), 4.19-4.06 (m, 7H), 3.72-3.54 (m, 6H), 3.17-3.04 (m, 4H), 2.80-2.73 (m, 2H), 2.10-2.00 (m, 6H), 1.65-1.51 (m, 24H), 1.51-1.42 (m, 11H), 1.38-1.24 (m, 11H), 0.92-0.86 (m, 3H). LCMS: calculated m/z (M+H)=767.6, found 767.7, RT=3.15 min.

The following examples 2-28 were prepared using similar procedures as Example 1, varying the carboxylic acid building block used in the final step.

Example 2: 3-(2-((3r,5r,7r)-adamantan-1-yl)acetoxy)-2-((((9Z,12Z)-octadeca-9,12-dienoyl)oxy)methyl)propyl 1-methylpiperidine-4-carboxylate (2)

(2)

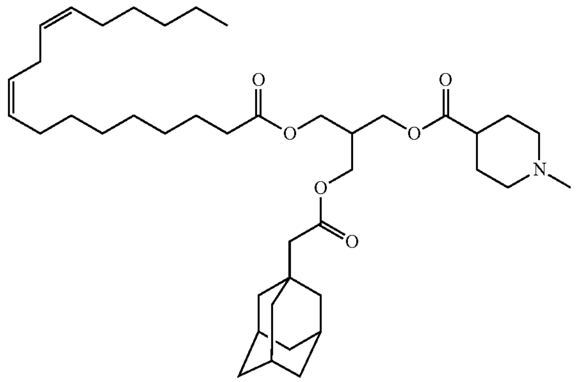

Prepared from 3-(2-((3r,5r,7r)-adamantan-1-yl)acetoxy)-2-(hydroxymethyl)propyl (9Z,12Z)-octadeca-9,12-dienoate using 1-methylpiperidine-4-carboxylic acid hydrochloride on a 0.18 mmol scale. Isolated 109 mg (89% yield) of the product. LCMS: calculated m/z (M+H)=670.5, found 670.5, RT=3.75 min.

Example 3: 3-(2-((3r,5r,7r)-adamantan-1-yl)acetoxy)-2-(((3-(4-methylpiperazin-1-yl)propanoyl)oxy)methyl)propyl (9Z,12Z)-octadeca-9,12-dienoate (3)

(3)

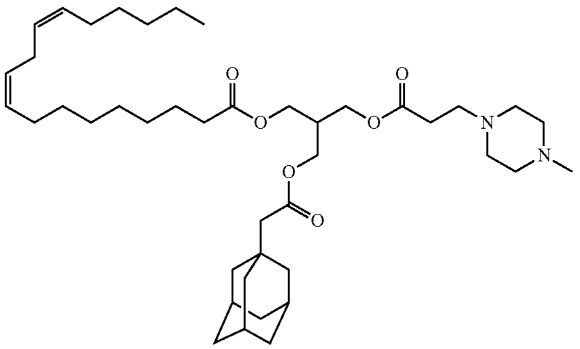

Prepared from 3-(2-((3r,5r,7r)-adamantan-1-yl)acetoxy)-2-(hydroxymethyl)propyl (9Z,12Z)-octadeca-9,12-dienoate using 3-(4-methylpiperazin-1-yl)propanoic acid dihydrochloride on a 0.18 mmol scale. Isolated 54 mg (42% yield) of the product. LCMS: calculated m/z (M+H)=699.5, found 699.5, RT=3.63 min.

Example 4: 3-(2-((3r,5r,7r)-adamantan-1-yl)acetoxy)-2-(((4-(dimethylamino)butanoyl)oxy)methyl)propyl (9Z,12Z)-octadeca-9,12-dienoate (4)

(4)

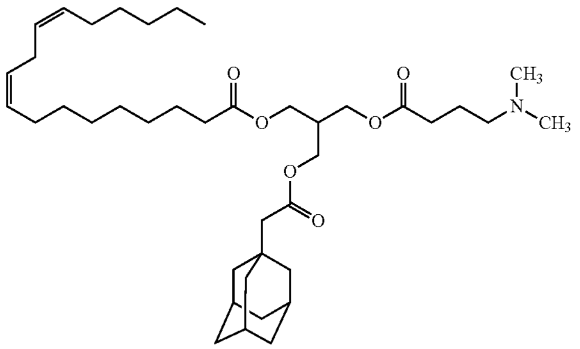

Prepared from 3-(2-((3r,5r,7r)-adamantan-1-yl)acetoxy)-2-(hydroxymethyl)propyl (9Z,12Z)-octadeca-9,12-dienoate using 4-(dimethylamino)butanoic acid hydrochloride on a 0.18 mmol scale. Isolated 105 mg (87% yield) of the product. LCMS: calculated m/z (M+H)=658.5, found 658.3, RT=3.60 min.

Example 5: 3-(2-((3r,5r,7r)-adamantan-1-yl)acetoxy)-2-(((dimethylglycyl)oxy)methyl)propyl (9Z,12Z)-octadeca-9,12-dienoate (5)

(5)

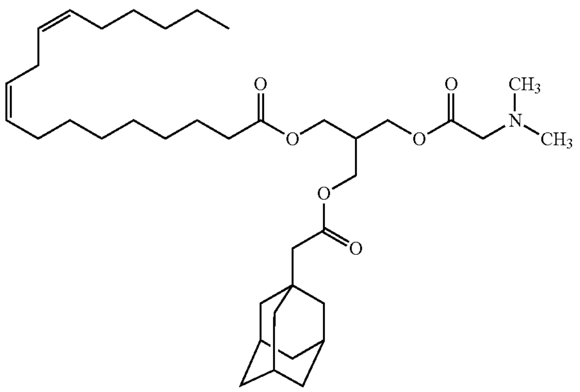

Prepared from 3-(2-((3r,5r,7r)-adamantan-1-yl)acetoxy)-2-(hydroxymethyl)propyl (9Z,12Z)-octadeca-9,12-dienoate using 2-(dimethylamino)acetic acid on a 0.18 mmol scale using N,N-dimethylformamide as the solvent rather than dichloromethane. Isolated 6.4 mg (6% yield) of the product. LCMS: calculated m/z (M+H)=630.5, found 630.4, RT=3.76 min.

Example 6: 3-(2-((3r,5r,7r)-adamantan-1-yl)acetoxy)-2-(((3-(ethyl(methyl)amino)propanoyl)oxy)methyl)propyl (9Z,12Z)-octadeca-9,12-dienoate (6)

(6)

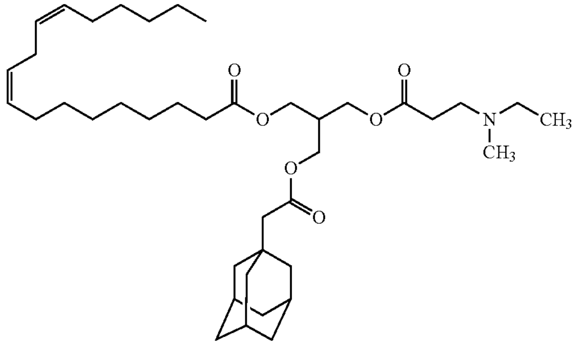

Prepared from 3-(2-((3r,5r,7r)-adamantan-1-yl)acetoxy)-2-(hydroxymethyl)propyl (9Z,12Z)-octadeca-9,12-dienoate using 3-[ethyl(methyl)amino]propanoic acid hydrochloride on a 0.18 mmol scale. Isolated 30 mg (25% yield) of the product. LCMS: calculated m/z (M+H)=658.5, found 658.7, RT=3.68 min.

Example 7: 3-(2-((3r,5r,7r)-adamantan-1-yl)acetoxy)-2-(((3-(pyrrolidin-1-yl)propanoyl)oxy)methyl)propyl (9Z,12Z)octadeca-9,12-dienoate (7)

(7)

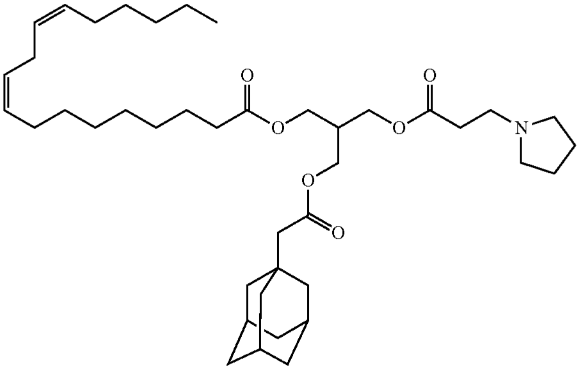

Prepared from 3-(2-((3r,5r,7r)-adamantan-1-yl)acetoxy)-2-(hydroxymethyl)propyl (9Z,12Z)-octadeca-9,12-dienoate using 3-(pyrrolidin-1-yl)propanoic acid hydrochloride on a 0.18 mmol scale. Isolated 18 mg (15% yield) of the product. LCMS: calculated m/z (M+H)=670.5, found 670.6, RT=3.46 min.

Example 8: 3-(2-((3r,5r,7r)-adamantan-1-yl)acetoxy)-2-((((9Z,12Z)-octadeca-9,12-dienoyl)oxy)methyl)propyl 1-isopropylpiperidine-4-carboxylate (8)

(8)

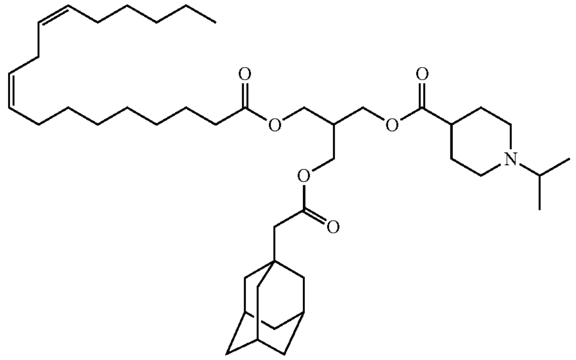

Prepared from 3-(2-((3r,5r,7r)-adamantan-1-yl)acetoxy)-2-(hydroxymethyl)propyl (9Z,12Z)-octadeca-9,12-dienoate using 1-(propan-2-yl)piperidine-4-carboxylic acid hydrochloride on a 0.18 mmol scale. Isolated 88 mg (68% yield) of the product. LCMS: calculated m/z (M+H)=698.5, found 698.4, RT=3.48 min.

Example 9: 3-(2-((3r,5r,7r)-adamantan-1-yl)acetoxy)-2-(((3-(piperidin-1-yl)propanoyl)oxy)methyl)propyl (9Z,12Z)-octadeca-9,12-dienoate (9)

(9)

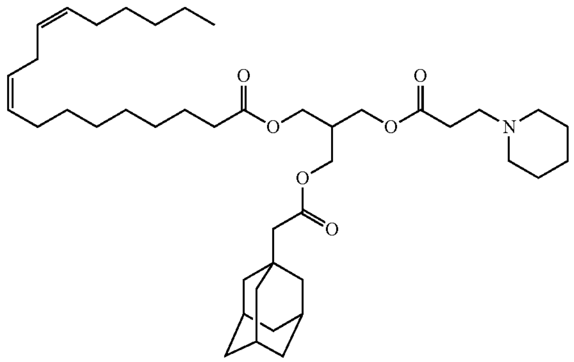

Prepared from 3-(2-((3r,5r,7r)-adamantan-1-yl)acetoxy)-2-(hydroxymethyl)propyl (9Z,12Z)-octadeca-9,12-dienoate using 3-(piperidin-1-yl)propanoic acid hydrochloride on a 0.18 mmol scale. Isolated 97 mg (77% yield) of the product. LCMS: calculated m/z (M+H)=684.5, found 684.3, RT=3.46 min.

Example 10: 3-(2-((3r,5r,7r)-adamantan-1-yl)acetoxy)-2-(((4-(piperidin-1-yl)butanoyl)oxy)methyl)propyl (9Z,12Z)-octadeca-9,12-dienoate (10)

(10)

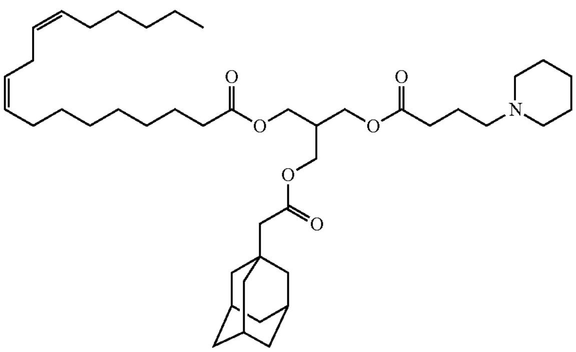

Prepared from 3-(2-((3r,5r,7r)-adamantan-1-yl)acetoxy)-2-(hydroxymethyl)propyl (9Z,12Z)-octadeca-9,12-dienoate using 4-(piperidin-1-yl)butanoic acid hydrochloride on a 0.18 mmol scale. Isolated 97 mg (76% yield) of the product. LCMS: calculated m/z (M+H)=698.5, found 698.4, RT=3.46 min.

Example 11: 3-(2-((3r,5r,7r)-adamantan-1-yl)acetoxy)-2-((((9Z,12Z)-octadeca-9,12-dienoyl)oxy)methyl)propyl 1-propylpiperidine-4-carboxylate (11)

(11)

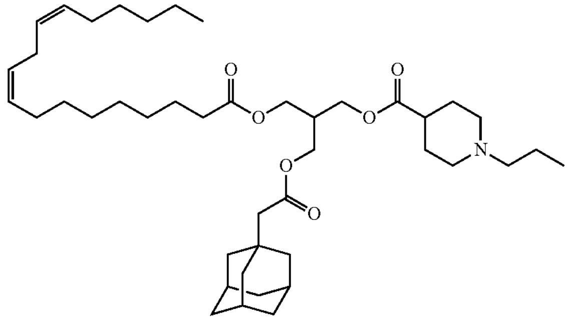

Prepared from 3-(2-((3r,5r,7r)-adamantan-1-yl)acetoxy)-2-(hydroxymethyl)propyl (9Z,12Z)-octadeca-9,12-dienoate using 1-propylpiperidine-4-carboxylic acid hydrochloride on a 0.18 mmol scale. Isolated 111 mg (87% yield) of the product. LCMS: calculated m/z (M+H)=698.5, found 698.4, RT=3.48 min.

Example 12: 3-(2-((3r,5r,7r)-adamantan-1-yl)acetoxy)-2-(((3-(dimethylamino)propanoyl)oxy)methyl)propyl (9Z,12Z)-octadeca-9,12-dienoate (12)

(12)

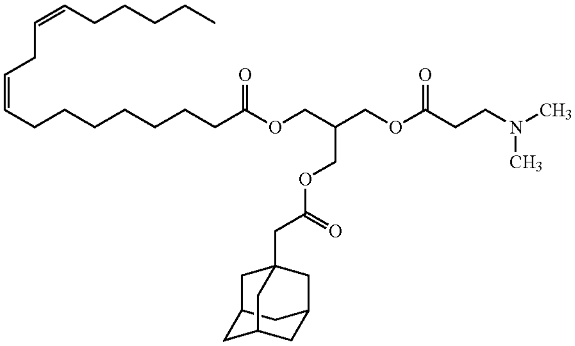

Prepared from 3-(2-((3r,5r,7r)-adamantan-1-yl)acetoxy)-2-(hydroxymethyl)propyl (9Z,12Z)-octadeca-9,12-dienoate using 3-(dimethylamino)propanoic acid hydrochloride on a 0.18 mmol scale. Isolated 63 mg (54% yield) of the product. LCMS: calculated m/z (M+H)=644.5, found 644.7, RT=3.62 min.

Example 13: 3-(2-((3r,5r,7r)-adamantan-1-yl)acetoxy)-2-(((N-methyl-N-propylglycyl)oxy)methyl)propyl (9Z,12Z)-octadeca-9,12-dienoate (13)

(13)

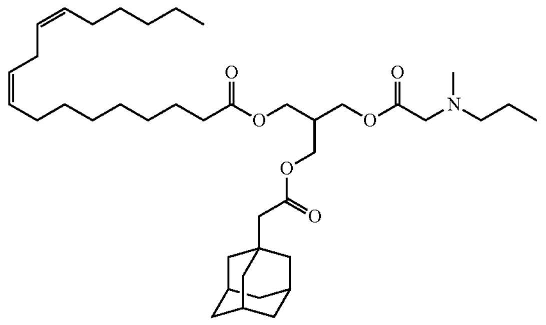

Prepared from 3-(2-((3r,5r,7r)-adamantan-1-yl)acetoxy)-2-(hydroxymethyl)propyl (9Z,12Z)-octadeca-9,12-dienoate using 2-[methyl(propyl)amino]acetic acid hydrochloride on a 0.18 mmol scale. Isolated 25 mg (20% yield) of the product. LCMS: calculated m/z (M+H)=658.5, found 658.5, RT=3.77 min.

Example 14: 3-(2-((3r,5r,7r)-adamantan-1-yl)acetoxy)-2-(((diethylglycyl)oxy)methyl)propyl (9Z,12Z)-octadeca-9,12-dienoate (14)

(14)

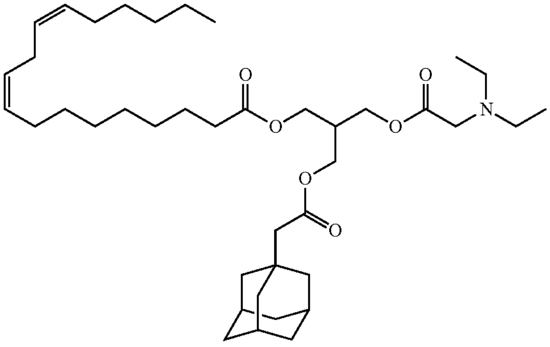

Prepared from 3-(2-((3r,5r,7r)-adamantan-1-yl)acetoxy)-2-(hydroxymethyl)propyl (9Z,12Z)-octadeca-9,12-dienoate using 2-(diethylamino)acetic acid on a 0.18 mmol scale. Isolated 34 mg (28% yield) of the product. LCMS: calculated m/z (M+H)=658.5, found 658.8, RT=3.82 min.

Example 15: 3-(2-((3r,5r,7r)-adamantan-1-yl)acetoxy)-2-(((3-(diethylamino)propanoyl)oxy)methyl)propyl (9Z,12Z)-octadeca-9,12-dienoate (15)

(15)

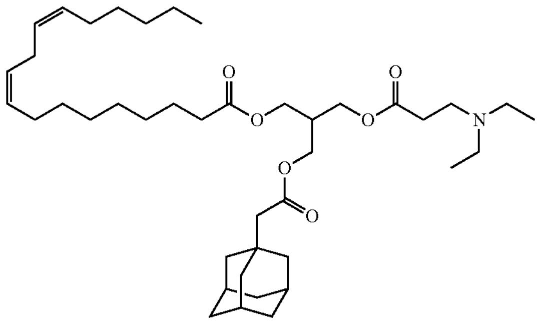

Prepared from 3-(2-((3r,5r,7r)-adamantan-1-yl)acetoxy)-2-(hydroxymethyl)propyl (9Z,12Z)-octadeca-9,12-dienoate using 3-(diethylamino)propanoic acid hydrochloride on a 0.18 mmol scale. Isolated 96 mg (78% yield) of the product. LCMS: calculated m/z (M+H)=672.5, found 672.4, RT=3.64 min.

Example 16: 3-(2-(1H-imidazol-1-yl)acetoxy)-2-((2-((3r,5r,7r)-adamantan-1-yl)acetoxy)methyl)propyl (9Z,12Z)-octadeca-9,12-dienoate (16)

(16)

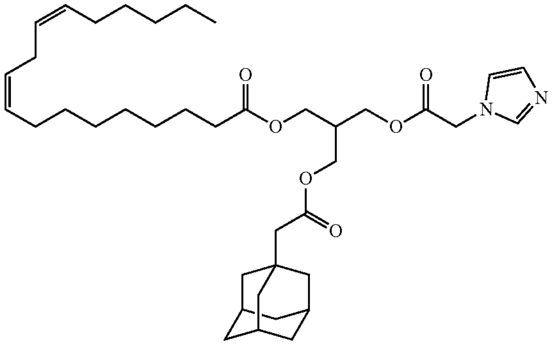

Prepared from 3-(2-((3r,5r,7r)-adamantan-1-yl)acetoxy)-2-(hydroxymethyl)propyl (9Z,12Z)-octadeca-9,12-dienoate using 1H-imidazole-1-acetic acid on a 0.18 mmol scale. Isolated 19 mg (16% yield) of the product. LCMS: calculated m/z (M+H)=653.5, found 653.5, RT=3.92 min.

Example 17: 3-(2-((3r,5r,7r)-adamantan-1-yl)acetoxy)-2-((2-(4-methylpiperazin-1-yl)acetoxy)methyl)propyl (9Z,12Z)-octadeca-9,12-dienoate (17)

(17)

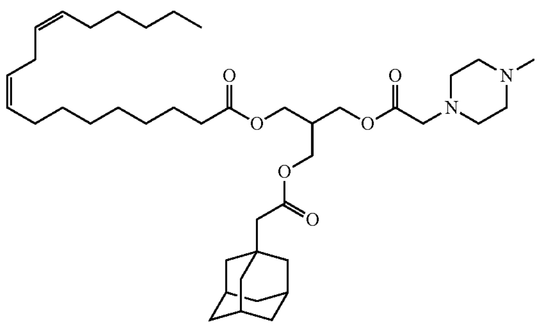

Prepared from 3-(2-((3r,5r,7r)-adamantan-1-yl)acetoxy)-2-(hydroxymethyl)propyl (9Z,12Z)-octadeca-9,12-dienoate using 2-(4-methylpiperazin-1-yl)acetic acid dihydrochloride on a 0.09 mmol scale. Isolated 47 mg (75% yield) of the product. LCMS: calculated m/z (M+H)=685.5, found 685.6, RT=3.90 min.

Example 18: 3-(2-((3r,5r,7r)-adamantan-1-yl)acetoxy)-2-(((4-(pyrrolidin-1-yl)butanoyl)oxy)methyl)propyl (9Z,12Z)-octadeca-9,12-dienoate (18)

(18)

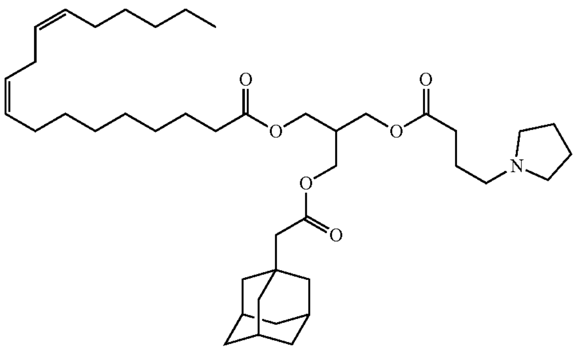

Prepared from 3-(2-((3r,5r,7r)-adamantan-1-yl)acetoxy)-2-(hydroxymethyl)propyl (9Z,12Z)-octadeca-9,12-dienoate using 4-(pyrrolidin-1-yl)butanoic acid hydrochloride on a 0.09 mmol scale. Isolated 40 mg (64% yield) of the product. LCMS: calculated m/z (M+H)=684.5, found 684.5, RT=3.72 min.

Example 19: 3-(2-((3r,5r,7r)-adamantan-1-yl)acetoxy)-2-(((4-(dipropylamino)butanoyl)oxy)methyl)propyl (9Z,12Z)-octadeca-9,12-dienoate (19)

(19)

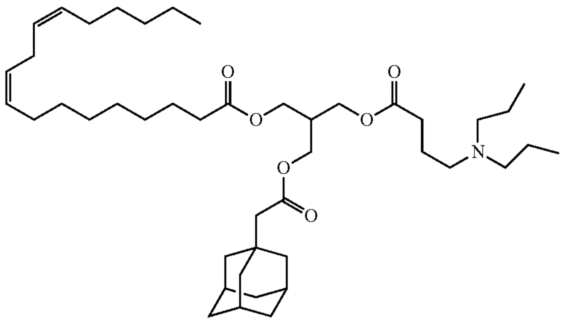

Prepared from 3-(2-((3r,5r,7r)-adamantan-1-yl)acetoxy)-2-(hydroxymethyl)propyl (9Z,12Z)-octadeca-9,12-dienoate using 4-(dipropylamino)butanoic acid hydrochloride on a 0.09 mmol scale. Isolated 59 mg (90% yield) of the product. LCMS: calculated m/z (M+H)=714.6, found 714.6, RT=3.66 min.

Example 20: 3-(2-((3r,5r,7r)-adamantan-1-yl)acetoxy)-2-((((9Z,12Z)-octadeca-9,12-dienoyl)oxy)methyl)propyl quinuclidine-4-carboxylate (20)

(20)

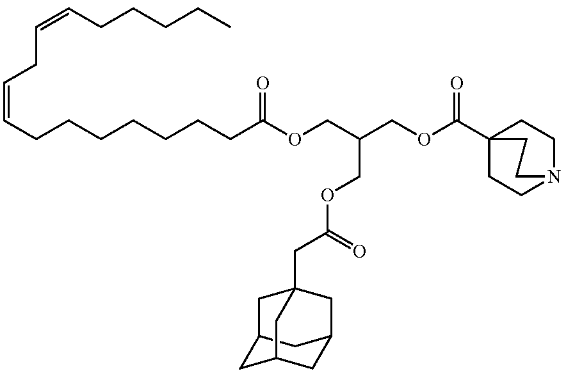

Prepared from 3-(2-((3r,5r,7r)-adamantan-1-yl)acetoxy)-2-(hydroxymethyl)propyl (9Z,12Z)-octadeca-9,12-dienoate using quinuclidine-4-carboxylic acid hydrochloride on a 0.09 mmol scale. Isolated 8.0 mg (13% yield) of the product. LCMS: calculated m/z (M+H)=682.5, found 682.4, RT=3.66 min.

Example 21: 3-(2-((3r,5r,7r)-adamantan-1-yl)acetoxy)-2-((((9Z,12Z)-octadeca-9,12-dienoyl)oxy)methyl)propyl 1-methylpiperidine-3-carboxylate (21)

(21)

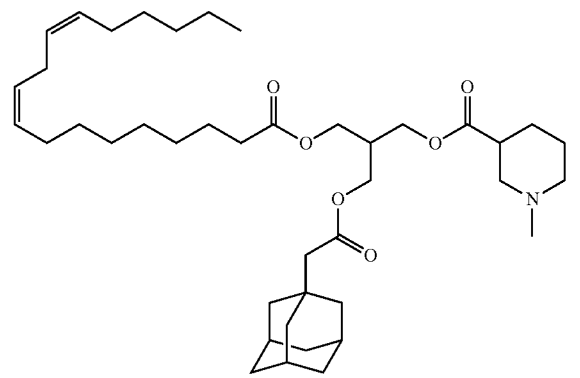

Prepared from 3-(2-((3r,5r,7r)-adamantan-1-yl)acetoxy)-2-(hydroxymethyl)propyl (9Z,12Z)-octadeca-9,12-dienoate using 1-methylpiperidine-3-carboxylic acid on a 0.09 mmol scale. Isolated 55 mg (89% yield) of the product. LCMS: calculated m/z (M+H)=670.5, found 670.4, RT=3.58 min.

Example 22: 3-(2-((3r,5r,7r)-adamantan-1-yl)acetoxy)-2-((((9Z,12Z)-octadeca-9,12-dienoyl)oxy)methyl)propyl 1,3-dimethylpyrrolidine-3-carboxylate (22)

(22)

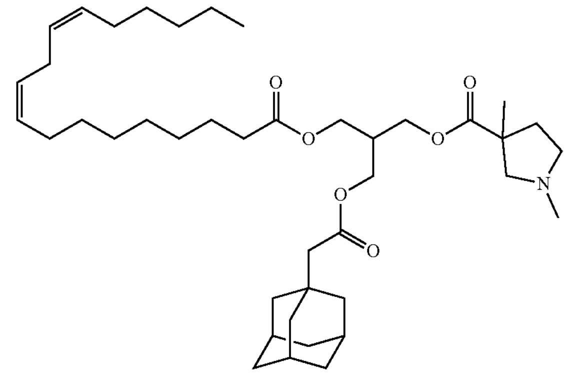

Prepared from 3-(2-((3r,5r,7r)-adamantan-1-yl)acetoxy)-2-(hydroxymethyl)propyl (9Z,12Z)-octadeca-9,12-dienoate using 1,3-dimethylpyrrolidine-3-carboxylic acid on a 0.09 mmol scale. Isolated 21 mg (34% yield) of the product. LCMS: calculated m/z (M+H)=670.5, found 670.5, RT=3.54 min.

Example 23: 3-(2-((3r,5r,7r)-adamantan-1-yl)acetoxy)-2-((2-(1-methylpiperidin-4-yl)acetoxy)methyl)propyl (9Z,12Z)-octadeca-9,12-dienoate (23)

(23)

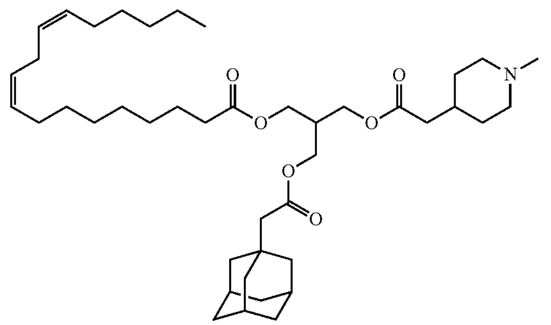

Prepared from 3-(2-((3r,5r,7r)-adamantan-1-yl)acetoxy)-2-(hydroxymethyl)propyl (9Z,12Z)-octadeca-9,12-dienoate using 2-(1-methylpiperidin-4-yl)acetic acid on a 0.09 mmol scale. Isolated 37 mg (59% yield) of the product. LCMS: calculated m/z (M+H)=684.5, found 684.5, RT=3.53 min.

Example 24: 3-(2-((3S,5S,7S)-adamantan-1-yl)acetoxy)-2-(((Nα,Nα-dimethyl-L-histidyl)oxy)methyl)propyl (9Z,12Z)-octadeca-9,12-dienoate (24)

(24)

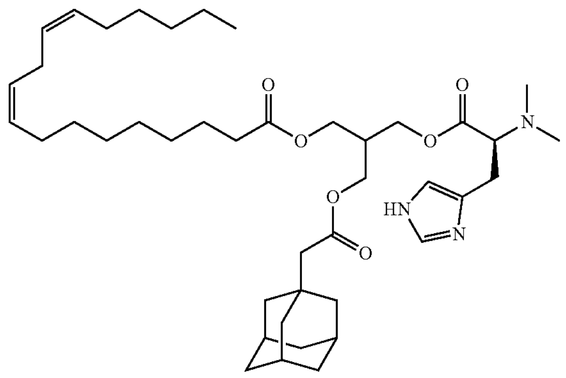

Prepared from 3-(2-((3r,5r,7r)-adamantan-1-yl)acetoxy)-2-(hydroxymethyl)propyl (9Z,12Z)-octadeca-9,12-dienoate using Nα,Nα-dimethyl-L-histidine on a 0.09 mmol scale. Isolated 2.7 mg (4% yield) of the product. LCMS: calculated m/z (M+H)=710.5, found 710.4, RT=3.70 min.

Example 25: 3-(2-((3r,5r,7r)-adamantan-1-yl)acetoxy)-2-((((9Z,12Z)-octadeca-9,12-dienoyl)oxy)methyl)propyl 1-(pyridin-4-yl)piperidine-4-carboxylate (25)

(25)

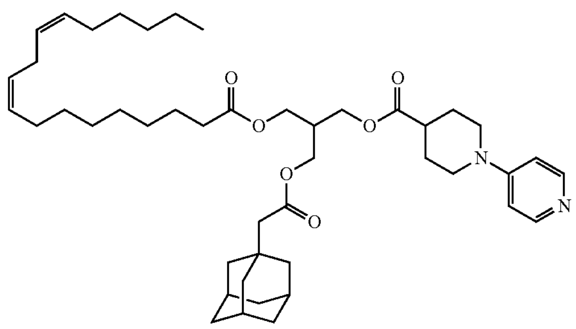

Prepared from 3-(2-((3r,5r,7r)-adamantan-1-yl)acetoxy)-2-(hydroxymethyl)propyl (9Z,12Z)-octadeca-9,12-dienoate using 1-(pyridin-4-yl)piperidine-4-carboxylic acid on a 0.09 mmol scale. Isolated 37 mg (55% yield) of the product. LCMS: calculated m/z (M+H)=733.5, found 733.4, RT=3.76 min.

Example 26: 3-(2-((3r,5r,7r)-adamantan-1-yl)acetoxy)-2-(((5-morpholinopentanoyl)oxy)methyl)propyl (9Z,12Z)-octadeca-9,12-dienoate (26)

(26)

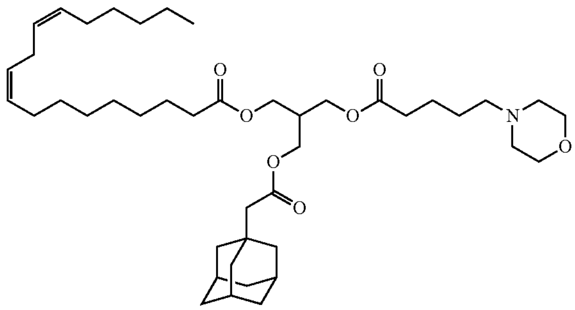

Prepared from 3-(2-((3r,5r,7r)-adamantan-1-yl)acetoxy)-2-(hydroxymethyl)propyl (9Z,12Z)-octadeca-9,12-dienoate using 5-morpholinopentanoic acid hydrochloride on a 0.09 mmol scale. Isolated 64 mg (98% yield) of the product. LCMS: calculated m/z (M+H)=714.5, found 714.5, RT=3.77 min.

Example 27: 3-(2-((3r,5r,7r)-adamantan-1-yl)acetoxy)-2-(((5-(dimethylamino)pentanoyl)oxy)methyl)propyl (9Z,12Z)-octadeca-9,12-dienoate (27)

(27)

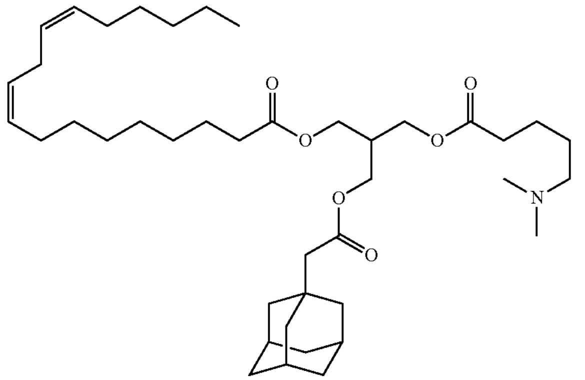

Prepared from 3-(2-((3r,5r,7r)-adamantan-1-yl)acetoxy)-2-(hydroxymethyl)propyl (9Z,12Z)-octadeca-9,12-dienoate using 5-(dimethylamino)pentanoic acid on a 0.09 mmol scale. Isolated 31 mg (50% yield) of the product. LCMS: calculated m/z (M+H)=672.5, found 672.5, RT=3.61 min.

Example 28: 3-(2-((3r,5r,7r)-adamantan-1-yl)acetoxy)-2-((2-(pyridin-4-yloxy)acetoxy)methyl)propyl (9Z,12Z)-octadeca-9,12-dienoate (28)

(28)

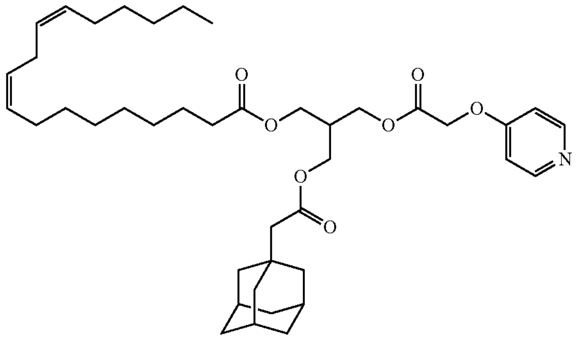

Prepared from 3-(2-((3r,5r,7r)-adamantan-1-yl)acetoxy)-2-(hydroxymethyl)propyl (9Z,12Z)-octadeca-9,12-dienoate using 2-(pyridin-4-yloxy)acetic acid on a 0.09 mmol scale. Isolated 2.7 mg (4% yield) of the product. LCMS: calculated m/z (M+H)=680.4, found 680.3, RT=4.01 min.

Example 29: 3-(((9Z,12Z)-octadeca-9,12-dienoyl)oxy)-2-((((1r,1's,4R,4'R)-4'-pentyl-[1,1'-bi(cyclohexane)]-4-carbonyl)oxy)methyl)propyl 1'-ethyl-[1,4'-bipiperidine]-4-carboxylate (29)

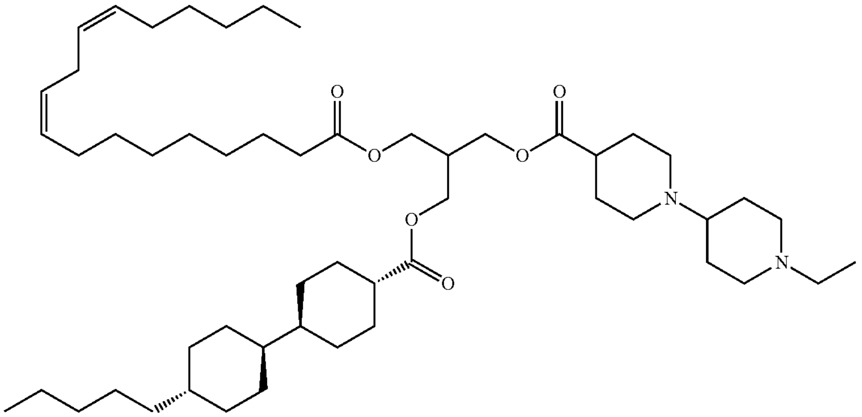

(29)

Step 1: 3-hydroxy-2-((((9Z,12Z)-octadeca-9,12-dienoyl)oxy)methyl)propyl 1'-ethyl-[1,4'-bipiperidine]-4-carboxylate

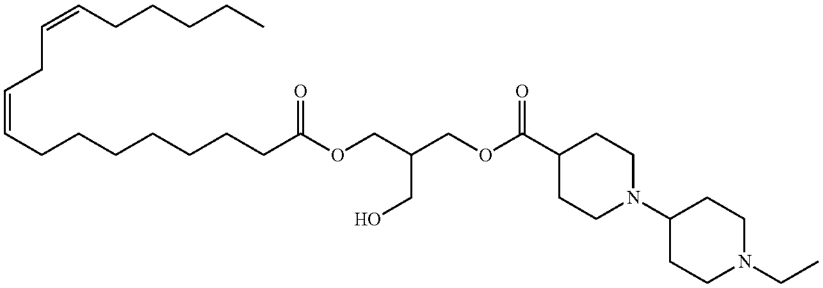 [SMILES: CCCCC/C=C\C/C=C\CCCCCCCC(=O)OCC(CO)COC(=O)C1CCN(C2CCN(CC)CC2)CC1]

To a solution of 3-hydroxy-2-(hydroxymethyl)propyl (9Z,12Z)-octadeca-9,12-dienoate (1.0 g, 1 Eq, 2.7 mmol) in dichloromethane (30 mL) was added 1'-ethyl-[1,4'-bipiperidine]-4-carboxylic acid dihydrochloride (0.85 g, 1 Eq, 2.7 mmol), DIPEA (1.2 g, 1.7 mL, 3.5 Eq, 9.5 mmol), and DMAP (66 mg, 0.2 Eq, 0.54 mmol). Added EDC (0.78 g, 1.5 Eq, 4.1 mmol) last, stirred at 23° C. for 18 h. After this time, the reaction mixture was concentrated and purified by flash column chromatography (100 g silica, 0 to 40% methanol in dichloromethane over 30 minutes). Obtained 3-hydroxy-2-((((9Z,12Z)-octadeca-9,12-dienoyl)oxy)methyl)propyl 1'-ethyl-[1,4'-bipiperidine]-4-carboxylate (540 mg, 34%) as a colorless oil. LCMS: calculated m/z (M+H)=591.5, found 591.6, RT=2.67 min.

Step 2: 3-(((9Z,12Z)-octadeca-9,12-dienoyl)oxy)-2-((((1r,1's,4R,4'R)-4'-pentyl-[1,1'-bi(cyclohexane)]-4-carbonyl)oxy)methyl)propyl 1'-ethyl-[1,4'-bipiperidine]-4-carboxylate (29)

(29)

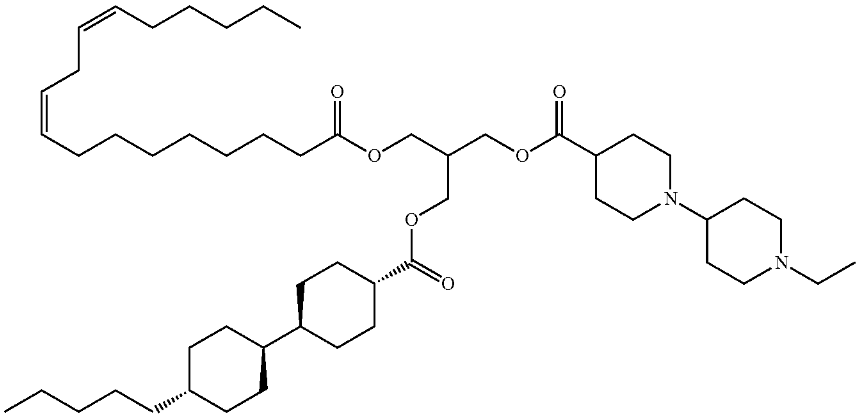

To a solution of 3-hydroxy-2-((((9Z,12Z)-octadeca-9,12-dienoyl)oxy)methyl)propyl 1'-ethyl-[1,4'-bipiperidine]-4-carboxylate (59 mg, 1 Eq, 0.10 mmol) in dichloromethane (1 mL) was added (1r,1's,4R,4'R)-4'-pentyl-[1,1'-bi(cyclohexane)]-4-carboxylic acid (28 mg, 1 Eq, 0.10 mmol), DIPEA (39 mg, 3 Eq, 0.30 mmol), and DMAP (2.4 mg, 0.2 Eq, 20 μmol). Added EDC (38 mg, 2 Eq, 0.20 mmol) last, stirred at 23° C. for 18 h. Purified directly by flash column chromatography (10 g silica, 0 to 30% methanol in dichloromethane over 12 minutes). Obtained 3-(((9Z,12Z)-octadeca-9,12-dienoyl)oxy)-2-((((1 r,1's,4R,4'R)-4'-pentyl-[1,1'-bi(cyclohexane)]-4-carbonyl)oxy)methyl)propyl 1'-ethyl-[1,4'-bipiperidine]-4-carboxylate (31 mg, 36%) as a colorless oil. $^1$H NMR (500 MHz, Chloroform-d) δ 5.42-5.29 (m, 4H), 4.16-4.09 (m, 6H), 3.85 (t, 0.1=6.9 Hz, 2H), 3.67-3.51 (m, 2H), 3.35-2.94 (m, 7H), 2.83-2.74 (m, 5H), 2.69-2.46 (m, 2H), 2.39 (p, J=6.0 Hz, 1H), 2.31 (t, J=7.6 Hz, 2H), 2.26-2.16 (m, 2H), 2.05 (q, J=7.0 Hz, 4H), 1.97 (d, J=13.0 Hz, 2H), 1.85-1.39 (m, 11H), 1.39-1.08 (m, 28H), 1.08-0.80 (m, 14H). LCMS: calculated m/z (M+H)=853.7, found 853.7, RT=3.54 min.

The following examples 30-37 were prepared using similar procedures as Example 29, varying the carboxylic acid building block used in the final step.

Example 30: 3-(2-((1r,3r)-adamantan-2-yl)acetoxy)-2-((((9Z,12Z)-octadeca-9,12-dienoyl)oxy)methyl)propyl 1'-ethyl-[1,4'-bipiperidine]-4-carboxylate (30)

(30)

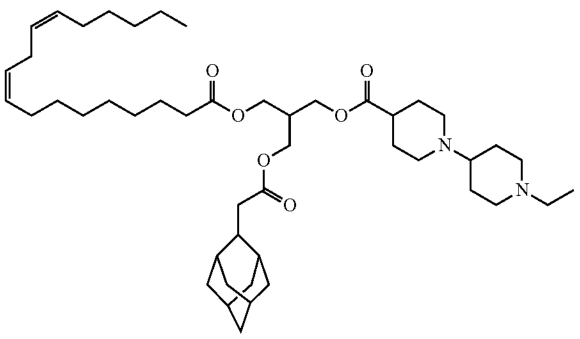

Prepared from 3-hydroxy-2-((((9Z,12Z)-octadeca-9,12-dienoyl)oxy)methyl)propyl 1'-ethyl-[1,4'-bipiperidine]-4-carboxylate using 2-(adamantan-2-yl)acetic acid on a 0.10 mmol scale. Isolated 32 mg (42% yield) of the product. LCMS: calculated m/z (M+H)=767.6, found 767.6, RT=3.17 min.

Example 31: 3-((3-((3r,5r,7r)-adamantan-1-yl)propanoyl)oxy)-2-((((9Z,12Z)-octadeca-9,12-dienoyl)oxy)methyl)propyl 1'-ethyl-[1,4'-bipiperidine]-4-carboxylate (31)

(31)

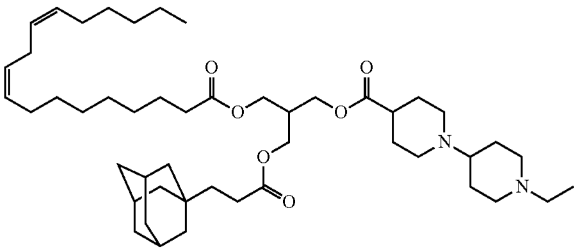

Prepared from 3-hydroxy-2-((((9Z,12Z)-octadeca-9,12-dienoyl)oxy)methyl)propyl 1'-ethyl-[1,4'-bipiperidine]-4-carboxylate using 3-(adamantan-1-yl)propanoic acid on a 0.10 mmol scale. Isolated 34 mg (44% yield) of the product. LCMS: calculated m/z (M+H)=781.6, found 781.7, RT=3.24 min.

Example 32: 3-((3,5-di-tert-butylbenzoyl)oxy)-2-((((9Z,12Z)-octadeca-9,12-dienoyl)oxy)methyl)propyl 1'-ethyl-[1,4'-bipiperidine]-4-carboxylate (32)

(32)

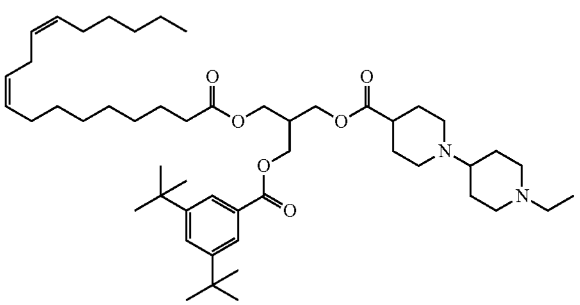

Prepared from 3-hydroxy-2-((((9Z,12Z)-octadeca-9,12-dienoyl)oxy)methyl)propyl 1'-ethyl-[1,4'-bipiperidine]-4-carboxylate using 3,5-di-tert-butylbenzoic acid on a 0.10 mmol scale. Isolated 21 mg (26% yield) of the product. LCMS: calculated m/z (M+H)=807.6, found 807.6, RT=3.29 min.

Example 33: 3-((2,3-diphenylpropanoyl)oxy)-2-((((9Z,12Z)-octadeca-9,12-dienoyl)oxy)methyl)propyl 1'-ethyl-[1,4'-bipiperidine]-4-carboxylate (33)

(33)

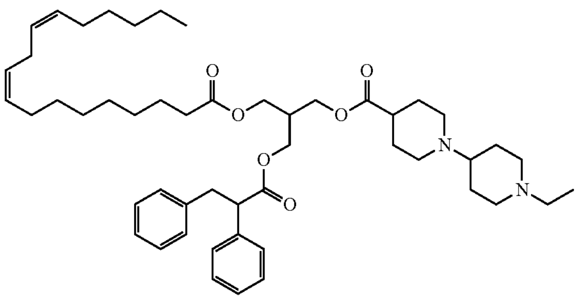

Prepared from 3-hydroxy-2-((((9Z,12Z)-octadeca-9,12-dienoyl)oxy)methyl)propyl 1'-ethyl-[1,4'-bipiperidine]-4-carboxylate using 2,3-diphenylpropanoic acid on a 0.10 mmol scale. Isolated 39 mg (49% yield) of the product. LCMS: calculated m/z (M+H)=799.6, found 799.4, RT=3.06 min.

Example 34: 3-(((9Z,12Z)-octadeca-9,12-dienoyl)oxy)-2-((((1R,2S,3s,4R,5S)-tricyclo[3.2.1.02,4]octane-3-carbonyl)oxy)methyl)propyl 1'-ethyl-[1,4'-bipiperidine]-4-carboxylate (34)

(34)

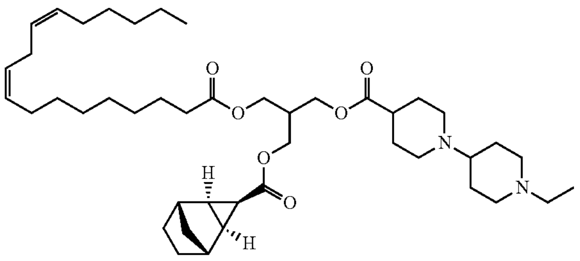

Prepared from 3-hydroxy-2-((((9Z,12Z)-octadeca-9,12-dienoyl)oxy)methyl)propyl 1'-ethyl-[1,4'-bipiperidine]-4-carboxylate using rac-(1R,2S,3R,4R,5S)-tricyclo[3.2.1.0,2,4]octane-3-carboxylic acid on a 0.10 mmol scale. Isolated 20 mg (28% yield) of the product. LCMS: calculated m/z (M+H)=725.5, found 725.4, RT=3.04 min.

Example 35: 3-(2-((1r,3R,5S,7r)-3,5-dimethyladamantan-1-yl)acetoxy)-2-((((9Z,12Z)-octadeca-9,12-dienoyl)oxy)methyl)propyl 1'-ethyl-[1,4'-bipiperidine]-4-carboxylate (35)

(35)

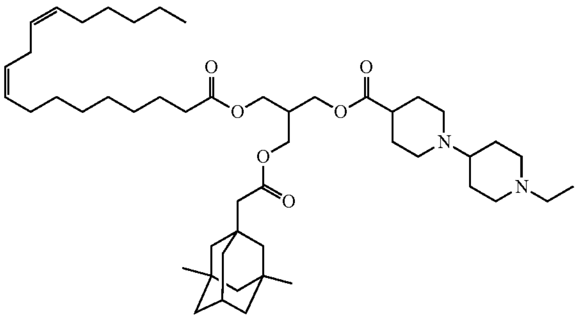

Prepared from 3-hydroxy-2-((((9Z,12Z)-octadeca-9,12-dienoyl)oxy)methyl)propyl 1'-ethyl-[1,4'-bipiperidine]-4-carboxylate using 2-(3,5-dimethyladamantan-1-yl)acetic acid on a 0.10 mmol scale. Isolated 43 mg (54% yield) of the product. LCMS: calculated m/z (M+H)=795.6, found 795.8, RT=3.32 min.

Example 36: 3-((bicyclo[3.3.1]nonane-3-carbonyl)oxy)-2-((((9Z,12Z)-octadeca-9,12-dienoyl)oxy)methyl)propyl 1'-ethyl-[1,4'-bipiperidine]-4-carboxylate (36)

(36)

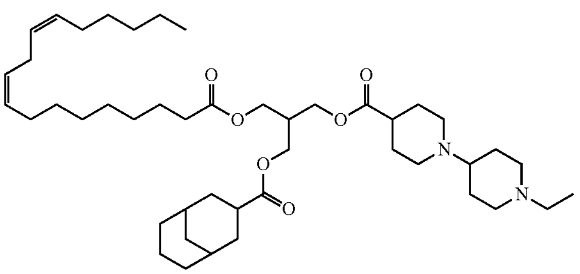

Prepared from 3-hydroxy-2-(((9Z,12Z)-octadeca-9,12-dienoyl)oxy)methyl)propyl 1'-ethyl-[1,4'-bipiperidine]-4-carboxylate using bicyclo[3.3.1]nonane-3-carboxylic acid on a 0.10 mmol scale. Isolated 37 mg (50% yield) of the product. LCMS: calculated m/z (M+H)=741.6, found 741.5, RT=3.12 min.

Example 37: 3-(((9Z,12Z)-octadeca-9,12-dienoyl)oxy)-2-((((3as,6as)-octahydro-2,5-methanopentalene-3a-carbonyl)oxy)methyl)propyl 1'-ethyl-[1,4'-bipiperidine]-4-carboxylate (37)

(37)

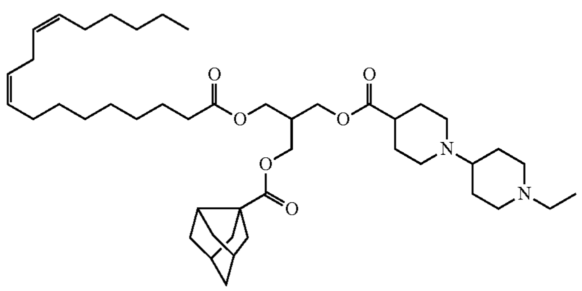

Prepared from 3-hydroxy-2-((((9Z,12Z)-octadeca-9,12-dienoyl)oxy)methyl)propyl 1'-ethyl-[1,4'-bipiperidine]-4-carboxylate using 3-noradamantanecarboxylic acid on a 0.10 mmol scale. Isolated 45 mg (61% yield) of the product. LCMS: calculated m/z (M+H)=739.6, found 739.3, RT=3.10 min.

Example 38: 3-((3-((3r,5r,7r)-adamantan-1-yl)propanoyl)oxy)-2-(((4-(dimethylamino)butanoyl)oxy)methyl)propyl (9Z,12Z)-octadeca-9,12-dienoate (38)

(38)

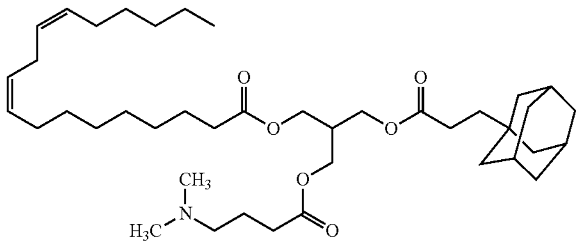

Step 1: 3-((4-(dimethylamino)butanoyl)oxy)-2-(hydroxymethyl)propyl (9Z,12Z)-octadeca-9,12-dienoate

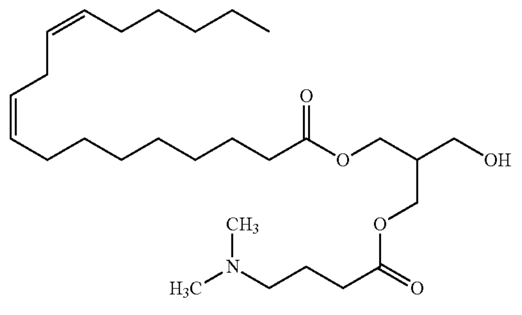 [SMILES: CCCCC/C=C\C/C=C\CCCCCCCC(=O)OCC(CO)COC(=O)CCCN(C)C]

To a solution of 3-hydroxy-2-(hydroxymethyl)propyl (9Z,12Z)-octadeca-9,12-dienoate (1000 mg, 1 Eq, 2.713 mmol) in dichloromethane (24 mL) was added 4-(dimethylamino)butanoic acid (355.9 mg, 1 Eq, 2.713 mmol), DIPEA (1.753 g, 2.35 mL, 5 Eq, 13.57 mmol), and DMAP (66.30 mg, 0.2 Eq, 542.7 μmol). Added EDC (1.040 g, 2 Eq, 5.427 mmol) last, stirred at 23° C. for 18 h. After this time, the reaction mixture was concentrated and purified by flash column chromatography (100 g silica, 0 to 30% methanol in dichloromethane over 20 minutes). Obtained 3-((4-(dimethylamino)butanoyl)oxy)-2-(hydroxymethyl)propyl (9Z,12Z)-octadeca-9,12-dienoate (0.447 g, 34%) as a pale yellow oil. LCMS: calculated m/z (M+H)=482.4, found 482.4, RT=3.15 min.

Step 2: 3-((3-((3r,5r,7r)-adamantan-1-yl)propanoyl)oxy)-2-(((4-(dimethylamino)butanoyl)oxy)methyl)propyl (9Z,12Z)-octadeca-9,12-dienoate (38)

(38)

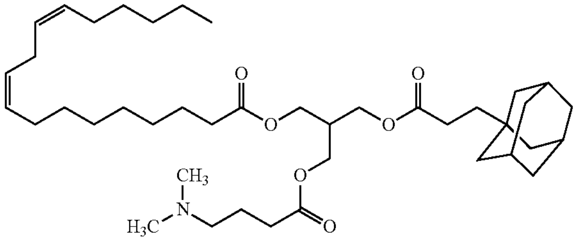

To a solution of 3-((4-(dimethylamino)butanoyl)oxy)-2-(hydroxymethyl)propyl (9Z,12Z)-octadeca-9,12-dienoate (0.050 g, 1 Eq, 0.10 mmol) in dichloromethane (1 mL) was added 3-((3r,5r,7r)-adamantan-1-yl)propanoic acid (22 mg, 1 Eq, 0.10 mmol), DIPEA (67 mg, 90 μL, 5 Eq, 0.52 mmol), and DMAP (2.5 mg, 0.2 Eq, 21 μmol). Added EDC (40 mg, 2 Eq, 0.21 mmol) last, stirred at 23° C. for 18 h. After this time, the reaction mixture was concentrated and purified by flash column chromatography (10 g silica, 0 to 20% methanol in dichloromethane over 12 minutes). Obtained 3-((3-((3r,5r,7r)-adamantan-1-yl)propanoyl)oxy)-2-(((4-(dimethylamino)butanoyl)oxy)methyl)propyl (9Z,12Z)-octadeca-9,12-dienoate (28 mg, 41%) as a pale yellow oil. $^1H$ NMR (500 MHz, Chloroform-d) δ 5.43-5.29 (m, 4H), 4.24-4.12 (m, 4H), 3.62 (t, J=5.6 Hz, 2H), 2.77 (t, J=6.7 Hz, 2H), 2.36-2.25 (m, 4H), 2.24-2.16 (m, 3H), 2.05 (q, J=6.8 Hz, 4H), 1.98-1.94 (m, 3H), 1.71 (d, J=12.3 Hz, 3H), 1.64-1.59 (m, 6H), 1.57 (s, 3H), 1.48-1.40 (m, 12H), 1.38-1.26 (m, 16H), 0.89 (t, J=6.9 Hz, 3H). LCMS: calculated m/z (M+H)=672.5, found 672.4, RT=3.84 min.

The following examples 39-46 were prepared using similar procedures as Example 38, varying the carboxylic acid building block used in the final step.

Example 39: 3-((4-(dimethylamino)butanoyl)oxy)-2-((((9Z,12Z)-octadeca-9,12-dienoyl)oxy)methyl)propyl (1r,3R,5S)-adamantane-1-carboxylate (39)

(39)

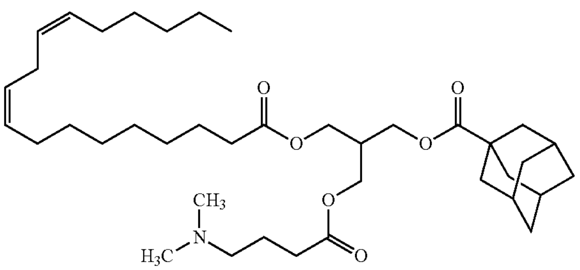

Prepared from 3-((4-(dimethylamino)butanoyl)oxy)-2-(hydroxymethyl)propyl (9Z,12Z)-octadeca-9,12-dienoate using 1-adamantanecarboxylic acid on a 0.10 mmol scale. Isolated 22 mg (34% yield) of the product. LCMS: calculated m/z (M+H)=644.5, found 644.4, RT=3.55 min.

Example 40: 3-(2-((1R,3S,5r,7r)-adamantan-2-yl)acetoxy)-2-(((4-(dimethylamino)butanoyl)oxy)methyl)propyl (9Z,12Z)-octadeca-9,12-dienoate (40)

(40)

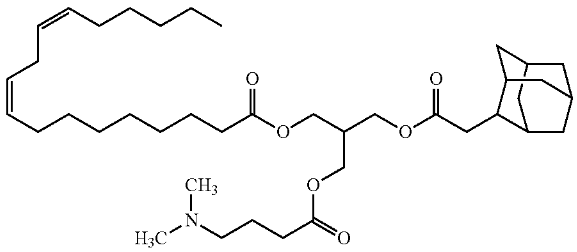

Prepared from 3-((4-(dimethylamino)butanoyl)oxy)-2-(hydroxymethyl)propyl (9Z,12Z)-octadeca-9,12-dienoate using 2-(adamantan-2-yl)acetic acid on a 0.10 mmol scale. Isolated 27 mg (40%/o yield) of the product. LCMS: calculated m/z (M+H)=658.5, found 658.5, RT=3.60 min.

Example 41: 3-((4-(dimethylamino)butanoyl)oxy)-2-((((9Z,12Z)-octadeca-9,12-dienoyl)oxy)methyl)propyl 3,5-di-tert-butylbenzoate (41)

(41)

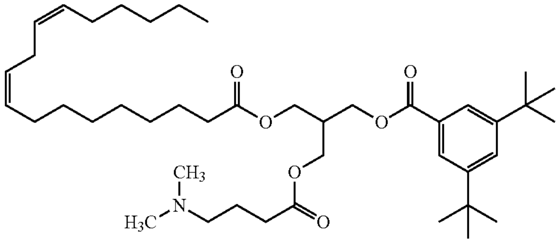

Prepared from 3-((4-(dimethylamino)butanoyl)oxy)-2-(hydroxymethyl)propyl (9Z,12Z)-octadeca-9,12-dienoate using 3,5-di-tert-butylbenzoic acid on a 0.10 mmol scale. Isolated 31 mg (43% yield) of the product. LCMS: calculated m/z (M+H)=698.5, found 698.6, RT=3.47 min.

Example 42: 3-(2-((1r,3R,5S,7r)-3,5-dimethyladamantan-1-yl)acetoxy)-2-(((4-(dimethylamino)butanoyl)oxy)methyl)propyl (9Z,12Z)-octadeca-9,12-dienoate (42)

(42)

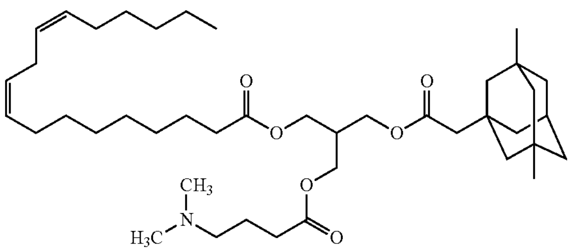

Prepared from 3-((4-(dimethylamino)butanoyl)oxy)-2-(hydroxymethyl)propyl (9Z,12Z)-octadeca-9,12-dienoate using 2-(3,5-dimethyladamantan-1-yl)acetic acid on a 0.10 mmol scale. Isolated 33 mg (46% yield) of the product. LCMS: calculated m/z (M+H)=686.5, found 686.4, RT=3.68 min.

Example 43: 3-((4-(dimethylamino)butanoyl)oxy)-2-((((9Z,12Z)-octadeca-9,12-dienoyl)oxy)methyl)propyl (2R,3as,5S,6as)-hexahydro-2,5-methanopentalene-3a(1H)-carboxylate (43)

(43)

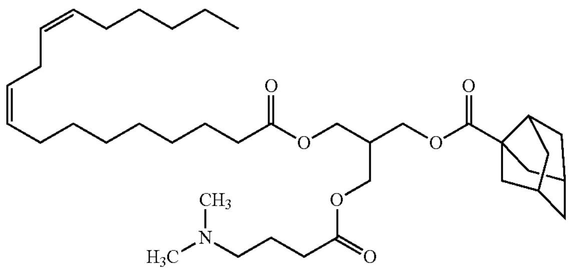

Prepared from 3-((4-(dimethylamino)butanoyl)oxy)-2-(hydroxymethyl)propyl (9Z,12Z)-octadeca-9,12-dienoate using 3-noradamantanecarboxylic acid on a 0.10 mmol scale. Isolated 30 mg (46% yield) of the product. LCMS: calculated m/z (M+H)=630.5, found 630.4, RT=3.54 min.

Example 44: 3-((4-(dimethylamino)butanoyl)oxy)-2-((((9Z,12Z)-octadeca-9,12-dienoyl)oxy)methyl) propyl bicyclo[3.3.1]nonane-3-carboxylate (44)

(44)

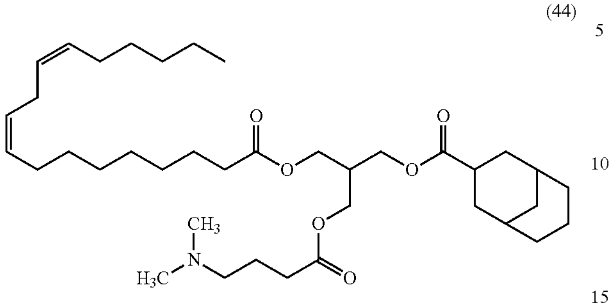

Prepared from 3-((4-(dimethylamino)butanoyl)oxy)-2-(hydroxymethyl)propyl (9Z,12Z)-octadeca-9,12-dienoate using bicyclo[3.3.1]nonane-3-carboxylic acid on a 0.10 mmol scale. Isolated 27 mg (41% yield) of the product. LCMS: calculated m/z (M+H)=632.5, found 632.8, RT=3.57 min.

Example 45: 3-((4-(dimethylamino)butanoyl)oxy)-2-((((9Z,12Z)-octadeca-9,12-dienoyl)oxy)methyl) propyl (1R,2S,3s,4R,5S)-tricyclo[3.2.1.02,4]octane-3-carboxylate (45)

(45)

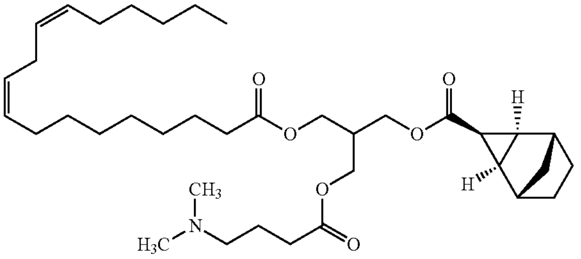

Prepared from 3-((4-(dimethylamino)butanoyl)oxy)-2-(hydroxymethyl)propyl (9Z,12Z)-octadeca-9,12-dienoate using rac-(1R,2S,3R,4R,5S)-tricyclo[3.2.1.0,2,4]octane-3-carboxylic acid on a 0.10 mmol scale. Isolated 28 mg (44% yield) of the product. LCMS: calculated m/z (M+H)=616.4, found 616.4, RT=3.50 min.

Example 46: 3-((4-(dimethylamino)butanoyl)oxy)-2-((((9Z,12Z)-octadeca-9,12-dienoyl)oxy)methyl) propyl (1r,1's,4R,4'R)-4'-pentyl-[1,1'-bi(cyclohexane)]-4-carboxylate (46)

(46)

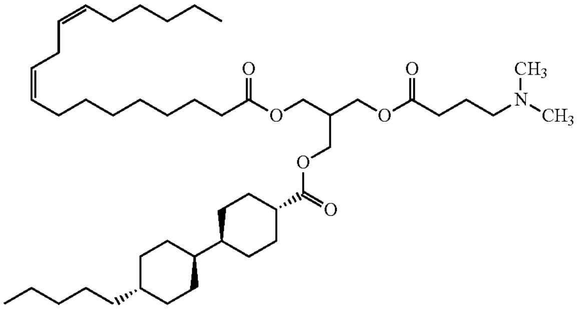

Prepared from 3-((4-(dimethylamino)butanoyl)oxy)-2-(hydroxymethyl)propyl (9Z,12Z)-octadeca-9,12-dienoate using trans,trans-4'-pentylbicyclohexyl-4-carboxylic Acid on a 0.10 mmol scale. Isolated 41 mg (54% yield) of the product. LCMS: calculated m/z (M+H)=744.6, found 744.8, RT=3.75 min.

Example 47: 3-(((9Z,12Z)-octadeca-9,12-dienoyl) oxy)-2-(((4-(pyrrolidin-1-yl)butanoyl)oxy)methyl) propyl 3,5-di-tert-butylbenzoate (47)

(47)

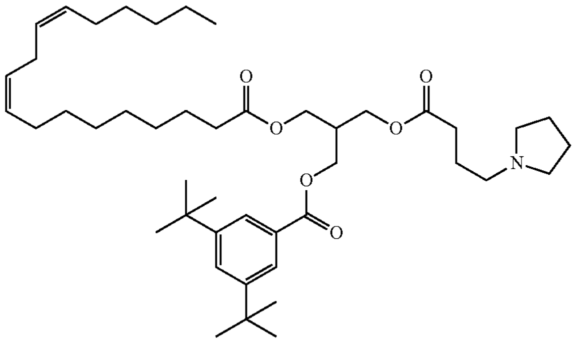

Step 1: 3-hydroxy-2-((((9Z,12Z)-octadeca-9,12-dienoyl)oxy)methyl)propyl 3,5-di-tert-butylbenzoate

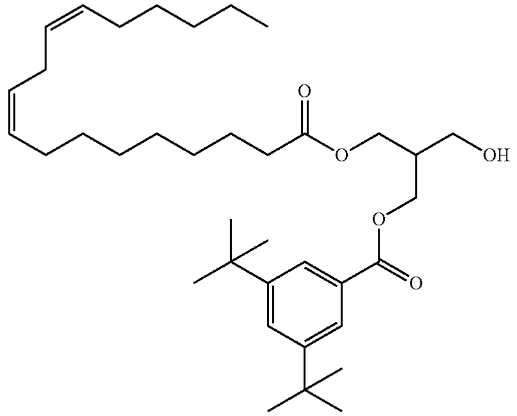 [SMILES: CCCCC/C=C\C/C=C\CCCCCCCC(=O)OCC(CO)COC(=O)c1cc(C(C)(C)C)cc(C(C)(C)C)c1]

To a solution of 3-hydroxy-2-(hydroxymethyl)propyl (9Z,12Z)-octadeca-9,12-dienoate (800 mg, 1 Eq, 2.17 mmol) in dichloromethane (5 mL) was added 3,5-di-tert-butylbenzoic acid (509 mg, 1 Eq, 2.17 mmol), DIPEA (561 mg, 0.76 mL, 2 Eq, 4.34 mmol), and DMAP (53.0 mg, 0.2 Eq, 434 μmol). Added EDC (624 mg, 1.5 Eq, 3.26 mmol) last, stirred at 23° C. for 18 h. After this time, the reaction mixture was concentrated and purified by flash column chromatography (50 g silica, 0 to 30% ethyl acetate in hexanes over 20 minutes). Obtained 3-hydroxy-2-((((9Z,12Z)-octadeca-9,12-dienoyl)oxy)methyl)propyl 3,5-di-tert-butylbenzoate (630 mg, 49.6%) as a colorless oil. $^1$H NMR (500 MHz, Chloroform-d) δ 7.88 (d, J=1.9 Hz, 2H), 7.65 (t, J=1.9 Hz, 1H), 5.43-5.30 (m, 4H), 4.45 (dd, J=6.0, 1.5 Hz, 2H), 4.33-4.22 (m, 2H), 3.70 (d, J=5.5 Hz, 2H), 2.80-2.74 (m, 2H), 2.49 (s, 1H), 2.39-2.30 (m, 3H), 2.08-2.01 (m, 5H), 1.62 (qd, J=7.5, 3.1 Hz, 2H), 1.41-1.21 (m, 31H), 0.92-0.86 (m, 3H).

Step 2: 3-(((9Z,12Z)-octadeca-9,12-dienoyl)oxy)-2-(((4-(pyrrolidin-1-yl)butanoyl)oxy)methyl)propyl 3,5-di-tert-butylbenzoate (47)

(47)

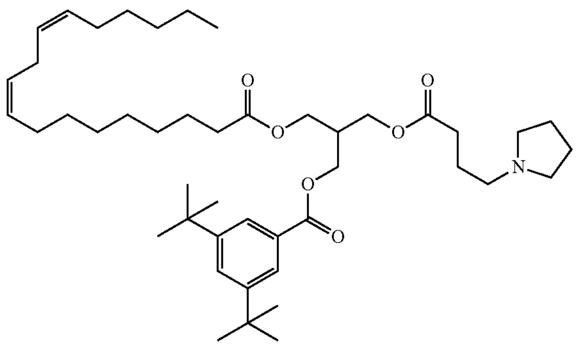

To a solution of 3-hydroxy-2-((((9Z,12Z)-octadeca-9,12-dienoyl)oxy)methyl)propyl 3,5-di-tert-butylbenzoate (50 mg, 1 Eq, 85 μmol) in dichloromethane (1 mL) was added 4-(pyrrolidin-1-yl)butanoic acid hydrochloride (17 mg, 1 Eq, 85 μmol), DIPEA (33 mg, 45 μL, 3 Eq, 0.26 mmol), and N,N-dimethylpyridin-4-amine (2.1 mg, 0.2 Eq, 17 μmol). Added EDC (33 mg, 2 Eq, 0.17 mmol) last, stirred at 23° C. for 18 h. After this time, the reaction mixture was purified directly by flash column chromatography (10 g silica, 0 to 25% methanol in dichloromethane over 12 minutes). Obtained 3-(((9Z,12Z)-octadeca-9,12-dienoyl)oxy)-2-(((4-(pyrrolidin-1-yl)butanoyl)oxy)methyl)propyl 3,5-di-tert-butylbenzoate (44 mg, 71%) as a colorless oil. $^1$H NMR (500 MHz, Chloroform-d) δ 7.90-7.84 (m, 2H), 7.65 (t, J=1.9 Hz, 1H), 5.42-5.28 (m, 4H), 4.43-4.36 (m, 2H), 4.23 (dd, J=6.0, 3.2 Hz, 4H), 2.86 (s, 4H), 2.77 (t, J=6.7 Hz, 2H), 2.57 (hept, J=6.1 Hz, 1H), 2.46 (t, J=6.9 Hz, 2H), 2.38-2.28 (m, 2H), 2.11-1.93 (m, 8H), 1.60 (q, J=7.1 Hz, 4H), 1.40-1.22 (m, 34H), 0.89 (t, J=6.9 Hz, 3H). LCMS: calculated m/z (M+H)=724.5, found 724.6, RT=3.57 min.

The following examples 48 and 49 were prepared using similar procedures as Example 47, varying the carboxylic acid building block used in the final step.

Example 48: 3-((3,5-di-tert-butylbenzoyl)oxy)-2-((((9Z,12Z)-octadeca-9,12-dienoyl)oxy)methyl)propyl 1-(pyridin-4-yl)piperidine-4-carboxylate (48)

(48)

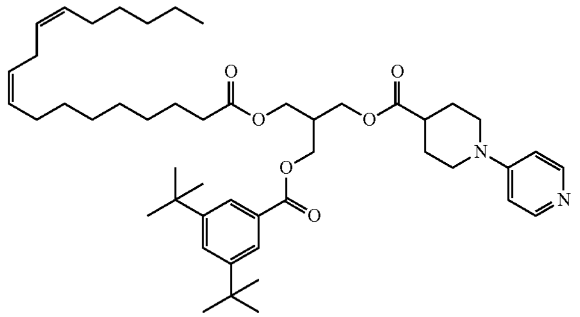

Prepared from 3-hydroxy-2-((((9Z,12Z)-octadeca-9,12-dienoyl)oxy)methyl)propyl 3,5-di-tert-butylbenzoate using 1-(pyridin-4-yl)piperidine-4-carboxylic acid on a 0.085 mmol scale. Isolated 14 mg (21% yield) of the product. LCMS: calculated m/z (M+H)=773.5, found 773.7, RT=3.61 min.

Example 49: 3-((Nα,Nα-dimethyl-L-histidyl)oxy)-2-((((9Z,12Z)-octadeca-9,12-dienoyl)oxy)methyl)propyl 3,5-di-tert-butylbenzoate (49)

(49)

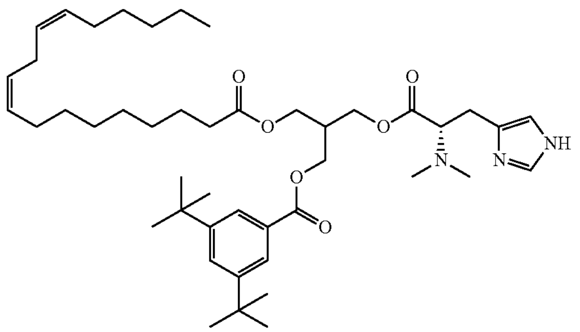

Prepared from 3-hydroxy-2-((((9Z,12Z)-octadeca-9,12-dienoyl)oxy)methyl)propyl 3,5-di-tert-butylbenzoate using Nα,Nα-dimethyl-L-histidine on a 0.085 mmol scale, using AOP instead of EDC as the coupling agent and N,N-dimethylformamide instead of dichloromethane as the solvent. Isolated 13 mg (20% yield) of the product. LCMS: calculated m/z (M+H)=750.5, found 750.6, RT=3.59 min.

Example 50: 3-(((9Z,12Z)-octadeca-9,12-dienoyl)oxy)-2-(((4-(pyrrolidin-1-yl)butanoyl)oxy)methyl)propyl (1r,1's,4R,4'R)-4'-pentyl-[1,1'-bi(cyclohexane)]-4-carboxylate (50)

(50)

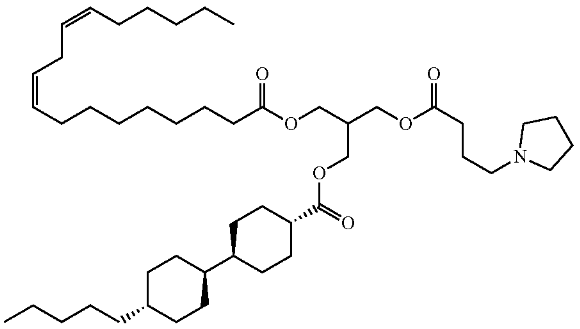

Step 1: 3-hydroxy-2-((((9Z,12Z)-octadeca-9,12-dienoyl)oxy)methyl)propyl (1r,1's,4R,4'R)-4'-pentyl-[1,1'-bi(cyclohexane)]-4-carboxylate

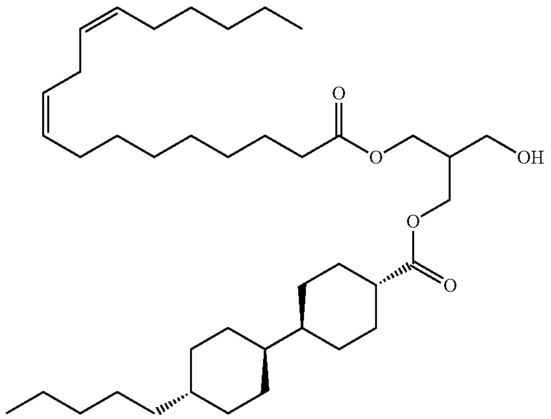 [SMILES: CCCCC/C=C\C/C=C\CCCCCCCC(=O)OCC(CO)COC(=O)[C@H]1CC[C@H]([C@H]2CC[C@H](CCCCC)CC2)CC1]

To a solution of 3-hydroxy-2-(hydroxymethyl)propyl (9Z,12Z)-octadeca-9,12-dienoate (800 mg, 1 Eq, 2.17 mmol) in dichloromethane (6 mL) was added (1r,1's,4R,4'R)-4'-pentyl-[1,1'-bi(cyclohexane)]-4-carboxylic acid (609 mg, 1 Eq, 2.17 mmol), DIPEA (561 mg, 0.76 mL, 2 Eq, 4.34 mmol), and DMAP (53.0 mg, 0.2 Eq, 434 μmol). Added EDC (624 mg, 1.5 Eq, 3.26 mmol) last, stirred at 23° C. for 18 h. After this time, the reaction mixture was concentrated and purified by flash column chromatography (50 g silica, 0 to 30% ethyl acetate in hexanes over 20 minutes). Obtained 3-hydroxy-2-((((9Z,12Z)-octadeca-9,12-dienoyl)oxy)methyl)propyl (1r,1's,4R,4'R)-4'-pentyl-[1,1'-bi(cyclohexane)]-4-carboxylate (686 mg, 50.1%) as a colorless oil. $^1$H NMR (500 MHz, Chloroform-d) δ 5.42-5.27 (m, 4H), 4.22-4.08 (m, 5H), 3.63-3.56 (m, 2H), 2.77 (dddt, J=7.8, 6.9, 1.4, 0.8 Hz, 2H), 2.35-2.28 (m, 2H), 2.27-2.14 (m, 2H), 2.08-2.01 (m, 4H), 2.01-1.94 (m, 2H), 1.81-1.56 (m, 8H), 1.44-1.16 (m, 27H), 1.16-0.92 (m, 6H), 0.92-0.80 (m, 6H).

Step 2: 3-(((9Z,12Z)-octadeca-9,12-dienoyl)oxy)-2-(((4-(pyrrolidin-1-yl)butanoyl)oxy)methyl)propyl (1r,1's,4R,4'R)-4'-pentyl-[1,1'-bi(cyclohexane)]-4-carboxylate (50)

(50)

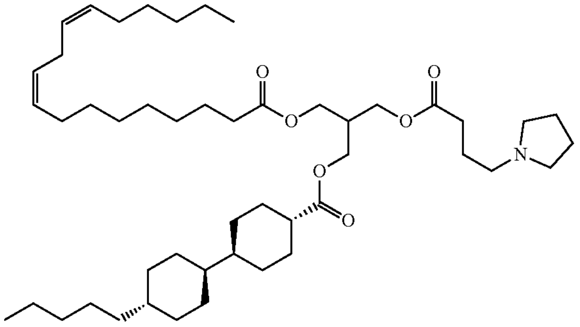

To a solution of 3-hydroxy-2-((((9Z,12Z)-octadeca-9,12-dienoyl)oxy)methyl)propyl (1r,1's,4R,4'R)-4'-pentyl-[1,1'-bi(cyclohexane)]-4-carboxylate (50 mg, 1 Eq, 79 μmol) in dichloromethane (1 mL) was added 4-(pyrrolidin-1-yl)butanoic acid hydrochloride (15 mg, 1 Eq, 79 μmol), DIPEA (31 mg, 41 μL, 3 Eq, 0.24 mmol), and DMAP (1.9 mg, 0.2 Eq, 16 μmol). Added EDC (30 mg, 2 Eq, 0.16 mmol) last, stirred at 23° C. for 18 h. After this time, the reaction mixture was purified directly by flash column chromatography (10 g silica, 0 to 25% methanol in dichloromethane over 12 minutes). Obtained 3-(((9Z,12Z)-octadeca-9,12-dienoyl)oxy)-2-(((4-(pyrrolidin-1-yl)butanoyl)oxy)methyl)propyl (1r,1's,4R,4'R)-4'-pentyl-[1,1'-bi(cyclohexane)]-4-carboxylate (41 mg, 67%) as a colorless oil. $^1$H NMR (500 MHz, Chloroform-d) δ 5.43-5.29 (m, 4H), 4.14-4.09 (m, 6H), 2.77 (t, J=6.7 Hz, 7H), 2.45-2.36 (m, 2H), 2.31 (q, J=7.5 Hz, 2H), 2.21 (tt, J=11.9, 3.5 Hz, 1H), 2.05 (q, J=6.9 Hz, 4H), 2.01-1.83 (m, 7H), 1.82-1.51 (m, 9H), 1.44-1.18 (m, 25H), 1.17-0.92 (m, 9H), 0.88 (q, J=6.8 Hz, 7H). LCMS: calculated m/z (M+H)=770.6, found 770.7, RT=4.08 min.

The following examples 51 and 52 were prepared using similar procedures as Example 50, varying the carboxylic acid building block used in the final step.

Example 51: 3-(((9Z,12Z)-octadeca-9,12-dienoyl)oxy)-2-((((1r,1's,4R,4'R)-4'-pentyl-[1,1'-bi(cyclohexane)]-4-carbonyl)oxy)methyl)propyl 1-(pyridin-4-yl)piperidine-4-carboxylate (51)

(51)

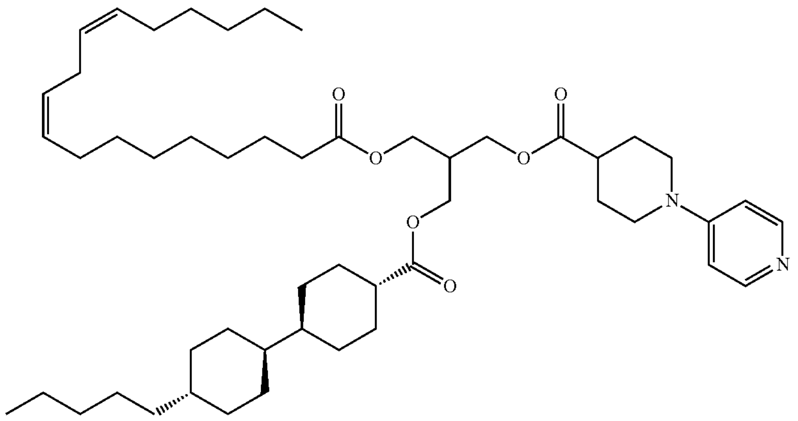

Prepared from 3-hydroxy-2-((((9Z,12Z)-octadeca-9,12-dienoyl)oxy)methyl)propyl (1r,1's,4R,4'R)-4'-pentyl-[1,1'-bi(cyclohexane)]-4-carboxylate using 1-(pyridin-4-yl)piperidine-4-carboxylic acid on a 0.079 mmol scale. Isolated 10 mg (15% yield) of the product. LCMS: calculated m/z (M+H)=819.6, found 819.7, RT=4.01 min.

Example 52: 3-((Nα,Nα-dimethyl-L-histidyl)oxy)-2-((((9Z,12Z)-octadeca-9,12-dienoyl)oxy)methyl)propyl (1S,1's,4R,4'S)-4'-pentyl-[1,1'-bi(cyclohexane)]-4-carboxylate (52)

(52)

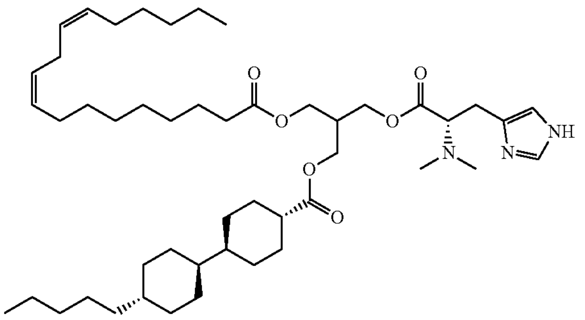

Prepared from 3-hydroxy-2-((((9Z,12Z)-octadeca-9,12-dienoyl)oxy)methyl)propyl (1r,1's,4R,4'R)-4'-pentyl-[1,1'-bi(cyclohexane)]-4-carboxylate using Nα,Nα-dimethyl-L-histidine on a 0.079 mmol scale, using AOP instead of EDC as the coupling agent and N,N-dimethylformamide instead of dichloromethane as the solvent. Isolated 2.7 mg (4% yield) of the product. LCMS: calculated m/z (M+H)=796.6, found 796.6, RT=4.30 min.

Example 53: 3-(2-((1S,2R,5R)-adamantan-2-yl)acetoxy)-2-(((4-(pyrrolidin-1-yl)butanoyl)oxy)methyl)propyl (9Z,12Z)-octadeca-9,12-dienoate (53)

(53)

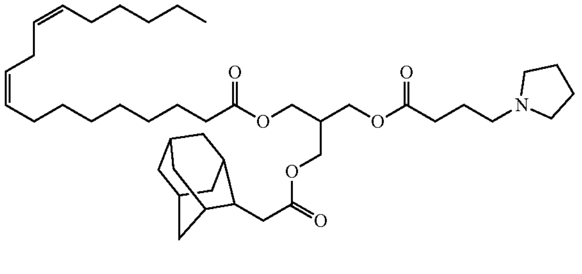

Step 1: 3-(2-((1S,2R,5R)-adamantan-2-yl)acetoxy)-2-(hydroxymethyl)propyl (9Z,12Z)-octadeca-9,12-dienoate

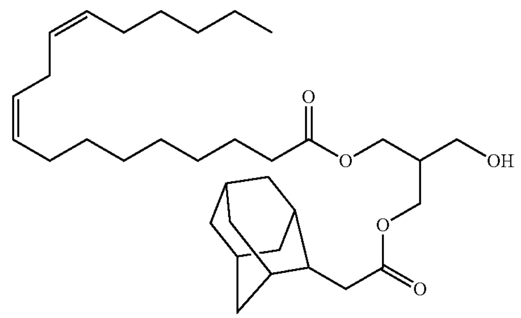 [SMILES: CCCCC/C=C\C/C=C\CCCCCCCC(=O)OCC(CO)COC(=O)CC1C2CC3CC(C2)CC1C3]

To a solution of 2-(adamantan-2-yl)acetic acid (213 mg, 1 Eq, 1.10 mmol) in dichloromethane (35 mL) was added 3-hydroxy-2-(hydroxymethyl)propyl (9Z,12Z)-octadeca-9,12-dienoate (405 mg, 1 Eq, 1.10 mmol), DIPEA (426 mg, 572 μL, 3 Eq, 3.30 mmol), and DMAP (13.4 mg, 0.1 Eq, 110 μmol). Added EDC (316 mg, 1.5 Eq, 1.65 mmol) last, stirred at 23° C. for 18 h. After this time, the reaction mixture was concentrated and purified by flash column chromatography (100 g silica, 0 to 40% ethyl acetate in hexanes over 20 minutes). Obtained 3-(2-((1r,5R,7S)-adamantan-2-yl)acetoxy)-2-(hydroxymethyl)propyl (9Z,12Z)-octadeca-9,12-dienoate (287 mg, 48.0%) as a colorless oil. $^1$H NMR (500 MHz, Chloroform-d) δ 5.43-5.28 (m, 4H), 4.23-4.12 (m, 4H), 3.64-3.58 (m, 2H), 2.77 (dddt, J=8.4, 7.0, 1.5, 0.8 Hz, 2H), 2.48 (d, J=7.6 Hz, 2H), 2.36-2.29 (m, 2H), 2.26-2.15 (m, 3H), 2.09-2.01 (m, 4H), 1.91-1.75 (m, 8H), 1.75-1.66 (m, 5H), 1.65-1.50 (m, 4H), 1.40-1.24 (m, 13H), 0.92-0.86 (m, 3H).

Step 2: 3-(2-((1S,2R,5R)-adamantan-2-yl)acetoxy)-2-(((4-(pyrrolidin-1-yl)butanoyl)oxy)methyl)propyl (9Z,12Z)-octadeca-9,12-dienoate (53)

(53)

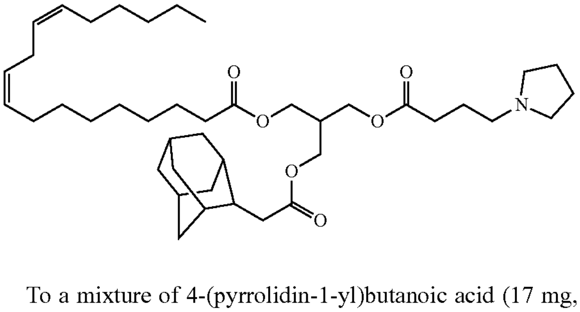

To a mixture of 4-(pyrrolidin-1-yl)butanoic acid (17 mg, 1 Eq, 0.11 mmol) in dichloromethane (1 mL) was added 3-(2-((1R,2r,3S,5r)-adamantan-2-yl)acetoxy)-2-(hydroxymethyl)propyl (9Z,12Z)-octadeca-9,12-dienoate (0.060 g, 1 Eq, 0.11 mmol), DIPEA (43 mg, 57 μL, 3 Eq, 0.33 mmol), and DMAP (2.7 mg, 0.2 Eq, 22 μmol). Added EDC (32 mg, 1.5 Eq, 0.17 mmol) last, stirred at 23° C. for 18 h. After this time, the reaction mixture was concentrated and purified by flash column chromatography (10 g silica, 0 to 10% methanol in dichloromethane over 10 minutes). Obtained 3-(2-((1S,2R,5R)-adamantan-2-yl)acetoxy)-2-(((4-(pyrrolidin-1-yl)butanoyl)oxy)methyl)propyl (9Z,12Z)-octadeca-9,12-dienoate (75 mg, 99%) as a colorless oil. $^{1}H$ NMR (500 MHz, Chloroform-d) δ 5.43-5.29 (m, 4H), 4.25-4.09 (m, 6H), 3.61 (d, J=5.6 Hz, 1H), 2.77 (t, J=6.7 Hz, 2H), 2.48 (t, J=7.8 Hz, 3H), 2.43-2.36 (m, 2H), 2.32 (dt, J=9.1, 7.5 Hz, 2H), 2.25-2.16 (m, 2H), 2.05 (q, J=7.0 Hz, 4H), 1.92-1.75 (m, 12H), 1.75-1.51 (m, 11H), 1.40-1.22 (m, 17H), 0.89 (t, J=6.9 Hz, 3H). LCMS: calculated m/z (M+H)=684.5, found 684.6, RT=3.49 min.

The following examples 54 and 55 were prepared using similar procedures as Example 53, varying the carboxylic acid building block used in the final step.

Example 54: 3-(2-((1S,2R,5R)-adamantan-2-yl)acetoxy)-2-((((9Z,12Z)-octadeca-9,12-dienoyl)oxy)methyl)propyl 1-(pyridin-4-yl)piperidine-4-carboxylate (54)

(54)

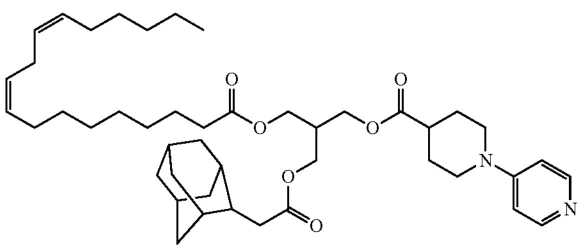

Prepared from 3-(2-((1R,2r,3S,5r)-adamantan-2-yl)acetoxy)-2-(hydroxymethyl)propyl (9Z,12Z)-octadeca-9,12-dienoate using 1-(pyridin-4-yl)piperidine-4-carboxylic acid on a 0.11 mmol scale. Isolated 40 mg (49% yield) of the product. LCMS: calculated m/z (M+H)=733.5, found 733.7, RT=3.54 min.

Example 55: 3-(2-((1S,2R,5R)-adamantan-2-yl)acetoxy)-2-(((Nα,Nα-dimethyl-L-histidyl)oxy)methyl)propyl (9Z,12Z)-octadeca-9,12-dienoate (55)

(55)

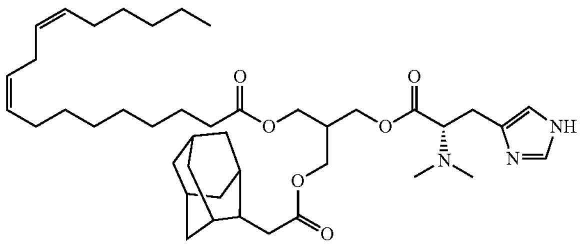

Prepared from 3-(2-((1R,2r,3S,5r)-adamantan-2-yl)acetoxy)-2-(hydroxymethyl)propyl (9Z,12Z)-octadeca-9,12-dienoate using Nα,Nα-dimethyl-L-histidine on a 0.11 mmol scale, using AOP instead of EDC as the coupling agent and N,N-dimethylformamide instead of dichloromethane as the solvent. Isolated 6 mg (8% yield) of the product. LCMS: calculated m/z (M+H)=710.5, found 710.6, RT=3.48 min.

Example 56: 3-((3-((3r,5r,7r)-adamantan-1-yl)propanoyl)oxy)-2-(((4-(pyrrolidin-1-yl)butanoyl)oxy)methyl)propyl (9Z,12Z)-octadeca-9,12-dienoate (56)

(56)

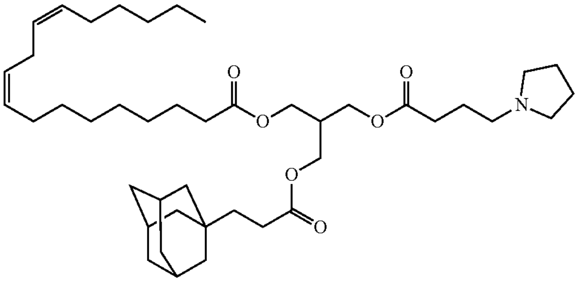

Step 1: 3-((3-((3r,5r,7r)-adamantan-1-yl)propanoyl)oxy)-2-(hydroxymethyl)propyl (9Z,12Z)-octadeca-9,12-dienoate

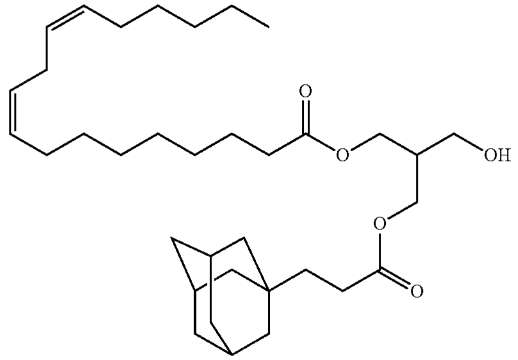 [SMILES: CCCCC/C=C\C/C=C\CCCCCCCC(=O)OCC(CO)COC(=O)CCC12CC3CC(CC(C3)C1)C2]

To a mixture of 3-(adamantan-1-yl)propanoic acid (396 mg, 1 Eq, 1.90 mmol) in dichloromethane (20 mL) was added 3-hydroxy-2-(hydroxymethyl)propyl (9Z,12Z)-octadeca-9,12-dienoate (700 mg, 1 Eq, 1.90 mmol), DIPEA (736 mg, 989 μL, 3 Eq, 5.70 mmol), and DMAP (23 mg, 0.1 Eq, 190 μmol). Added EDC (546 mg, 1.5 Eq, 2.85 mmol) last, stirred at 23° C. for 18 h. After this time, the reaction mixture was concentrated and purified by flash column chromatography (50 g silica, 0 to 40% ethyl acetate in hexanes over 16 minutes). Obtained 3-((3-((1s,3R,5S)-adamantan-1-yl)propanoyl)oxy)-2-(hydroxymethyl)propyl (9Z,12Z)-octadeca-9,12-dienoate (0.305 g, 28.7%) as a colorless oil. $^{1}H$ NMR (500 MHz, Chloroform-d) δ 5.41-5.28 (m, 4H), 4.22-4.10 (m, 4H), 3.61 (t, J=5.9 Hz, 2H), 2.76 (td, J=6.8, 1.1 Hz, 2H), 2.35-2.24 (m, 6H), 2.23-2.14 (m, 1H), 2.04 (dt, J=8.1, 6.2 Hz, 4H), 1.96-1.93 (m, 4H), 1.75-1.67 (m, 4H), 1.65-1.55 (m, 5H), 1.48-1.37 (m, 10H), 1.37-1.22 (m, 9H), 0.92-0.85 (m, 3H).

Step 2: 3-((3-((3r,5r,7r)-adamantan-1-yl)propanoyl)oxy)-2-(((4-(pyrrolidin-1-yl)butanoyl)oxy)methyl)propyl (9Z,12Z)-octadeca-9,12-dienoate (56)

(56)

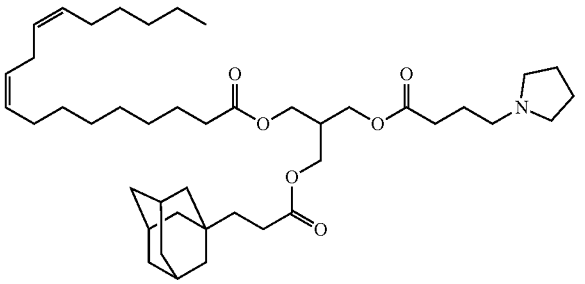

To a mixture of 4-(pyrrolidin-1-yl)butanoic acid (18 mg, 1 Eq, 0.12 mmol) in dichloromethane (20 mL) was added 3-((3-((3r,5r,7r)-adamantan-1-yl)propanoyl)oxy)-2-(hydroxymethyl)propyl (9Z,12Z)-octadeca-9,12-dienoate (0.065 g, 1 Eq, 0.12 mmol), DIPEA (45 mg, 61 μL, 3 Eq, 0.35 mmol), and DMAP (2.8 mg, 0.2 Eq, 23 μmol). Added EDC (33 mg, 1.5 Eq, 0.17 mmol) last, stirred at 23° C. for 18 h. After this time, the reaction mixture was concentrated and purified by flash column chromatography (10 g silica, 0 to 10% methanol in dichloromethane over 10 minutes). Obtained 3-((3-((3r,5r,7r)-adamantan-1-yl)propanoyl)oxy)-2-(((4-(pyrrolidin-1-yl)butanoyl)oxy)methyl)propyl (9Z,12Z)-octadeca-9,12-dienoate (70 mg, 87%) as a colorless oil. $^{1}$H NMR (500 MHz, Chloroform-d) δ 5.43-5.29 (m, 4H), 4.24-4.08 (m, 6H), 2.77 (t, J=6.7 Hz, 2H), 2.51 (d, J=18.9 Hz, 5H), 2.43-2.24 (m, 7H), 2.09-2.01 (m, 4H), 1.97-1.94 (m, 3H), 1.90-1.75 (m, 4H), 1.75-1.54 (m, 12H), 1.50-1.22 (m, 21H), 0.89 (t, J=6.9 Hz, 3H). LCMS: calculated m/z (M+H)=698.5, found 698.7, RT=3.56 min.

The following examples 57 and 58 were prepared using similar procedures as Example 56, varying the carboxylic acid building block used in the final step.

Example 57: 3-((3-((3r,5r,7r)-adamantan-1-yl)propanoyl)oxy)-2-((((9Z,12Z)-octadeca-9,12-dienoyl)oxy)methyl)propyl 1-(pyridin-4-yl)piperidine-4-carboxylate (57)

(57)

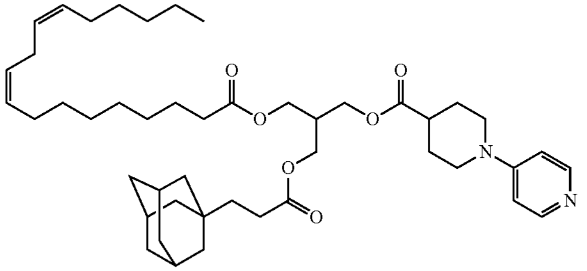

Prepared from 3-((3-((3r,5r,7r)-adamantan-1-yl)propanoyl)oxy)-2-(hydroxymethyl)propyl (9Z,12Z)-octadeca-9,12-dienoate using 1-(pyridin-4-yl)piperidine-4-carboxylic acid on a 0.11 mmol scale. Isolated 44 mg (50% yield) of the product. LCMS: calculated m/z (M+H)=747.5, found 747.7, RT=3.61 min.

Example 58: 3-((3-((3S,5S,7S)-adamantan-1-yl)propanoyl)oxy)-2-(((Nα,Nα-dimethyl-L-histidyl)oxy)methyl)propyl (9Z,12Z)-octadeca-9,12-dienoate (58)

(58)

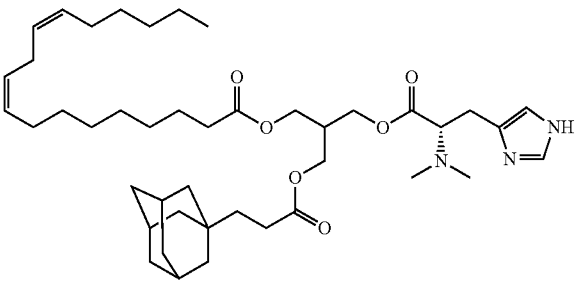

Prepared from 3-((3-((3r,5r,7r)-adamantan-1-yl)propanoyl)oxy)-2-(hydroxymethyl)propyl (9Z,12Z)-octadeca-9,12-dienoate using Nα,Nα-dimethyl-L-histidine on a 0.11 mmol scale, using AOP instead of EDC as the coupling agent and N,N-dimethylformamide instead of dichloromethane as the solvent. Isolated 12 mg (14% yield) of the product. LCMS: calculated m/z (M+H)=724.5, found 724.6, RT=3.56 min.

Example 59: 3-(2-((3r,5r,7r)-adamantan-1-yl)acetoxy)-2-((((2-(4-methylpiperazin-1-yl)ethoxy)carbonyl)oxy)methyl)propyl (9Z,12Z)-octadeca-9,12-dienoate (59)

(59)

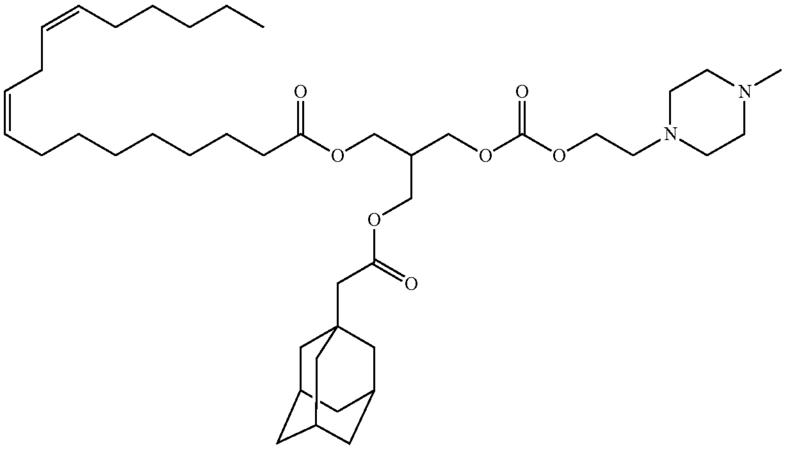

To a solution of 3-(2-((3r,5r,7r)-adamantan-1-yl)acetoxy)-2-(hydroxymethyl)propyl (9Z,12Z)-octadeca-9,12-dienoate (100 mg, 1 Eq, 184 μmol) in dichloromethane (1 mL) was added pyridine (29.0 mg, 30 μL, 2 Eq, 367 μmol), DMAP (6.73 mg, 0.3 Eq, 55.1 μmol), and 4-nitrophenyl chloroformate (74.0 mg, 2 Eq, 367 μmol). The resulting mixture was stirred for 1 h at 23° C. After this time, to it was added DIPEA (94.9 mg, 0.13 mL, 4 Eq, 734 μmol) and 2-(4-methylpiperazin-1-yl)ethan-1-ol (106 mg, 4 Eq, 734 μmol). The resulting mixture was stirred for an additional 18 h at 23° C. After this time, the reaction mixture was diluted with dichloromethane (10 mL), washed with 0.75 M aqueous sodium carbonate solution (3×10 mL), water (10 mL), and saturated aqueous sodium chloride (10 mL). The resulting organic layer was dried over sodium sulfate, concentrated, and the residue purified by flash column chromatography (10 g silica, 0 to 25% methanol in dichloromethane over 12 minutes). Obtained 3-(2-((3r,5r,7r)-adamantan-1-yl)acetoxy)-2-((((2-(4-methylpiperazin-1-yl)ethoxy)carbonyl)oxy)methyl)propyl (9Z,12Z)-octadeca-9,12-dienoate (50 mg, 38%) as a pale yellow oil. $^{1}$H NMR (500 MHz, Chloroform-d) δ 5.42-5.29 (m, 4H), 4.25 (td, 0.1=5.9, 1.2 Hz, 2H), 4.21 (dd, J=6.1, 1.1 Hz, 2H), 4.15 (dd, J=6.1, 1.2 Hz, 2H), 4.13 (dd, J=5.9, 1.2 Hz, 2H), 2.77 (t, J=6.7 Hz, 2H), 2.67 (td, J=5.9, 1.2 Hz, 2H), 2.48-2.38 (m, 1H), 2.33-2.28 (m, 5H), 2.10-2.02 (m, 6H), 1.97 (s, 4H), 1.70 (d, 0.1=12.5 Hz, 6H), 1.65-1.57 (m, 14H), 1.40-1.25 (m, 15H), 0.89 (t, J=7.1 Hz, 3H). LCMS: calculated m/z (M+H)=715.5, found 715.5, RT=3.62 min.

The following examples 60-82 were prepared using similar procedures as Example 59, varying the alcohol reactant (all intermediates described in procedures for earlier examples or prepared as shown below) and the amino alcohol building block used in the final step.

Example 60: 3-(2-((3r,5r,7r)-adamantan-1-yl)acetoxy)-2-(((((1-ethylpyrrolidin-3-yl)methoxy)carbonyl)oxy)methyl)propyl (9Z,12Z)-octadeca-9,12-dienoate (60)

(60)

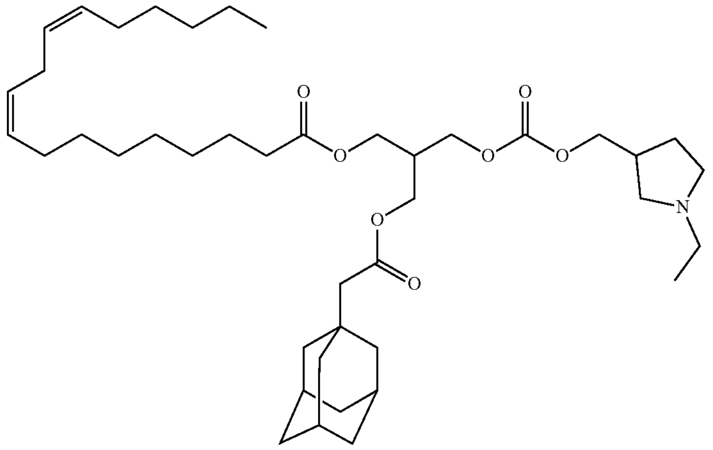

Prepared from 3-(2-((3r,5r,7r)-adamantan-1-yl)acetoxy)-2-(hydroxymethyl)propyl (9Z,12Z)-octadeca-9,12-dienoate using (1-ethylpyrrolidin-3-yl)methanol on a 0.18 mmol scale. Isolated 30 mg (23% yield) of the product. LCMS: calculated m/z (M+H)=700.5, found 700.7, RT=3.71 min.

Example 61: 3-(2-((3r,5r,7r)-adamantan-1-yl)acetoxy)-2-(((((1-isopropylpiperidin-4-yl)oxy)carbonyl)oxy)methyl)propyl (9Z,12Z)-octadeca-9,12-dienoate (61)

(61)

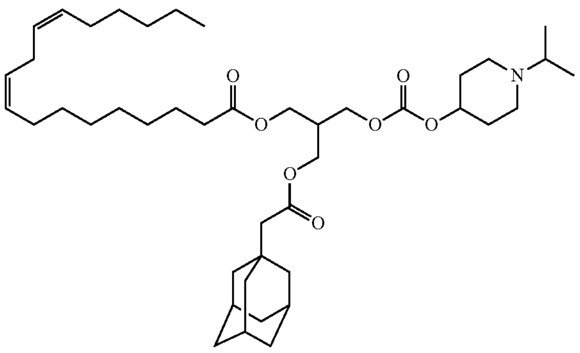

Prepared from 3-(2-((3r,5r,7r)-adamantan-1-yl)acetoxy)-2-(hydroxymethyl)propyl (9Z,12Z)-octadeca-9,12-dienoate using 1-isopropylpiperidin-4-ol on a 0.18 mmol scale. Isolated 67 mg (51% yield) of the product. LCMS: calculated m/z (M+H)=714.5, found 714.6, RT=3.64 min.

Example 62: 3-(2-((3r,5r,7r)-adamantan-1-yl)acetoxy)-2-((((3-(4-methylpiperazin-1-yl)propoxy)carbonyl)oxy)methyl)propyl (9Z,12Z)-octadeca-9,12-dienoate (62)

(62)

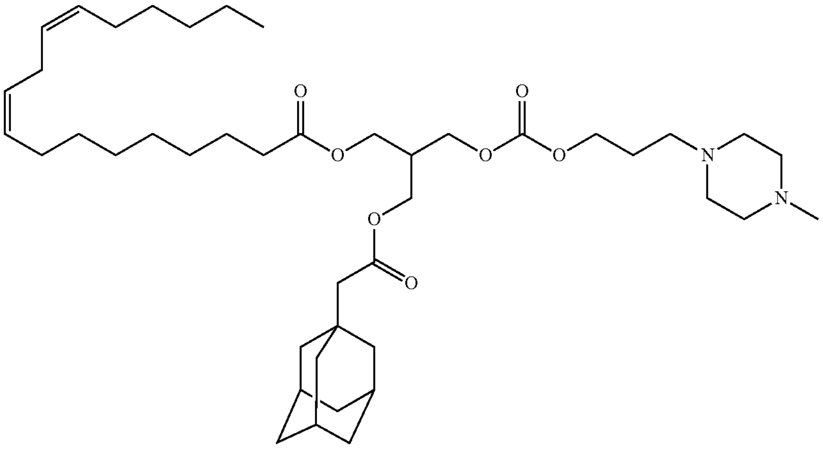

Prepared from 3-(2-((3r,5r,7r)-adamantan-1-yl)acetoxy)-2-(hydroxymethyl)propyl (9Z,12Z)-octadeca-9,12-dienoate using 3-(4-methylpiperazin-1-yl)propan-1-ol on a 0.18 mmol scale. Isolated 59 mg (44% yield) of the product. LCMS: calculated m/z (M+H)=729.5, found 729.4, RT=3.69 min.

Example 63: 3-(2-((3r,5r,7r)-adamantan-1-yl)acetoxy)-2-(((((1-ethylpiperidin-3-yl)oxy)carbonyl)oxy)methyl)propyl (9Z,12Z)-octadeca-9,12-dienoate (63)

(63)

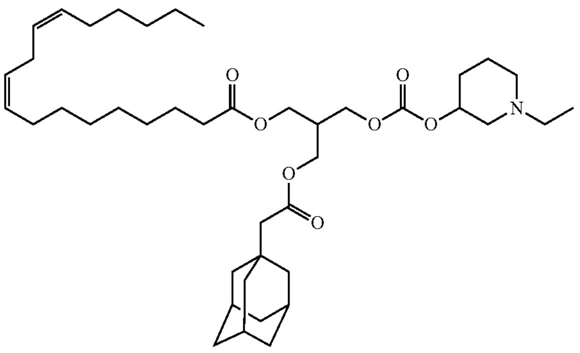

Prepared from 3-(2-((3r,5r,7r)-adamantan-1-yl)acetoxy)-2-(hydroxymethyl)propyl (9Z,12Z)-octadeca-9,12-dienoate using 1-ethylpiperidin-3-ol on a 0.18 mmol scale. Isolated 50 mg (39% yield) of the product. LCMS: calculated m/z (M+H)=700.5, found 700.8, RT=3.58 min.

Example 64: 3-(2-((3r,5r,7r)-adamantan-1-yl)acetoxy)-2-((((2-(1-methylpyrrolidin-2-yl)ethoxy)carbonyl)oxy)methyl)propyl (9Z,12Z)-octadeca-9,12-dienoate (64)

(64)

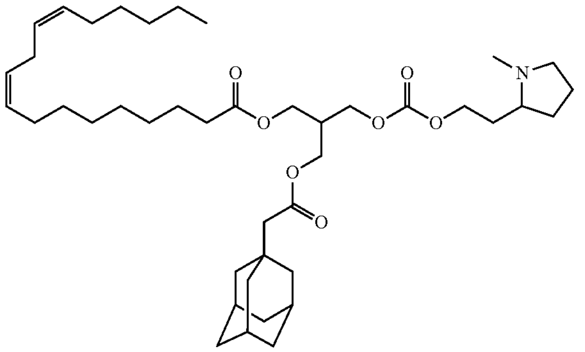

Prepared from 3-(2-((3r,5r,7r)-adamantan-1-yl)acetoxy)-2-(hydroxymethyl)propyl (9Z,12Z)-octadeca-9,12-dienoate using 2-(1-methylpyrrolidin-2-yl)ethan-1-ol on a 0.18 mmol scale. Isolated 44 mg (34% yield) of the product. LCMS: calculated m/z (M+H)=700.5, found 700.2, RT=3.63 min.

Example 65: 3-(2-((3r,5r,7r)-adamantan-1-yl)acetoxy)-2-((((4-(dimethylamino)butoxy)carbonyl)oxy)methyl)propyl (9Z,12Z)-octadeca-9,12-dienoate (65)

(65)

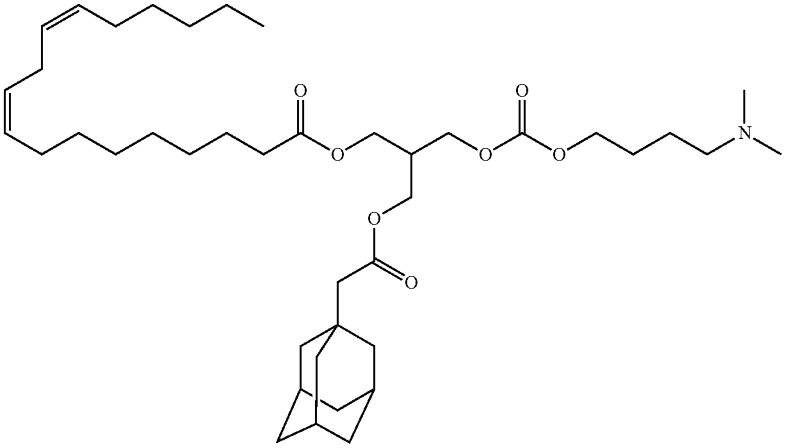

Prepared from 3-(2-((3r,5r,7r)-adamantan-1-yl)acetoxy)-2-(hydroxymethyl)propyl (9Z,12Z)-octadeca-9,12-dienoate using 4-(dimethylamino)butan-1-ol on a 0.18 mmol scale. Isolated 37 mg (29% yield) of the product. LCMS: calculated m/z (M+H)=688.5, found 688.3, RT=3.62 min.-

Example 66: 13-((2-((3r,5r,7r)-adamantan-1-yl)acetoxy)methyl)-2,5-dimethyl-10-oxo-9,11-dioxa-2,5-diazatetradecan-14-yl (9Z,12Z)-octadeca-9,12-dienoate (66)

(66)

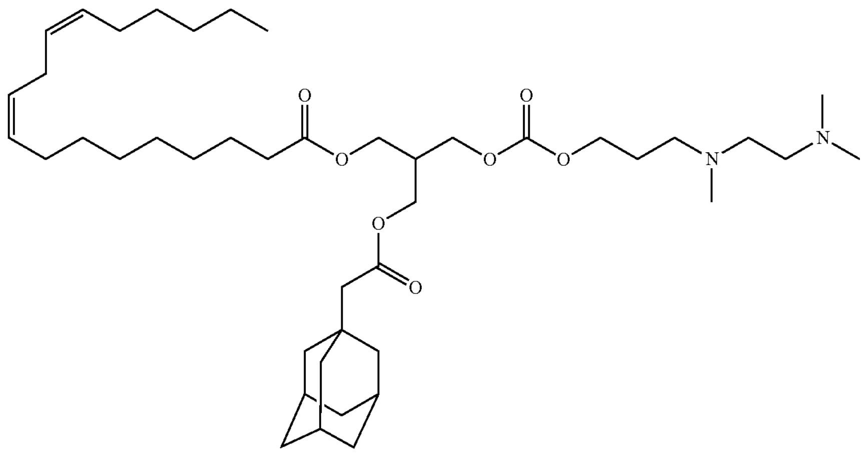

Prepared from 3-(2-((3r,5r,7r)-adamantan-1-yl)acetoxy)-2-(hydroxymethyl)propyl (9Z,2Z)-octadeca-9,12-dienoate using 3-((2-(dimethylamino)ethyl)(methyl)amino)propan-1-ol on a 0.18 mmol scale. Isolated 32 mg (24% yield) of the product. LCMS: calculated m/z (M+H)=731.5, found 731.5, RT=3.59 min.

Example 67: 3-(((3-(diethylamino)propoxy)carbonyl)oxy)-2-((((9Z,12Z)-octadeca-9,12-dienoyl)oxy)methyl)propyl 3,5-di-tert-butylbenzoate (67)

(67)

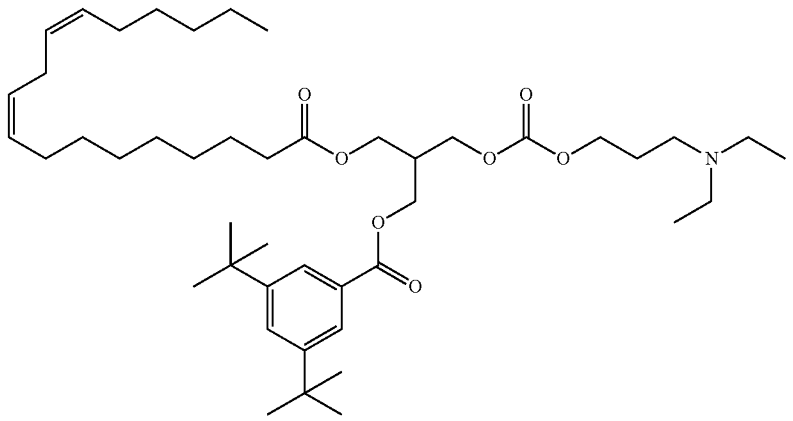

Prepared from 3-hydroxy-2-((((9Z,12Z)-octadeca-9,12-dienoyl)oxy)methyl)propyl 3,5-di-tert-butylbenzoate using 3-(diethylamino)-1-propanol on a 0.17 mmol scale. Isolated 95 mg (75% yield) of the product. LCMS: calculated m/z (M+H)=742.6, found 742.7, RT=3.60 min.

Example 68: 3-(((3-(diethylamino)propoxy)carbonyl)oxy)-2-((((9Z,12Z)-octadeca-9,12-dienoyl)oxy)methyl)propyl (1r,1's,4R,4'R)-4'-pentyl-[1,1'-bi(cyclohexane)]-4-carboxylate (68)

-

(68)

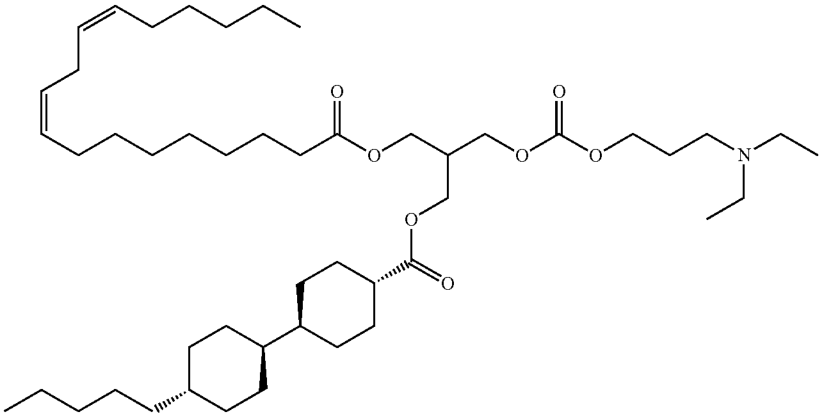

Prepared from 3-hydroxy-2-((((9Z,12Z)-octadeca-9,12-dienoyl)oxy)methyl)propyl (1r,1's,4R,4'R)-4'-pentyl-[1,1'-bi(cyclohexane)]-4-carboxylate using 3-(diethylamino)-1-propanol on a 0.16 mmol scale. Isolated 98 mg (78% yield) of the product. LCMS: calculated m/z (M+H)=788.6, found 788.7, RT=4.05 min.

Example 69: 3-(2-((1r,3r)-adamantan-2-yl)acetoxy)-2-((((3-(diethylamino)propoxy)carbonyl)oxy)methyl)propyl (9Z,12Z)-octadeca-9,12-dienoate (69)

(69)

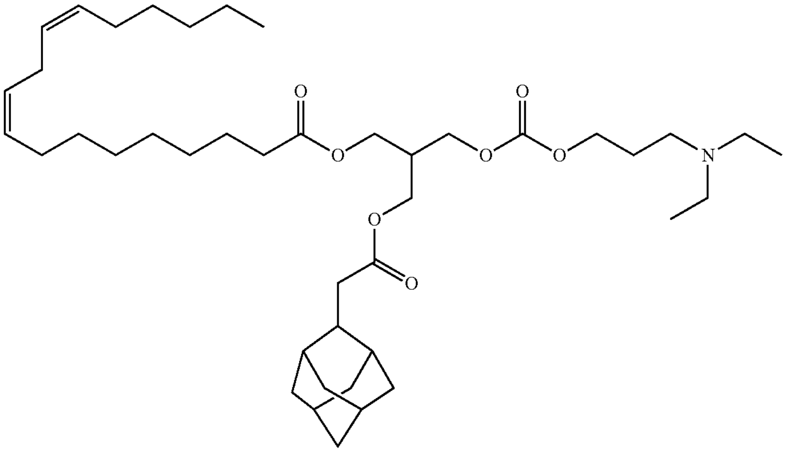

Prepared from 3-(2-((1S,2R,5R)-adamantan-2-yl)acetoxy)-2-(hydroxymethyl)propyl (9Z,12Z)-octadeca-9,12-dienoate using 3-(diethylamino)-1-propanol on a 0.09 mmol scale. Isolated 53 mg (82% yield) of the product. LCMS: calculated m/z (M+H)=702.5, found 702.6, RT=3.50 min.

Example 70: 3-((3-((1r,3s)-adamantan-1-yl)propanoyl)oxy)-2-((((3-(diethylamino)propoxy)carbonyl)oxy)methyl)propyl (9Z,12Z)-octadeca-9,12-dienoate (70)

(70)

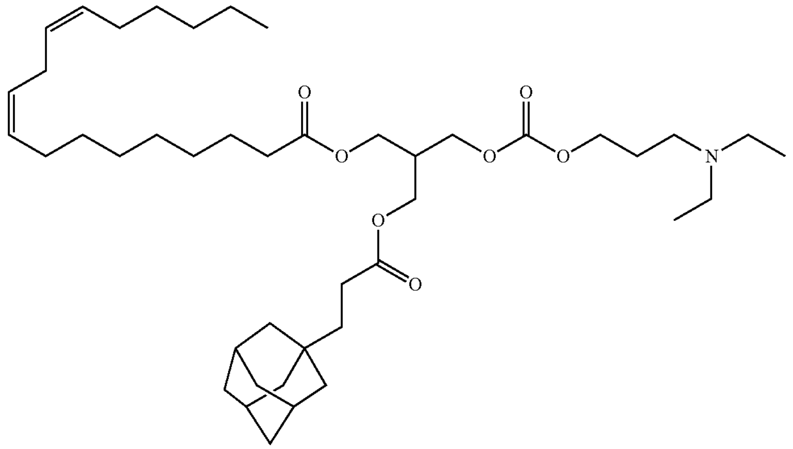

Prepared from 3-(2-((1S,2R,5R)-adamantan-2-yl)acetoxy)-2-(hydroxymethyl)propyl (9Z,12Z)-octadeca-9,12-dienoate using 3-(diethylamino)-1-propanol on a 0.09 mmol scale. Isolated 50 mg (78% yield) of the product. LCMS: calculated m/z (M+H)=716.5, found 716.6, RT=3.59 min.

Example 71: 3-(2-((3r,5r,7r)-adamantan-1-yl)acetoxy)-2-(((((1-ethylpiperidin-3-yl)methoxy)carbonyl)oxy)methyl)propyl (9Z,12Z)-octadeca-9,12-dienoate (71)

(71)

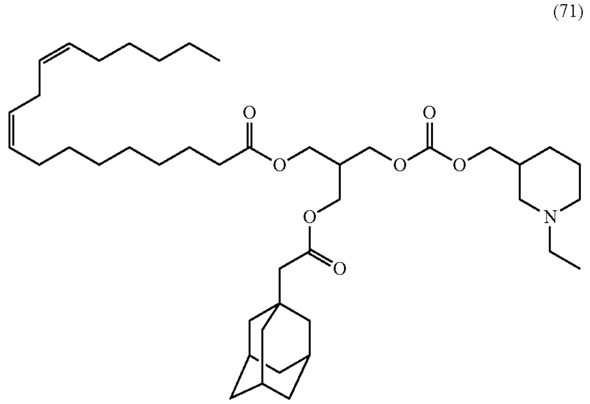 [SMILES: CCCCC/C=C\C/C=C\CCCCCCCC(=O)OCC(COC(=O)CC12CC3CC(CC(C3)C1)C2)COC(=O)OCC1CCCN(CC)C1]

Prepared from 3-(2-((3r,5r,7r)-adamantan-1-yl)acetoxy)-2-(hydroxymethyl)propyl (9Z,12Z)-octadeca-9,12-dienoate using (1-ethylpiperidin-3-yl)methanol on a 0.70 mmol scale. Isolated 163 mg (33% yield) of the product. LCMS: calculated m/z (M+H)=714.5, found 714.5, RT=3.50 min.

Example 72: 3-(2-((1r,3r)-adamantan-2-yl)acetoxy)-2-(((((1-ethylpiperidin-3-yl)methoxy)carbonyl)oxy)methyl)propyl (9Z,12Z)-octadeca-9,12-dienoate (72)

(72)

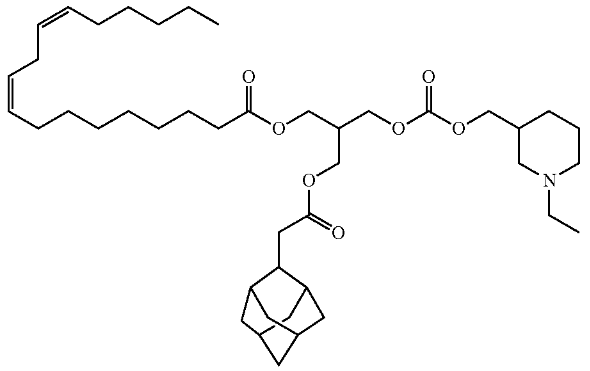

Prepared from 3-(2-((1S,2R,5R)-adamantan-2-yl)acetoxy)-2-(hydroxymethyl)propyl (9Z,12Z)-octadeca-9,12-dienoate using (1-ethylpiperidin-3-yl)methanol on a 0.59 mmol scale. Isolated 238 mg (56% yield) of the product. LCMS: calculated m/z (M+H)=714.5, found 714.5, RT=3.46 min.

Example 73: 3-((3-((1r,3s)-adamantan-1-yl)propanoyl)oxy)-2-(((((1-ethylpiperidin-3-yl)methoxy)carbonyl)oxy)methyl)propyl (9Z,12Z)-octadeca-9,12-dienoate (73)

(73)

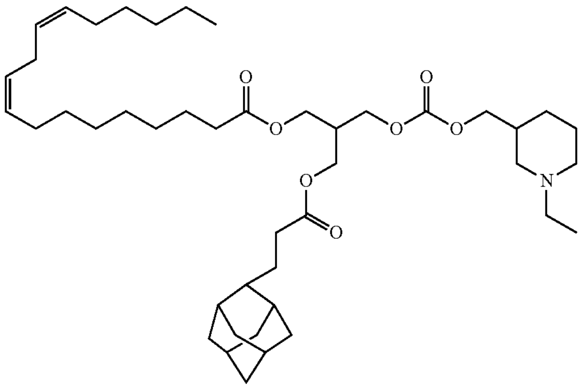

Prepared from 3-(2-((1S,2R,5R)-adamantan-2-yl)acetoxy)-2-(hydroxymethyl)propyl (9Z,12Z)-octadeca-9,12-dienoate using (1-ethylpiperidin-3-yl)methanol on a 0.36 mmol scale. Isolated 207 mg (79% yield) of the product. LCMS: calculated m/z (M+H)=728.5, found 728.7, RT=3.52 min.

Example 74: 3-((((1-ethylpiperidin-3-yl)methoxy)carbonyl)oxy)-2-((((9Z,12Z)-octadeca-9,12-dienoyl)oxy)methyl)propyl (1r,1's,4R,4'R)-4'-pentyl-[1,1'-bi(cyclohexane)]-4-carboxylate (74)

(74)

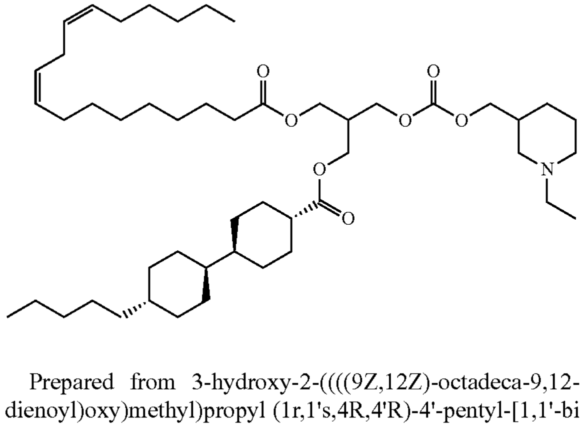

Prepared from 3-hydroxy-2-((((9Z,12Z)-octadeca-9,12-dienoyl)oxy)methyl)propyl (1r,1's,4R,4'R)-4'-pentyl-[1,1'-bi(cyclohexane)]-4-carboxylate using (1-ethylpiperidin-3-yl)methanol on a 0.32 mmol scale. Isolated 186 mg (73% yield) of the product. LCMS: calculated m/z (M+H)=800.6, found 800.8, RT=4.24 min.

Example 75: 2-((((3-(diethylamino)propoxy)carbonyl)oxy)methyl)propane-1,3-diyl bis(2-((3r,5r,7r)-adamantan-1-yl)acetate) (75)

(75)

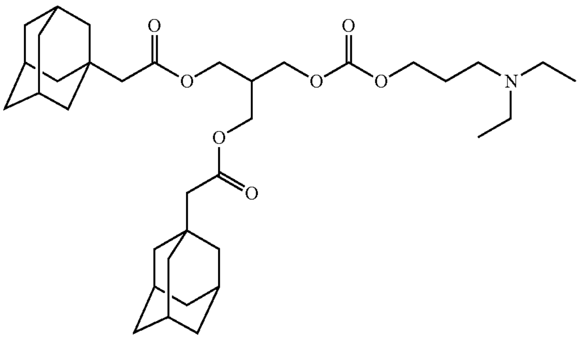

Step 1: 2-(hydroxymethyl)propane-1,3-diyl bis(2-((3r,5r,7r)-adamantan-1-yl)acetate)

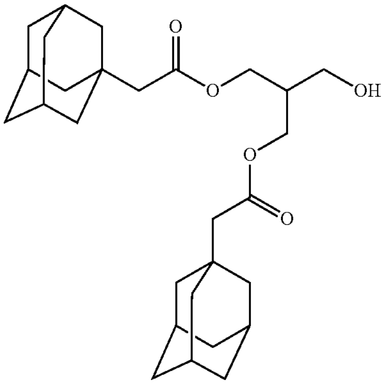 [SMILES: O=C(CC12CC3CC(CC(C3)C1)C2)OCC(CO)COC(=O)CC12CC3CC(CC(C3)C1)C2]

To a solution of trimethylolmethane (5.00 g, 1 Eq, 47.1 mmol) in dichloromethane (125 mL) and tetrahydrofuran (125 mL) was added 1-adamantaneacetic acid (9.15 g, 1 Eq, 47.1 mmol), DIPEA (9.13 g, 12.3 mL, 1.5 Eq, 70.7 mmol), and DMAP (576 mg, 0.1 Eq, 4.71 mmol). Added EDC (9.94 g, 1.1 Eq, 51.8 mmol) last, stirred at 23° C. for 18 h. Concentrated by rotary evaporation, then added 5% aqueous citric acid (250 mL), extracted with ethyl acetate (200 mL×2). Washed combined organics with 5% citric acid, water, and brine. Dried over sodium sulfate and concentrated. The crude residue was purified by flash column chromatography (200 g silica, 0 to 90% ethyl acetate in hexanes over 25 minutes). Obtained 2-(hydroxymethyl)propane-1,3-diyl bis(2-((3r,5r,7r)-adamantan-1-yl)acetate) (5.1 g, 24%) as a colorless oil.

Step 2: 2-(((((1-ethylpiperidin-3-yl)methoxy)carbonyl)oxy)methyl)propane-1,3-diyl bis(2-((3r,5r,7r)-adamantan-1-yl)acetate) (75)

Prepared from 2-(hydroxymethyl)propane-1,3-diyl bis(2-((3r,5r,7r)-adamantan-1-yl)acetate) using 3-(diethylamino)-1-propanol on a 0.11 mmol scale. Isolated 31 mg (46% yield) of the product. LCMS: calculated m/z (M+H)=616.4, found 616.6, RT=2.94 min.

Example 76: 3-(((3-(diethylamino)propoxy)carbonyl)oxy)-2-((((9Z,12Z)-octadeca-9,12-dienoyl)oxy)methyl)propyl (1r,1'r,4R,4'R)-4'-ethyl-[1,1'-bi(cyclohexane)]-4-carboxylate (76)

-

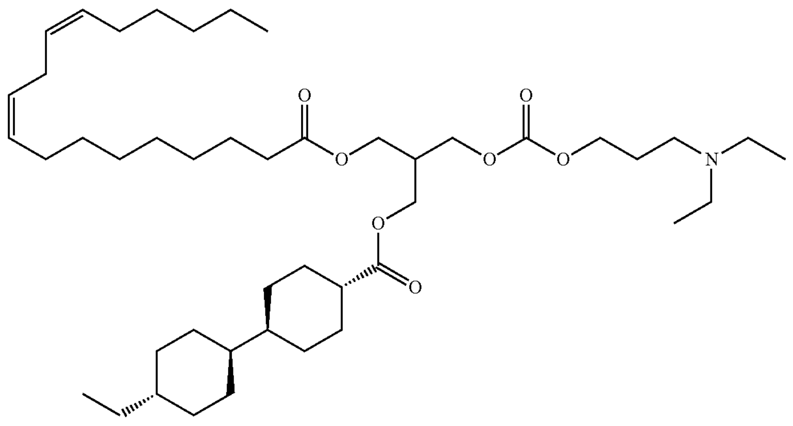

(76)

Step 1: 3-hydroxy-2-((((9Z,12Z)-octadeca-9,12-dienoyl)oxy)methyl)propyl (1r,1'r,4R,4'R)-4'-ethyl-[1,1'-bi(cyclohexane)]-4-carboxylate

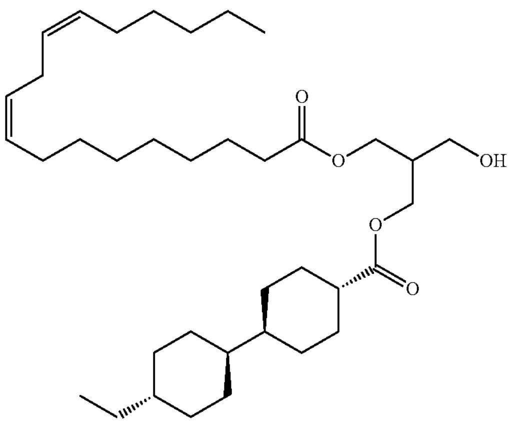 [SMILES: CCCCC/C=C\C/C=C\CCCCCCCC(=O)OCC(CO)COC(=O)[C@H]1CC[C@H]([C@H]2CC[C@H](CC)CC2)CC1]

Prepared from 3-hydroxy-2-(hydroxymethyl)propyl (9Z,12Z)-octadeca-9,12-dienoate using trans,trans-4'-ethyl-[1,1'-bi(cyclohexane)]-4-carboxylic acid on a 0.53 mmol scale. Isolated 161 mg (51% yield).

Step 2: 3-(((3-(diethylamino)propoxy)carbonyl)oxy)-2-((((9Z,12Z)-octadeca-9,12-dienoyl)oxy)methyl)propyl (1r,1'r,4R,4'R)-4'-ethyl-[1,1'-bi(cyclohexane)]-4-carboxylate (76)

Prepared from 3-hydroxy-2-((((9Z,12Z)-octadeca-9,12-dienoyl)oxy)methyl)propyl (1r,1'r,4R,4'R)-4'-ethyl-[1,1'-bi(cyclohexane)]-4-carboxylate using 3-(diethylamino)-1-propanol on a 0.27 mmol scale. Isolated 178 mg (87% yield) of the product. LCMS: calculated m/z (M+H)=746.6, found 746.7, RT=3.92 min.

(77)

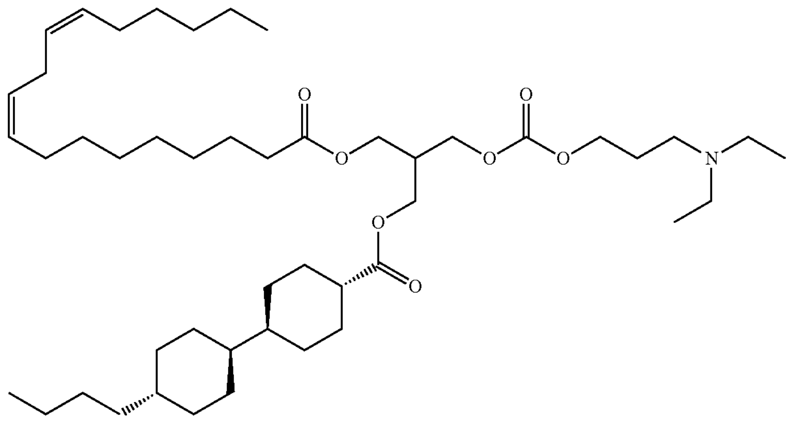

Step 1: 3-hydroxy-2-((((9Z,12Z)-octadeca-9,12-dienoyl)oxy)methyl)propyl (1r,1's,4R,4'R)-4'-butyl-[1,1'-bi(cyclohexane)]-4-carboxylate

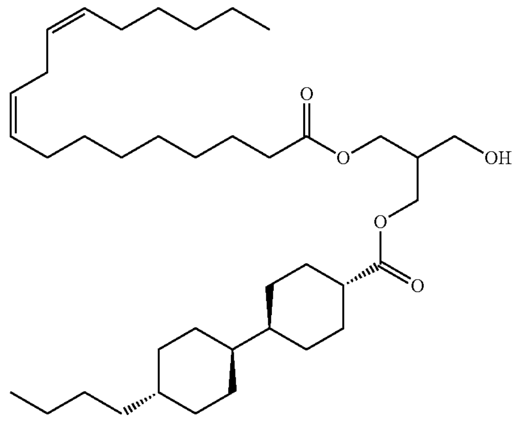 [SMILES: CCCCC/C=C\C/C=C\CCCCCCCC(=O)OCC(CO)COC(=O)[C@H]1CC[C@H]([C@H]2CC[C@H](CCCC)CC2)CC1]

Prepared from 3-hydroxy-2-(hydroxymethyl)propyl (9Z,12Z)-octadeca-9,12-dienoate using trans,trans-4'-butyl-[1,1'-bi(cyclohexane)]-4-carboxylic acid on a 0.54 mmol scale. Isolated 159 mg (48% yield).

Step 2: 3-(((3-(diethylamino)propoxy)carbonyl)oxy)-2-((((9Z,12Z)-octadeca-9,12-dienoyl)oxy)methyl)propyl (1r,1's,4R,4'R)-4'-butyl-[1,1'-bi(cyclohexane)]-4-carboxylate (77)

Prepared from 3-hydroxy-2-((((9Z,12Z)-octadeca-9,12-dienoyl)oxy)methyl)propyl (1r,1's,4R,4'R)-4'-butyl-[1,1'-bi(cyclohexane)]-4-carboxylate using 3-(diethylamino)-1-propanol on a 0.26 mmol scale. Isolated 153 mg (77% yield) of the product. LCMS: calculated m/z (M+H)=774.6, found 774.7, RT=4.02 min.

Example 78: 3-((5-cyclohexylpentanoyl)oxy)-2-((((3-(diethylamino)propoxy)carbonyl)oxy)methyl)propyl (9Z,12Z)-octadeca-9,12-dienoate (78)

(78)

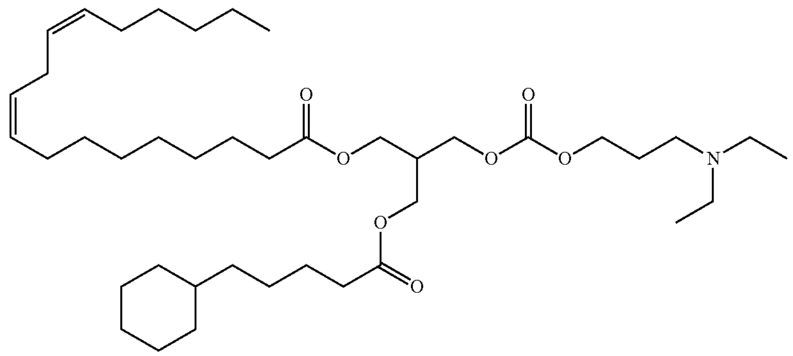

Step 1: 3-((5-cyclohexylpentanoyl)oxy)-2-(hydroxymethyl)propyl (9Z,12Z)-octadeca-9,12-dienoate

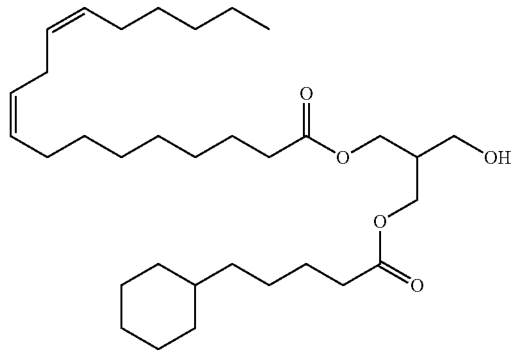 [SMILES: CCCCC/C=C\C/C=C\CCCCCCCC(=O)OCC(CO)COC(=O)CCCCC1CCCCC1]

Prepared from 3-hydroxy-2-(hydroxymethyl)propyl (9Z, 12Z)-octadeca-9,12-dienoate using 5-cyclohexylpentanoic acid on a 0.54 mmol scale. Isolated 140 mg (48% yield).

Step 2: 3-((5-cyclohexylpentanoyl)oxy)-2-((((3-(diethylamino)propoxy)carbonyl)oxy)methyl)propyl (9Z,12Z)-octadeca-9,12-dienoate (78)

Prepared from 3-((5-cyclohexylpentanoyl)oxy)-2-(hydroxymethyl)propyl (9Z,12Z)-octadeca-9,12-dienoate using 3-(diethylamino)-1-propanol on a 0.26 mmol scale. Isolated 155 mg (86% yield) of the product. LCMS: calculated m/z (M+H)=692.5, found 692.7, RT=3.48 min.

Example 79: 3-(((3-(diethylamino)propoxy)carbonyl)oxy)-2-((((9Z,12Z)-octadeca-9,12-dienoyl)oxy)methyl)propyl 4-propylcyclohexane-1-carboxylate (79)

Step 1: 3-hydroxy-2-((((9Z,12Z)-octadeca-9,12-dienoyl)oxy)methyl)propyl 4-propylcyclohexane-1-carboxylate

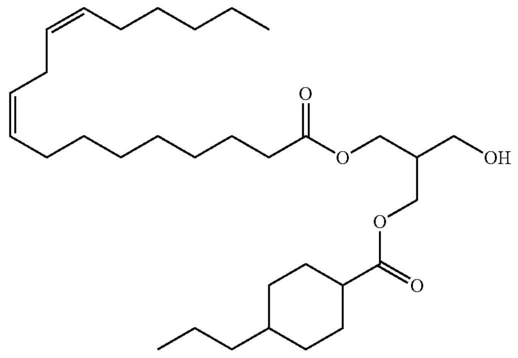 [SMILES: CCCCC/C=C\C/C=C\CCCCCCCC(=O)OCC(CO)COC(=O)C1CCC(CCC)CC1]

Prepared from 3-hydroxy-2-(hydroxymethyl)propyl (9Z, 12Z)-octadeca-9,12-dienoate using 4-propylcyclohexane-1-carboxylic acid on a 0.54 mmol scale. Isolated 142 mg (50% yield).

Step 2: 3-(((3-(diethylamino)propoxy)carbonyl)oxy)-2-((((9Z,12Z)-octadeca-9,12-dienoyl)oxy)methyl)propyl 4-propylcyclohexane-1-carboxylate (79)

Prepared from 3-hydroxy-2-((((9Z,12Z)-octadeca-9,12-dienoyl)oxy)methyl)propyl 4-propylcyclohexane-1-carboxylate using 3-(diethylamino)-1-propanol on a 0.27 mmol scale. Isolated 108 mg (58% yield) of the product. LCMS: calculated m/z (M+H)=678.5, found 678.7, RT=3.38 min.

(79)

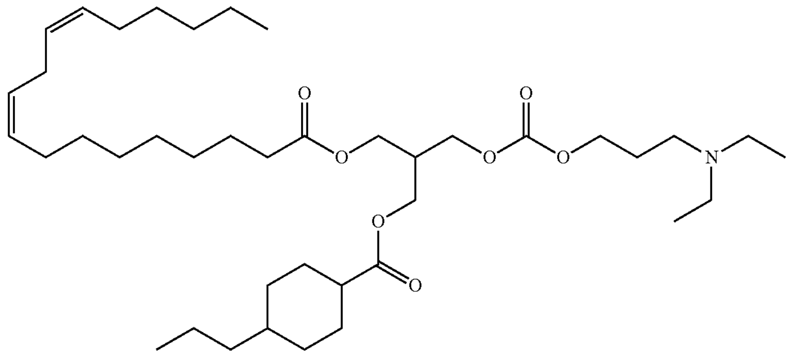

Example 80: 3-(((3-(diethylamino)propoxy)carbonyl)oxy)-2-((((9Z,12Z)-octadeca-9,12-dienoyl)oxy)methyl)propyl 4-butylcyclohexane-1-carboxylate (80)

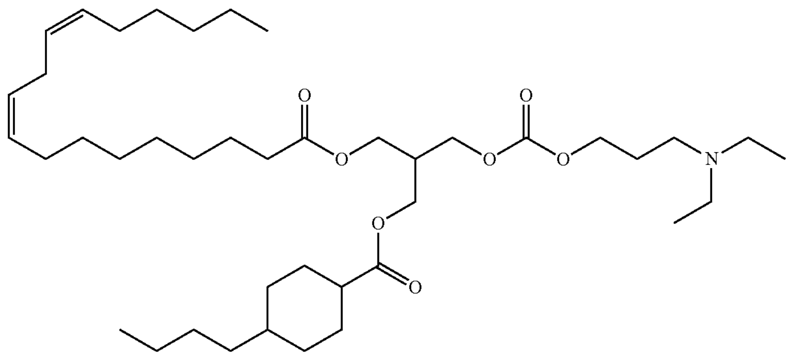

(80)

Step 1: 3-hydroxy-2-((((9Z,12Z)-octadeca-9,12-dienoyl)oxy)methyl)propyl 4-butylcyclohexane-1-carboxylate

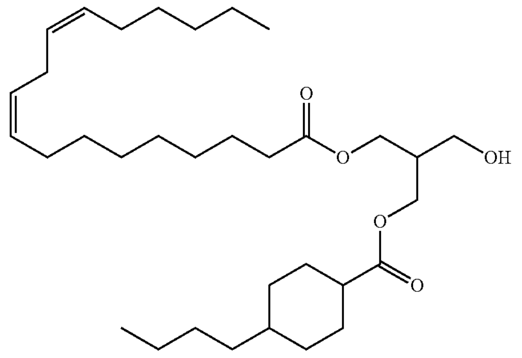 [SMILES: CCCCC/C=C\C/C=C\CCCCCCCC(=O)OCC(CO)COC(=O)C1CCC(CCCC)CC1]

Prepared from 3-hydroxy-2-(hydroxymethyl)propyl (9Z,12Z)-octadeca-9,12-dienoate using 4-butylcyclohexane-1-carboxylic acid on a 0.54 mmol scale. Isolated 142 mg (49% yield).

Step 2: 3-(((3-(diethylamino)propoxy)carbonyl)oxy)-2-((((9Z,12Z)-octadeca-9,12-dienoyl)oxy)methyl)propyl 4-butylcyclohexane-1-carboxylate (80)

Prepared from 3-hydroxy-2-((((9Z,12Z)-octadeca-9,12-dienoyl)oxy)methyl)propyl 4-butylcyclohexane-1-carboxylate using 3-(diethylamino)-1-propanol on a 0.27 mmol scale. Isolated 111 mg (60% yield) of the product. LCMS: calculated m/z (M+H)=692.5, found 692.7, RT=3.48 min.

Example 81: 3-(((3-(diethylamino)propoxy)carbonyl)oxy)-2-((((9Z,12Z)-octadeca-9,12-dienoyl)oxy)methyl)propyl 4-(tert-butyl)cyclohexane-1-carboxylate (81)

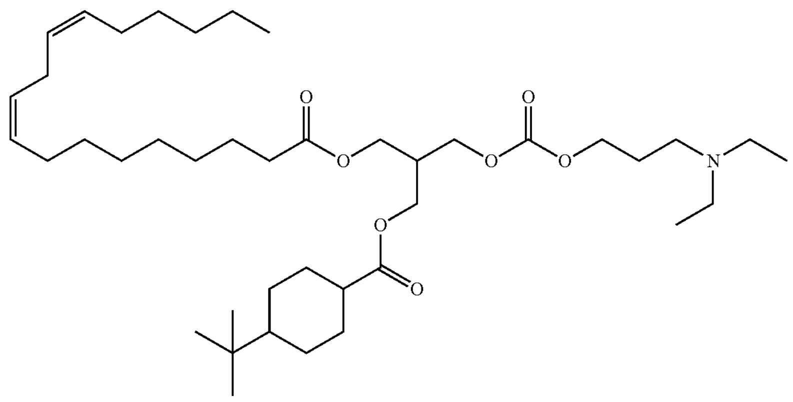

(81)

Step 1: 3-hydroxy-2-((((9Z,12Z)-octadeca-9,12-dienoyl)oxy)methyl)propyl 4-(tert-butyl)cyclohexane-1-carboxylate Prepared from 3-hydroxy-2-(hydroxymethyl)propyl (9Z,12Z)-octadeca-9,12-dienoate using 4-tert-butylcyclohexane-1-carboxylic acid on a 0.54 mmol scale. Isolated 151 mg (52% yield).

Step 2: 3-(((3-(diethylamino)propoxy)carbonyl)oxy)-2-((((9Z,12Z)-octadeca-9,12-dienoyl)oxy)methyl)propyl 4-(tert-butyl)cyclohexane-1-carboxylate (81)

Prepared from 3-hydroxy-2-((((9Z,12Z)-octadeca-9,12-dienoyl)oxy)methyl)propyl 4-(tert-butyl)cyclohexane-1-carboxylate using 3-(diethylamino)-1-propanol on a 0.28 mmol scale. Isolated 123 mg (63% yield) of the product. LCMS: calculated m/z (M+H)=692.5, found 692.7, RT=3.43 min.

Example 82: 3-(((3-(diethylamino)propoxy)carbonyl)oxy)-2-((((9Z,12Z)-octadeca-9,12-dienoyl)oxy)methyl)propyl 4-pentylcyclohexane-1-carboxylate (82)

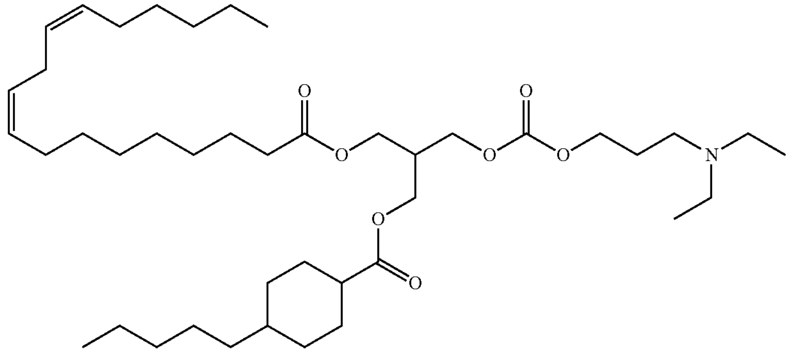

(82)

Step 1: 3-hydroxy-2-((((9Z,12Z)-octadeca-9,12-dienoyl)oxy)methyl)propyl 4-pentylcyclohexane-1-carboxylate

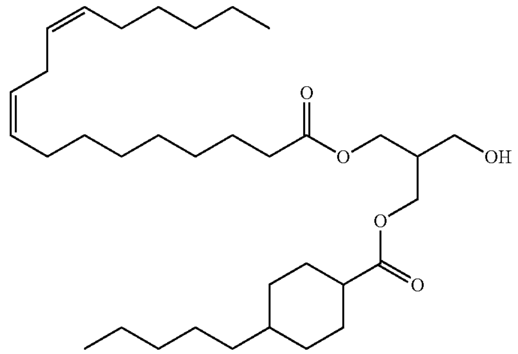 [SMILES: CCCCC/C=C\C/C=C\CCCCCCCC(=O)OCC(CO)COC(=O)C1CCC(CCCCC)CC1]

Prepared from 3-hydroxy-2-(hydroxymethyl)propyl (9Z,12Z)-octadeca-9,12-dienoate using 4-pentylcyclohexane-1-carboxylic acid on a 0.54 mmol scale. Isolated 139 mg (47% yield).

Step 2: 3-(((3-(diethylamino)propoxy)carbonyl)oxy)-2-((((9Z,12Z)-octadeca-9,12-dienoyl)oxy)methyl)propyl 4-pentylcyclohexane-1-carboxylate (82)

Prepared from 3-hydroxy-2-((((9Z,12Z)-octadeca-9,12-dienoyl)oxy)methyl)propyl 4-pentylcyclohexane-1-carboxylate using 3-(diethylamino)-1-propanol on a 0.25 mmol scale. Isolated 106 mg (59% yield) of the product. LCMS: calculated m/z (M+H)=706.6, found 706.72, RT=3.55 min.

Example 83: 2-((2-((3r,5r,7r)-adamantan-1-yl)acetoxy)methyl)-4-((4-(pyrrolidin-1-yl)butanoyl)oxy)butyl (9Z,12Z)-octadeca-9,12-dienoate (83)

Step 2: 2-(2,2-dimethyl-1,3-dioxan-5-yl)ethan-1-ol

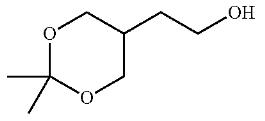

To a stirred solution of 2-(hydroxymethyl)butane-1,4-diol (1.7 g, 14.1 mmol) and 2,2-dimethoxypropane (4.3 mL, 35.3 mmol) in THF (10 mL) was added p-toluenesulfonic acid monohydrate (0.36 g, 3.1 mmol) at 25° C. under argon atmosphere. The reaction mixture was stirred at 25° C. for (83)

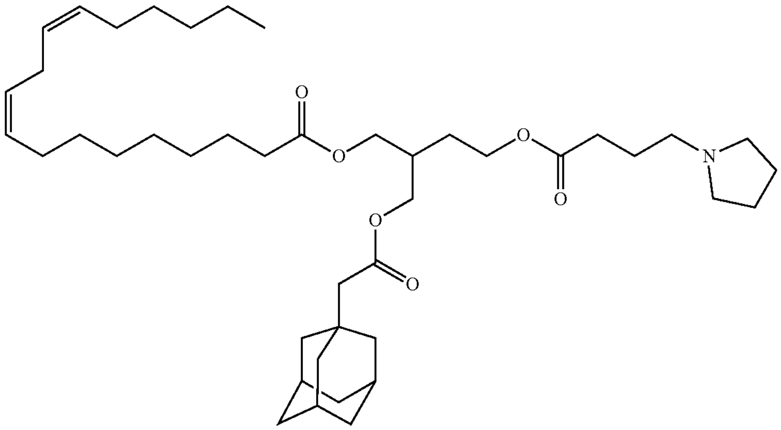

Step 1: 2-(hydroxymethyl)butane-1,4-diol

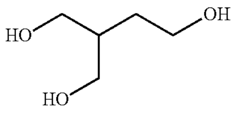

To a stirred solution of triethyl ethane-1,1,2-tricarboxylate (5 g, 20.3 mmol) in tert-butanol (80 mL) was added $NaBH_4$ (2.3 g, 60.9 mmol) under argon atmosphere at 25° C. The resulting suspension was heated to reflux and methanol (3 mL) was added drop wise in three portions within 30 min. The resulting solution was heated to reflux for another 3 h. Then the reaction mixture was cooled to 25° C. and neutralized with 5N HCl (2.5 mL). The precipitate was filtered and the filtrate was evaporated to afford crude material which was purified by combiflash column chromatography, eluted with 10-15% MeOH in DCM to afford 2-(hydroxymethyl)butane-1,4-diol (1.7 g, 69%) as a yellow liquid. $^1H$ NMR (400 MHz, DMSO-$d_6$): δ 1.34-1.46 (m, 2H), 1.49-1.63 (m, J H), 3.27-3.48 (m, 6H), 4.34 (t, J=5.2 Hz, 2H), 4.40 (t, J=5.1 Hz, 1H).

16 h. After this time, the reaction was neutralized with triethylamine (5 mL). Solvent was removed under reduced pressure to afford crude material which was purified by combiflash column chromatography eluted with 15% ethyl acetate-hexane to afford 2-(2,2-dimethyl-1,3-dioxan-5-yl)ethan-1-ol (1.2 g, 53%) as a pale yellow liquid. $^1H$ NMR (400 MHz, $CDCl_3$): δ 1.41 (s, 6H), 1.50-1.60 (m, 2H), 1.88-1.98 (m, 1H), 3.63 (dd, J=7.9, 11.8 Hz, 2H), 3.70 (t, J=6.4 Hz, 2H), 3.93 (dd, J=4.5, 11.8 Hz, 2H).

Step 3: 2-(2,2-dimethyl-1,3-dioxan-5-yl)ethyl 4-(pyrrolidin-1-yl)butanoate

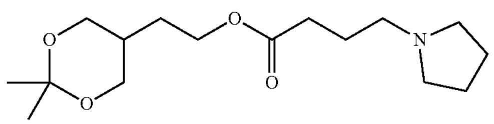 [SMILES: CC1(C)OCC(CCOC(=O)CCCN2CCCC2)CO1]

To a stirred solution of 4-(pyrrolidin-1-yl)butanoic acid (255 mg, 1.6 mmol) in DCM (5 mL) were added EDC (355 mg, 1.8 mmol) and DMAP (31 mg, 0.2 mmol) at 25° C. and stirred for 5 min. After this time, triethylamine (0.6 mL, 4.96 mmol) and 2-(2,2-dimethyl-1,3-dioxan-5-yl)ethan-1-ol (307 mg, 1.92 mmol) were added at 25° C. The reaction mass was stirred at 25° C. for 16 h. Reaction mixture was diluted with water and extracted with DCM (3×15 mL). Combined organic layer was washed with brine, dried over anhydrous $Na_2SO_4$, filtered and concentrated under reduced pressure.

Crude material thus obtained was purified by combiflash column chromatography eluted with 2% MeOH-DCM to afford 2-(2,2-dimethyl-1,3-dioxan-5-yl)ethyl 4-(pyrrolidin-1-yl)butanoate (140 mg, 38%) as a pale yellow liquid. LCMS: Column—YMC Triart C18 (33×2.1 mm, 3μ), (mobile phase: 98% [0.05% HCOOH in water] and 2% [$CH_3CN$] held for 0.75 min, then to 90% [0.05% HCOOH in water] and 10% [$CH_3CN$] in 1.0 min, to 2% [0.05% HCOOH in water] and 98% [$CH_3CN$] in 2.0 min, held this mobile phase composition up to 2.25 min and finally back to initial condition in 3.0 min). Flow=1.5 ml/min, 25° C.=1.22 min., calculated m/z [M+H]=300.2, found 300.5.

Step 4: 4-hydroxy-3-(hydroxymethyl)butyl 4-(pyrrolidin-1-yl)butanoate

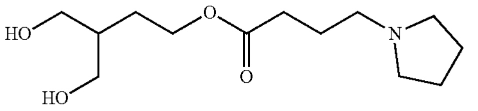 [SMILES: O=C(CCCN1CCCC1)OCCC(CO)CO]

To a stirred solution of 2-(2,2-dimethyl-1,3-dioxan-5-yl) ethyl 4-(pyrrolidin-1-yl)butanoate (140 mg, 0.3 mmol) in MeOH (1 mL) was added 1N HCl (0.9 mL, 0.9 mmol) at 25° C. The reaction was stirred for 4 h. After this time the reaction mixture was concentrated and azeotroped with toluene two times to afford crude product (120 mg) which was directly used in the next step without purification. LCMS: Column-YMC Triart C18 (33×2.1 mm, 3μ), (mobile phase: 98% [0.05% HCOOH in water] and 2% [$CH_3CN$] held for 0.75 min, then to 90% [0.05% HCOOH in water] and 10% [$CH_3CN$] in 1.0 min, further to 2% [0.05% HCOOH in water] and 98% [$CH_3CN$] in 2.0 min, held this mobile phase composition up to 2.25 min and finally back to initial condition in 3.0 min). Flow=1.5 ml/min, 25° C.=0.50 min., calculated m/z [M+H]=260.2, found 260.2.

Step 5: 2-(hydroxymethyl)-4-((4-(pyrrolidin-1-yl) butanoyl)oxy)butyl (9Z,12Z)-octadeca-9,12-dienoate

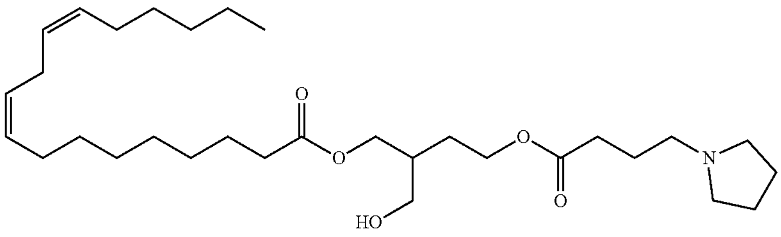 [SMILES: CCCCC/C=C\C/C=C\CCCCCCCC(=O)OCC(CO)CCOC(=O)CCCN1CCCC1]

To a stirred solution of linoleic acid (0.32 mL, 1.0 mmol) in DCM (4 mL) were added DIPEA (0.5 mL, 2.8 mmol), EDC (333 mg, 1.8 mmol) and DMAP (14 mg, 0.16 mmol) at 0° C. and stirred for 5 min. After this time, 4-hydroxy-3-(hydroxymethyl)butyl 4-(pyrrolidin-1-yl)butanoate (crude from Step 4, 115 mg) was added at 0° C. The reaction mixture was stirred at 25° C. for 16 h. The reaction mixture was diluted with water and extracted with DCM (3×15 mL). Combined organic layers were washed with brine, dried over anhydrous $Na_2SO_4$, filtered and concentrated under reduced pressure. The crude material was purified by combiflash column chromatography, eluted with 2% MeOH-DCM to afford 2-(hydroxymethyl)-4-((4-(pyrrolidin-1-yl)butanoyl) oxy)butyl (9Z,12Z)-octadeca-9,12-dienoate (150 mg, 24%) as pale yellow liquid. LCMS: Column—YMC Triart C18 (33×2.1 mm, 3μ), (mobile phase: 98% [0.05% HCOOH in water] and 2% [$CH_3CN$] held for 0.75 min, then to 90% [0.05% HCOOH in water] and 10% [$CH_3CN$] in 1.0 min, further to 2% [0.05% HCOOH in water] and 98% [$CH_3CN$] in 2.0 min, held this mobile phase composition up to 2.25 min and finally back to initial condition in 3.0 min). Flow=1.5 ml/min, 25° C.=1.74 min., calculated m/z [M+H]=522.41, found 522.7.

Step 6: 2-((2-((3r,5r,7r)-adamantan-1-yl)acetoxy) methyl)-4-((4-(pyrrolidin-1-yl)butanoyl)oxy)butyl (9Z,12Z)-octadeca-9,12-dienoate (83)

To a stirred solution of 1-adamantane acetic acid (87.74 mg, 0.43 mmol) in DCM (2 mL), were added EDC (165.35 mg, 0.86 mmol), DIPEA (0.15 mL, 0.86 mmol) and DMAP (3.5 mg, 0.02 mmol) at 0° C. and stirred for 5 min. Then 2-(hydroxymethyl)-4-((4-(pyrrolidin-1-yl)butanoyl)oxy) butyl (9Z,12Z)-octadeca-9,12-dienoate (210 mg, 0.40 mmol) was added at 0° C. The reaction mixture was stirred at 25° C. for 16 h. After this time, the reaction mixture was diluted with water and extracted with DCM (3×15 mL). Combined organic layers were washed with brine, dried over anhydrous $Na_2SO_4$, filtered and concentrated under reduced pressure. The crude material was purified by Prep-HPLC to obtain 2-((2-((3r,5r,7r)-adamantan-1-yl)acetoxy)methyl)-4-((4-(pyrrolidin-1-yl)butanoyl)oxy)butyl (9Z,12Z)-octadeca-9,12-dienoate (22 mg, 8%) as yellow sticky liquid. Prep-HPLC method: Waters auto purification instrument. Column name: Xterra RP18(50×20 mm, 5μ) operating at 50° C. and flow rate of 16 mL/min. Mobile phase: A=0.1% Formic acid in water; B=70:30::Acetonitrile:THF+0.1% Formic acid; Gradient Profile: Mobile phase initial composition of 70% A and 30% B gradually increased 30% A and 70% B in 14 min., then to 100% B in 15 min. and continued in this composition up to 17 min for column washing, then returned to initial composition in 18 min and held till 20 min.

LCMS: Column—XTERRA RP 18 (4.6×50 mm), 5μ, (mobile phase: initially 80% [0.1% HCOOH in WATER] and 20% [0.1% HCOOH in (70:30) ACN:THF]; held this initial condition for 0.75 min; then to 65% [0.1% HCOOH in WATER] and 35% [0.1% HCOOH in (70:30) ACN:THF] in 3.0 min, then to 2% [0.1% HCOOH in WATER] and 98% [0.1% HCOOH in (70:30) ACN:THF] in 6.0 min, held this mobile phase composition up to 9.0 min, and finally back to initial condition, i.e.; 80% [0.1% HCOOH in WATER] and 20% [0.1% HCOOH in (70:30) ACN:THF] in 11.00 min, held this mobile phase composition up to 12.10 min. Flow=1.2 ml/min, RT=5.19 min., calculated m/z [M+H]=698.5, found 699.2.

Example 84: 2-((2-((3r,5r,7r)-adamantan-1-yl)acetoxy)methyl)-4-((3-(4-methylpiperazin-1-yl)propanoyl)oxy)butyl (9Z,12Z)-octadeca-9,12-dienoate (84)

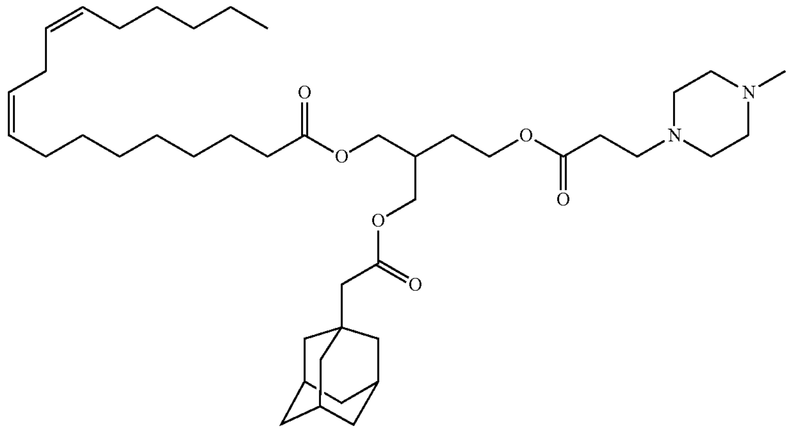

(84)

Prepared by similar procedures as illustrated for Example 83, substituting 3-(4-methylpiperazin-1-yl)propanoic acid for 4-(pyrrolidin-1-yl)butanoic acid in Step 3. Yield of final step: 38 mg, 14%. LCMS: Column—XTERRA RP 18 (4.6×50 mm), 5μ, (mobile phase: initially 95% [0.1% HCOOH in WATER] and 5% [0.1% HCOOH in (70:30) ACN:THF]; then to 70% [0.1% HCOOH in WATER] and 30% [0.1% HCOOH in (70:30) ACN:THF] in 0.75 min, then to 2% [0.1% HCOOH in WATER] and 98% [0.1% HCOOH in (70:30) ACN:THF] in 3.0 min, held this mobile phase composition up to 4.90 min, and finally back to initial condition, i.e; 95% [0.1% HCOOH in WATER] and 5% [0.1% HCOOH in (70:30) ACN:THF] in 5.10 min. Flow=1.2 mL/min, RT=2.57 min., calculated m/z [M+H]=713.5, MS found 713.7.

Example 85: 2-((2-((3r,5r,7r)-adamantan-1-yl)acetoxy)methyl)-4-((4-(dipropylamino)butanoyl)oxy) butyl (9Z,12Z)-octadeca-9,12-dienoate Prepared by similar procedures as illustrated for Example 83, substituting 4-(dipropylamino)butanoic acid for 4-(pyrrolidin-1-yl)butanoic acid in Step 3. Yield of final step: 21 mg, 7%. LCMS: Column—XTERRA RP 18 (4.6×50 mm), 5μ, (mobile phase: initially 80% [0.1% HCOOH in WATER] and 20% [0.1% HCOOH in (70:30) ACN:THF]; held this initial condition for 0.75 min; then to 65% [0.1% HCOOH in WATER] and 35% [0.1% HCOOH in (70:30) ACN:THF] in 3.0 min, then to 2% [0.1% HCOOH in WATER] and 98% [0.1% HCOOH in (70:30) ACN:THF] in 6.0 min, held this mobile phase composition up to 9.0 min, and finally back to initial condition, i.e.; 80% [0.1% HCOOH in WATER] and 20% [0.1% HCOOH in (70:30) ACN:THF] in 11.00 min, held this mobile phase composition up to 12.10 min. Flow=1.2 ml/min, RT=5.18 min., calculated m/z [M+H]=729.1, found 729.7.

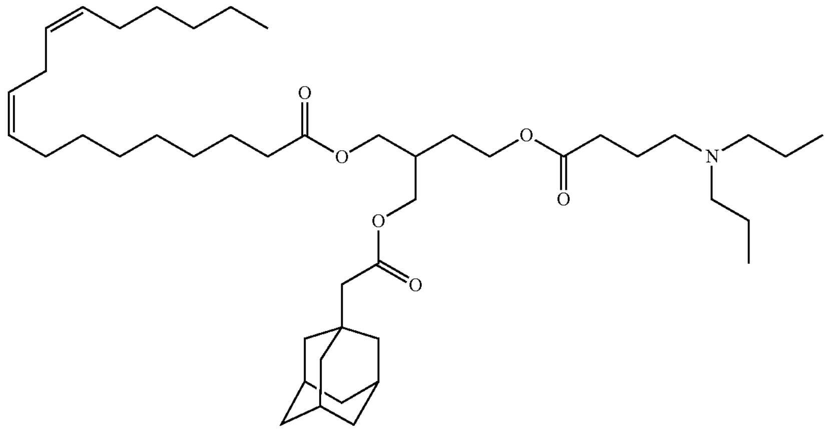

(85)

Example 86: 2-((2-((3r,5r,7r)-adamantan-1-yl)acetoxy)methyl)-4-(2-(4-methylpiperazin-1-yl)acetoxy)butyl (9Z,12Z)-octadeca-9,12-dienoate (86)

(86)

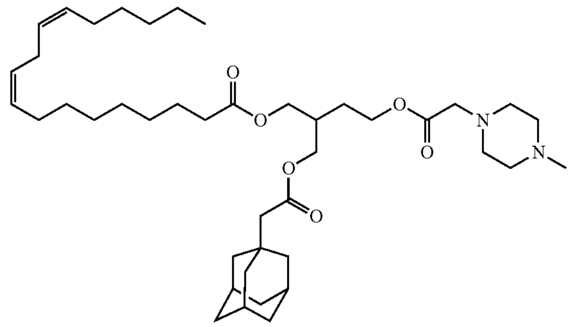

Prepared by similar procedures as illustrated for Example 83, substituting 2-(4-methylpiperazin-1-yl)acetic acid for 4-(pyrrolidin-1-yl)butanoic acid in Step 3. Yield of final step: 14 mg, 5%. LCMS: Column—XTERRA RP 18 (4.6×50 mm), 5μ, (mobile phase: initially 80% [0.1% HCOOH in WATER] and 20% [0.1% HCOOH in (70:30) ACN:THF]; held this initial condition for 0.75 min; then to 65% [0.1% HCOOH in WATER] and 35% [0.1% HCOOH in (70:30) ACN:THF] in 3.0 min, then to 2% [0.1% HCOOH in WATER] and 98% [0.1% HCOOH in (70:30) ACN:THF] in 6.0 min, held this mobile phase composition up to 9.0 min, and finally back to initial condition, i.e.; 80% [0.1% HCOOH in WATER] and 20% [0.1% HCOOH in (70:30) ACN:THF] in 11.00 min, held this mobile phase composition up to 12.10 min. Flow=1.2 ml/min, RT=2.51 min., calculated m/z [M+H]=699.5, found: 699.3.

Lipid Nanoparticles

Screening

F. LNP Formulation

The lipid nanoparticle components were dissolved in 100% ethanol at specified lipid component molar ratios. The nucleic acid (NA) cargo was dissolved in 10 mM citrate, 100 mM NaCl, pH 4.0, resulting in a concentration of NA cargo of approximately 0.22 mg/mL. In some embodiments, NA cargos consist of both a functional NA (e.g. siRNA, antisense, expressing DNA, mRNA) as well as a reporter DNA barcode (as previously described Sago, 2018 PNAS) mixed at mass ratios of 1:10 to 10:1 functional NA to barcode.

The LNPs were formulated with a total lipid to NA mass ratio of 11.7. The LNPs were formed by microfluidic mixing of the lipid and NA solutions using a Precision Nanosystems NanoAssemblr Spark or Benchtop Instrument, according to the manufacturers protocol. A 2:1 ratio of aqueous to organic solvent was maintained during mixing using differential flow rates. After mixing, the LNPs were collected, diluted in PBS (approximately 1:1 v/v), and further buffer exchange was conducted using dialysis in PBS at 4° C. for 8 to 24 hours against a 20 kDa filter. After this initial dialysis, each individual LNP formulation was characterized via DLS to measure the size and polydispersity, and the pKa of a subpopulation of LNPs were measured via TNS assay. LNPs falling within specific diameter and polydispersity ranges were pooled, and further dialyzed against PBS at 4° C. for 1 to 4 hours against a 100 kDa dialysis cassette. After the second dialysis, LNPs were sterile filtered using 0.22 μM filter and stored at 4° C. for further use.

G. LNP Characterization

DLS—LNP hydrodynamic diameter and polydispersity percent (PDI %) were measured using high throughput dynamic light scattering (DLS) (DynaPro plate reader II, Wyatt). LNPs were diluted 1×PBS to an appropriate concentration and analyzed.

Concentration & Encapsulation Efficiency—Concentration of NA was determined by Qubit microRNA kit (for siRNA) or HS RNA kit (for mRNA) per manufacturer's instructions. Encapsulation efficiency was determined by measuring unlysed and lysed LNPs.

pKa—A stock solution of 10 mM HEPES (Sigma Aldrich), 10 mM MES (Sigma Aldrich), 10 mM sodium acetate (Sigma), and 140 nM sodium chloride (Sigma Aldrich) was prepared and pH adjusted using hydrogen chloride and sodium hydroxide to a range of pH 4-10. Using 4 replicates for each pH, 140 μL pH-adjusted buffer was added to a 96-well plate, followed by the addition 5 μL of 2-(p-toluidino)-6-napthalene sulfonic acid (60 μg/mL). 5 μL of LNP were added to each well. After 5 min of incubation under gentle shaking, fluorescence was measured using an excitation wavelength of 325 nm and emission wavelength of 435 nm (BioTek Synergy H4 Hybrid).

LNP Administration—Male and female mice aged approximately 8-12 weeks were used for all studies. Each mouse was temporarily restrained, and pooled LNP was administered IV via tail vein injection in up to five animals per experiment. Age-matched mice were also used to administer vehicle (1×PBS) via tail vein injection in up to three animals per experiment. At 72 hours post-dose, tissues including liver, spleen, bone marrow and blood were collected for analysis.

Information related to LNP formulation, as well as LNP characterization can be found in FIG. 1. The lipid number corresponds to the numbering in the Examples section.

Flow—Liver tissues were mechanically, and then enzymatically digested using a mixture of proteinases, then passed through a 70 uM filter to generate single cell suspensions. Spleen tissues were mechanically digested to generate single cell suspensions. All tissues were treated with ACK buffer to lyse red blood cells, and then stained with fluorescently-labeled antibodies for flow cytometry and fluorescence-activated cell sorting (FACS). All antibodies were commercially available antibodies. Using a BD FACSMelody (Becton Dickinson), all samples were acquired via flwo cytometry to generate gates prior to sorting. In general, the gating structure was size→singlet cells→live cells→cells of interest. T cells were defined as CD45+CD3+, monocytes were defined as CD45+CD11b+, and B cells were defined as CD45+CD19+. In the liver, endothelial cells were defined as CD31+, Kupffer cells as CD45+CD11b+ and hepatocytes as CD31−/CD45−. For siRNA studies, we gated for downregulation of the target gene, whereas for mRNA studies, we gated for upregulation of the target gene. Tissues from vehicle-dosed mice were used to set the gates for sorting. Up to 20,000 cells of each cell subset with the correct phenotype was sorted into 1×PBS. After sorting, cells were pelleted via centrifugation and DNA was extracted using Quick Extract DNA Extraction Solution (Lucigen) according to manufacturers protocol. DNA was stored at −20° C.

Barcoding Sequencing—DNA (genomic and DNA barcodes) were isolated using QuickExtract (Lucigen) and sequenced using Illumina MiniSeq as previously described (Sago et al. PNAS 2018, Sago et al. JACs 2018, Sago, Lokugamage et al. Nano Letters 2018), normalizing frequency DNA barcode counts in FACS isolated samples to frequency in injected input. These data are plotted as 'Normalized Fold Above Input', selected in vivo data from experiments 71, 72, 73, and 74 can be found in FIGS. 2-5.

H. Confirmation

LNP Formulation

The lipid nanoparticle components were dissolved in 100% ethanol at specified lipid component molar ratios. The nucleic acid (NA) cargo was dissolved in 10 mM citrate, 100 mM NaCl, pH 4.0, resulting in a concentration of NA cargo of approximately 0.22 mg/mL. In some embodiments, NA cargos consist of both a functional NA (e.g. siRNA, antisense, expressing DNA, mRNA) as well as a reporter DNA barcode (as previously described Sago, 2018 PNAS) mixed at mass ratios of 1:10 to 10:1 functional NA to barcode. The LNPs were formulated with a total lipid to NA mass ratio of 11.7. The LNPs were formed by microfluidic mixing of the lipid and NA solutions using a Precision Nanosystems NanoAssemblr Spark or Benchtop Instrument, according to the manufacturers protocol. A 3:1 ratio of aqueous to organic solvent was maintained during mixing using differential flow rates. After mixing, the LNPs were collected, diluted in PBS (approximately 1:1 v/v), and further buffer exchange was conducted using dialysis in PBS at 4° C. for 8 to 24 hours against a 20 kDa filter. After this initial dialysis, each individual LNP formulation was characterized via DLS to measure the size and polydispersity, and the pKa of a subpopulation of LNPs were measured via TNS assay. After dialysis, LNPs were sterile filtered using 0.22 micron sterile filter and stored at 4° C. for further use.

LNP Characterization

DLS—LNP hydrodynamic diameter and polydispersity percent (PDI %) were measured using high throughput dynamic light scattering (DLS) (DynaPro plate reader II, Wyatt). LNPs were diluted 1×PBS to an appropriate concentration and analyzed.

Concentration & Encapsulation Efficiency—Concentration of NA was determined by Qubit microRNA kit (for siRNA) or HS RNA kit (for mRNA) per manufacturer's instructions. Encapsulation efficiency was determined by measuring unlysed and lysed LNPs.

pKa—A stock solution of 10 mM HEPES (Sigma Aldrich), 10 mM MES (Sigma Aldrich), 10 mM sodium acetate (Sigma), and 140 nM sodium chloride (Sigma Aldrich) was prepared and pH adjusted using hydrogen chloride and sodium hydroxide to a range of pH 4-10. Using 4 replicates for each pH, 140 μL pH-adjusted buffer was added to a 96-well plate, followed by the addition 5 μL of 2-(p-toluidino)-6-napthalene sulfonic acid (60 μg/mL). 5 μL of LNP were added to each well. After 5 min of incubation under gentle shaking, fluorescence was measured using an excitation wavelength of 325 nm and emission wavelength of 435 nm (BioTek Synergy H4 Hybrid).

LNP Administration—Male and female mice aged approximately 8-12 weeks were used for all studies. Each mouse was temporarily restrained, and pooled LNP was administered IV via tail vein injection in up to five animals per experiment. Age-matched mice were also used to administer vehicle (OX PBS) via tail vein injection in up to three animals per experiment. At 72 hours post-dose, tissues including liver, spleen, bone marrow and blood were collected for analysis.

Figure 3:
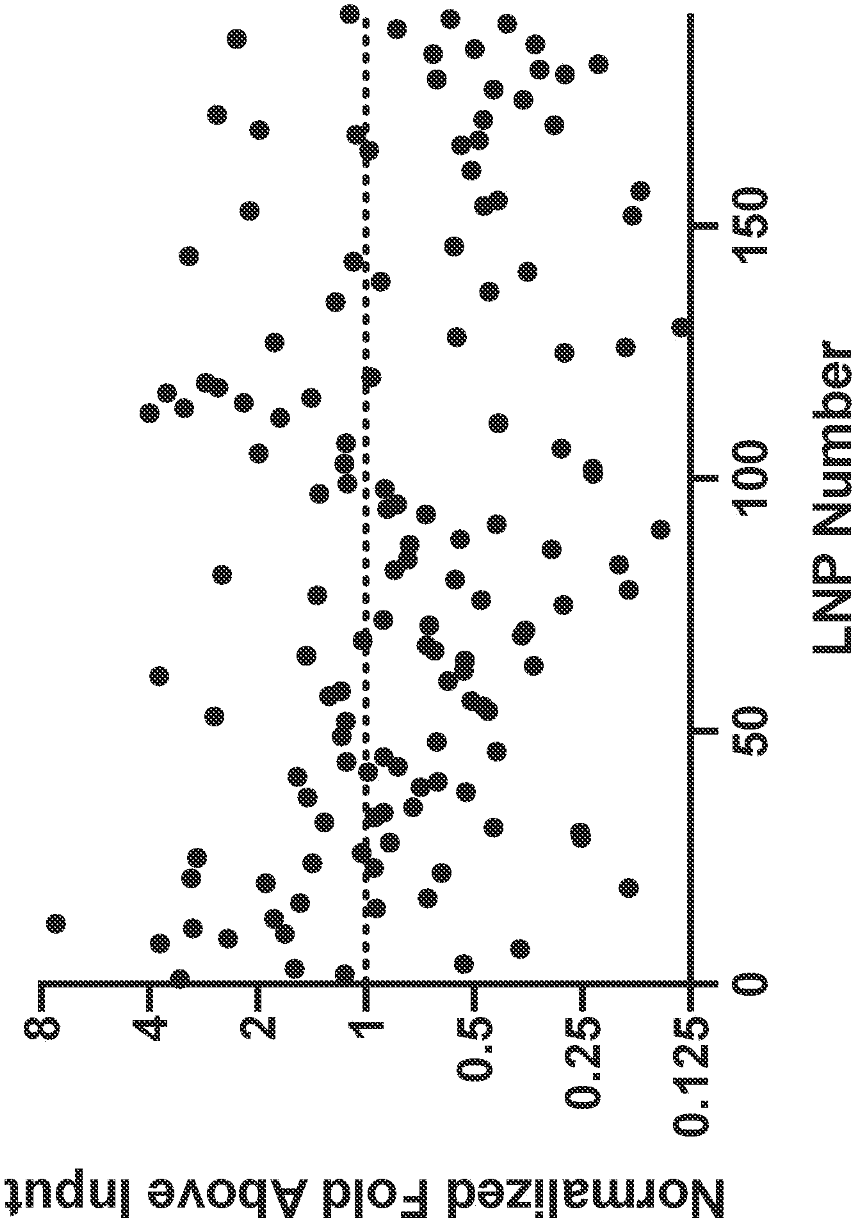
FIG. 3 is a graph showing the normalized frequency DNA barcode counts in FACS isolated samples as compared to the frequency in injected input for selected LNPs as tested in spleen CD11b cells.
Figure 4:
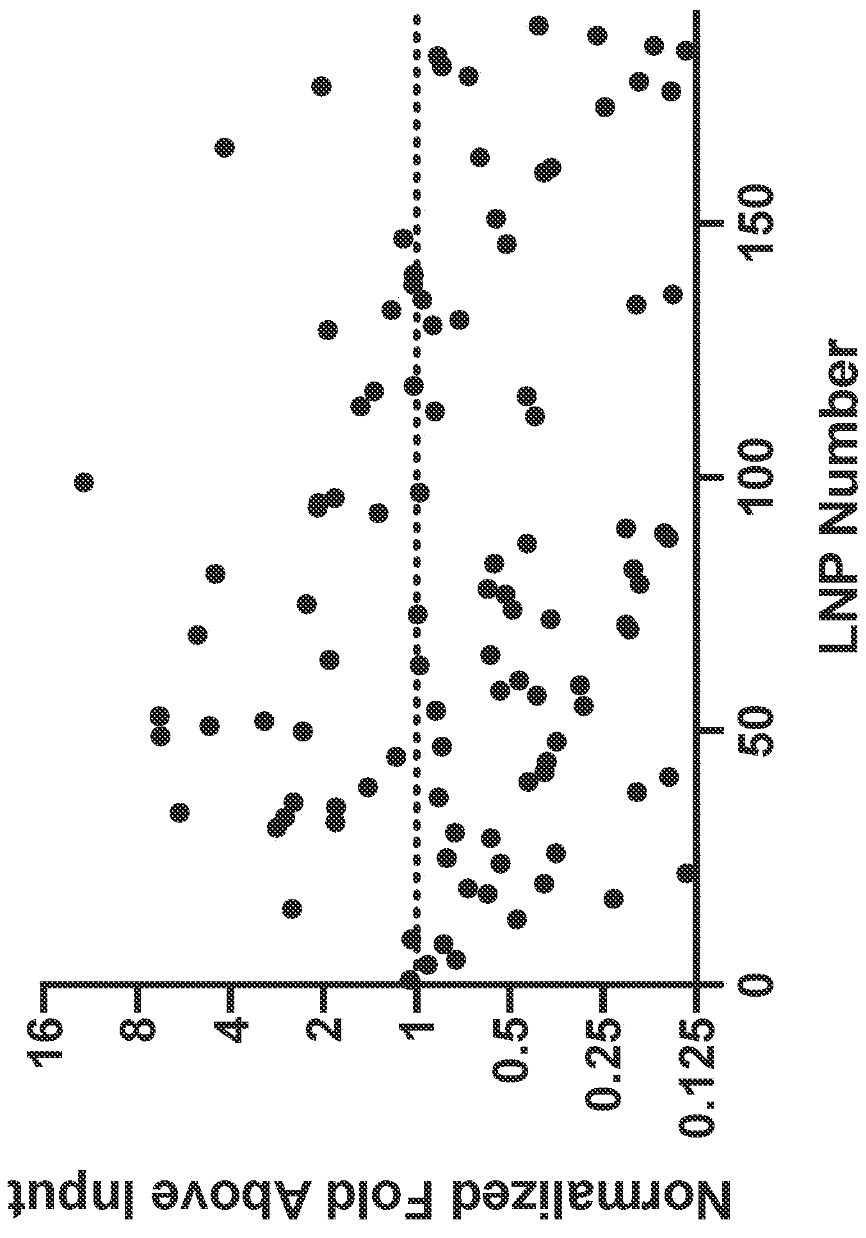
FIG. 4 is a graph showing the normalized frequency DNA barcode counts in FACS isolated samples as compared to the frequency in injected input for selected LNPs as tested in spleen CD19 cells.
Figure 5:
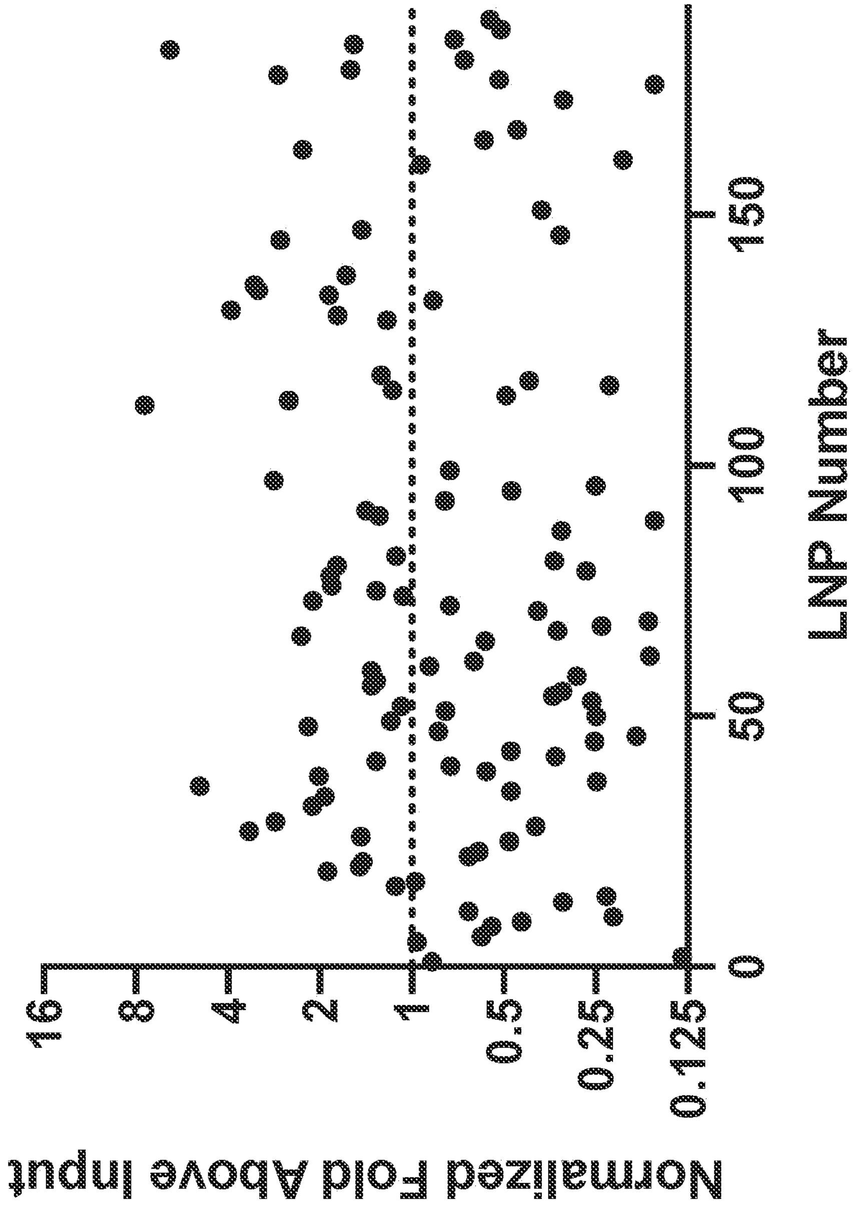
FIG. 5 is a graph showing the normalized frequency DNA barcode counts in FACS isolated samples as compared to the frequency in injected input for selected LNPs as tested in liver endothelial cells.
Figure 6:
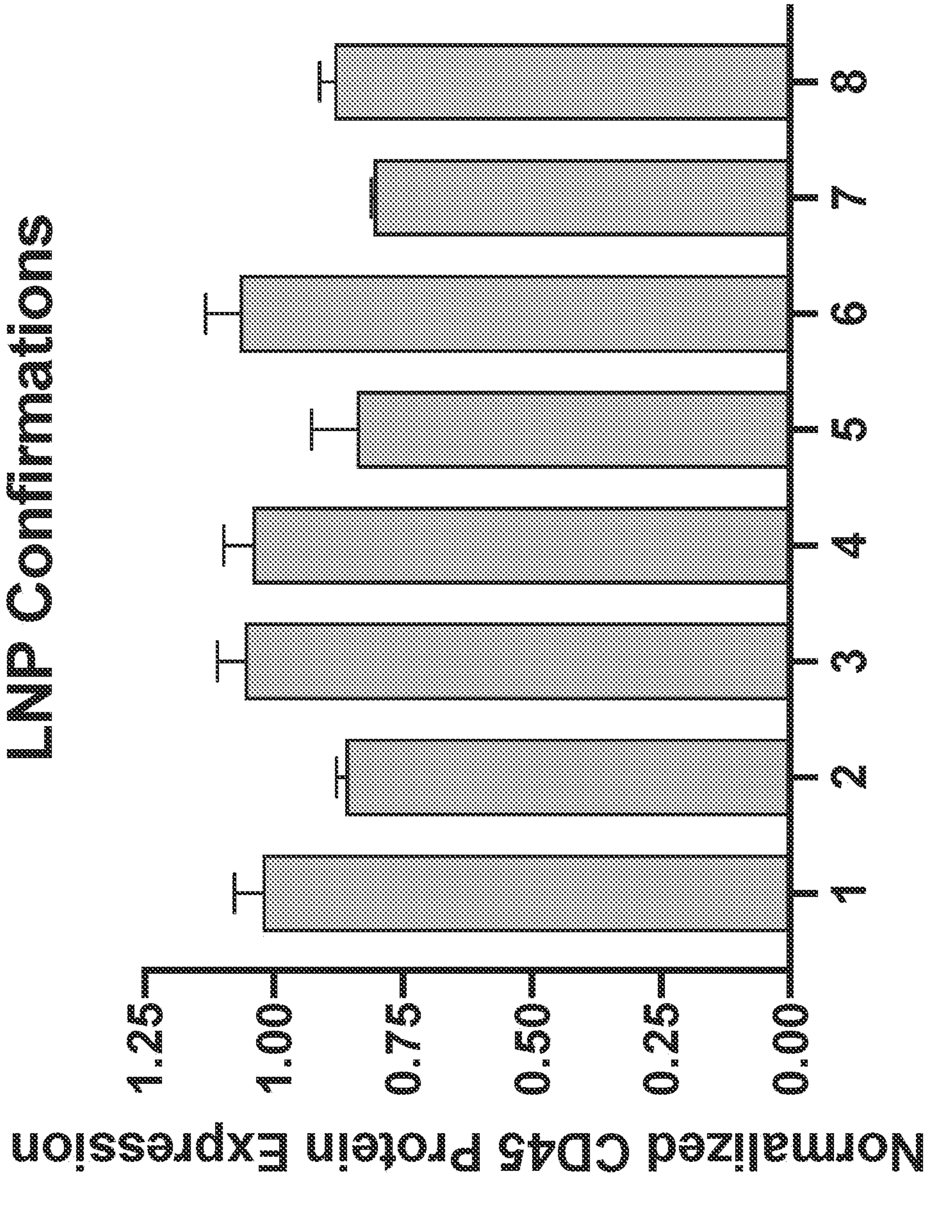
FIG. 6 is a graph showing the CD45 protein expression in CD3-positive cells isolated from mice spleens for LNP formulations as described in Table 1.

Flow—Liver tissues were mechanically, and then enzymatically digested using a mixture of proteinases, then passed through a 70 uM filter to generate single cell suspensions. Spleen tissues were mechanically digested to generate single cell suspensions. All tissues were treated with ACK buffer to lyse red blood cells, and then stained with fluorescently-labeled antibodies for flow cytometry and FACS sorting. All antibodies were commercially available antibodies. Using a BD FACSMelody (Becton Dickinson), all samples were acquired via flow cytometry to generate gates prior to sorting. In general, the gating structure was size→singlet cells→live cells→cells of interest. T cells were defined as CD45+CD3+, monocytes were defined as CD45+ CD11b+, and B cells were defined as CD45+CD19+. In the liver, LSECs were defined as CD31+, Kupffer cells as CD45+CD11b+ and hepatocytes as CD31−/CD45−. For siRNA studies, we gated for downregulation of the target gene, whereas for mRNA studies, we gated for upregulation of the target gene. Tissues from vehicle-dosed mice were used to set the gates for sorting. Data are recorded as MFI by flow cytometry. Selected in vivo data are shown in FIG. 3 for CD45 protein expression in CD3-positive cells isolated from mice spleens, corresponding to the formulations shown in Table 2. The lipid number corresponds to the numbering in the Examples section. In FIG. 6, group 1 is PBS-treated animals, while groups 2-8 are LNPs 1 to 7, respectively. In each of LNPs 1-7, the cholesterol used is cholesterol, the PEG used is DMG-PEG2000, the phospholipid used is DSPC, and the ratio of lipid:cholesterol:PEG:phospholipid is 35:46.5:3.5:16. The ratio of lipid to nucleic acid is 11.7 to 1.

TABLE 2

| LNP | Lipid | Diameter | Encapsulation % | Dose Administered (mg/kg) | Payload |
|---|---|---|---|---|---|
| 1 | 70 | 101.7 | 96.53 | 0.2 | siCD45 |
| 2 | 19 | 92.2 | 73.13 | 0.3 | siCD45 |
| 3 | 29 | 85.7 | 94.03 | 0.2 | siCD45 |
| 4 | 18 | 114 | 80.74 | 0.3 | siCD45 |
| 5 | 1 | 149.1 | 87.23 | 0.2 | siITGB1 |
| 6 | 53 | 140.5 | 92.13 | 0.2 | siCD45 |
| 7 | 68 | 66 | 93.92 | 0.2 | siCD45 |

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A compound of Formula (IIb):

(IIb)

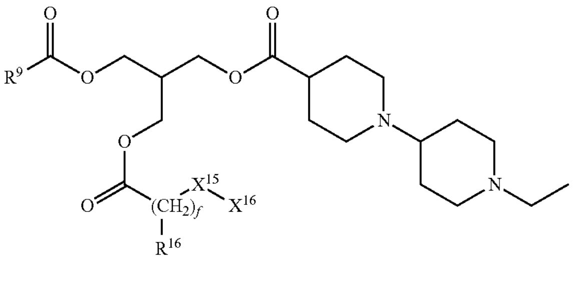

wherein:

$R^9$ is $C_9$-$C_{20}$ alkyl optionally fused with 1-4 $C_3$-$C_6$ cycloalkyl groups, $C_9$-$C_{20}$ alkenyl with 1-3 units of unsaturation, or —$(CH_2)_g$—$X^{17}$, wherein $X^{17}$ is optionally substituted $C_4$-$C_{12}$ cycloalkyl;

f is independently an integer from 0-6;

$R^{16}$ is hydrogen or optionally substituted $C_5$-$C_6$ aryl;

$X^{15}$ is optionally substituted $C_4$-$C_{12}$ cycloalkyl or optionally substituted $C_5$-$C_{10}$ aryl; and $X^{16}$ is hydrogen or optionally substituted $C_4$-$C_{12}$ cycloalkyl;

provided that when f is 1 and $R^9$ is

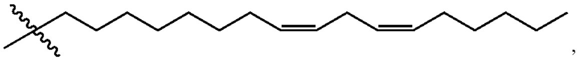

, $X^{15}$ is not

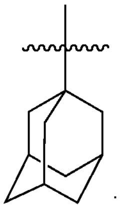 [SMILES: *C12CC3CC(CC(C3)C1)C2]

.

2. The compound of claim 1, wherein the compound is selected from the group consisting of:

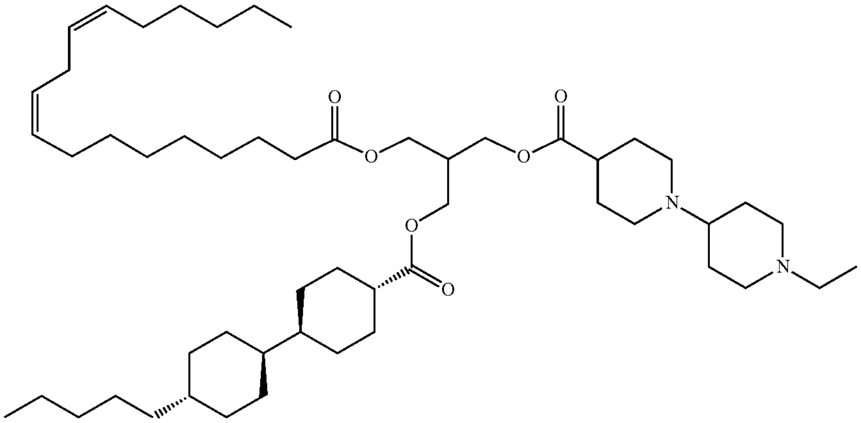

,

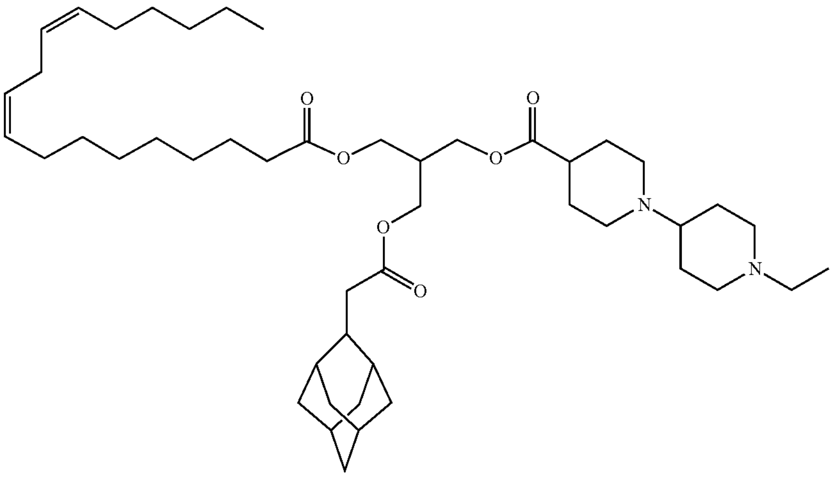

,

-continued
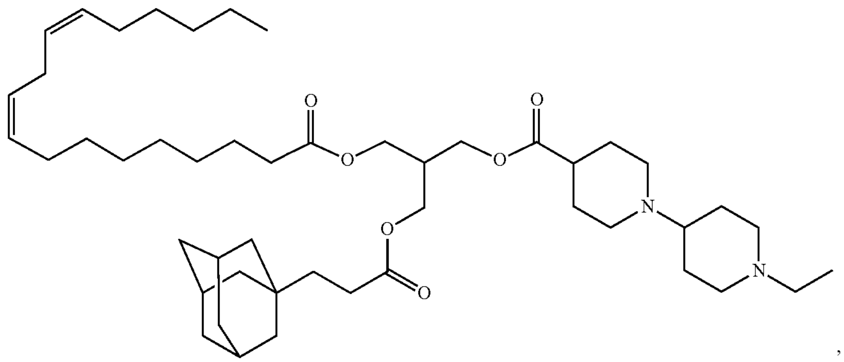
,
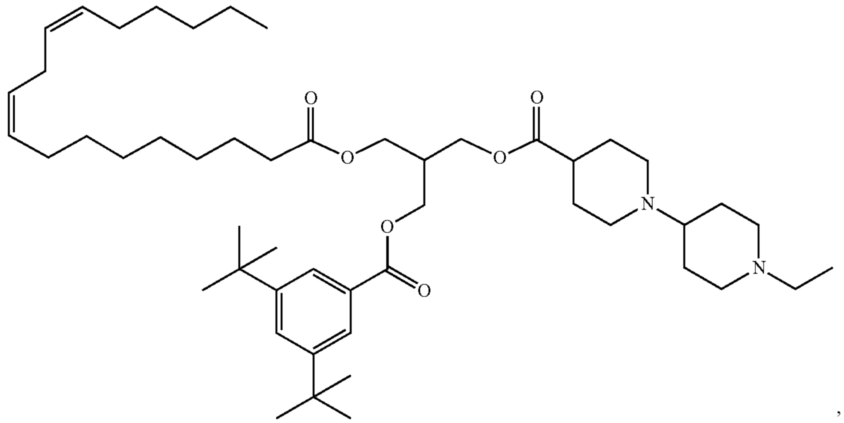
,
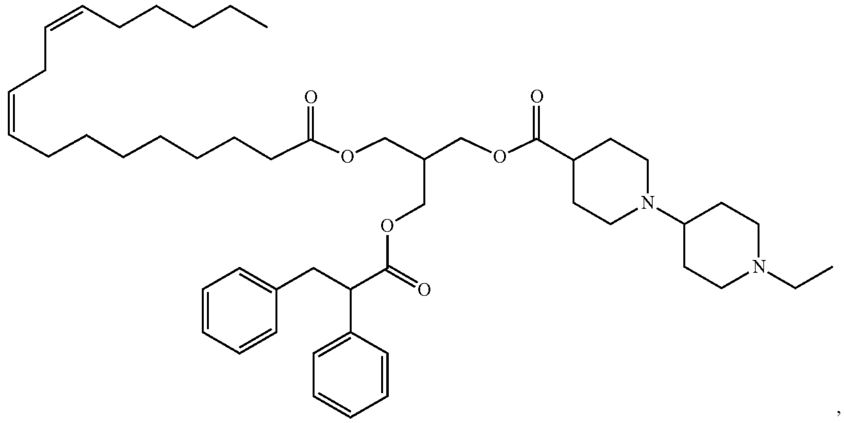
,
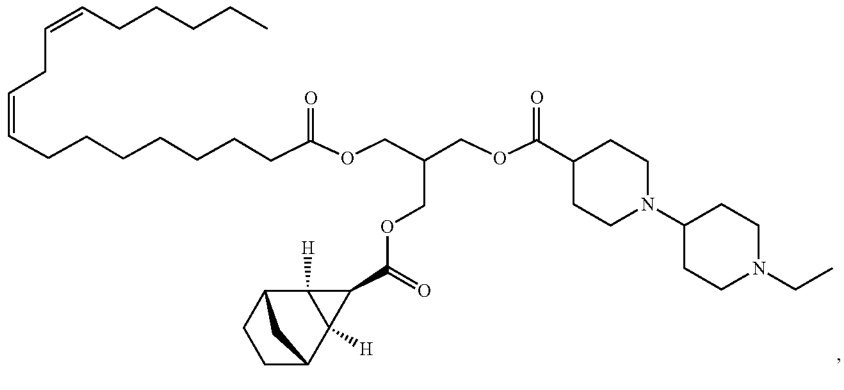
,

-continued
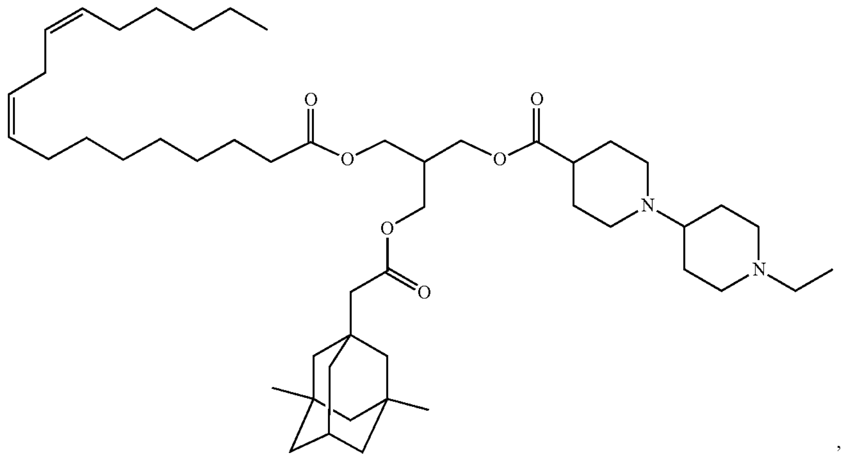
,
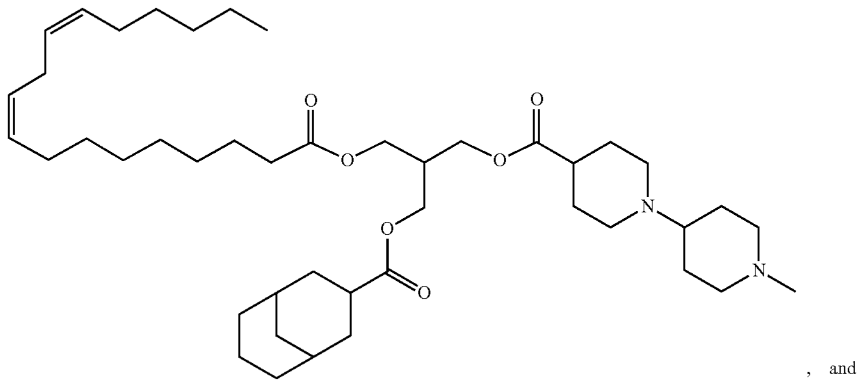
, and
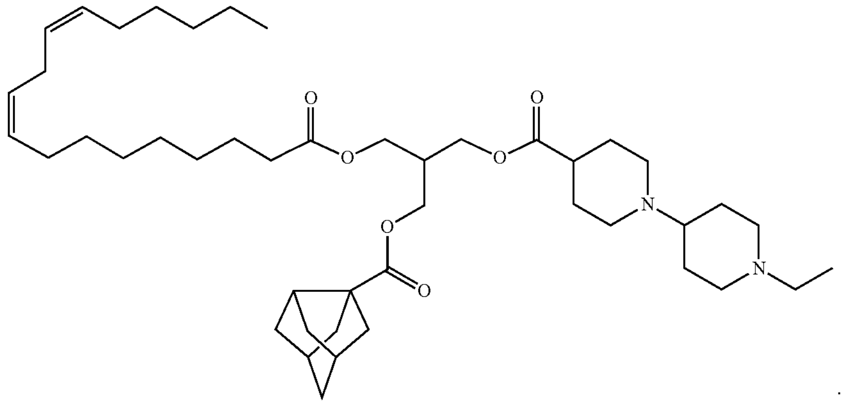
.

3. The compound of claim 2, having the following structure
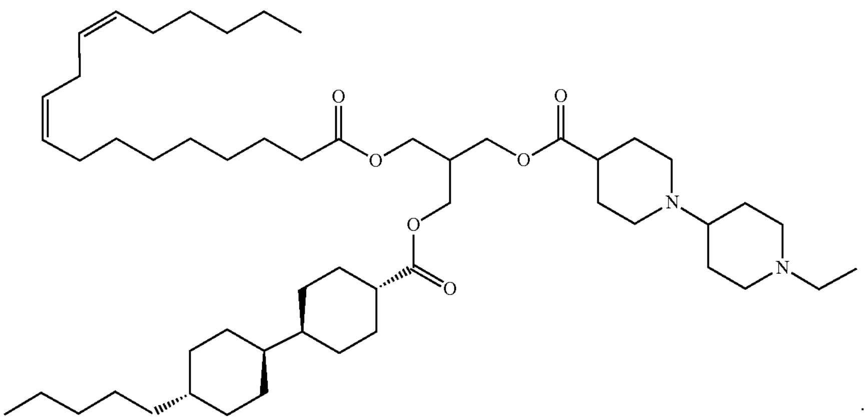 [SMILES: CCCCC/C=C\C/C=C\CCCCCCCC(=O)OCC(COC(=O)C1CCN(C2CCN(CC)CC2)CC1)COC(=O)[C@H]1CC[C@H]([C@H]2CC[C@H](CCCCC)CC2)CC1]
4. The compound of claim 2, having the following structure
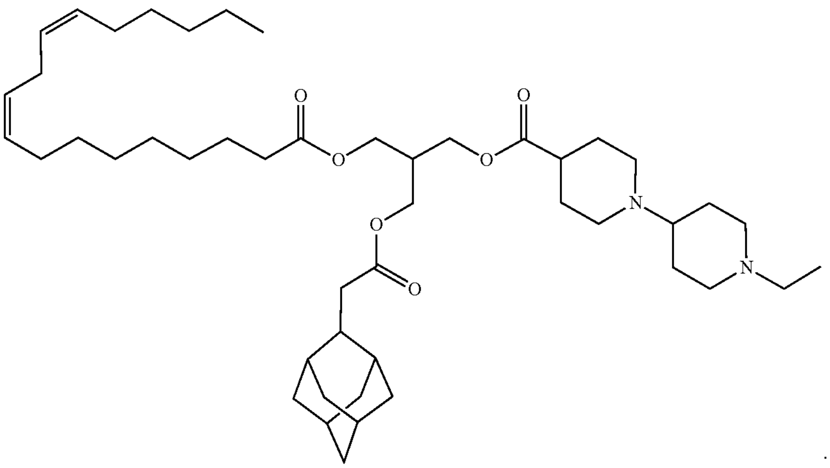 [SMILES: CCCCC/C=C\C/C=C\CCCCCCCC(=O)OCC(COC(=O)CC1C2CC3CC(C2)CC1C3)COC(=O)C1CCN(C2CCN(CC)CC2)CC1]
5. The compound of claim 2, having the following structure
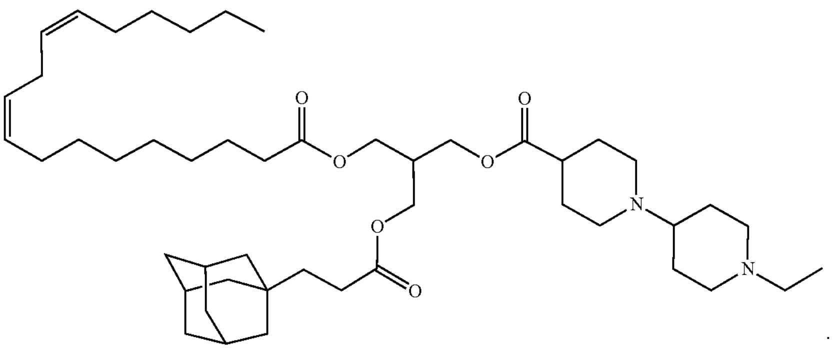 [SMILES: CCCCC/C=C\C/C=C\CCCCCCCC(=O)OCC(COC(=O)CCC12CC3CC(CC(C3)C1)C2)COC(=O)C1CCN(C2CCN(CC)CC2)CC1]
6. The compound of claim 2, having the following structure

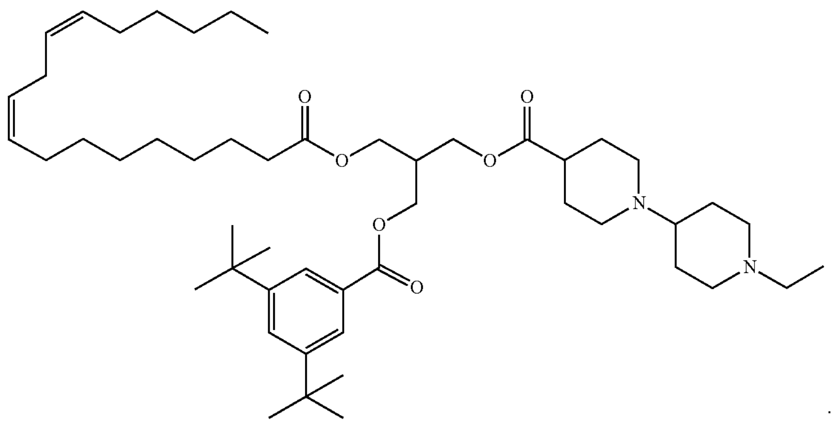 [SMILES: CCCCC/C=C\C/C=C\CCCCCCCC(=O)OCC(COC(=O)c1cc(C(C)(C)C)cc(C(C)(C)C)c1)COC(=O)C1CCN(C2CCN(CC)CC2)CC1]
7. The compound of claim 2, having the following structure
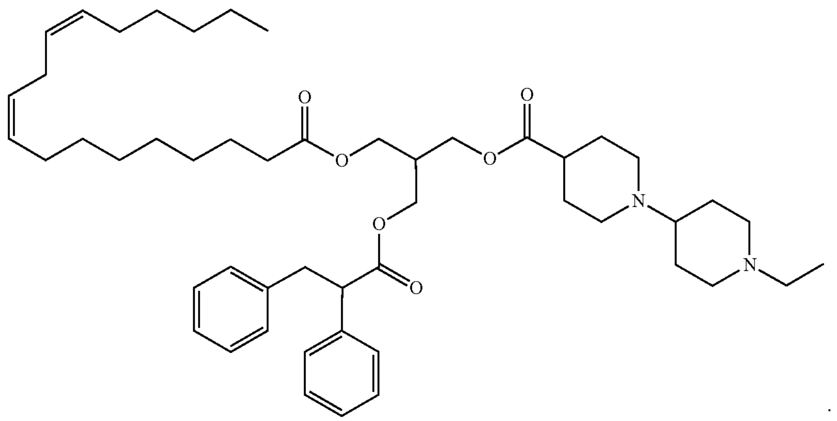 [SMILES: CCCCC/C=C\C/C=C\CCCCCCCC(=O)OCC(COC(=O)C1CCN(C2CCN(CC)CC2)CC1)COC(=O)C(Cc1ccccc1)c1ccccc1]
8. The compound of claim 2, having the following structure
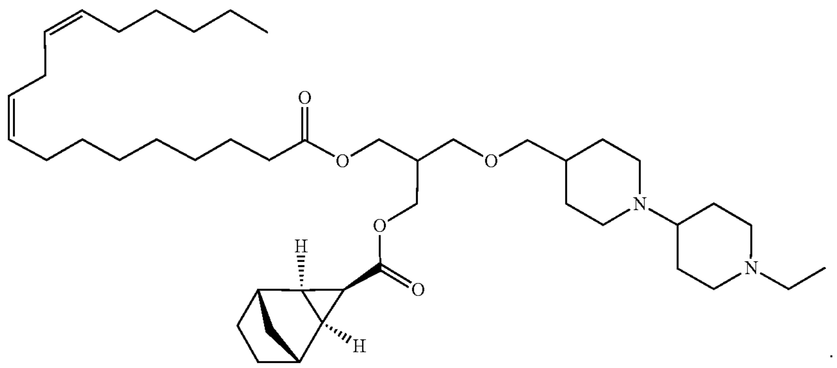 [SMILES: CCCCC/C=C\C/C=C\CCCCCCCC(=O)OCC(COCC1CCN(C2CCN(CC)CC2)CC1)COC(=O)[C@H]1[C@H]2[C@@H]3CC[C@@H](C3)[C@@H]12]
9. The compound of claim 2, having the following structure

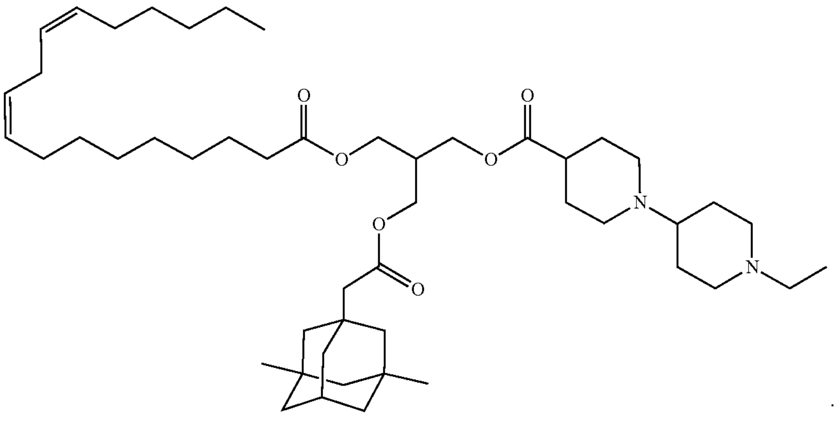 [SMILES: CCCCC/C=C\C/C=C\CCCCCCCC(=O)OCC(COC(=O)CC12CC3CC(C)(CC(C)(C3)C1)C2)COC(=O)C1CCN(C2CCN(CC)CC2)CC1]

10. The compound of claim 2, having the following structure

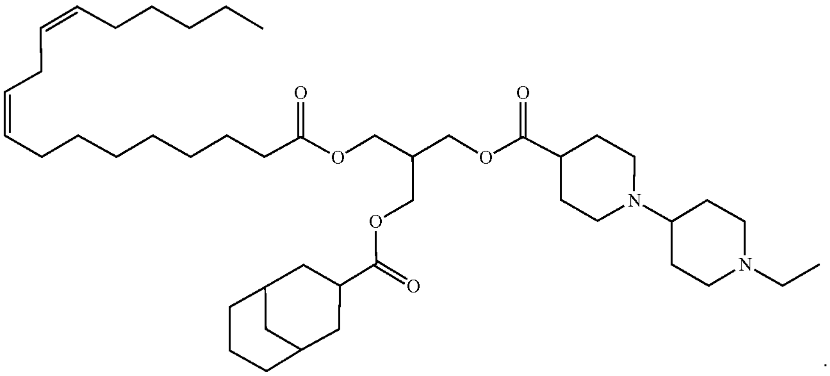 [SMILES: CCCCC/C=C\C/C=C\CCCCCCCC(=O)OCC(COC(=O)C1CCN(C2CCN(CC)CC2)CC1)COC(=O)C1CC2CCCC(C2)C1]

11. The compound of claim 2, having the following structure

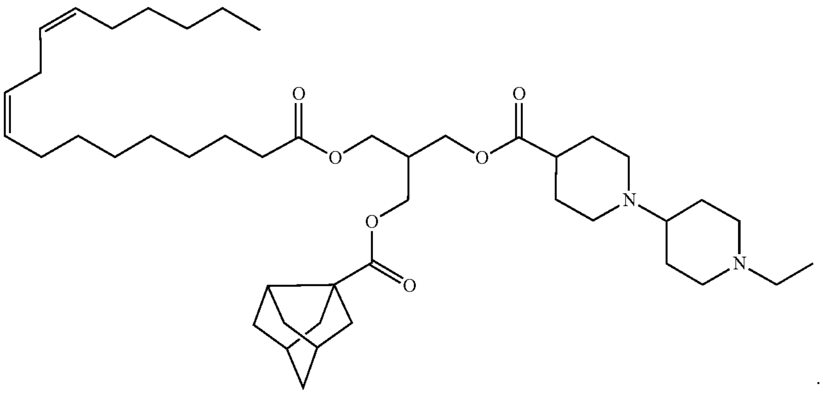 [SMILES: CCCCC/C=C\C/C=C\CCCCCCCC(=O)OCC(COC(=O)C1CCN(C2CCN(CC)CC2)CC1)COC(=O)C12CC3CC(CC1C3)C2]

12. A lipid nanoparticle composition comprising:

an ionizable lipid that is the compound of claim 1;

a phospholipid;

a polyethylene glycol-lipid; and a cholesterol.

13. The lipid nanoparticle composition of claim 1, further comprising a nucleic acid.

14. The lipid nanoparticle composition of claim 12, wherein the amount of ionizable lipid is present in the range of about 35 to 65 mole percent, based on total moles.

15. The lipid nanoparticle composition of claim 12, wherein the phospholipid is DSPC.

16. The lipid nanoparticle composition of claim 12, wherein the phospholipid is DMPC.

17. A method of delivering a nucleic acid to a subject in need thereof, comprising administering to the subject the lipid nanoparticle composition of claim 12.

18. The lipid nanoparticle composition of claim 13, wherein the nucleic acid is siRNA, miRNA, anti-sense oligonucleotide, or immunostimulatory oligonucleotide.

19. The lipid nanoparticle composition of claim 12, wherein the polyethylene glycol-lipid is DMG-PEG2000.

20. The lipid nanoparticle composition of claim 12, wherein the polyethylene glycol-lipid is DSG-PEG2000.

* * * * *